United States Patent
Lippa et al.

(10) Patent No.: US 10,428,072 B2
(45) Date of Patent: Oct. 1, 2019

(54) INHIBITING THE TRANSIENT RECEPTOR POTENTIAL A1 ION CHANNEL

(71) Applicant: Eli Lilly and Company, Indianapolis, IN (US)

(72) Inventors: Blaise S. Lippa, Concord, MA (US); Xinyuan Wu, Newton, MA (US); Qingyi Li, Somerville, MA (US); Iwona Wrona, Sharon, MA (US); Andrew J. Jackson, Waltham, MA (US); Bertrand L. Chenard, Waterford, CT (US); Christopher M. Liu, Somerville, MA (US); Guohua Liang, Acton, MA (US); Matthew F. Baevsky, Northborough, MA (US); Richard A. Earl, Westford, MA (US); Lisa Mcqueen, Phoenixville, PA (US); Jared Smit, Lafayette, IN (US); Brett A. Cowans, Lafayette, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 15/940,253

(22) Filed: Mar. 29, 2018

(65) Prior Publication Data
US 2018/0230149 A1    Aug. 16, 2018

Related U.S. Application Data

(63) Continuation of application No. 15/305,892, filed as application No. PCT/US2015/027353 on Apr. 23, 2015, now abandoned.

(60) Provisional application No. 61/983,223, filed on Apr. 23, 2014, provisional application No. 61/987,272, filed on May 1, 2014.

(51) Int. Cl.
C07D 473/08    (2006.01)
A61K 31/522    (2006.01)

(52) U.S. Cl.
CPC ........ *C07D 473/08* (2013.01); *C07B 2200/13* (2013.01)

(58) Field of Classification Search
None
See application file for complete search history.

(56) References Cited

FOREIGN PATENT DOCUMENTS

| WO | 2009/002933 A1 | 12/2008 |
|----|----------------|---------|
| WO | 2009/140517 A1 | 11/2009 |
| WO | 2013023102 A1  | 2/2013  |
| WO | 2014/113671 A1 | 7/2014  |

OTHER PUBLICATIONS

Chen et al. "TRPA1 as a drug target—promises and challenges," Naunyn-Schmiedeberg's Arch Pharmacol, 2015, 388:451-463.
International Preliminary Report on Patentability for International Application No. PCT/US2015/027353, dated Oct. 25, 2016.
International Search Report and Written Opinon issued for PCT/US2015/027353, dated Sep. 2, 2015.
WebMD. "What is Inflammation," (2016). Web: <http://www.webmd.com/arthritis/about-inflammation#2>.

*Primary Examiner* — Emily A Bernhardt
*Assistant Examiner* — Laura M Daniel
(74) *Attorney, Agent, or Firm* — Nelsen L Lentz

(57) ABSTRACT

The present invention relates to compounds of the Formula (I), or a pharmaceutically acceptable salt, pharmaceutical preparation, or pharmaceutical composition thereof, and their use for the treatment of pain, inflammatory disease, neuropathy, dermatological disorders, pulmonary conditions, and cough, as well as inhibiting the Transient Receptor Potential A1 ion channel (TRPA1).

58 Claims, 23 Drawing Sheets

Pain Behaviors (flinch, lift, lick, bite) monitored for 5 min. following intraplantar formalin (mean ± sd)
* $p<0.05$;  $p<0.01$; * $p<0.001$ versus vehicle; Plasma LLQ ~ 1 ng/mL

INHIBITING THE TRANSIENT RECEPTOR POTENTIAL A1 ION CHANNEL

CLAIM OF PRIORITY

This application is a continuation of U.S. patent application Ser. No. 15/305,892, filed Oct. 21, 2016, which is a U.S. National Stage Application under 35. U.S.C. § 371 of International Application No. PCT/US2015/027353, filed Apr. 23, 2015, which claims priority to U.S. Provisional Application No. 61/983,223, filed Apr. 23, 2014, and U.S. Provisional Application No. 61/987,272, filed May 1, 2014. The disclosures of each of the foregoing applications are herein incorporated by reference in their entirety.

TECHNICAL FIELD

The present invention relates to compounds of the Formula (I), or a pharmaceutically acceptable salt, pharmaceutical preparation, or pharmaceutical composition thereof, and their use for the treatment of pain, inflammatory disease, neuropathy, dermatological disorders, pulmonary conditions, and cough, as well as inhibiting the Transient Receptor Potential A1 ion channel (TRPA1).

BACKGROUND

Transient Receptor Potential A1 (herein, "TRPA1") is a non-selective cation channel related to pain sensation in humans. TRPA1 is found in sensory neurons and functions as a detector that helps link detection of noxious chemicals, tissue damage, and inflammation to pain. Activation of TRPA1 is believed to cause pain by inducing firing of nociceptive neurons and driving central sensitization in the spinal cord. TRPA1 stimulation can also increase firing of sensory neurons, leading to the release of pro-inflammatory neuropeptides such as NK-A, substance P and CGRP, which induce vasodilation and help recruit immune cells. A variety of endogenous reactive compounds produced during inflammation activate TRPA1, including 4-hydroxynonenal released during liposome peroxidation; cyclopentane prostaglandins synthesized by COX enzymes; hydrogen peroxide produced by oxidative stress. Activation of TRPA1 also sensitizes TRPA1 to cold. Furthermore, a gain-of-function mutation in TRPA1 causes familial episodic pain syndrome; patients suffering from this condition have episodic pain that may be triggered by cold. Thus, TRPA1 is considered to play a role in pain related to nerve damage, cold allodynia, and inflammatory pain.

Compounds that inhibit the TRPA1 ion channel can be useful, for example, in treating conditions ameliorated, eliminated, or prevented by inhibition of the TRPA1 ion channel. For example, pharmaceutical compositions that inhibit TRPA1 can be used to treat pain. Inhibition of TRPA1 (e.g., by genetic ablation and chemical antagonism) has been shown to result in reduced pain behavior in mice and rats. Knockout mice lacking functional TRPA1 have diminished nociceptive responses to TRPA1 activators, including AITC, formalin, acrolein, 4-hydroxynonenal, and, in addition, have greatly reduced thermal and mechanical hypersensitivity in response to the inflammatory mediator bradykinin (e.g., Kwan, K. Y. et al. Neuron 2006, 50, 277-289; Bautista, D. M. et al. Cell 2006, 124, 1269-1282). In animal pain models, down regulation of TRPA1 expression by gene specific antisenses prevented and reversed cold hyperalgesia induced by inflammation and nerve injury (see, e.g., Obata, K. et al., *J Clin Invest* (2005) 115, 2393-2401; Jordt, S. E. et al., *Nature* (2004), 427, 260-265; Katsura, H. et al., *Explor Neurol* (2006), 200, 112-123). TRPA1 inhibitor compounds are effective in a variety of rodent pain models. TRPA1 inhibitors have been shown to reduce mechanical hypersensitivity and cold allodynia following inflammation induced by Complete Freund's Adjuvant without altering normal cold sensation in naïve animals and also to improve function in the rat mono-iodoacetate osteoarthritis model (see, e.g., Materazzi, S et al., *Eur J Physiol* (2012), 463(4):561-9; Wei H et al., *Anesthesiology* 2012, 117(1):137-48; Koivisto, A et al., *Pharmacol Res* (2012), 65(1):149-58). TRPA1 inhibitor compounds have demonstrated reduced pain behavior in rodents injected with AITC (mustard oil), formalin, cinnamaldehyde, acrolein, and other TRPA1 activators. TRPA1 inhibitor compounds have also demonstrated efficacy in rodent models for post operative pain, (see, e.g., Wei et al., *Anesthesiology* (2012), 117(1):137-48); chemotherapy induced peripheral neuropathy (see, e.g., Trevisan, et al., *Cancer Res* (2013) 73(10):3120-31), and painful diabetic neuropathy (see, e.g., Koivisto et al., *Pharmacol Res* (2011) 65:149-158).

SUMMARY

The compounds described herein can be useful in the treatment of disorders wherein inhibition of the TRPA1 ion channel is beneficial, for example, in the treatment of pain. In some embodiments, a compound described herein has preferable properties over other compounds in the art that inhibit TRPA1. For example, in some embodiments, a compound described herein inhibits the TRPA1 ion channel without elevating serum biomarkers of hepatotoxicity. In some embodiments, a compound as described herein, e.g., a compound of Formula (I), has desirable aqueous solubility (including compounds with aqueous solubility suitable for pharmaceutical compositions formulated for intravenous administration) relative to other compounds in the art that inhibit TRPA1.

Described herein is a compound of the Formula (I) and pharmaceutically acceptable salts thereof:

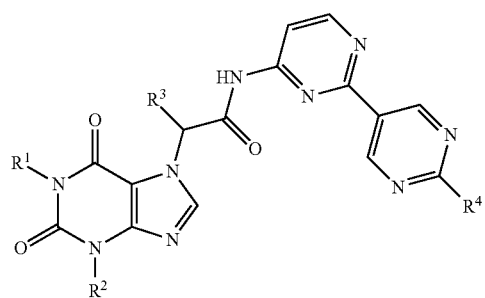

Formula (I)

wherein each of the variables above are as described herein, for example, in the detailed description below.

Also described herein are purified pharmaceutical preparations and pharmaceutical compositions comprising a compound of Formula (I) or a pharmaceutical salt thereof.

The compounds and compositions described herein can be used to treat various disorders in a subject. For example, described herein are methods of treatment such as a method of treating a TRPA1 mediated disorder in a subject, the method comprising administering an effective amount of a compound of Formula (I), or a pharmaceutically acceptable salt thereof. Methods of treating pain in a subject, the method comprising administering an effective amount of a compound of Formula (I), or a pharmaceutically acceptable salt thereof are also described herein. Exemplary types of pain include neuropathic pain, e.g., painful diabetic neuropathy, chemotherapy-induced peripheral neuropathy, lower back pain, trigeminal neuralgia, post-herpetic neuralgia, sciatica, and complex regional pain syndrome; inflammatory pain, e.g., from rheumatoid arthritis, osteoarthritis, temperomandibular disorder; PDN or CIPN; visceral pain, e.g., from pancreatitis, inflammatory bowel disease, colitis, Crohn's disease, endometriosis, pelvic pain, and angina; pain selected from the group: cancer pain, burn pain, oral pain, crush and injury-induced pain, incisional pain, bone pain, sickle cell disease pain, fibromyalgia and musculoskeletal pain; or pain from hyperalgesia or allodynia.

In some embodiments the methods include treating inflammatory disease in a subject, the method comprising administering an effective amount of a compound of Formula (I), or a pharmaceutically acceptable salt thereof.

In some embodiments the methods include treating neuropathy in a subject, the method comprising administering an effective amount of a compound of Formula (I), or a pharmaceutically acceptable salt thereof. In some embodiments, the neuropathy is from diabetes, chemical injury, chemotherapy, and or trauma.

In some embodiments the methods include treating a dermatogological disorder in a subject, the method comprising administering an effective amount of a compound of Formula (I), or a pharmaceutically acceptable salt thereof. Exemplary dermatogological disorders include atopic dermatitis, acute pruritus, psoriasis, hives, eczema, dyshidrotic eczema, mouth ulcers, and diaper rash.

In some embodiments the methods include treating a pulmonary condition in a subject, the method comprising administering an effective amount of a compound of Formula (I), or a pharmaceutically acceptable salt thereof. Exemplary pulmonary conditions include obstructive diseases such as chronic obstructive pulmonary disease. Additional exemplary pulmonary conditions include asthma and cough.

In addition, a compound as described herein, e.g., a compound of Formula (I), are useful in the manufacture of a pharmaceutical composition formulated for oral administration. In some embodiments, a compound described herein can be formulated into a composition for intravenous administration. In embodiments, a compound or composition described herein can be used to treat pain A compound as described herein, e.g., a compound of Formula (I), can include molecules having one or more chiral centers. For example, unless otherwise stated, a composition of Formula (I) can contain various amounts of stereoisomers of Formula (Ia), (Ib), (IIa) and (IIb). In an embodiment, a composition comprising a compound of Formula (Ia) or (IIa) preferably contains a therapeutically effective amount of the compound having the stereochemistry indicated in Formula (Ia) or (IIa) (e.g., an enantiomeric excess or a diastereomeric excess of a particular isomer of Formula (Ia) or (IIa) over the corresponding stereoisomer of Formula (Ib) or (IIb)). In an embodiment, a composition comprising a compound of Formula (I) contains a therapeutically effective amount of the compound having the stereochemistry indicated in Formula (Ib) or (IIb) (e.g., an enantiomeric excess or a diastereomeric excess of a particular isomer of Formula (Ib) or (IIb) over the corresponding stereoisomer of Formula (Ia)).

In addition, compounds of Formula (I) can include one or more isotopes of the atoms present in Formula (I). For example, compounds of Formula (I) can include: those in which H (or hydrogen) is replaced with any isotopic form of hydrogen including $^1H$, $^2H$ or D (Deuterium), and $^3H$ (Tritium); those in which C is replaced with any isotopic form of carbon including $^{12}C$, $^{13}C$, and $^{14}C$; those in which O is replaced with any isotopic form of oxygen including $^{16}O$, $^{17}O$ and $^{18}O$; those in which N is replaced with any isotopic form of nitrogen including $^{13}N$, $^{14}N$ and $^{15}N$; those in which P is replaced with any isotopic form of phosphorous including $^{31}P$ and $^{32}P$; those in which S is replaced with any isotopic form of sulfur including $^{32}S$ and $^{35}S$; those in which F is replaced with any isotopic form of fluorine including $^{19}F$ and $^{18}F$; and the like. In an embodiment, compounds represented by Formula (I) comprise isomers of the atoms therein in their naturally occurring abundance.

DETAILED DESCRIPTION

Definitions

Figure 1:
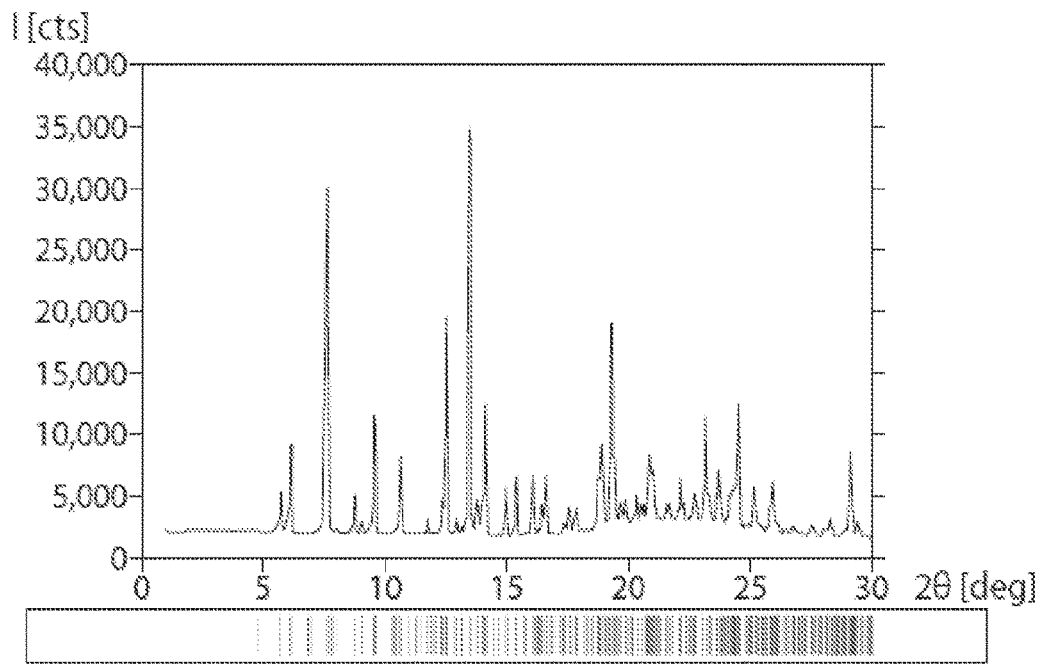
FIG. 1 is a spectrum depicting the X-ray powder diffraction (XRPD) pattern of a solid crystalline form of Compound 2 (Form A) after slurry treatment in ethanol.

This disclosure is not limited in its application to the details of the methods and compositions described herein. Also, the phraseology and terminology used herein is for the purpose of description and should not be regarded as limiting.

As used herein, the articles "a" and "an" refer to one or to more than one (e.g., to at least one) of the grammatical object of the article.

"About" and "approximately" shall generally mean an acceptable degree of error for the quantity measured given the nature or precision of the measurements. Exemplary degrees of error are within 20 percent (%), typically, within 10%, and more typically, within 5% of a given value or range of values.

As used herein, an amount of a compound or combination effective to treat a disorder (e.g., a disorder as described herein), "therapeutically effective amount", "effective amount" or "effective course" refers to an amount of the compound or combination which is effective, upon single or multiple dose administration(s) to a subject, in treating a subject, or in curing, alleviating, relieving or improving a subject with a disorder (e.g., a disorder as described herein) beyond that expected in the absence of such treatment.

The term "pharmaceutically acceptable," as used herein, refers to a compound or carrier (e.g., excipient) that may be administered to a subject, together with a compound described herein (e.g., a compound of Formula (I)), and which does not destroy the pharmacological activity thereof and is nontoxic when administered in doses sufficient to deliver a therapeutic amount of the compound.

As set out above, certain embodiments of the present compounds may contain a basic functional group, such as amino or alkylamino, and are thus capable of forming pharmaceutically acceptable salts with pharmaceutically acceptable acids. The term "pharmaceutically acceptable salts" in this respect, refers to the relatively non-toxic, inorganic and organic acid addition salts of compounds disclosed herein. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J Pharm Sci* 66:1-19.)

In other cases, the compounds disclosed herein may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of compounds disclosed herein. These salts can likewise be prepared in situ during the final isolation and purification of the compounds, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

The term, "treat" or "treatment," as used herein, refers to the application or administration of a compound, alone or in combination with, an additional agent to a subject, e.g., a subject who has a disorder (e.g., a disorder as described herein), a symptom of a disorder, or a predisposition toward a disorder, with the purpose to cure, heal, alleviate, relieve, alter, remedy, ameliorate, improve or affect the disorder.

As used herein, the term "subject" is intended to include human and non-human animals. Exemplary human subjects include a human subject having a disorder, e.g., a disorder described herein. The term "non-human animals" of the invention includes all vertebrates, e.g., non-mammals (such as chickens, amphibians, reptiles) and mammals, such as non-human primates, domesticated and/or agriculturally useful animals, e.g., sheep, dog, cat, cow, pig, etc.

The terms "antagonist" and "inhibitor" are used interchangeably to refer to an agent that decreases or suppresses a biological activity, such as to repress an activity of an ion channel, such as TRPA1. TRPA1 inhibitors include inhibitors having any combination of the structural and/or functional properties disclosed herein.

An "effective amount" of, e.g., a TRPA1 antagonist, with respect to the subject methods of inhibition or treatment, refers to an amount of the antagonist in a preparation which, when applied as part of a desired dosage regimen brings about a desired clinical or functional result. Without being bound by theory, an effective amount of a TRPA1 antagonist for use in the methods of the present invention includes an amount of a TRPA1 antagonist effective to decrease one or more in vitro or in vivo functions of a TRPA1 channel. Exemplary functions include, but are not limited to, membrane polarization (e.g., an antagonist may prevent depolarization of a cell), ion flux, ion concentration in a cell, outward current, and inward current. Compounds that antagonize TRPA1 function include compounds that antagonize an in vitro or in vivo functional activity of TRPA1. When a particular functional activity is only readily observable in an in vitro assay, the ability of a compound to inhibit TRPA1 function in that in vitro assay serves as a reasonable proxy for the activity of that compound. In certain embodiments, an effective amount is an amount sufficient to inhibit a TRPA1-mediated current and/or the amount sufficient to inhibit TRPA1 mediated ion flux.

The term "hydrate" as used herein, refers to a compound formed by the union of water with the parent compound.

The term "preventing," when used in relation to a condition, such as a local recurrence (e.g., pain), a disease such as cancer, a syndrome complex such as heart failure or any other medical condition, is well understood in the art and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

The term "prodrug" is intended to encompass compounds that, under physiological conditions, are converted into the therapeutically active agents of the present invention. A common method for making a prodrug is to include selected moieties that are hydrolyzed under physiological conditions to reveal the desired molecule. In other embodiments, the prodrug is converted by an enzymatic activity in the host animal.

The term "solvate" as used herein, refers to a compound formed by solvation (e.g., a compound formed by the combination of solvent molecules with molecules or ions of the solute).

The terms "TRPA1", "TRPA1 protein", and "TRPA1 channel" are used interchangeably throughout the application. These terms refer to an ion channel (e.g., a polypeptide) comprising the amino acid sequence set forth in SEQ ID NO: 1, SEQ ID NO: 3, or SEQ ID NO: 5 of WO 2007/073505, or an equivalent polypeptide, or a functional bioactive fragment thereof. In certain embodiments, the term refers to a polypeptide comprising, consisting of, or consisting essentially of, the amino acid sequence set forth in SEQ ID NO: 1, SEQ ID NO: 3, or SEQ ID NO: 5. TRPA1 includes polypeptides that retain a function of TRPA1 and comprise (i) all or a portion of the amino acid sequence set forth in SEQ ID NO: 1, SEQ ID NO: 3 or SEQ ID NO: 5; (ii) the amino acid sequence set forth in SEQ ID NO: 1, SEQ ID NO: 3 or SEQ ID NO: 5 with 1 to about 2, 3, 5, 7, 10, 15, 20, 30, 50, 75 or more conservative amino acid substitutions; (iii) an amino acid sequence that is at least 70%, 75%, 80%, 90%, 95%, 96%, 97%, 98%, or 99% identical to SEQ ID NO: 1, SEQ ID NO: 3 or SEQ ID NO: 5; and (iv) functional fragments thereof. Polypeptides of the invention also include homologs, e.g., orthologs and paralogs, of SEQ ID NO: 1, SEQ ID NO: 3 or SEQ ID NO: 5.

The "enantiomeric excess" or "% enantiomeric excess" of a composition can be calculated using the equation shown below. In the example shown below a composition contains 90% of one enantiomer, e.g., the S enantiomer, and 10% of the other enantiomer, i.e., the R enantiomer.

$$ee=(90-10)/100=80\%.$$

Thus, a composition containing 90% of one enantiomer and 10% of the other enantiomer is said to have an enantiomeric excess of 80%.

The "diastereomeric excess" or "% diastereomeric excess" of a composition can be calculated using the equation shown below. In the example shown below a composition contains 90% of one diastereomer, and 10% of another enantiomer.

$$de=(90-10)/100=80\%.$$

Thus, a composition containing 90% of one diastereomer and 10% of the other diastereomer is said to have a diastereomeric excess of 80%.

Chemical Definitions

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

For compounds of the invention in which a variable appears more than once, each variable can be a different moiety selected from the Markush group defining the variable. For example, where a structure is described having two R groups that are simultaneously present on the same compound; the two R groups can represent different moieties selected from the Markush group defined for R.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

As used herein, "alkyl," by itself or as part of another substituent, means, unless otherwise stated, a straight or branched chain, and can have a number of carbon atoms optionally designated (i.e., $C_1$-$C_6$ means one to six carbons). Examples of saturated hydrocarbon groups include, but are not limited to, groups such as methyl, ethyl, n-propyl, isopropyl, n-butyl, t-butyl, isobutyl, sec-butyl, n-pentyl, isopentyl, homologs and isomers of, for example, n-pentyl, n-hexyl, and the like.

As used herein, "alkylene" refers to a divalent alkyl, e.g., —$CH_2$—, —$CH_2CH_2$—, —$CH_2CH_2CH_2$—, —$CH_2CH_2CH_2CH_2$—, —$CH_2CH_2CH_2CH_2CH_2$—, and —$CH_2CH_2CH_2CH_2CH_2CH_2$—.

As used herein, "alkenyl" can be a straight or branched hydrocarbon chain, containing at least one double bond, and having from two to six carbon atoms (i.e. $C_2$-$C_6$ alkenyl). Examples of alkenyl groups, include, but are not limited to, groups such as ethenyl (i.e., vinyl), prop-1-enyl (i.e., allyl), but-1-enyl, pent-1-enyl, penta-1,4-dienyl, and the like.

As used herein, "alkoxy" can be a straight chain or branched alkoxy group having from one to six carbon atoms (i.e., $C_1$-$C_6$ alkoxy). Examples of alkoxy groups, include, but are not limited to, groups such as methoxy, ethoxy, propyloxy, isopropyloxy, butyloxy, isobutyloxy, tert-butyloxy, pentyloxy, or hexyloxy, and the like.

As used herein, "alkynyl" can be a straight or branched hydrocarbon chain, containing at least one triple bond, having from two to six carbon atoms (i.e. $C_2$-$C_6$ alkynyl). Examples of alkynyl groups, include, but are not limited to, groups such as ethynyl, propynyl, butynyl, pentynyl, hexynyl, and the like.

As used herein, "amino" or "amine" refers to a —$NH_2$ radical group.

As used herein, "aryl" refers to a polyunsaturated, aromatic, hydrocarbon moiety which can be a single ring or multiple rings (e.g., 1 to 2 rings) which are fused together or linked covalently, having from six to twelve carbon atoms (i.e. $C_6$-$C_{12}$ aryl). Non-limiting examples of aryl groups include phenyl, 1-naphthyl, 2-naphthyl, and 4-biphenyl.

As used herein, "cycloalkyl" refers to a monocyclic or polycyclic radical that contains only carbon and hydrogen, and may be saturated, or partially unsaturated. Cycloalkyl groups include groups having from 3 to 10 ring atoms (i.e. $C_3$-$C_{10}$ cycloalkyl). Examples of cycloalkyl groups include, but are not limited to, groups such as cyclopropyl, cyclobutyl, cyclopentyl, cyclopentenyl, cyclohexyl, cyclohexenyl, cycloseptyl, cyclooctyl, cyclononyl, cyclodecyl, norbornyl, and the like.

As used herein, "halo" or "halogen," independently or as part of another substituent, mean, unless otherwise stated, a fluorine, chlorine, bromine, or iodine atom. The term "halide" by itself or as part of another substituent, refers to a fluoride, chloride, bromide, or iodide atom.

As used herein, "haloalkyl" and "haloalkoxy" can include alkyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine.

As used herein, "heteroalkyl" can include an optionally substituted alkyl, which has one or more skeletal chain atoms selected from an atom other than carbon, e.g., oxygen, nitrogen, sulfur, phosphorus or combinations thereof. A numerical range may be given, e.g. $C_1$-$C_6$ heteroalkyl which refers to the number of carbons in the chain, which in this example includes 1 to 6 carbon atoms. For example, a —$CH_2OCH_2CH_3$ radical is referred to as a "$C_3$" heteroalkyl. Connection to the rest of the molecule may be through either a heteroatom or a carbon in the heteroalkyl chain.

As used herein, "heteroaryl" refers to a 5- to 14-membered aromatic radical (e.g., $C_2$-$C_{13}$ heteroaryl) that includes one or more ring heteroatoms selected from nitrogen, oxygen and sulfur, and which may be a monocyclic or bicyclic ring system. Bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene. An N-containing "heteroaromatic" or "heteroaryl" moiety refers to an aromatic group in which at least one of the skeletal atoms of the ring is a nitrogen atom. The polycyclic heteroaryl group may be fused or non-fused. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryl groups include without limitation, pyridyl, pyrimidinyl, pyrazinyl, pyridazinyl, triazinyl, furyl (furanyl), quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like.

As used herein, "heterocyclyl" or "heterocycloalkyl" can be a stable 3- to 18-membered non-aromatic mono, di, or tricyclic heterocycle ring radical that comprises two to twelve carbon atoms and from one to six heteroatoms selected from nitrogen, oxygen and sulfur. Examples of heterocycloalkyl groups include, but are not limited to, groups such as dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, azetidinyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, and the like.

As used herein, "hydroxy" or "hydroxyl" refers to —OH.

As used herein, "cyano" refers to —CN.

As used herein, "nitro" refers to —$NO_2$.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds (e.g., alkyl, alkenyl, alkynyl, cycloalkyl, heterocycloalkyl, aryl, or heteroaryl, any of which may itself be further substituted), as well as halogen, carbonyl (e.g., aldehyde, ketone, ester, carboxyl, or formyl), thiocarbonyl (e.g., thioester, thiocarboxylate, or thioformate), amino (e.g., —N($R^b$)($R^c$), wherein each $R^b$ and $R^c$ is independently H or $C_1$-$C_6$ alkyl), cyano, nitro, —$SO_2N(R^b)(R^c)$, —$SOR^d$, and $S(O)_2R^d$, wherein each $R^b$, $R^c$, and $R^d$ is independently H or $C_1$-$C_6$ alkyl. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled Standard List of Abbreviations. The abbreviations contained in said list, and all abbreviations utilized by organic chemists of ordinary skill in the art are hereby incorporated by reference.

Contemplated equivalents of the compounds described above include compounds which otherwise correspond thereto, and which have the same general properties thereof (e.g., the ability to inhibit TRPA1 activity), wherein one or more simple variations of substituents are made which do not adversely affect the efficacy of the compound. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

For purposes of this invention, the chemical elements are identified in accordance with the Periodic Table of the Elements, CAS version, Handbook of Chemistry and Physics, 67th Ed., 1986-87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

Compounds

Described herein are compounds, which can be useful in the treatment of a disorder where inhibition of TRPA1 is beneficial. Such disorders are described herein.

The compounds include compounds of Formula (I)

Formula (I)

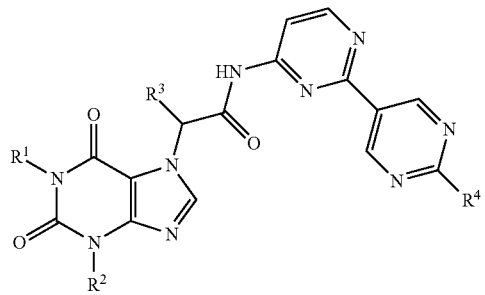

wherein:
$R^1$ is H, $C_1$-$C_6$ alkyl, $C_1$-$C_6$ alkenyl, or $C_1$-$C_6$ alkynyl;
$R^2$ is H, $C_1$-$C_6$ alkyl, $C_1$-$C_6$ alkenyl, or $C_1$-$C_6$ alkynyl optionally substituted with one or more $R^5$ groups;
$R^3$ is H, $C_1$-$C_6$ alkyl, $C_1$-$C_6$ alkenyl, or $C_1$-$C_6$ alkynyl;
$R^4$ is halo, hydroxy, alkoxy, thiol, alkylthio, amino, alkylamino, dialkylamino, cyano, nitro, amido, alkylamido, dialkylamido, thioyl, sulfonyl, cyclyl, heterocyclyl, aryl, or heteroaryl, optionally substituted at one or more positions with 1-4 $R^6$ groups;
$R^5$ is independently H, halogen, alkyl, aralkyl, alkenyl, alkynyl, hydroxy, amino, amido, phosphonate, carboxyl, ether, alkylthio, haloalkyl, and cyano; and
$R^6$ is independently H, halogen, alkyl, aralkyl, alkenyl, alkynyl, cycloalkyl, hydroxy, amino, nitro, sulfhydryl, imino, amido, phosphate, phosphonate, phosphinate, carbonyl, carboxyl, silyl, ether, alkylthio, sulfonyl, ketone, aldehyde, ester, heterocycle, an aromatic or heteroaromatic ring, haloalkyl, and cyano.

In some embodiments, $R^1$ is $C_1$-$C_6$ alkyl, for example, —$CH_3$. In some embodiments, $R^1$ is H.

In some embodiments, $R^2$ is H or $C_1$-$C_6$ alkyl, for example, —$CH_3$, —$CD_3$, or —$CHF_2$.

In some embodiments, each $R^1$ and $R^2$ is independently $C_1$-$C_6$ alkyl, for example, —$CH_3$.

In some embodiments, each $R^1$ and $R^2$ is independently —$CH_3$ and $R^3$ is H.

In some embodiments, $R^3$ is H. In some embodiments, $R^3$ is $C_1$-$C_6$ alkyl, for example, —$CH_3$.

In some embodiments, each of $R^1$ and $R^2$ and $R^3$ is independently $C_1$-$C_6$ alkyl, for example, —$CH_3$.

In some embodiments, the compound of the Formula (I) is the compound of the Formula (Ia):

Formula (Ia)

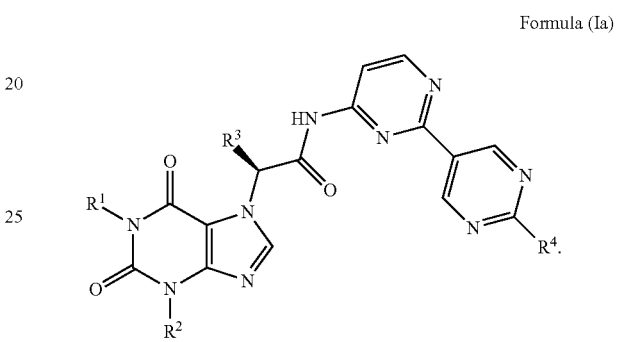

In some embodiments, each of $R^1$ and $R^2$ and $R^3$ is independently $C_1$-$C_6$ alkyl, for example, —$CH_3$.

In some embodiments, the compound of the Formula (I) of claim 1, is the compound of the Formula (Ib):

Formula (Ib)

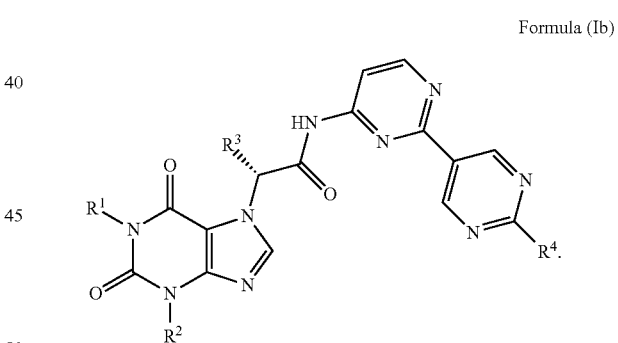

In some embodiments, each of $R^1$ and $R^2$ and $R^3$ is independently $C_1$-$C_6$ alkyl, for example, —$CH_3$.

In some embodiments, $R^4$ is heterocyclyl, for example, a 4 to 8-membered ring. In some embodiments, the heterocyclyl is linked through a nitrogen atom. In some embodiments, $R^4$ is substituted heterocyclyl. In some embodiments, $R^4$ is selected from the group:

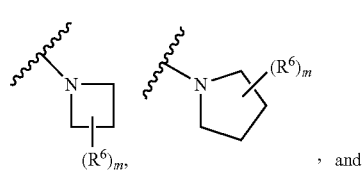

, and

-continued

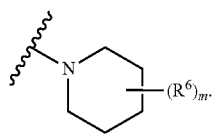

In some embodiments, $R^4$ is selected from the group:

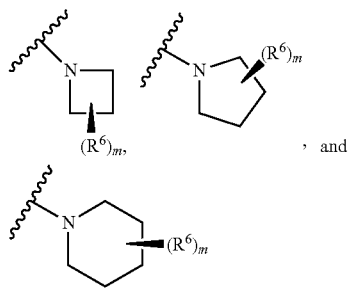

and m is 1.

In some embodiments, $R^4$ is selected from the group:

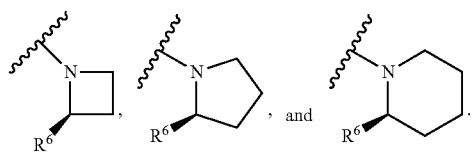

In some embodiments, $R^4$ is selected from the group:

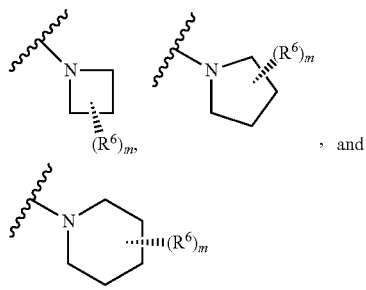

and m is 1.

In some embodiments, $R^4$ is selected from the group:

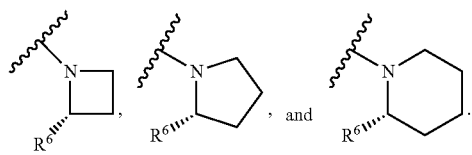

In some embodiments, m is 0. In some embodiments, m is 1.

In some embodiments, $R^6$ is, alkyl, haloalkyl, or cyano, for example, alkyl or haloalkyl, such as $-CF_3$.

In some embodiments, $R^4$ is selected from the group:

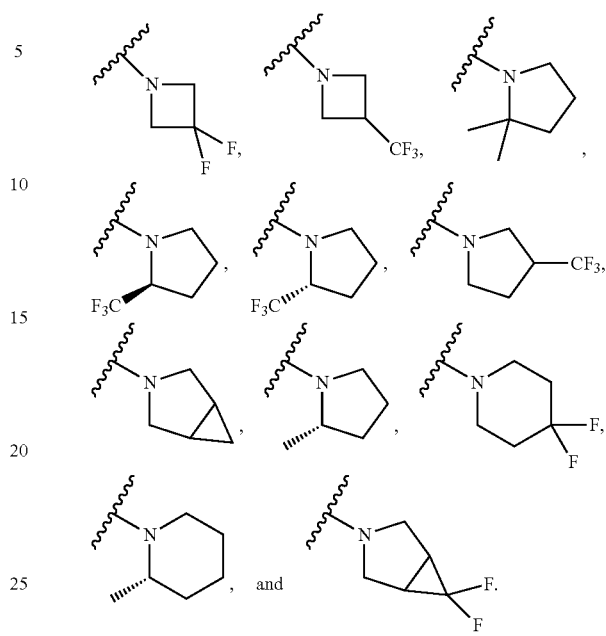

In some embodiments, the compound of Formula (I) is of the Formula (II):

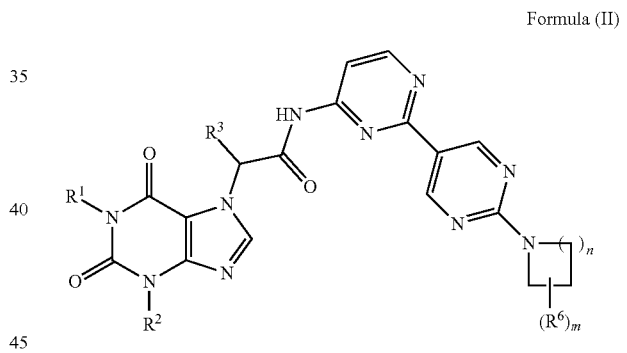

Formula (II)

wherein:
n is an integer from 0 to 4; and
m is selected from an integer from 0 to 4.

In some embodiments, the compound of Formula (I) is of the Formula (IIa):

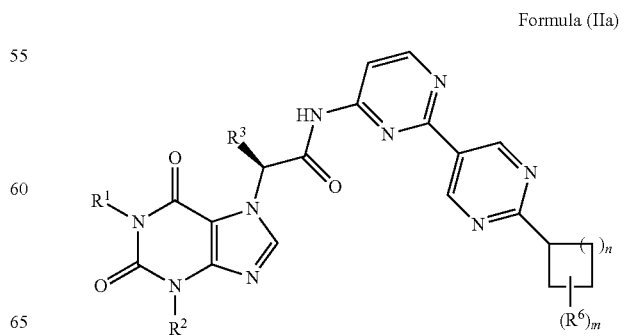

Formula (IIa)

wherein:
  n is an integer from 0 to 4; and
  m is selected from an integer from 0 to 4.
In some embodiments, the compound of Formula (I) is of the Formula (IIb):
Formula (IIb)
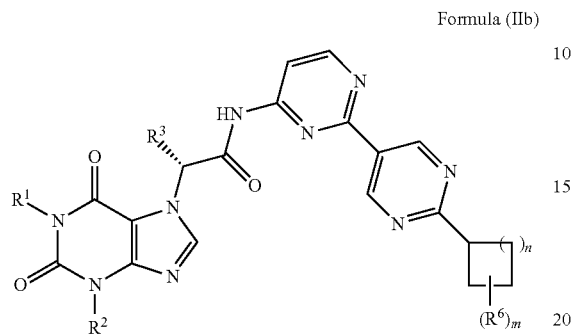
wherein:
  n is an integer from 0 to 4; and
  m is selected from an integer from 0 to 4.
In some embodiments, the compound is selected from the following group:
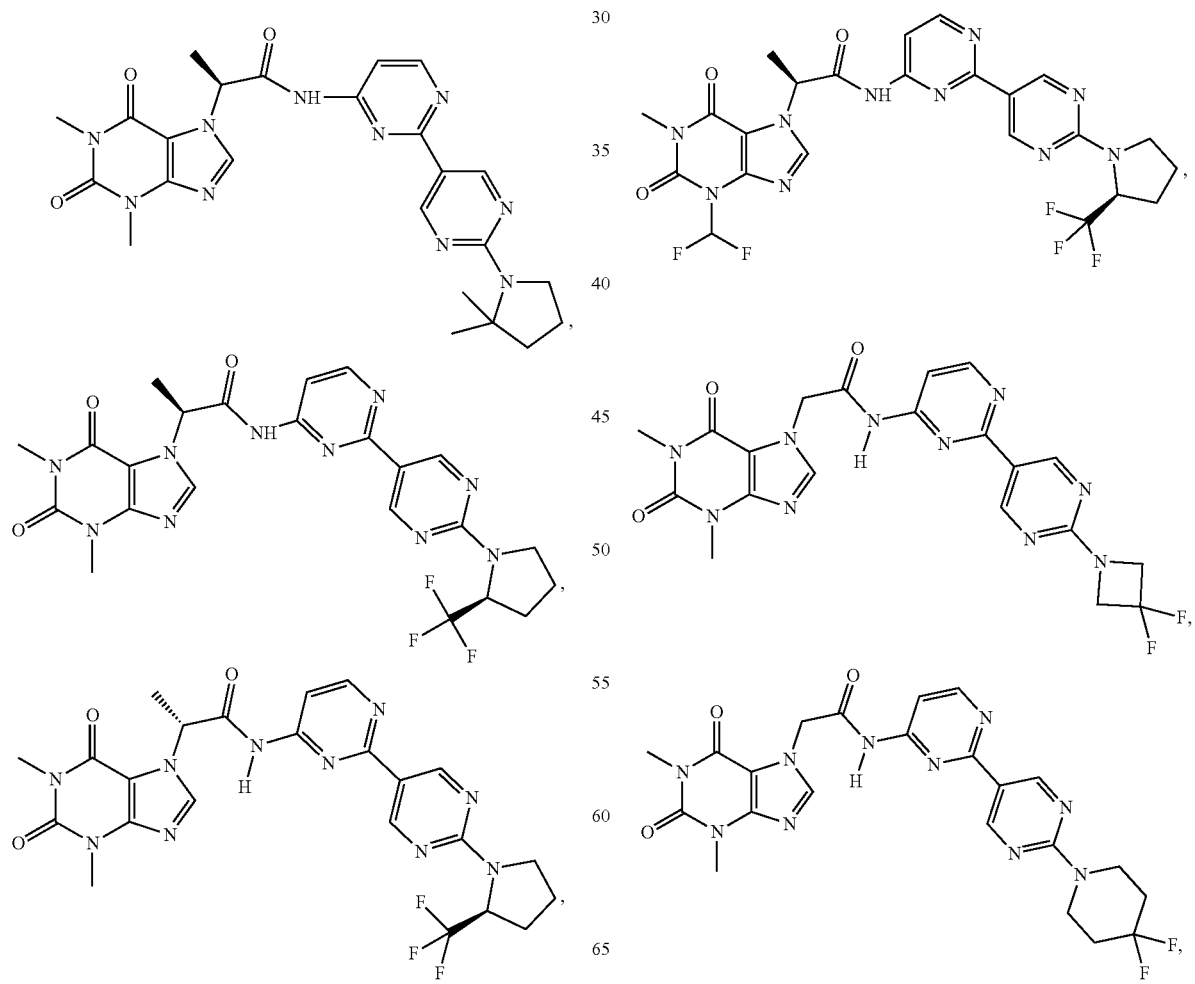
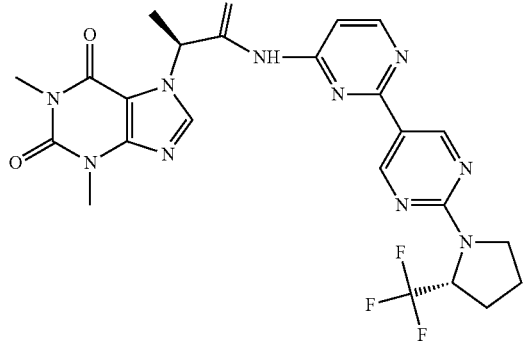
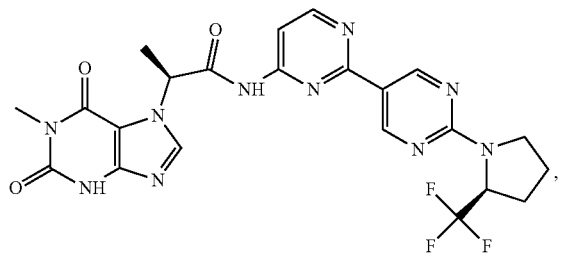

-continued
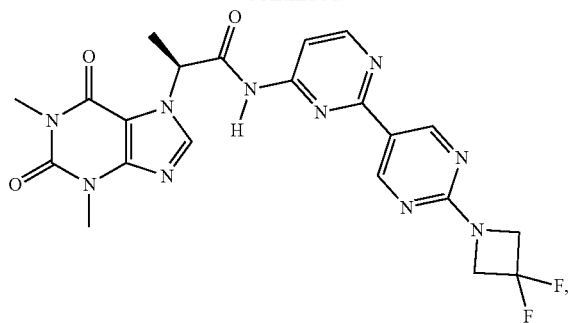
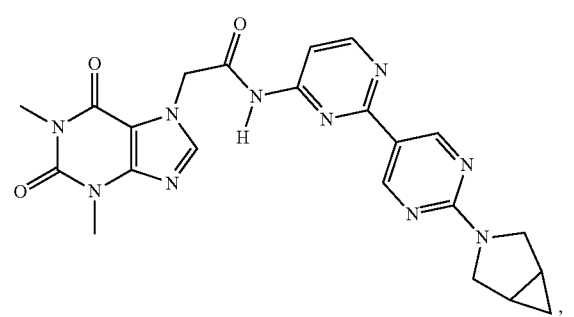
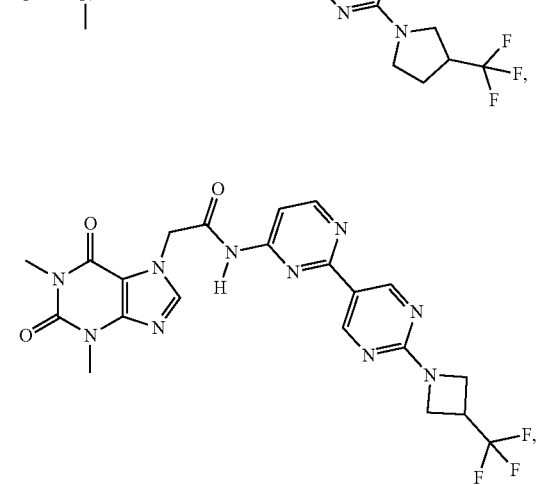
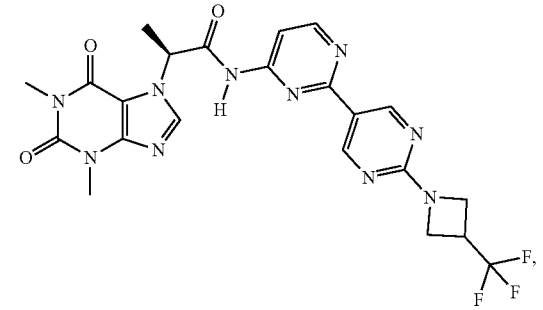
-continued
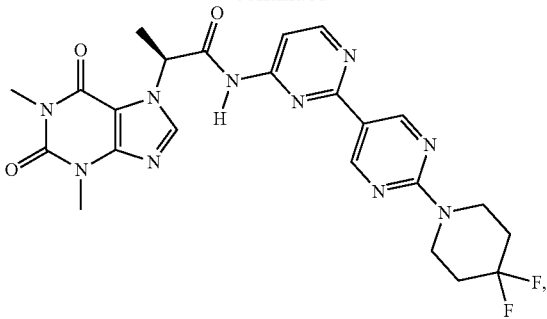
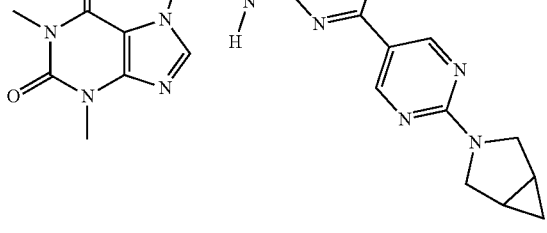
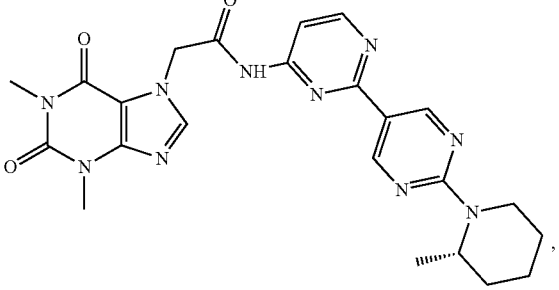
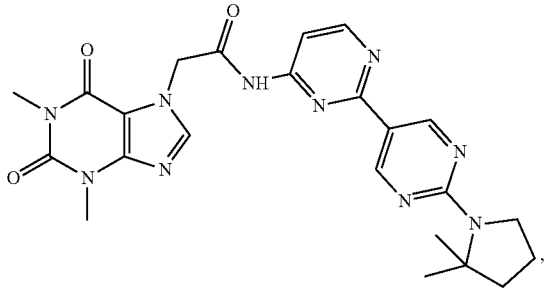

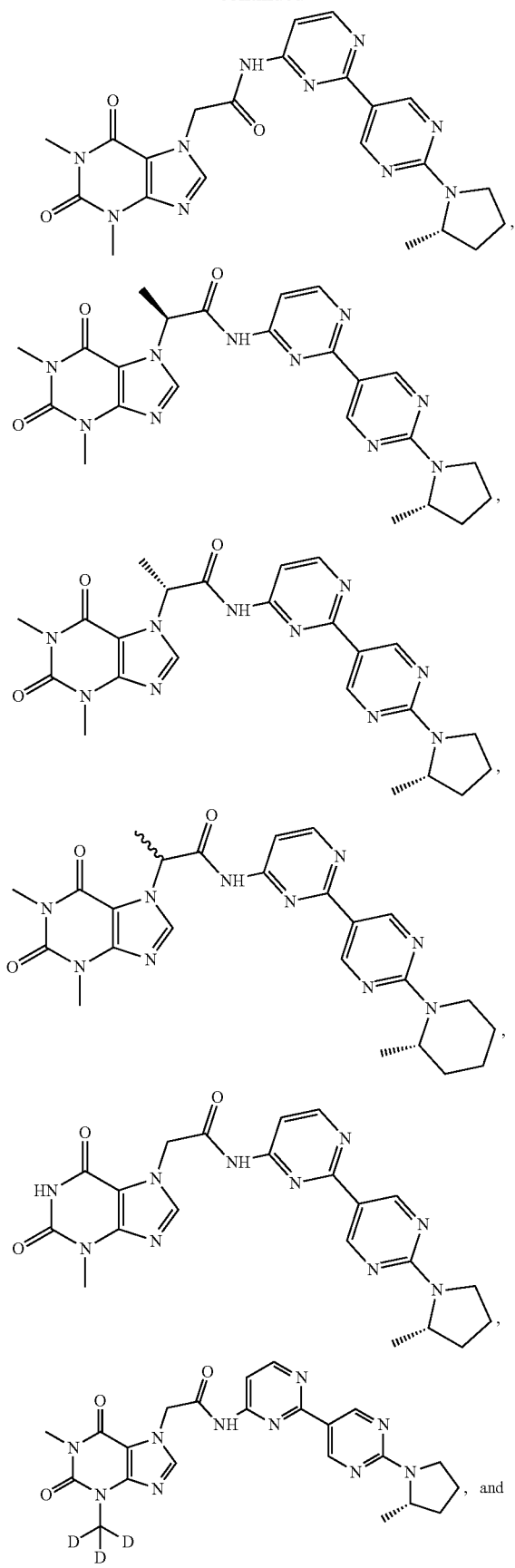

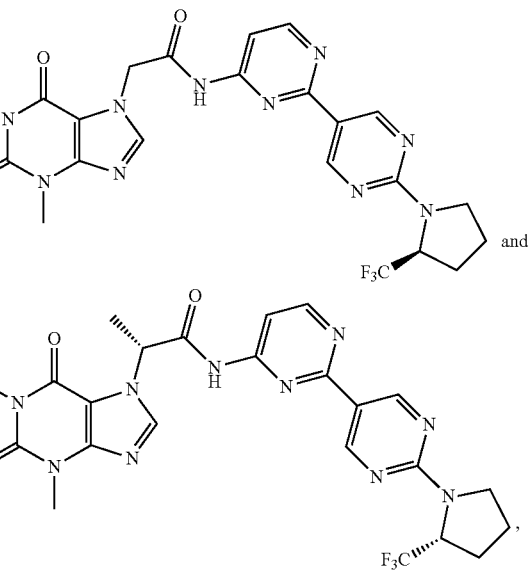

or a pharmaceutically acceptable salt thereof.

In some embodiments, the compound is selected from the following group:

or a pharmaceutically acceptable salt thereof.

In some embodiments, a compound of Formula (I) has a melting point greater than or equal to about 100° C. In some embodiments, said compound of Formula (I) has a melting point greater than or equal to about 125° C., about 150° C., about 175° C., or about 180° C. In some embodiments, said compound of Formula (I) has a melting point in the range of about 180° C. to about 205° C. In some embodiments, said compound of Formula (I) has a melting point in the range of about 190° C. to about 200° C. In some embodiments, said compound of Formula (I) has a melting point in the range of about 190° C. to about 196° C.

In some embodiments, a solid crystalline form of a compound of Formula (I) is produced upon slurry treatment with a suitable solvent (e.g., ethanol, water, or a combination thereof). In some embodiments, a solid crystalline form (e.g., an anhydrous solid crystalline form) of a compound of Formula (I) is produced upon slurry treatment with a suitable solvent (e.g., ethanol, water, or a combination thereof) followed by an additional treatment (e.g., vacuum treatment, e.g., −80° C. for one day).

In some embodiments, a solid crystalline form of a compound of Formula (I) (e.g., produced upon slurry treatment with a suitable solvent, e.g., ethanol, water, or a combination thereof, and optionally followed by an additional treatment, e.g., vacuum treatment, e.g., -80° C. for one day) has a melting point greater than or equal to about 100° C. In some embodiments, said solid crystalline form of a compound of Formula (I) has a melting point greater than or equal to about 125° C., about 150° C., about 175° C., or about 180° C. In some embodiments, said solid crystalline form of a compound of Formula (I) has a melting point in the range of about 180° C. to about 205° C. In some embodiments, said solid crystalline form of a compound of Formula (I) has a melting point in the range of about 190° C. to about 200° C. In some embodiments, said solid crystalline form of a compound of Formula (I) has a melting point in the range of about 190° C. to about 196° C.

In some embodiments, the compound of Formula (I) is:

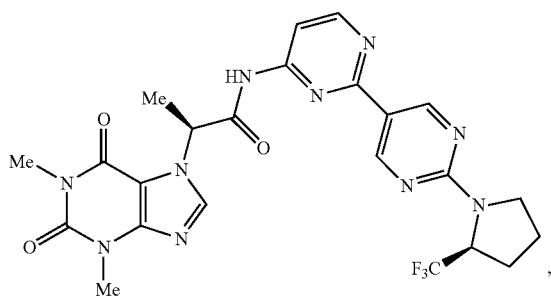 [SMILES: C[C@@H](C(=O)Nc1ccnc(-c2cnc(N3CCC[C@H]3C(F)(F)F)nc2)n1)n1cnc2c1c(=O)n(C)c(=O)n2C]

or a pharmaceutically acceptable salt thereof, which is referred to as Compound 2, Example 2, or Compound of Example 2 herein.

In some embodiments, a solid crystalline form of Compound 2 (e.g., Form A) is produced upon slurry treatment with a suitable solvent (e.g., ethanol, water, or a combination thereof). In some embodiments, said solid crystalline form of Compound 2 (e.g., Form A) has an X-ray powder diffraction pattern comprising characteristic peaks, expressed in terms of 2θ, at one or more of the following angles: about 7.67°, about 12.52°, about 13.49°, and about 19.31°. In some embodiments, said solid crystalline form of Compound 2 (e.g., Form A) has characteristic peaks as shown in FIG. 1.

Figure 2:
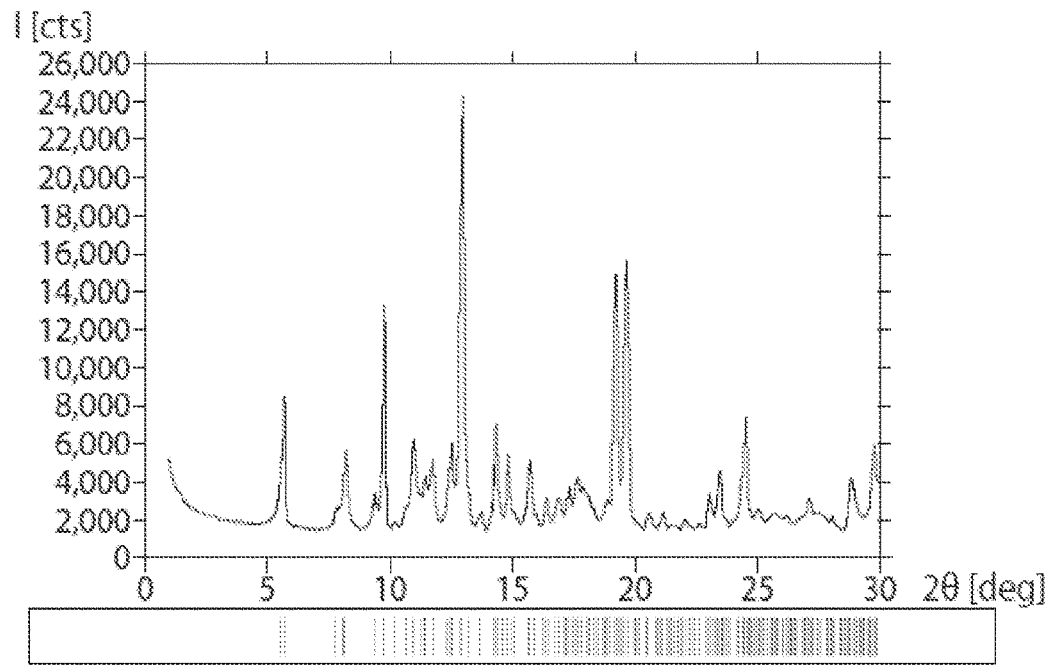
FIG. 2 is a spectrum depicting the X-ray powder diffraction pattern of an anhydrous solid crystalline form of Compound 2 (Form B) after slurry treatment in 97% ethanol/3% water and drying under vacuum (−80° C. for one day).

In some embodiments, a solid crystalline form of Compound 2 (e.g., an anhydrous solid crystalline form of Compound 2, e.g., Form B) is produced upon slurry treatment with a suitable solvent (e.g., ethanol, water, or a combination thereof) followed by an additional treatment (e.g., vacuum treatment, e.g., -80° C. for one day). In some embodiments, said solid crystalline form of Compound 2 (e.g., an anhydrous solid crystalline form of Compound 2, e.g., Form B) has an X-ray powder diffraction pattern comprising characteristic peaks, expressed in terms of 2θ, at one or more of the following angles: about 9.78°, about 12.98°, about 19.20°, and about 19.67°. In some embodiments, said solid crystalline form of Compound 2 (e.g., an anhydrous solid crystalline form of Compound 2, e.g., Form B) has characteristic peaks as shown in FIG. 2.

Figure 3:
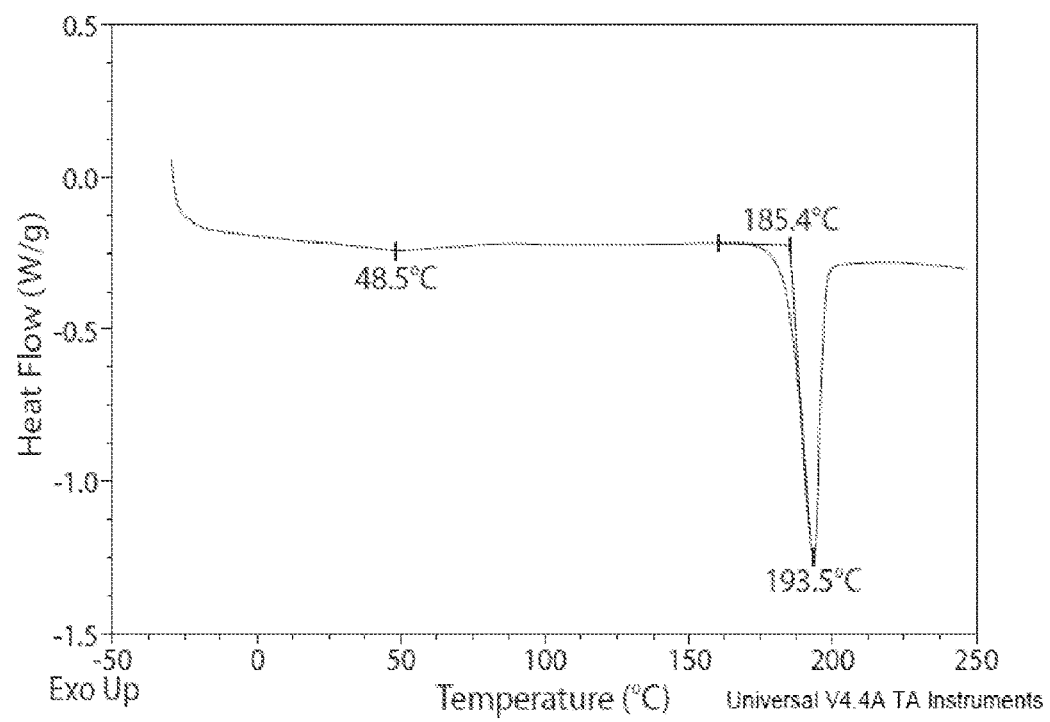
FIG. 3 is a graph depicting the results of differential scanning calorimetry (DSC) analysis on an anhydrous solid crystalline form of Compound 2 (Form B).

In some embodiments, a solid crystalline form of Compound 2 (e.g., an anhydrous solid crystalline form of Compound 2, e.g., Form B) has a melting point greater than or equal to about 100° C. In some embodiments, said solid crystalline form of Compound 2 (e.g., an anhydrous solid crystalline form of Compound 2, e.g., Form B) has a melting point greater than or equal to about 125° C., about 150° C., about 175° C., or about 180° C. In some embodiments, said solid crystalline form of Compound 2 (e.g., an anhydrous solid crystalline form of Compound 2, e.g., Form B) has a melting point in the range of about 180° C. to about 205° C. In some embodiments, said solid crystalline form of Compound 2 (e.g., an anhydrous solid crystalline form of Compound 2, e.g., Form B) has a melting point in the range of about 190° C. to about 200° C. In some embodiments, said solid crystalline form of Compound 2 (e.g., an anhydrous solid crystalline form of Compound 2, e.g., Form B) has a melting point in the range of about 190° C. to about 196° C. In some embodiments, said solid crystalline form of Compound 2 (e.g., an anhydrous solid crystalline form of Compound 2, e.g., Form B) has a differential scanning calorimetry trace as shown in FIG. 3.

In some embodiments, a solid crystalline form of Compound 2 (e.g., an anhydrous solid crystalline form of Compound 2, e.g., Form B) is produced upon slurry treatment with a suitable solvent (e.g., ethanol, water, or a combination thereof) followed by an additional treatment (e.g., vacuum treatment, e.g., -80° C. for one day) wherein said solid crystalline form of Compound 2 (e.g., an anhydrous solid crystalline form of Compound 2, e.g., Form B) has a melting point greater than or equal to about 150° C. and an X-ray powder diffraction pattern comprising characteristic peaks, expressed in terms of 2θ, at one or more of the following angles: about 9.78°, about 12.98°, about 19.20°, and about 19.67°. In some embodiments, a solid crystalline form of Compound 2 (e.g., an anhydrous solid crystalline form of Compound 2, e.g., Form B) is produced upon slurry treatment with a suitable solvent (e.g., ethanol, water, or a combination thereof) followed by an additional treatment (e.g., vacuum treatment, e.g., -80° C. for one day) wherein said solid crystalline form of Compound 2 (e.g., an anhydrous solid crystalline form of Compound 2, e.g., Form B) has a melting point in the range of 185° C. to about 205° C. and an X-ray powder diffraction pattern comprising characteristic peaks, expressed in terms of 2θ, at one or more of the following angles: about 9.78°, about 12.98°, about 19.20°, and about 19.67°.

Certain embodiments of the present invention comprise a purified pharmaceutical preparation comprising a compound of Formula (I). In some embodiments, the pharmaceutical preparation comprises a diastereomeric excess of greater than or equal to about 55% (e.g., about 60%, about 70%, about 80%, about 90%, about 95%, about 99%, or about 99.5%) of one diastereomer over another diastereomer. In some embodiments, the pharmaceutical preparation comprises a diastereomeric excess of greater than or equal to about 95% of one diastereomer over another diastereomer. In some embodiments, the pharmaceutical preparation comprises a diastereomeric excess of greater than or equal to about 99% of one diastereomer over another diastereomer.

In some embodiments, the pharmaceutical preparation comprises less than or equal to about 10% moisture content (e.g., water content). In some embodiments, the pharmaceutical composition comprises less than or equal to about 9%, about 8%, about 7%, about 6%, about 5%, about 4%, about 3%, about 2%, about 1%, about 0.5%, about 0.1%, about 0.05%, about 0.01%, or about 0.001% moisture content (e.g., water content). In some embodiments, the pharmaceutical preparation is substantially free of moisture (e.g., water).

In some embodiments, the pharmaceutical preparation comprises a compound of Formula (I), wherein the compound is:

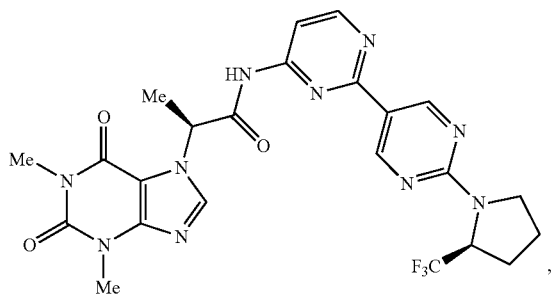 [SMILES: C[C@@H](C(=O)Nc1ccnc(-c2cnc(N3CCC[C@H]3C(F)(F)F)nc2)n1)n1cnc2c1c(=O)n(C)c(=O)n2C]

or a pharmaceutically acceptable salt thereof, which is referred to as Compound 2, Example 2, or Compound of Example 2 herein.

In some embodiments, the pharmaceutical preparation comprises a compound of Formula (I), wherein the compound is Compound 2, or a pharmaceutically acceptable salt thereof, and the preparation has a diastereomeric excess of Compound 2 greater than or equal to about 99%. In some embodiments, the pharmaceutical preparation comprises a compound of Formula (I), wherein the compound is Compound 2, or a pharmaceutically acceptable salt thereof, and the preparation has a moisture content (e.g., water content) of less than or equal to about 0.1%. In some embodiments, the pharmaceutical preparation comprises a compound of Formula (I), wherein the compound is Compound 2, or a pharmaceutically acceptable salt thereof, and the preparation has a diastereomeric excess of Compound 2 greater than or equal to about 99% and a moisture content (e.g., water content) of less than or equal to about 0.1%.

In some embodiments, the pharmaceutical preparation comprises a solid crystalline form of Compound 2 (e.g., Form A) that has an X-ray powder diffraction pattern comprising characteristic peaks, expressed in terms of 2θ, at one or more of the following angles: about 7.67°, about 12.52°, about 13.49°, and about 19.31°, and the preparation has a diastereomeric excess of Compound 2 greater than or equal to about 99% and a moisture content (e.g., water content) of less than or equal to about 0.1%.

In some embodiments, the pharmaceutical preparation comprises a solid crystalline form of Compound 2 (e.g., Form B) that has a melting point in the range of 185° C. to about 205° C. and an X-ray powder diffraction pattern comprising characteristic peaks, expressed in terms of 2θ, at one or more of the following angles: about 9.78°, about 12.98°, about 19.20°, and about 19.67°, and the preparation has a diastereomeric excess of Compound 2 greater than or equal to about 99% and a moisture content (e.g., water content) of less than or equal to about 0.1%.

Compounds of Formula (I) include molecules having an aqueous solubility suitable for oral or parenteral (e.g., intravenous) administration leading to or resulting in the treatment of a disorder described herein, for example the treatment of pain. In some embodiments, the compound is formulated into a composition suitable for oral administration. The potency in inhibiting the TRPA1 ion channel of compounds of Formula (I) described herein was measured using the method of Example 33. Table 14 discloses the TRPA1 inhibition in vitro potency of exemplary compounds (measured by the method of Example 33).

Preferred compounds of Formula (I) include compounds that inhibit the TRPA1 ion channel with a $IC_{50}$ value obtained by the method of Example 33 of less than about 100 nM (preferably, less than about 75 nM, more preferably less than about 25 nM).

Compounds of Formula (I) can inhibit the TRPA1 ion channel. In some embodiments, a compound of Formula (I) can be administered as part of an oral or parenteral (e.g., intravenous) pharmaceutical composition to treat a disorder described herein (e.g., pain) in a therapeutically effective manner.

Certain compounds disclosed herein may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. For example, if one chiral center is present in a molecule, the invention includes racemic mixtures, enantiomerically enriched mixtures, and substantially enantiomerically or diastereomerically pure compounds. The composition can contain, e.g., more than 50%, more than 60%, more than 70%, more than 80%, more than 90%, more than 95%, or more than 99% of a single enantiomer or diastereomer. Additional asymmetric carbon atoms may be present in a substituent such as an alkyl group. All such isomers, as well as mixtures thereof, are intended to be included in this invention.

The compounds described herein may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds disclosed herein, whether radioactive or not, are intended to be encompassed within the scope of the present invention. For example, deuterated compounds and compounds incorporated $^{13}C$ are intended to be encompassed within the scope of the invention.

Certain compounds disclosed herein can exist in unsolvated forms as well as solvated forms, including hydrated forms. In general, the solvated forms are equivalent to unsolvated forms and are encompassed within the scope of the present invention. Certain compounds disclosed herein may exist in multiple crystalline or amorphous forms. In general, all physical forms are equivalent for the uses contemplated by the present invention and are intended to be within the scope of the present invention.

Pharmaceutical Compositions

Pharmaceutical compositions containing compounds described herein such as a compound of Formula (I) or pharmaceutically acceptable salt thereof can be used to treat or ameliorate a disorder described herein, for example, a disorder responsive to the inhibition of the TRPA1 ion channel in subjects (e.g., humans and animals).

The amount and concentration of compounds of Formula (I) in the pharmaceutical compositions, as well as the quantity of the pharmaceutical composition administered to a subject, can be selected based on clinically relevant factors, such as medically relevant characteristics of the subject (e.g., age, weight, gender, other medical conditions, and the like), the solubility of compounds in the pharmaceutical compositions, the potency and activity of the compounds, and the manner of administration of the pharmaceutical compositions. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

While it is possible for a compound disclosed herein to be administered alone, it is preferable to administer the compound as a pharmaceutical formulation, where the compound is combined with one or more pharmaceutically acceptable excipients or carriers. The compounds disclosed herein may be formulated for administration in any convenient way for use in human or veterinary medicine. In certain embodiments, the compound included in the pharmaceutical preparation may be active itself, or may be a prodrug, e.g., capable of being converted to an active compound in a physiological setting.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Examples of pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; (21) cyclodextrins such as Captisol®; and (22) other non-toxic compatible substances employed in pharmaceutical formulations.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Solid dosage forms (e.g., capsules, tablets, pills, dragees, powders, granules and the like) can include one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents.

Liquid dosage forms can include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

The tablets, and other solid dosage forms of the pharmaceutical compositions disclosed herein, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The formulations disclosed herein can be delivered via a device. Exemplary devices include, but are not limited to, a catheter, wire, stent, or other intraluminal device. Further exemplary delivery devices also include a patch, bandage, mouthguard, or dental apparatus. Transdermal patches have the added advantage of providing controlled delivery of a compound disclosed herein to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, drops, solutions and the like, are also contemplated as being within the scope of this invention.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

When the compounds disclosed herein are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The formulations can be administered topically, orally, transdermally, rectally, vaginally, parenterally, intranasally, intrapulmonary, intraocularly, intravenously, intramuscularly, intraarterially, intrathecally, intracapsularly, intraorbitally, intracardiacly, intradermally, intraperitoneally, transtracheally, subcutaneously, subcuticularly, intraarticularly, subcapsularly, subarachnoidly, intraspinally, intrasternally or by inhalation.

One specific embodiment is an antitussive composition for peroral administration comprising an agent that inhibits both a TRPA1-mediated current with an $IC_{50}$ of 1 micromolar or less, and an orally-acceptable pharmaceutical carrier in the form of an aqueous-based liquid, or solid dissolvable in the mouth, selected from the group consisting of syrup, elixer, suspension, spray, lozenge, chewable lozenge, powder, and chewable tablet. Such antitussive compositions can include one or more additional agents for treating cough, allergy or asthma symptom selected from the group consisting of: antihistamines, 5-lipoxygenase inhibitors, leukotriene inhibitors, H3 inhibitors, β-adrenergic receptor agonists, xanthine derivatives, α-adrenergic receptor agonists, mast cell stabilizers, expectorants, and NK1, NK2 and NK3 tachykinin receptor antagonists.

Still another embodiment is a metered dose aerosol dispenser containing an aerosol pharmaceutical composition for pulmonary or nasal delivery comprising an agent that inhibits a TRPA1-mediated current with an $IC_{50}$ of 1 micromolar or less. For instance, it can be a metered dose inhaler, a dry powder inhaler or an air-jet nebulizer.

Dosages

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound disclosed herein employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound that is the lowest dose effective to produce a therapeutic effect. Such an effective dose will generally depend upon the factors described above. Generally, intravenous, intracerebroventricular, intrathecal and subcutaneous doses of the compounds described herein for a subject will range from about 0.0001 to about 100 mg per kilogram of body weight per day. For example, the dose can be 1-50, 1-25, or 5-10 mg/kg. Generally, oral doses of the compounds described herein for a subject will range from about 1 to about 1,000 mg/day (e.g., from about 5 to about 500 mg/day.

If desired, the effective daily dose of the active compound may be administered as two, three, four, five, six or more sub-doses administered separately at appropriate intervals throughout the day, optionally, in unit dosage forms.

Methods of Treatment

The compounds described herein can be used to treat or prevent a disorder described herein. For example, compounds with TRPA1 inhibitory activity are provided herein for the prevention, treatment, or alleviating symptoms of a disease or condition associated with TRPA1. Compounds of Formula (I), or pharmaceutical compositions containing one or more compounds of Formula (I), can be administered to treat disorders, conditions, or diseases described herein such as those treatable by the inhibition of TRPA1. For example, the pharmaceutical compositions comprising compounds of Formula (I), or pharmaceutically acceptable salts thereof, are useful as a perioperative analgesic, for example in the management of mild to moderate acute post-operative pain and management of moderate to severe acute pain as an adjunct to opioid analgesics. The pharmaceutical compositions comprising a therapeutically-effective dose of compounds of Formula (I), can be administered to a patient for treatment of pain in a clinically safe and effective manner, including one or more separate administrations of the pharmaceutical compositions comprising compounds of Formula (I). Additional exemplary methods include the treatment of peripheral diabetic neuropathy (PDN) and chemotherapy induced peripheral neuropathy (CIPN). For example, a pharmaceutical composition comprising a therapeutically effective dose of compounds of Formula (I), or pharmaceutically acceptable salts thereof can be administered (e.g., intravenously) to a subject in need thereof multiple times per day (e.g., BID) over a course of treatment of one or more days to treat pain in the subject. Pharmaceutical compositions comprising compounds of Formula (I) can also be used to treat or ameliorate pulmonary conditions, such as obstructive diseases, e.g., chronic obstructive pulmonary disease (COPD), asthma (e.g., cold induced asthma, exercise-induced asthma, allergy-induced asthma, and occupational asthma), and cough.

Those of skill in the treatment of diseases linked to the mediation of the TRPA1 receptor will be able to determine the therapeutically effective amount of a compound of Formula (I) from the test results presented hereinafter. In general, a suitable daily dose of a compound of the invention will be that amount of the compound that is the lowest dose able to produce a therapeutic effect. Such an effective dose will generally depend upon various factors. Generally, oral, sublingual, rectal, intravenous, topical, transdermal, inhaled and intracerebroventricular doses of the compounds of this invention for a patient will range from about 0.0001 to about 100 mg per kilogram of body weight per day. For example, the dose can be 1-50, 1-25, or 5-10 mg/kg. It is contemplated, for instance, that a therapeutically effective dose will be from about 0.001 mg/kg to about 50 mg/kg per kg of body weight, more preferably from about 0.01 mg/kg to about 10 mg/kg per kg of body weight of the patient to be treated. It may be appropriate to administer the therapeutically effective dose in the form of two or more sub-doses at appropriate intervals throughout the day. Said sub-doses may be formulated as unit dosage forms, for example each containing from about 0.1 mg to about 1000 mg, more particularly from about 1 to about 500 mg, of the active ingredient per unit dosage form.

The exact dosage and frequency of administration depends on the particular compound of formula (I) used, the particular condition being treated, the severity of the condition being treated, the age, weight and general physical condition of the particular patient as well as the other medication the patient may be taking, as is well known to those skilled in the art. Furthermore, said "therapeutically effective amount" may be lowered or increased depending on the response of the treated patient and/or depending on the evaluation of the physician prescribing the compounds of the instant invention. The effective daily amount ranges mentioned hereinabove are therefore only guidelines. A physician or veterinarian having ordinary skill in the art can readily determine and prescribe the effective amount of the pharmaceutical composition required.

Exemplary disorders suitable for treatment with a compound or composition described herein are provided below.
Pain The compounds of Formula (I) that are useful in the modulation of TRPA1 can be used in the formulation of analgesic pharmaceuticals suitable for the treatment and/or prophylaxis of pain in mammals, especially in humans. Endogenous activators of TRPA1 are produced during many pathological conditions including tissue injury, inflammation, and metabolic stress. Compounds and pharmaceutical compositions of the present invention can be administered to treat pain resulting from activation of TRPA1 including neuropathic pain. Relevant neuropathic pain conditions include, but are not limited to, painful diabetic neuropathy, chemotherapy-induced peripheral neuropathy, lower back pain, trigeminal neuralgia, post-herpetic neuralgia, sciatica, and complex regional pain syndrome Compositions and methods provided herein may also be used in connection with treatment of in the treatment of inflammation and inflammatory pain. Such disorders include rheumatoid arthritis, osteoarthritis, temperomandibular disorder. In some embodiments, the compositions and methods provided herein may be used to treat headache pain, e.g., migraine.

Disclosed compounds also may be useful in the treatment of visceral pain and inflammation. Relevant diseases include pancreatitis, inflammatory bowel disease, colitis, Crohn's disease, endometriosis, pelvic pain, and angina.

Additional exemplary pain indications for which compounds disclosed herein can be used include temperomandibular disorder, cancer pain (resulting either from the underlying disease or from the treatments), burn pain, oral pain, oral pain due to cancer treatment, crush and injury induced pain, incisional pain, bone pain, sickle cell disease pain, fibromyalgia and musculoskeletal pain. TRPA1 has been show to play a role in cancer related pain (see, e.g., Trevisan et al., *Cancer Res* (2013) 73(10):3120-3131); postoperative pain (see, e.g., Wei et al, *Anasthesiology* (2012) 117:137-148); pathological pain (see, e.g., Chen et al, *Pain* (2011) 152:2549-2556); and pain related to chemical injury (see, e.g., Macpherson et al, *J Neurosci* (2007) 27(42): 11412-11415).

Hyperalgesia (e.g., mechanical hyperalegsia, cold hyperalegsia) or increased sensitivity to pain (e.g., acute, chronic). Multiple Chemical Sensitivity is a disorder linked to chemical exposure with multi-organ symptoms including respiratory symptoms and headache.

Allodynia (e.g., cutaneous allodynia, e.g., cephalic, extracephalic) is a pain due to a stimulus which does not normally provoke pain, e.g., temperature or physical stimuli, and differs from hyperalgesia, which generally refers to an extreme, exaggerated reaction to a stimulus which is normally painful.
Migraine The compounds of Formula (I) that are useful in the modulation of TRPA1 can be used in the formulation of pharmaceuticals suitable for the treatment and/or prophylaxis of migraine in mammals, especially in humans. Exposure to TRPA1 activators has been shown to trigger migraine in susceptible populations. Such activators include but are not limited to umbellulone, nitroglycerin, cigarette smoke, and formaldehyde. Accordingly, TRPA1 antagonists of the invention represent a significant possible therapeutic for the treatment of both chronic and acute migraine.
Inflammatory Diseases and Disorders Compositions and methods provided herein may also be used in connection with treatment of inflammatory diseases. These diseases include but are not limited to asthma, chronic obstructive pulmonary disease, rheumatoid arthritis, osteoarthritis, inflammatory bowel disease, glomerulonephritis, neuroinflammatory diseases such as multiple sclerosis, and disorders of the immune system. TRPA1 has been show to play a role in pancreatic pain and inflammation (see, e.g., Schwartz et al., *Gastroenterology* (2011) 140(4):1283-1291).

Peripheral neuropathy, for example diabetic neuropathy (e.g., painful diabetic neuropathy), is a particular condition that involves both a neuronal and an inflammatory component. Without being bound by a mechanistic theory, the TRPA1 antagonists of the invention may be useful in treating peripheral neuropathies including, but not limited to, diabetic neuropathy. In addition to their use in the treatment of peripheral neuropathies (e.g., reducing inflammation), the subject inhibitors may also be useful in reducing the pain associated with peripheral neuropathy. TRPA1 has been show to play a role in neuropathy and neuropathic pain (see, e.g., Wei et al, *Anesthesiology* (2009) 111:147-54; Koivisto et al., *Pharmacol Res* (2011) 65:149-158).

Neurogenic inflammation often occurs when neuronal hyperexcitability leads to the release of peptides that trigger inflammation. These peptides include substance P and CGRP. Blocking TRPA1 would reduce neuronal activity and thus could block neurogenic inflammation. For example, neurogenic inflammation in the respiratory tract, can result in asthma and allergic rhinitis symptoms, and neurogenic inflammation in the dura may also mediate migraine pain.

Pancreatitis

Pancreatitis is an inflammation of the pancreas. The pancreas is a large gland behind the stomach and close to the duodenum. Normally, digestive enzymes do not become active until they reach the small intestine, where they begin digesting food. But if these enzymes become active inside the pancreas, they start "digesting" the pancreas itself. TRPA1 has been show to play a role in pancreatic pain and inflammation (see, e.g., Schwartz et al., *Gastroenterology* (2011) 140(4):1283-1291.).

Acute pancreatitis is usually, although not exclusively, caused by gallstones or by alcohol abuse. Acute pancreatitis usually begins with pain in the upper abdomen that may last for a few days. The pain may be severe and may become constant. The pain may be isolated to the abdomen or it may reach to the back and other areas. Sometimes, and for some patients, the pain is sudden and intense. Other times, or for other patients, the pain begins as a mild pain that worsens after eating. Someone with acute pancreatitis often looks and feels very sick. Other symptoms may include swollen and tender abdomen, nausea, vomiting, fever, and rapid pulse. Severe cases of acute pancreatitis may cause dehydration and low blood pressure, and may even lead to organ failure, internal bleeding, or death.

During acute pancreatitis attacks, the blood levels of amylase and lipase are often increased by at least 3-fold. Changes may also occur in blood levels of glucose, calcium, magnesium, sodium, potassium, and bicarbonate.

The current treatment depends on the severity of the attack. Treatment, in general, is designed to support vital bodily functions, manage pain, and prevent complications. Although acute pancreatitis typically resolved in a few days, pain management during an attack is often required. The compounds disclosed herein can be used to relieve the pain associated with acute pancreatitis.

Chronic pancreatitis may develop if injury to the pancreas continues. Chronic pancreatitis occurs when digestive enzymes attack and destroy the pancreas and nearby tissues, causing scarring and pain. Chronic pancreatitis may be caused by alcoholism, or by blocked, damaged, or narrowed pancreatic ducts. Additionally, hereditary factors appear to influence the disease, and in certain cases, there is no identifiable cause (so called idiopathic pancreatitis).

Most people with chronic pancreatitis have abdominal pain. The pain may get worse when eating or drinking, spread to the back, or become constant and disabling. Other symptoms include nausea, vomiting, weight loss, and fatty stools.

Relieving pain is the first step in treating chronic pancreatitis. Once the pain has been managed, a high carbohydrate and low fat dietary plan is put in place. Pancreatic enzymes may be used to help compensate for decrease enzyme production from the injured pancreas. Sometimes insulin or other drugs are needed to control blood glucose.

Although pain is typically managed using drug therapy, surgery may be necessary to relieve pain. Surgery may be necessary to drain an enlarged pancreatic duct or even to removing a portion of a seriously injured pancreas.

Pain is frequently present with chronic pancreatitis. For example, pain is present for approximately 75% of patients with alcoholic chronic pancreatitis, 50% of patients with lateonset idiopathic chronic pancreatitis, and 100% of patients with early-onset idiopathic chronic pancreatitis (DiMagno, *Gastroenterology* (1999) 116(5):1252-1257).

A minority of patients with pain have readily identifiable lesions which are relatively easy to treat surgically or endoscopically. In other patients, pain is often thought to result from a variety of causes, including elevated intrapancreatic pressure, ischemia, and fibrosis. Without being bound by theory, however, these phenomena are not likely the underlying cause of the pain. Rather, pain may result from a background of neuronal sensitization induced by damage to the perineurium and subsequent exposure of the nerves to mediators and products of inflammation.

Given the importance of effective pain management in patients with chronic pancreatitis, additional therapies for treating painful symptoms are important and useful. The compounds disclosed herein can be used to manage the pain associated with chronic pancreatitis; they can be used alone or as part of an overall therapeutic treatment plan to manage patients with chronic pancreatitis. For example, the compounds can be administered with pancreatic enzymes and/or insulin as part of a therapeutic regimen designed to manage patients with chronic pancreatitis.

Cancer treatments are not only painful, but they may even be toxic to healthy tissue. Some chemotherapeutic agents can cause painful neuropathy. Accordingly, the compounds disclosed herein could represent a significant possible therapeutic for the treatment of the pain and/or inflammation associated with cancer treatments that cause neuropathy.

A major function of prostaglandins is to protect the gastric mucosa. Included in this function is the modulation of intracellular calcium level in human gastric cells which plays a critical role in cell proliferation. Consequently, inhibition of prostaglandins by nonsteroidal anti-inflammatory drugs (NSAIDs) can inhibit calcium influx in gastric cells (Kokoska et al. (1998) *Surgery* (St Louis) 124(2):429-437). The NSAIDs that relieve inflammation most effectively also produce the greatest gastrointestinal damage (Canadian Family Physician, 5 Jan. 1998, p. 101). Thus, the ability to independently modulate calcium channels in specific cell types may help to alleviate such side effect of anti-inflammatory therapy. Additionally or alternatively, administration of TRPA1 inhibitory compounds disclosed herein may be used in combination with NSAIDs, thus promoting pain relief using reduced dosage of NSAIDs.

TRPA1 may mediate ongoing nociception in chronic pancreatitis; and may be involved in transforming acute into chronic inflammation and hyperalgesia in pancreatitis. TRPA1 may also mediate irritation and burning in the e.g., nasal and oral mucosa and respiratory lining.

Neuropathy

Because TRPA1 overactivity can lead to a toxic calcium overload, TRPA1 antagonists also have utility in the prevention of neuropathy associated with diabetes, chemical injury, chemotherapy, medicines such as statins, HIV/AIDS, Fabry's disease, vitamin deficiency, inherited polyneuropathy such as Marie-Charcot Tooth disease, and trauma. Peripheral neurodegenerative diseases such as Amyotrophic Lateral Sclerosis may also be amenable to treatment with a TRPA1 antagonist.

Pulmonary Disease and Cough

Compositions and methods provided herein may also be used in connection with the treatment of pulmonary diseases, including, but not limited to, asthma (including exercise-induced asthma, atopic asthma, allergic asthma), Chronic Obstructive Pulmonary disease (COPD), emphysema, cystic fibrosis, bronchiectasis, bronchiolitis, allergic bronchopulmonary aspergillosis, bronchiolitis obliterans (popcorn worker lung), diseases due to chemical exposure including exposures to diacetyl, formaldehyde, and other irritants. These conditions also include tuberculosis, restrictive lung disease including asbestosis, radiation fibrosis, hypersensitivity pneumonitis, infant respiratory distress syndrome, idiopathic pulmonary fibrosis, idiopathic interstial pneumonia sarcoidosis, eosinophilic pneumonia, lymphangioleiomyomatosis, pulmonary Langerhan's cell histiocytosis, and pulmonary alveolar proteinosis; respiratory tract infections including upper respiratory tract infections (e.g., common cold, sinusitis, tonsillitis, pharyngitis and laryngitis) and lower respiratory tract infections (e.g., pneumonia); respiratory tumors whether malignant (e.g., small cell lung cancer, non-small cell lung cancer, adenocarcinoma, squamous cell carcinoma, large cell undifferentiated carcinoma, carcinoid, mesothelioma, metastatic cancer of the lung, metastatic germ cell cancer, metastatic renal cell carcinoma) or benign (e.g., pulmonary hamartoma, congenital malformations such as pulmonary sequestration and congenital cystic adenomatoid malformation (CCAM)); pleural cavity diseases (e.g., empyema and mesothelioma); and pulmonary vascular diseases, e.g, pulmonary embolism such as thromboembolism, and air embolism (iatrogenic), pulmonary arterial hypertension, pulmonary edema, pulmonary hemorrhage, inflammation and damage to capillaries in the lung resulting in blood leaking into the alveoli. Other conditions that may be treated include disorders that affect breathing mechanics (e.g., obstructive sleep apnea, central sleep apnea, Guillan-Barre syndrome, and myasthenia gravis).

The present compounds can also be useful for treating, reducing, or preventing cough (with or without the production of sputum), cough associated with asthma, cough associated with influenza, coughing blood (haemoptysis), cough of unknown etiology, allergy-induced cough, and cough due to chemical exposures.

Dermatological Disorders

A number of agents that cause itch activate TRPA1 directly or via activation of receptors which couple to TRPA1 downstream. Compositions and methods provided herein may also be used in connection with the treatment of itch. Indications include, but are not limited to, conditions triggered by exposure to exogenous chemicals such as contact dermatitis, poison ivy, itch due to cancer including lymphomas, itch caused by medications such as chloroquine, itch due to reactive drug metabolites or itch due to dry skin.

Additional exemplary indications include atopic dermatitis, psoriasis, hives, eczema, dyshidrotic eczema, mouth ulcers, diaper rash.

Itch

Itch, or acute pruritus, while serving an important protective function by e.g., warning against harmful agents in the environment, can also be a debilitating condition that e.g., accompanies numerous skin, systemic and nervous system disorders. Some forms of itch are mediated by histamine signaling as such are susceptible to treatment with e.g., antihistamines. However, most pathophysiological itch conditions are insensitive to antihistamine treatment. Compounds and pharmaceutical compositions of the present invention can be administered to treat itch.

Atopic dermatitis (AD) is a chronic itch and inflammatory disorder of the skin. Patients with severe AD can develop asthma and allergic rhinitis, also known as atopic march. Skin rash and pruritus may be associated with atopic disease. Chronic itch, e.g., in AD and psoriasis; includes pathophysiological hallmarks such as robust scratching, extensive epidermal hyperplasia from e.g., eczema, kidney failure, cirrhosis, nervous system disorders, some cancers.

Allergic contact dermatitis is a common skin disease associated with inflammation and persistent pruritus.

Methods as disclosed herein may inhibit skin edema, keratinocyte hyperplasia, nerve growth, leukocyte infiltration, and antihistamine-resistant scratching behavior. Methods as disclosed herein may inhibit allergic response to e.g., exogenous stimulants, e.g., haptens, oxazolone, urushiol (e.g., from poison ivy).

Disease and Injury Models

Compounds that antagonize TRPA1 function may be useful in the prophylaxis and treatment of any of the foregoing injuries, diseases, disorders, or conditions. In addition to in vitro assays of the activity of these compounds, their efficacy can be readily tested in one or more animal models. There are numerous animal models for studying pain. The various models use various agents or procedures to simulate pain resulting from injuries, diseases, or other condition (see, e.g., Blackburn-Munro (2004) *Trends in Pharmacol Sci* (2004) 25:299-305 (e.g., Tables 1, 3, or 4). Behavioral characteristics of challenged animals can then be observed. Compounds or procedures that may reduce pain in the animals can be readily tested by observing behavioral characteristics of challenged animals in the presence versus the absence of the test compound(s) or procedure.

Exemplary behavioral tests used to study chronic pain include tests of spontaneous pain, allodynia, and hyperalgesia. Id. To assess spontaneous pain, posture, gait, nocifensive signs (e.g., paw licking, excessive grooming, excessive exploratory behavior, guarding of the injured body part, and self-mutilation) can be observed. To measure evoked pain, behavioral responses can be examined following exposure to heat (e.g., thermal injury model).

Exemplary animal models of pain include, but are not limited to, the models described in the Trevisan model, and the Koivisto references including streptozotocin induced painful diabetic neuropathy, bortexomib induced peripheral neuropathy and oxaliplatin induced peripheral neuropathy; the Chung model, the spared nerve injury model, the carageenan induced hyperalgesia model, the Freund's complete adjuvant induced hyperalgesia model, the thermal injury model, the formalin model and the Bennett Model.

In the Trevisan reference, chemotherapy-induced peripheral neuropathy model involves the induction if a CIPN phenotype in mice by treatment with bortexomib or oxaliplatin (Trevisan et al, *Cancer Res* (2013) 73: 3120-3131). Treatment of an animal with an inhibitor of TRPA1 can be evaluated using any of a variety of nociceptive tests such as the Von Frey hair test, the hot plate test, cold simulation, chemical hyperalgesia, or the rotarod test.

The model of peripheral diabetic neuropathy (PDN) in the Koivisto reference involves induction of diabetes mellitus (DM) in rats with streptozotocin, and assessing axon reflex induced by intraplantar injection of a TRPA1 agonist (Koivisto et al., *Pharmacol Res* (2011) 65:149-158). Treatment with a compound that inhibits TRPA1 can be evaluated for the reduction in DM-induced attenuation of the cutaneous axon reflex.

The Chung model of neuropathic pain (without inflammation) involves ligating one or more spinal nerves (see, e.g., Chung et al. *Methods Mol Med* (2004) 99: 35-45; Kim and Chung, *Pain* (1992) 50: 355-363). Ligation of the spinal nerves results in a variety of behavioral changes in the animals including heat hyperalgesia, cold allodynia, and ongoing pain. Compounds that antagonize TRPA1 can be administered to ligated animals to assess whether they diminish these ligation-induced behavioral changes in comparison to that observed in the absence of compound.

Carageenan induced hyperalgesia and Freund's complete adjuvant (CFA) induced hyperalgesia are models of inflammatory pain (see, e.g., Walker et al. *J Pharmacol Exp Ther* (2003) 304:56-62; McGaraughty et al. *Br J Pharmacol* (2003) 140:1381-1388; Honore et al. *J Pharmacol Exp Ther* (2005) 314:410-421). Compounds that antagonize TRPA1 can be administered to carrageenan or CFA challenged animals to assess whether they diminish cold, mechanical or heat hypersensitivity in comparison to that observed in the absence of compound. In addition, the ability of compounds that antagonize TRPA1 function to diminish cold and/or mechanical hypersensitivity can also be assessed in these models. Typically, the carrageenan induced hyperalgesia model is believed to mimic acute inflammatory pain and the CFA model is believed to mimic chronic pain and chronic inflammatory pain.

Exemplary models of inflammatory pain include the rat model of intraplantar bradykinin injection. Briefly, the baseline thermal sensitivity of the animals is assessed on a Hargreave's apparatus. TRPA1 blockers are then administered systemically. Bradykinin is subsequently injected into the paw and a hyperalgesia is allowed to develop. Thermal escape latency is then measured at multiple time points over the next few hours (Chuang et al., 2001; Vale et al., 2004).

Inflammation is often an important contributing factor to pain. As such, it is useful to identify compounds that act as anti-inflammatories. Many compounds that reduce neural activity also prevent neurogenic inflammation. To measure inflammation directly, the volume of a rat paw can be assessed using a plethysmometer. After baseline measurement is taken, carrageenan can be injected into the paw and the volume can be monitored over the course of hours in animals that have been treated with vehicle or drug. Drugs that reduce the paw swelling are considered to be anti-inflammatory.

Migraines are associated with significant pain and inability to complete normal tasks. Several models of migraine exist including the rat neurogenic inflammation model (see e.g., Buzzi et al *Br J Pharmacol* (1990) 99:202-206) and the Burstein Model (see, e.g., Strassman et al., *Nature* (1996) 384: 560-564).

The Bennett model uses prolonged ischemia of the paw to mirror chronic pain (see, e.g., Xanthos et al. *J Pain* (2004) 5: S1). This provides an animal model for chronic pain including post-operative pain, complex regional pain syndrome, and reflex sympathetic dystrophy. Prolonged ischemia induces behavioral changes in the animals including hyperalgesia to mechanical stimuli, sensitivity to cold, pain behaviors (e.g., paw shaking, licking, and/or favoring), and hyperpathia. Compounds that antagonize TRPA1 can be administered to challenged animals to assess whether they diminish any or all of these behaviors in comparison to that observed in the absence of compound. Similar experiments can be conducted in a thermal injury or UV-burn model which can be used to mimic post-operative pain.

Additional models of neuropathic pain include central pain models based on spinal cord injury. Chronic pain is generated by inducing a spinal cord injury, for example, by dropping a weight on a surgically exposed area of spinal cord (e.g., weight-drop model). Spinal cord injury can additionally be induced by crushing or compressing the spinal cord, by delivering neurotoxin, using photochemicals, or by hemisecting the spinal cord.

Additional models of neuropathic pain include peripheral nerve injury models. Exemplary models include, but are not limited to, the neuroma model, the Bennett model, the Seltzer model, the Chung model (ligation at either L5 or L5/L6), the sciatic cryoneurolysis model, the inferior caudal trunk resection model, and the sciatic inflammatory neuritis model. Id.

Exemplary models of neuropathic pain associated with particular diseases are also available. Diabetes and shingles are two diseases often accompanied by neuropathic pain. Even following an acute shingles episodes, some patients continue to suffer from postherpetic neuralgia and experience persistent pain lasting years. Neuropathic pain caused by shingles and/or postherpetic neuralgia can be studied in the postherpetic neuralgia model (PHN). Diabetic neuropathy can be studied in diabetic mouse models, as well as chemically induced models of diabetic neuropathy.

As outlined above, cancer pain may have any of a number of causes, and numerous animal models exist to examine cancer pain related to, for example, chemotherapeutics or tumor infiltration. Exemplary models of toxin-related cancer pain include the vincristine-induced peripheral neuropathy model, the taxol-induced peripheral neuropathy model, and the cisplatin-induced peripheral neuropathy model. An exemplary model of cancer pain caused by tumor infiltration is the cancer invasion pain model (CIP). Id.

Primary and metastatic bone cancers are associated with tremendous pain. Several models of bone cancer pain exist including the mouse femur bone cancer pain model (FBC), the mouse calcaneus bone cancer pain model (CBC), and the rat tibia bone cancer model (TBC). Id.

An additional model of pain is the formalin model like the carrageenan and CFA models, the formalin model involves injection of an irritant intradermally or intraperitoneally into an animal. Injection of formalin, a 37 percent solution of formaldehyde, is the most commonly used agent for intradermal paw injection (the formalin test). Injection of a 0.5 to 15 percent solution of formalin (usually about 3.5%) into the dorsal or plantar surface of the fore- or hindpaw produces a biphasic painful response of increasing and decreasing intensity for about 60 minutes after the injection. Typical responses include the paw being lifted, licked, nibbled, or shaken. These responses are considered nociceptive. The initial phase of the response (also known as the Early Phase), which lasts 3 to 5 minutes, is probably due to direct chemical stimulation of nociceptors. This is followed by 10 to 15 minutes during which animals display little behavior suggestive of nociception. The second phase of this response (also known as the Late Phase) starts about 15 to 20 minutes after the formalin injection and lasts 20 to 40 minutes, initially rising with both number and frequency of nociceptive behaviors, reaching a peak, then falling off. The intensities of these nociceptive behaviors are dependent on the concentration of formalin used. The second phase involves a period of sensitization during which inflammatory phenomena occur. The two phases of responsiveness to formalin injection makes the formalin model an appropriate model for studying nociceptive and acute inflammatory pain. It may also model, in some respects, neuropathic pain.

In addition to any of the foregoing models of chronic pain, compounds that antagonize TRPA1 function can be tested in one or more models of acute pain (see, e.g., Valenzano et al. (2005) *Neuropharmacology* 48:658-672). Regardless of whether compounds are tested in models of chronic pain, acute pain, or both, these studies are typically (though not exclusively) conducted, for example, in mice, rats, or guinea pigs. Additionally, compounds can be tested in various cell lines that provide in vitro assays of pain.

Many individuals seeking treatment for pain suffer from visceral pain. Animal models of visceral pain include the rat model of inflammatory uterine pain (see, e.g., Wesselmann et al., *Pain* (1997) 73:309-317), injection of mustard oil into the gastrointestinal tract to mimic irritable bowel syndrome (see, e.g., Kimball et al., (2005) *Am J Physiol Gastrointest Liver Physiol,* 288(6):G1266-73), injection of mustard oil into the bladder to mimic overactive bladder or bladder cystitis (see, e.g., Riazimand (2004), *BJU Int* 94:158-163). The effectiveness of a TRPA1 compound can be assessed by a decrease in writhing, gastrointestinal inflammation or bladder excitability.

For testing the efficacy of TRPA1 antagonists for the treatment of cough, experiments using the conscious guinea pig model of cough can be readily conducted (see, e.g., Tanaka and Maruyama (2003) *J Pharmacol Sci* 93:465-470; McLeod et al. (2001) *Br J Pharmacol* 132: 1175-1178). Briefly, guinea pigs serve as a useful animal model for cough because, unlike other rodents such as mice and rats, guinea pigs actually cough. Furthermore, guinea pig coughing appears to mimic human coughing in terms of the posture, behavior, and appearance of the coughing animal.

To induce cough, conscious guinea pigs are exposed to an inducing agent such as citric acid or capsaicin. The response of the animal is measured by counting the number of coughs. The effectiveness of a cough suppressing agent, for example a compound that inhibits TRPA1, can be measured by administering the agent and assessing the ability of the agent to decrease the number of coughs elicited by exposure to citric acid, capsaicin, or other similar cough-inducing agent. In this way, TRPA1 inhibitors for use in the treatment of cough can be readily evaluated and identified.

Additional models of cough may also include the unconscious guinea pig model (see, e.g., Rouget et al. (2004) *Br J Pharmacol* 141: 1077-1083). Either of the foregoing models can be adapted for use with other animals capable of coughing. Exemplary additional animals capable of coughing include cats and dogs.

Compounds of the invention may be tested in multiple models of asthma. One example is the murine ovalbumin model of asthma (see, e.g., Caceres A I et al., *Proc Natl Acad Sci USA*. (2009) 106(22):9099-104). In this model, ovalbumin is injected into the intraperitoneal cavity several times over 2 weeks. Sometime in the third week, animals are challenged with intranasal ovalbumin an airway hyperresponsiveness, inflammation and inflammatory cytokine production may be measured. Compounds are dosed during the challenge phase of the model. Trpa1 knock-out mice may be substituted into the above models as reported by Caceres et al.

An example of a large animal model of asthma the conscious allergic sheep model as described in Abraham, W. M. et al. may be used to assess effects of compounds on the antigen-induced late stage response of asthma (Abraham W M., *Am J Respir Crit Care Med* (2000) 162(2):603-11). Briefly, baseline airway responsiveness is measured by plethysmograph in conscious sheep prior to a nebulized administration of Ascaris suum extract to induce asthma. After baseline readings are captured, animals are challenged with a nebulized dose of Ascaris suum. Antigen sensitivity is determined by decrease in pulmonary flow resistance from baseline. Once animals demonstrate antigen-sensitivity, test compounds may be administered and additional pulmonary flow resistance readings captured to assess changes airway responsiveness. Models in the horse and beagle dog are sometimes also used.

Additional models may include the Brown Norway rat model and the C57BL/6J mouse model of asthma as described in Raemdonck et al. (Raemdonck K et al., *Thorax* (2012) January; 67(1):19-25). Briefly Brown Norway rats and C57BL/6J mice may be sensitized and challenged with aerosol delivered ovalbumin. Once sensitivity is confirmed by a decrease in lung function as measured by whole body plethysmograph readings, compounds of the invention may be administered. Visual and audible signs of respiratory distress including wheezing may also be present.

Dermatitis

Multiple mouse models of dermatological disease currently exist. For example, Liu et al. describe multiple oxazolone and urushiol-induced contact dermatis models (see, e.g., Liu B et al., *FASEB J*. (2013) 27(9):3549-63). Briefly, Trpa1 knock-out mice receive topical administrations of oxazolone or urushiol to induce dermatitis and itch responses. Epidermis thickness may also be measured by taking ear punches and measurements of challenged areas compared with untreated ears. In vivo treatment compounds may be determined by administering compounds to the animals prior to or after ozazolone or urushiol treatments. Scratching behaviors are recorded by video cameras positioned above observation chambers. Observers blind to treatment groups record the time animals spend scratching over the course of thirty minutes.

An alternative mouse model of dry-skin evoking itch involves administration of acetone, ether, and water to the mouse as reported by Wilson et al. (Wilson S R et al., *J Neurosci* (2013) 33(22):9283-94) In this model, the area to be treated is shaved and mice receive topical administration of acetone and ether twice daily on the area to be observed, e.g. cheek or caudal back. In vivo efficacy of treatment compounds may be determined by administering compounds to the animals prior to or after acetone and ether administration. Scratching behavior is recorded by camera for a period of 20 minutes and quantified by observers blind to treatment groups.

In addition, pruritus may be induced by direct injection of an agent that causes itch. Examples of these agents may be found in Akayimo and Carstens, 2013. Some examples are: chloroquine (Wilson et al., 2011), bile acids, TSLP (Wilson et al., 2013), and IL-31 (Cevikbas et al., 2014). Typically scratching bouts in a defined period are recorded by an observed blinded to treatment group.

Numerous rodent models of incontinence exist. These include models of incontinence induced by nerve damage, urethral impingement and inflammation. Models of urethral impingement include the rat bladder outflow obstruction model (see, e.g., Pandita, R K, and Andersson K E. *J Urol* (1999) 162: 943-948). Inflammatory models include injection of mustard oil into the bladder.

To test the effectiveness of a TRPA1 inhibitor compound in treating incontinence, varying concentrations of compound (e.g., low, medium, and high concentration) can be administered to rats following surgical partial bladder outlet obstruction (BOO). Efficacy of the varying doses of TRPA1 inhibitory compound can be compared to controls administered excipients alone (sham control). Efficacy can further be compared to rats administered a positive control, such as atropine. Atropine is expected to decrease bladder overactivity following partial bladder outlet obstruction in the BOO model. Note that when testing compounds in the BOO model, compounds can be administered directly to the bladder or urethra (e.g., by catheter) or compounds can be administered systemically (e.g., orally, intraveneously, intraperitoneally, etc).

Several rat models of pancreatitic pain have recently been described (Lu, 2003, *Anesthesiology* 98(3):734-740; Winston et al., (2003) *Journal of Pain* 4(6): 329-337). Lu et al. induced pancreatitis by systemic delivery of dibutylin dichloride in rats. Rats showed an increase in withdrawal events after von Frey filament stimulation of the abdomen and decreased withdrawal latency after thermal stimulation during a period of 7 days. The pain state induced in these animals was also characterized by increased levels of substance P in spinal cords (Lu, et al., 2003). To test the efficacy of a TRPA1 inhibitor in this model, a TRPA1 inhibitor can be administered following or concurrently with delivery of dibutylin dichloride. Control animals can be administered a carrier or a known pain reliever. Indicia of pain can be measured. Efficacy of a TRPA1 inhibitor can be evaluated by comparing the indicia of pain observed in animals receiving a TRPA1 inhibitor to that of animals that did not receive a TRPA1 inhibitor. Additionally, efficacy of a TRPA1 inhibitor can be compared to that of known pain medicaments.

The efficacy of von Frey filament testing as a means to measure nociceptive behavior was also shown by inducing pancreatitis by systemic L-arginine administration (Winston et al, 2003). The efficacy of a TRPA1 inhibitor can similarly be tested following pancreatitis induced by systemic L-arginine administration.

Lu et al. also described direct behavioral assays for pancreatic pain using acute noxious stimulation of the pancreas via an indwelling ductal cannula in awake and freely moving rats. These assays included cage crossing, rearing, and hind limb extension in response to intrapancreatic bradykinin infusion. Intrathecal administration of either D-APV (NMDA receptor antagonist) or morphine alone partially reduced visceral pain behaviors in this model. Combinations of both reduced pain behaviors to baseline. The efficacy of a TRPA1 inhibitor can similarly be tested in this system.

Any of the foregoing animal models may be used to evaluate the efficacy of a TRPA1 inhibitor in treating pain associated with pancreatitis. The efficacy can be compared to a no treatment or placebo control. Additionally or alternatively, efficacy can be evaluated in comparison to one or more known pain relieving medicaments.

EXAMPLES

General Procedures

All reactions were run under an inert atmosphere, generally nitrogen. All non-aqueous reactions were run using anhydrous solvents. All reactions were stirred either with a magnetic stir bar or with overhead mechanical stirring. All saturated extraction solutions are assumed to be aqueous (saturated $NH_4Cl$ for example). All drying agents are anhydrous. Drying organic solutions with a drying agent implies that the drying agent was removed from the organic solution by filtration. Chromatography refers to column chromatography on silica gel. Preparative thin layer chromatography (TLC) was run on silica gel plates. Concentration of reaction mixtures implies concentration under reduced pressure and the use of a rotary evaporation instrument. Drying of final products implies drying under high vacuum conditions. Sonication implies the use of an ultrasonic bath. All $^1$H-NMR data were obtained at 400 MHz. Mass spectra were obtained in positive ion mode and are reported as the protonated species $MH^+$ unless otherwise indicated.

Abbreviations

DCM dichloromethane
DIC N,N'-diisopropylcarbodiimide
DIPEA N,N'-diisopropylethylamine
DMAP 4-dimethylaminopyridine
DMF N,N-dimethylformamide
EDC 1-ethyl-3-(3-dimethylaminopropyl)carbodiimide
EA ethyl acetate
Ether diethyl ether
h hours
HOAc acetic acid
HOAT 1-hydroxy-7-azabenzotriazole
LAH lithium aluminum hydride
MeOH methanol
min minutes
n-BuLi n-butyllithium
NMP N-methylpyrrolidinone
Pd/C palladium on activated carbon, generally 10% palladium load
PE petroleum ether
RT room temperature
TBAI tetrabutylammonium iodide
TEA triethylamine
TFA trifluoroacetic acid
TLC thin layer chromatography
THF tetrahydrofuran Preparation of Synthetic Intermediates Preparation 1 (2S)-2-(1,3-dimethyl-2,6-dioxo-3,4,5,6-tetrahydro-1H-purin-7(2H)-yl)propanoic acid

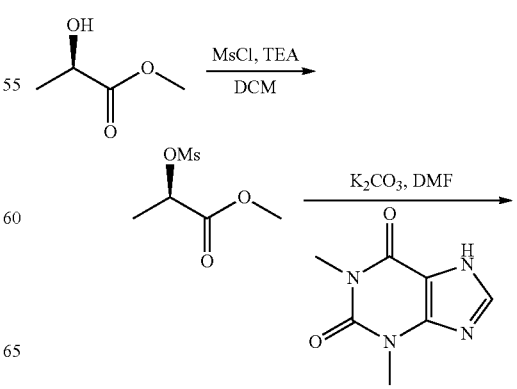

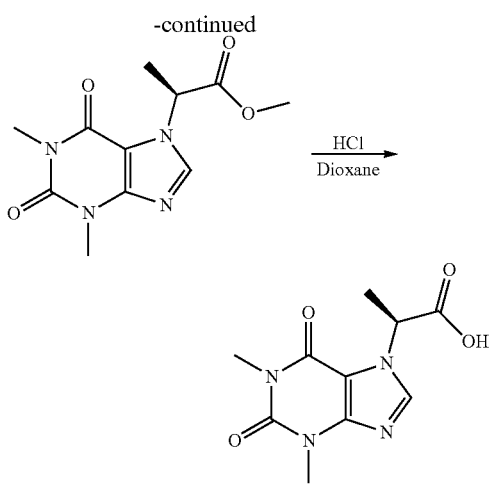

Step 1 (R)-methyl 2-(methylsulfonyloxy)propanoate

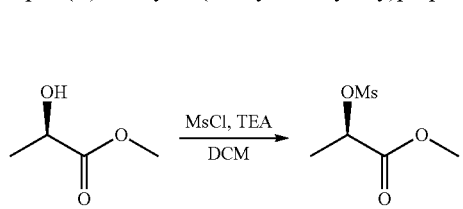

A solution of (R)-methyl 2-hydroxypropanoate (30 g, 0.28 mol) and TEA (80 mL, 0.56 mol) in DCM (300 mL) was chilled to 0° C. and methanesulfonyl chloride (33.6 mL, 0.42 mol) was added dropwise at 0° C. over 1 h. The mixture was stirred at 10-20° C. for 1.5 h. The resulting mixture was quenched with ice-water (100 mL). The organic layer was separated, washed with water (2×50 mL) and brine, dried over $Na_2SO_4$ and concentrated to afford the crude product (R)-methyl 2-(methylsulfonyloxy)propanoate (50 g, 95.2%) as brick red oil which was used without purification.

Step 2 (2S)-methyl 2-(1,3-dimethyl-2,6-dioxo-3,4,5,6-tetra-hydro-1H-purin-7(2H)-yl)propanoate

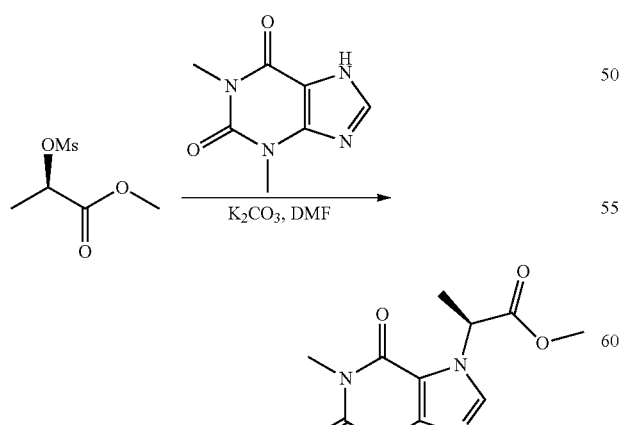

To a suspension of 1,3-dimethyl-3,4,5,7-tetrahydro-1H-purine-2,6-dione (112 g, 0.62 mol) and $K_2CO_3$ (171 g, 1.24 mol, 2 eq) in DMF (2.2 L) at 18° C. was added (R)-methyl 2-(methylsulfonyloxy)propanoate (226 g, 1.24 mol). The mixture was stirred at 18° C. overnight; then it was quenched with saturated $NH_4Cl$ (2 L). The resulting mixture was extracted with DCM (3×1 L). The combined organic phase was washed with water (5×500 mL) and brine, dried over $Na_2SO_4$ and concentrated. The residue was taken up in DCM and extracted with 6N HCl (2×200 mL). The combined aqueous phase was back-extracted with DCM (2×50 mL). The combined organic phase was dried over $Na_2SO_4$ and concentrated to give the desired product as a pale brown oil (65 g, 39.3%) which was used without further purification. $MH^+$ 267.

Step 3 (2S)-2-(1,3-dimethyl-2,6-dioxo-3,4,5,6-tetra-hydro-1H-purin-7(2H)-yl)propanoic acid

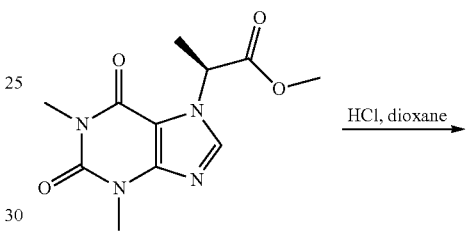

To a solution of (2S)-methyl 2-(1,3-dimethyl-2,6-dioxo-3,4,5,6-tetra-hydro-1H-purin-7(2H)-yl)propanoate (39 g, 145 mmol) in dioxane (400 mL) was added 6N HCl (200 mL). The mixture was refluxed for 3 h, cooled to room temperature and then concentrated to remove the dioxane and most of the aqueous phase. The residue was triturated in water (70 mL) and filtered. The solid was collected by filtration to give the title product (17.3 g, ee: 99%*). The filtrate was concentrated to dryness and the residue was purified by chromatography eluting with DCM/MeOH (40/1 to 15/1) to give an additional product (3.2 g, ee: 95%*). Total yield was 55.1%. $^1H$ NMR (DMSO-$d_6$) δ 13.28 (s, 1H), 8.21 (s, 1H), 5.47 (q, J=7.4 Hz, 1H), 3.44 (s, 3H), 3.21 (s, 3H), 1.76 (d, J=7.4 Hz, 3H). $MH^+$ 253.

* Chiral HPLC details: Chiralcel AD Column, 250*4.6 mm, 10 um. Mobile phase: hexane (0.1% TFA)/IPA (0.1% TFA) 70/30.

Preparation 2 5,5-dimethylpyrrolidin-2-one hydrochloride

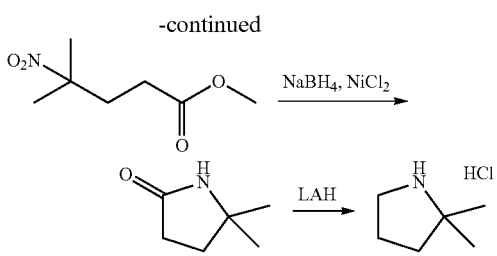

Step 1 methyl 4-methyl-4-nitropentanoate

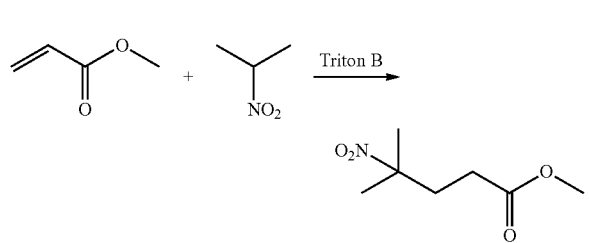

To a solution of 2-nitropropane (5.06 g, 56.84 mmol) in dioxane (3 mL) was added Triton B (0.55 mL, 40% aqueous). The reaction was warmed to 70° C. and methyl acrylate (4.78 g, 55.58 mmol) was added dropwise. After addition, the reaction was heated at 100° C. for 4 hrs. The reaction was cooled to RT, 1N HCl (2 mL) was added, the resulting mixture was partitioned between EA and water. The combined organic layer was washed with brine, dried over Na$_2$SO$_4$, and concentrated to afford the crude product (10 g, 100%) as an oil. $^1$H NMR (CDCl$_3$) δ 3.68 (s, 3H), 2.35-2.31 (m, 2H), 2.27-2.23 (m, 2H), 1.60 (s, 6H).

Step 2 5,5-dimethylpyrrolidin-2-one

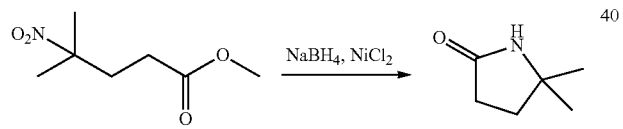

To a solution of NiCl$_2$ hexahydrate (0.67 g, 2.86 mmol) in MeOH (30 mL) was added NaBH$_4$ (0.33 g, 8.57 mmol) portionwise. The reaction was sonicated for 0.5 hr; then methyl 4-methyl-4-nitropentanoate (1.0 g, 5.77 mmol) was added dropwise. Additional NaBH$_4$ (0.66 g, 17.14 mmol) was added portionwise. The resulting mixture was stirred at room temperature overnight. The mixture was filtered through Celite and the filtrate was concentrated to one forth volume. The residue was partitioned between DCM and saturated NaHCO$_3$. The organic layer washed with brine, dried over Na$_2$SO$_4$, and concentrated to afford the crude product (0.35 g, 53.7%) as an oil. MH$^+$ 114.

Step 3 5,5-dimethylpyrrolidin-2-one hydrochloride

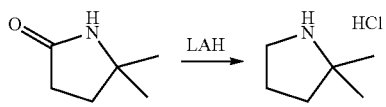

To a suspension of LAH (121 mg, 3.18 mmol) in THF (8 mL) was added 5,5-dimethylpyrrolidin-2-one (0.3 g, 2.65 mmol) and the reaction was heated at 60° C. overnight. The reaction was cooled to 0° C. and carefully quenched with water (0.2 mL) followed by 15% NaOH (0.2 mL). The mixture was filtered through celite. Concentrated hydrochloride acid was added to the filtrate. This mixture was concentrated to afford the crude product (0.2 g, 75.5%) as a white solid, which was used without purification. MH$^+$ 100.

Preparation 3 2'-(2,2-dimethylpyrrolidin-1-yl)-[2,5'-bipyrimidin]-4-amine

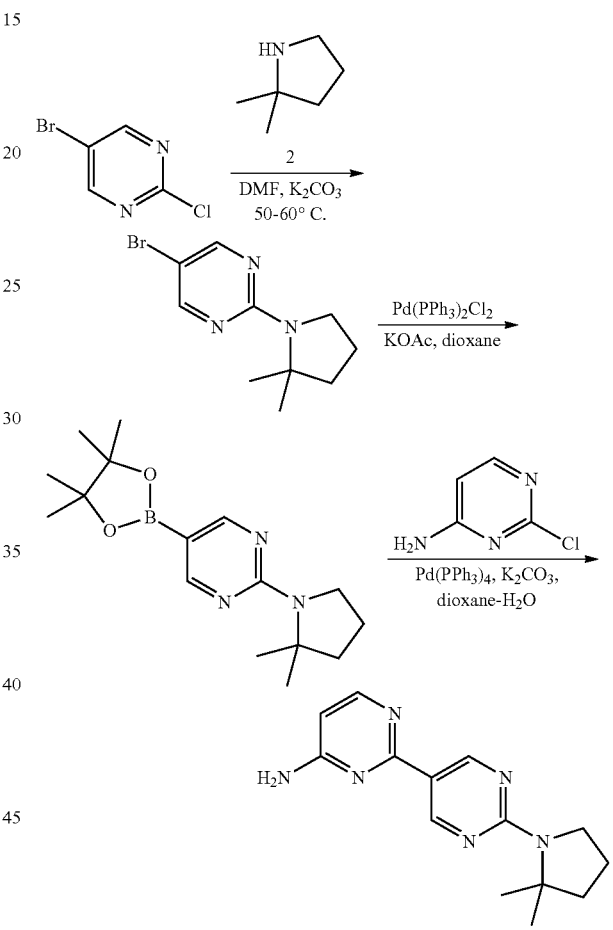

Step 1
5-bromo-2-(2,2-dimethylpyrrolidin-1-yl)pyrimidine

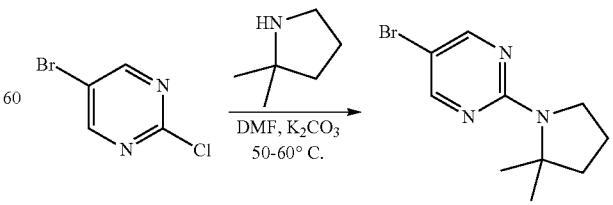

To a solution of 5-bromo-2-chloropyrimidine (2.3 g, 11.9 mmol) and K$_2$CO$_3$ (6.6 g, 47.6 mmol) in DMF (20 mL) was added a solution of 2,2-dimethylpyrrolidine (2.26 g, 16.7 mmol) in DMF (4 mL) at RT. The resulting reaction mixture was stirred at 50° C. for two days. The reaction was poured into ice water with stirring. The precipitate was collected to give crude 5-bromo-2-(2,2-dimethylpyrrolidin-1-yl)pyrimidine (2.3 g, 76.6%) as a light yellow solid, which was used for next step without any further purification. MH+ 256.

Step 2 2-(2,2-dimethylpyrrolidin-1-yl)-5-(4,4,5,5-tetramethyl-1,3,2-dioxaborolan-2-yl)pyrimidine A mixture of 5-bromo-2-(2,2-dimethylpyrrolidin-1-yl)pyrimidine (17.6 g, 68.9 mmol), bis(pinacolato)diboron (24.5 g, 96.5 mmol), and KOAc (13.5 g, 0.14 mol) in 1,4-dioxane (320 mL) was added Pd(PPh$_3$)$_2$Cl$_2$ (2.4 g, 3.45 mmol). The mixture was stirred at 80° C. for 20 h. The reaction was cooled to RT, poured into ice-water, and extracted with EA (4×200 mL). The combined organic layer was washed with brine, dried over Na$_2$SO$_4$, concentrated to give a dark residue. The residue was purified by chromatography eluting with PE/EA (40:1) to give 2-(2,2-dimethylpyrrolidin-1-yl)-5-(4,4,5,5-tetramethyl-1,3,2-dioxaborolan-2-yl)pyrimidine (11.5 g, 49% over two steps) as a yellow solid. $^1$H NMR (DMSO-d$_6$) δ 8.58 (s, 2H), 3.69 (m, 2H), 1.92 (m, 4H), 1.55 (s, 6H), 1.33 (s, 12H).

Step 3 2'-(2,2-dimethylpyrrolidin-1-yl)-[2,5'-bipyrimidin]-4-amine

To a mixture of 2-(2,2-dimethylpyrrolidin-1-yl)-5-(4,4,5,5-tetramethyl-1,3,2-dioxaborolan-2-yl)pyrimidine (9.5 g, 31 mmol) in 1,4-dioxane (140 mL) was added 4-amino-2-chloropyrimidine (4.5 g, 34.5 mmol) and 2M K$_2$CO$_3$ (20.4 mL, 40.7 mmol). The orange mixture was degassed with N$_2$; then Pd(PPh$_3$)$_4$ (3.65 g, 3.1 mmol) was added. The reaction was stirred at 80° C. overnight. The reaction was cooled to RT, poured into water and extracted with EtOAc (3×150 mL). The combined organic layer was washed with brine, dried over Na$_2$SO$_4$, and concentrated. The residue was purified by chromatography eluting with PE:EA (1:1) to afford compound 2'-(2,2-dimethylpyrrolidin-1-yl)-[2,5'-bipyrimidin]-4-amine (8.96 g, >100%) as a yellow solid. MH+ 271.

Preparation 4 (S)-2-(2-(2-(trifluoromethyl)pyrrolidin-1-yl)pyrimidin-5-yl)pyrimidin-4-amine

Step 1 (S)-5-bromo-2-(2-(trifluoromethyl)pyrrolidin-1-yl)pyrimidine

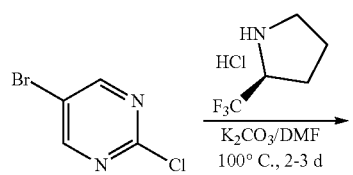

A mixture of (S)-2-(trifluoromethyl)pyrrolidine hydrochloride (40 g, 0.23 mol), K₂CO₃ (94.6 g, 0.68 mol) and 5-bromo-2-chloropyrimidine (48 g, 0.25 mol) in DMF (200 mL) was stirred at 100° C. for 24 hr, then $N_1,N_2$-dimethylethane-1,2-diamine (4 mL) was added and the reaction was stirred for another 2 h to consume excess 5-bromo-2-chloropyrimidine. The reaction was quenched with water (400 mL), and extracted with EA (3×500 mL). The combined organic phase was washed with 10% aqueous LiCl, dried over Na₂SO₄ and concentrated. The residue was purified by chromatography eluting with PE:EA (50:1) to afford (S)-5-bromo-2-(2-(trifluoromethyl) pyrrolidin-1-yl)pyrimidine (50 g, 74%) as a white solid. ¹H NMR (DMSO-d₆) δ 8.54 (s, 2H), 4.90-4.94 (m, 2H), 3.56-3.58 (m, 2H), 2.02-2.16 (m, 4H). MH⁺ 296.

Step 2 (S)-2-(2-(trifluoromethyl)pyrrolidin-1-yl)pyrimidin-5-ylboronic acid

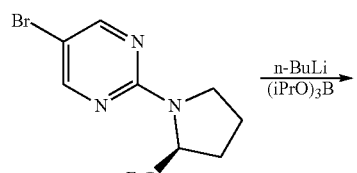

A solution of (S)-5-bromo-2-(2-(trifluoromethyl)pyrrolidin-1-yl)pyrimidine (50 g, 0.17 mol) and triisopropyl borate (44.4 g, 0.23 mol) in THF (400 mL) was cooled to −78° C. and n-BuLi (105 mL, 2.4 M in hexane) was added dropwise. The reaction was stirred 2 h at −78° C. The reaction was quenched with water (150 mL) and allowed to warm to RT. The reaction was concentrated to leave the aqueous phase. The aqueous phase was extracted with ether (2×50 mL) to remove impurities (product in aqueous layer). The pH was adjusted to 5 with 6 N HCl and then it was extracted with EA (3×100 mL). The combined organic phase was dried over Na₂SO₄ and concentrated to afford (S)-2-(2-(trifluoromethyl)pyrrolidin-1-yl) pyrimidin-5-ylboronic acid (45 g, quantitative yield) as an off-white solid. MH⁺ 262.

Step 3 (S)-2-(2-(2-(trifluoromethyl)pyrrolidin-1-yl)pyrimidin-5-yl)pyrimidin-4-amine

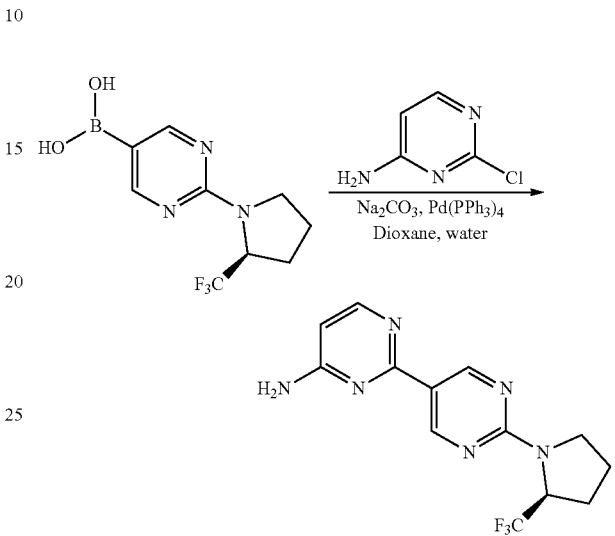

To a mixture of (S)-2-(2-(trifluoromethyl)pyrrolidin-1-yl) pyrimidin-5-ylboronic acid (9.5 g, 36.4 mmol), 2-chloropyrimidin-4-amine (4.3 g, 33.1 mmol) and Na₂CO₃ (7.0 g, 66.2 mmol) in dioxane (105 mL) and water (35 mL) was added Pd(PPh₃)₄ (3.8 mg, 3.31 mmol). The mixture was degassed with nitrogen and then stirred at 110° C. for 3 h. The reaction was cooled and filtered through Celite. The filtrate was partitioned with EA (300 mL) and water (150 mL). The organic phase was washed with brine (100 mL), dried over Na₂SO₄ and concentrated. The residue was purified by chromatography eluting with DCM/MeOH (100:1 to 80:1 to 70:1) to give (S)-2-(2-(2-(trifluoromethyl)pyrrolidin-1-yl) pyrimidin-5-yl)pyrimidin-4-amine (8 g, 78%) as a white solid. ¹H-NMR (CDCl₃) δ 9.16 (s, 2H), 8.13-8.14 (d, J=10 Hz, 1H), 6.97 (s, 2H), 6.34-6.35 (d, J=6 Hz, 1H), 5.09-5.13 (m, 1H), 3.67-3.72 (m, 2H), 2.06-2.21 (m, 4H). MH⁺ 311.

Preparation 5 (R)-2-(2-(2-(trifluoromethyl)pyrrolidin-1-yl)pyrimidin-5-yl)pyrimidin-4-amine

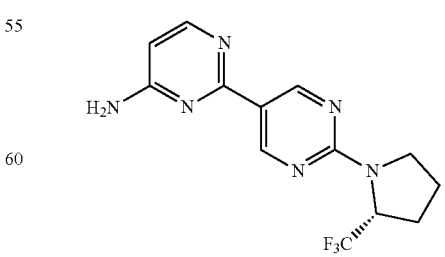

The title compound was prepared using the method of preparation 4. MH⁺ 311

Preparation 6 (2S)-2-(1-methyl-2,6-dioxo-3,4,5,6-tetrahydro-1H-purin-7(2H)-yl)propanoic acid

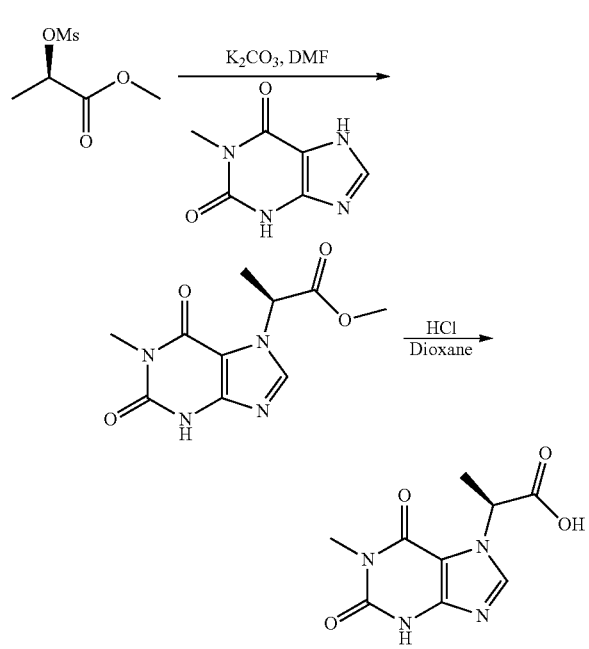

Step 1 (2S)-methyl 2-(1-methyl-2,6-dioxo-3,4,5,6-tetrahydro-1H-purin-7(2H)-yl)propanoate

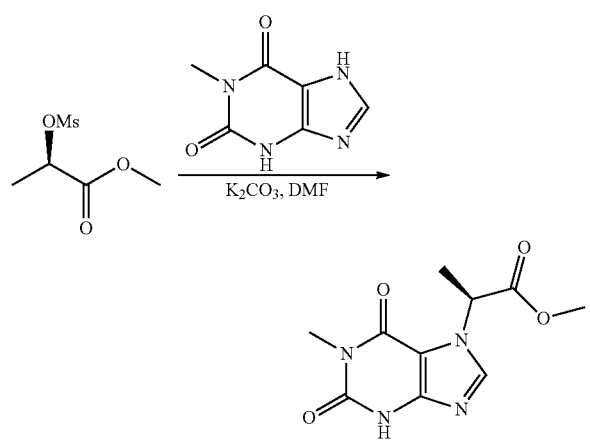

To a suspension of 1-methyl-3,4,5,7-tetrahydro-1H-purine-2,6-dione (6.904 g, 41.5 mmol) and K$_2$CO$_3$ (5.734 g, 41.5 mmol) in DMF (150 mL) at 50° C. was added (R)-methyl 2-(methylsulfonyloxy)propanoate (5.818 g, 32.0 mmol). The reaction was stirred at 50° C. overnight, then quenched with saturated NH$_4$Cl (2 L). The resulting mixture was extracted with EA (3×200 mL). The combined organic phase was washed with water (5×500 mL) and brine. The organic phase was dried over Na$_2$SO$_4$ and concentrated. The residue was purified by chromatography (0-3% MeOH: DCM) to give the title product as a white solid (1.649 g, 20%). MH$^+$ 253.

Step 2 (2S)-2-(1-methyl-2,6-dioxo-3,4,5,6-tetrahydro-1H-purin-7(2H)-yl)propanoic acid

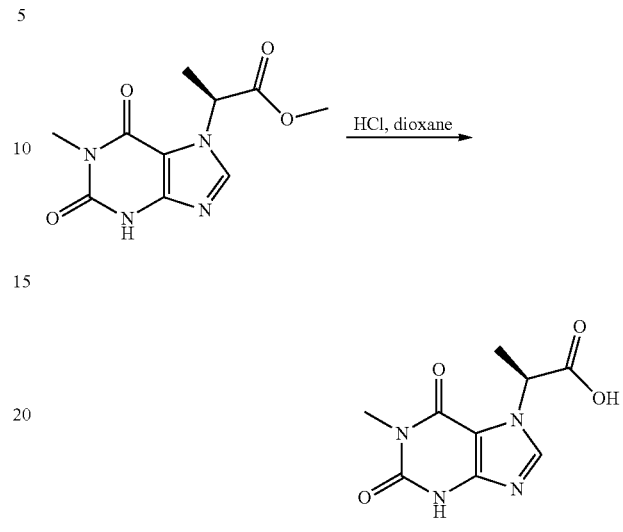

To a mixture of (2S)-methyl 2-(1-methyl-2,6-dioxo-3,4,5,6-tetrahydro-1H-purin-7(2H)-yl)propanoate (96.9 mg, 0.38 mmol) in dioxane (3 mL) was added 6N HCl (2 mL). The reaction was refluxed for 3 h, cooled to room temperature and concentrated to give the white solid product (92 mg, 100%); MH$^+$ 239.

Preparation 7 (S)-2-(3-(difluoromethyl)-1-methyl-2,6-dioxo-2,3-dihydro-1H-purin-7(6H)-yl)propanoic acid

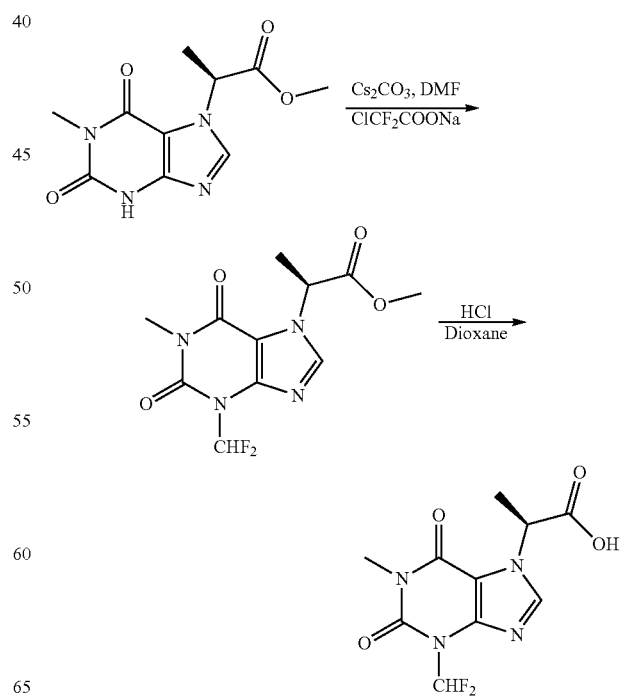

Step 1 (S)-methyl 2-(3-(difluoromethyl)-1-methyl-2,6-dioxo-2,3-dihydro-1H-purin-7(6H)-yl)propanoate

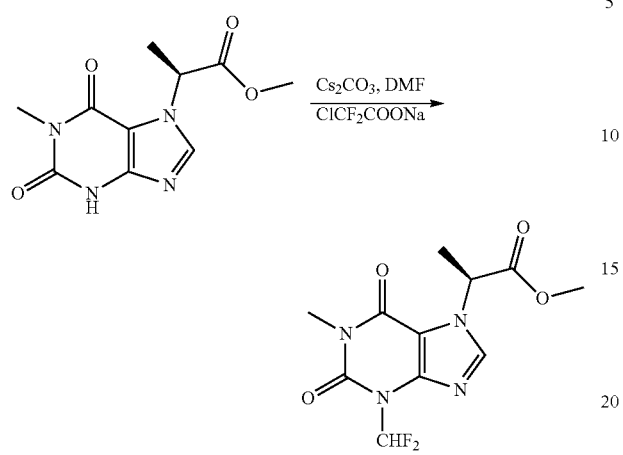

To a solution of (2S)-methyl 2-(1-methyl-2,6-dioxo-3,4,5,6-tetrahydro-1H-purin-7(2H)-yl)propanoate (600 mg, 2.38 mmol) in DMF (2 ml) at RT was added sodium 2-chloro-2,2-difluoroacetate (508 mg, 3.33 mmol) followed by $Cs_2CO_3$ (229 mg 3.81 mmol). The reaction was heated at 60° C. for 12 h. The reaction was cooled to RT, diluted with cold water and extracted with EA twice. The combined organic layer was washed with brine, dried over $MgSO_4$ and concentrated. The residue was purified by chromatography eluting with MeOH: DCM (0-3%) to give (S)-methyl 2-(3-(difluoromethyl)-1-methyl-2,6-dioxo-2,3-dihydro-1H-purin-7(6H)-yl)propanoate (164 mg, 23%) as colorless oil. $MH^+$ 303.

Step 2 (S)-2-(3-(difluoromethyl)-1-methyl-2,6-dioxo-2,3-dihydro-1H-purin-7(6H)-yl)propanoic acid

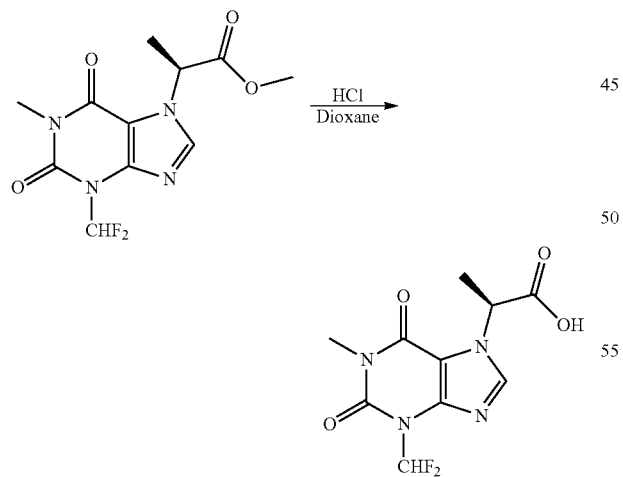

To a mixture of (S)-methyl 2-(3-(difluoromethyl)-1-methyl-2,6-dioxo-2,3-dihydro-1H-purin-7(6H)-yl)propanoate (64 mg, 0.21 mmol) in dioxane (1 mL) was added 6N HCl (1 mL). The reaction was refluxed for 3 h, cooled to RT and then concentrated. The precipitate was collected to give the white solid product (61 mg, 100%). $MH^+$ 289.

Preparation 8 2'-(3,3-difluoroazetidin-1-yl)-[2,5'-bipyrimidin]-4-amine

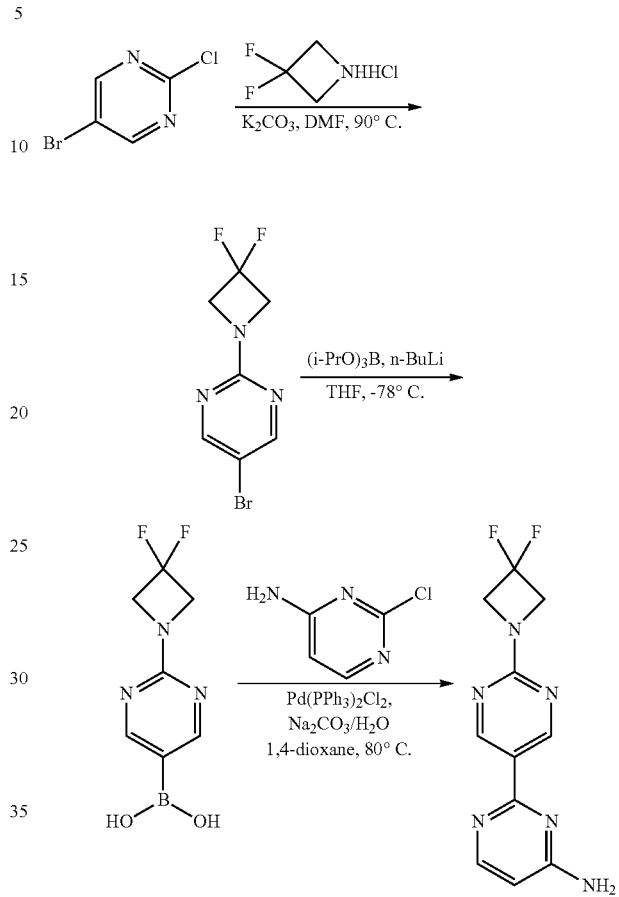

Step 1
5-bromo-2-(3,3-difluoroazetidin-1-yl)pyrimidine

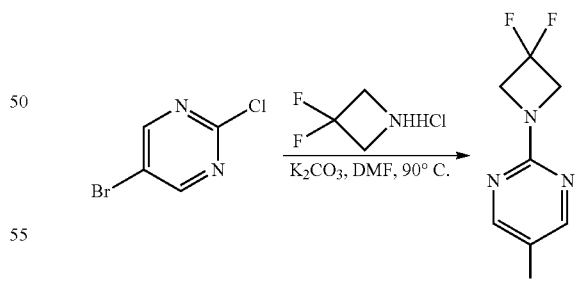

A sealed tube was charged with 5-bromo-2-chloropyrimidine (450 mg, 2.3 mmol), 3,3-difluoroazetidine hydrochloride (275.1 mg, 2.1 mmol), $K_2CO_3$ (589.3 mg, 4.3 mmol), and DMF (3 mL). The tube was sealed and stirred at 130° C. for 2 h. The reaction was cooled to RT and poured into water (4 mL). The solid was collected by filtration and dried to give 5-bromo-2-(3,3-difluoroazetidin-1-yl)pyrimidine (300 mg, 51.4%) as a white solid. $MH^+$ 250.

Step 2 (2-(3,3-difluoroazetidin-1-yl)pyrimidin-5-yl) boronic acid

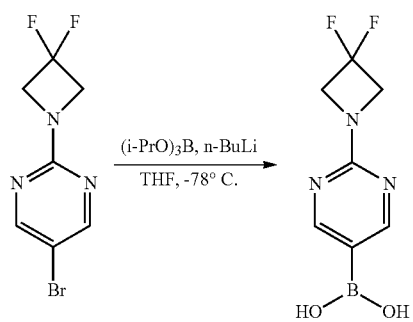 [SMILES: FC1(F)CN(c2ncc(Br)cn2)C1 ; OB(O)c1cnc(N2CC(F)(F)C2)nc1]

To a solution of 5-bromo-2-(3,3-difluoroazetidin-1-yl) pyrimidine (300 mg, 1.2 mmol) and triisopropyl borate (0.4 mL, 1.8 mmol) in THF (6 mL) was added n-BuLi (0.6 mL, 2.4 M in hexane, 1.5 mmol) dropwise at −78° C. The mixture was stirred at −78° C. for 2 h. The reaction was quenched with water and warmed to RT. The solvent was concentrated and the residual aqueous layer was extracted with ether (2×10 mL). The aqueous layer was adjusted to pH 6 with 1N HCl and extracted with EA (3×10 mL). The combined organic layer was washed with brine, dried over $Na_2SO_4$, and concentrated to give the product (170 mg, 65.6%) as a white solid. $MH^+$ 216.

Step 3 2'-(3,3-difluoroazetidin-1-yl)-[2,5'-bipyrimidin]-4-amine

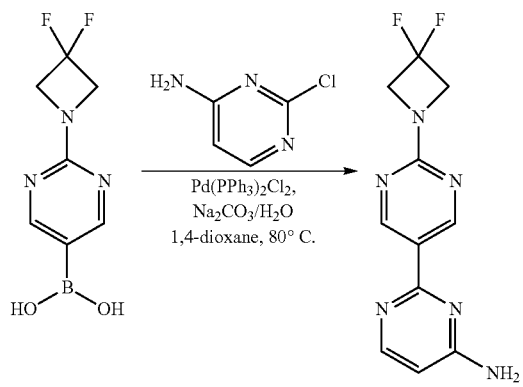 [SMILES: OB(O)c1cnc(N2CC(F)(F)C2)nc1 ; Nc1ccnc(Cl)n1 ; Nc1ccnc(-c2cnc(N3CC(F)(F)C3)nc2)n1]

A mixture of (2-(3,3-difluoroazetidin-1-yl)pyrimidin-5-yl)boronic acid (170.0 mg, 0.8 mmol), 4-amino-2-chloropyrimidine (102.4 mg, 0.8 mmol), $Pd(PPh_3)_2Cl_2$ (56.2 mg, 0.08 mmol) and $Na_2CO_3$ (167.5 mg, 1.6 mmol) in 1,4-dioxane (5 mL) and water (1 mL) was degassed with nitrogen and stirred at 90° C. overnight. The resulting mixture was cooled to RT and poured into EA. The organic phase was separated, washed with water and brine, dried over $Na_2SO_4$ and concentrated. The residue was dissolved in ether. An insoluble residue was removed by filtration and the filtrate was concentrated to give 2'-(3,3-difluoroazetidin-1-yl)[2,5'-bipyrimidin]-4-amine (130 mg, 62.3%) as a white solid. $MH^+$ 265.

Preparation 9 2-chloro-N-(2'-(3,3-difluoroazetidin-1-yl)-[2,5'-bipyrimidin]-4-yl)acetamide

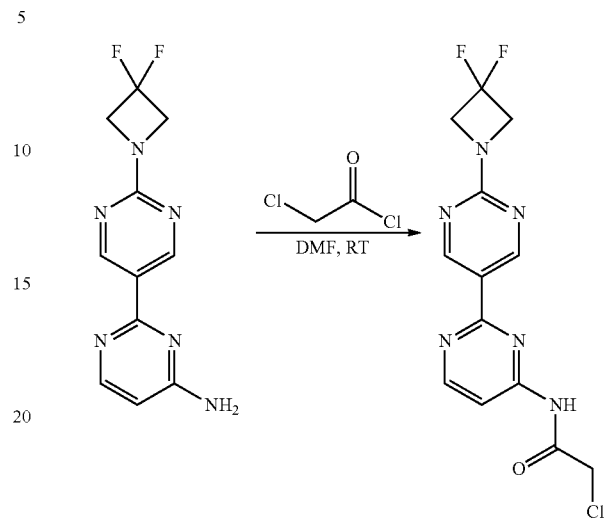

To a solution of 2'-(3,3-difluoroazetidin-1-yl)[2,5'-bipyrimidin]-4-amine (60 mg, 0.2 mmol) in DMF (2 mL) was added dropwise 2-chloroacetyl chloride (0.03 mL, 0.34 mmol) at 0° C. The reaction was stirred at RT for 2 h and then it was poured into EA. This organic phase was washed with water and brine, dried over $Na_2SO_4$, and concentrated to give 2-chloro-N-(2'-(3,3-difluoroazetidin-1-yl)-[2,5'-bipyrimidin]-4-yl)acetamide (50 mg, 64.7%) as a yellow solid. $MH^+$ 341.

Preparation 10 (2-(4,4-difluoropiperidin-1-yl)pyrimidin-5-yl)boronic acid

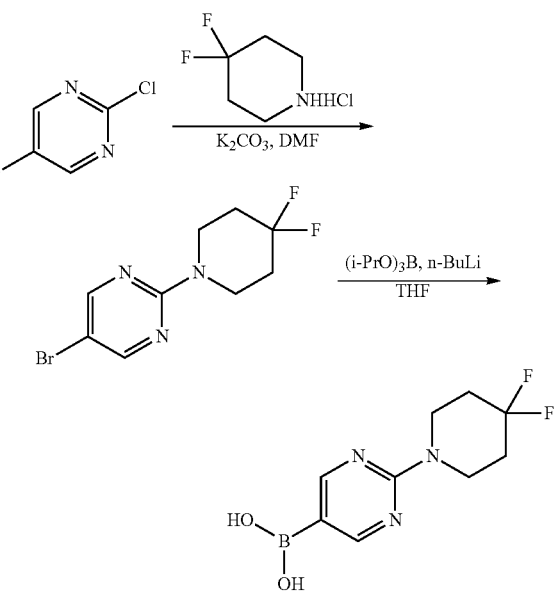

Step 1
5-bromo-2-(4,4-difluoropiperidin-1-yl)pyrimidine

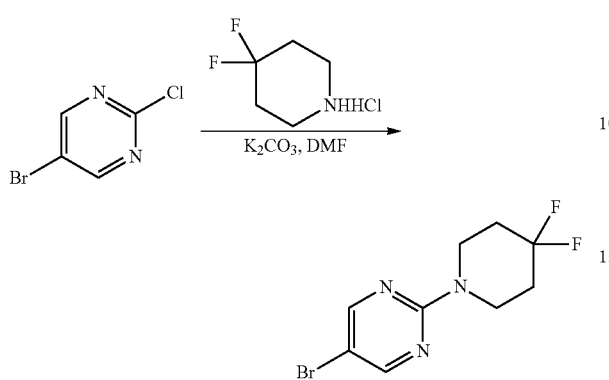

A sealed tube were charged with 5-bromo-2-chloropyrimidine (633.3 mg, 3.3 mmol), 4,4-difluoropiperidine hydrochloride (472.8 mg, 3.0 mmol), $K_2CO_3$ (829.3 mg, 6.0 mmol) and DMF (4 mL). The tube was sealed and stirred at 130° C. for 2 h; then it was cooled to RT and poured into water (5 mL). The solid precipitate was collected and dried to give 5-bromo-2-(4,4-difluoropiperidin-1-yl)pyrimidine (640 mg, 77%) as a white solid. $MH^+$ 278.

Step 2 (2-(4,4-difluoropiperidin-1-yl)pyrimidin-5-yl)boronic acid

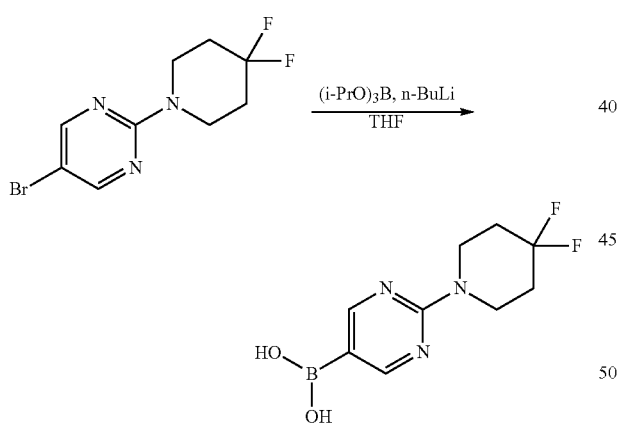

To a solution of 5-bromo-2-(4,4-difluoropiperidin-1-yl) pyrimidine (640 mg, 2.3 mmol) and triisopropyl borate (0.8 mL, 3.5 mmol) in THF (8 mL) was added n-BuLi (2 mL, 2.4 M in hexane, 1.5 mmol) dropwise at −78° C. The mixture was stirred at −78° C. for 2 h. This reaction was quenched with water and allowed to warm to RT. The reaction was concentrated and the residual aqueous mixture was extracted with ether (2×10 mL). The aqueous phase was adjusted to pH 6 with 1N HCl and extracted with EA (3×10 mL). The combined organic phase was washed with brine, dried over $Na_2SO_4$, and concentrated to give (2-(4,4-difluoropiperidin-1-yl)pyrimidin-5-yl)boronic acid (420 mg, 74.8%) as a white solid. $MH^+$ 244.

Preparation 11
2-chloro-N-(2-chloropyrimidin-4-yl)acetamide

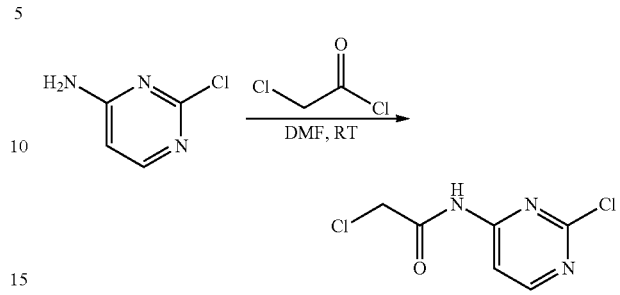

To a mixture of 4-amino-2-chloropyrimidine (2.0 g, 15.4 mmol) and DMF (25 mL) was added dropwise 2-chloroacetyl chloride (0.03 mL, 0.34 mmol) at 0° C. The reaction was stirred at RT overnight and then it was poured into EA. The organic phase was washed with water and brine, dried over $Na_2SO_4$, and concentrated. The residue was triturated with DCM and the solids were collected to give 2-chloro-N-(2-chloropyrimidin-4-yl)acetamide (1.3 g, 20.5%) as a yellow solid. $MH^+$ 206.

Preparation 12 N-(2-chloropyrimidin-4-yl)-2-(1,3-dimethyl-2,6-dioxo-2,3-dihydro-1H-purin-7(6H)-yl) acetamide

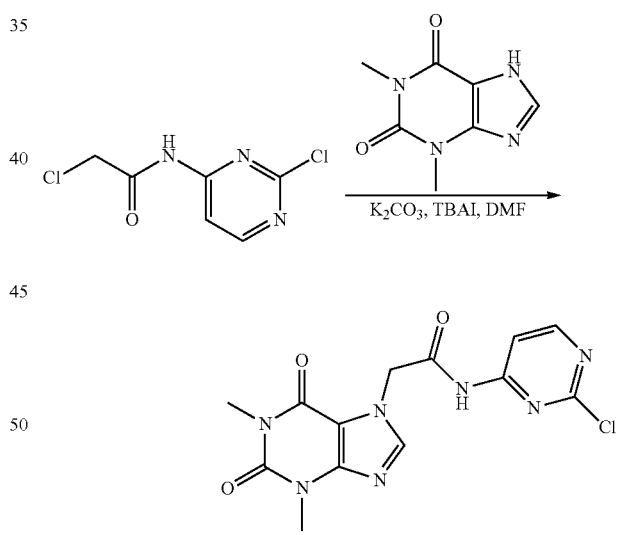

A mixture of 2-chloro-N-(2-chloropyrimidin-4-yl)acetamide (1.1 g, 5.4 mmol), 1,3-dimethyl-1H-purine-2,6(3H,7H)-dione (966.3 mg, 5.4 mmol), $K_2CO_3$ (1.1 g, 8.1 mmol), and TBAI (198.2 mg, 0.5 mmol) in DMF (20 mL) was stirred at 90° C. for 10 min. The reaction was cooled to RT and then diluted with EA. The resulting mixture was washed with water, saturated $NH_4Cl$ and brine, dried over $Na_2SO_4$ and concentrated. The residue was recrystallized from DCM to give N-(2-chloropyrimidin-4-yl)-2-(1,3-dimethyl-2,6-dioxo-2,3-dihydro-1H-purin-7(6H)-yl)-acetamide (1.3 g, 69.4%) as a white solid. $MH^+$ 350.

Preparation 13 3-azabicyclo[3.1.0]hexane hydrochloride

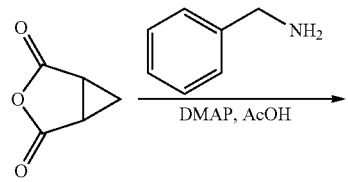

Step 1 3-benzyl-3-azabicyclo[3.1.0]hexane-2,4-dione

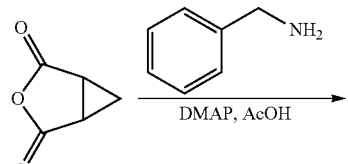

To a mixture of 3-oxabicyclo[3.1.0]hexane-2,4-dione (2.3 g, 20.5 mmol) in AcOH (30 mL) was added DMAP (150 mg) and benzylamine (2.2 mL, 20.5 mmol). The mixture was stirred at 100° C. for 40 hr; then cooled to RT. The reaction was concentrated and the residue was dissolved in EA. The organic phase was washed with water and brine, dried over $Na_2SO_4$ and concentrated. The residue was purified via chromatography eluting with PE:EA (8:1 to 5:1) to afford 3-benzyl-3-azabicyclo[3.1.0]hexane-2,4-dione (3.7 g, 89.6%) as a white solid. $MH^+$ 202.

Step 2 3-benzyl-3-azabicyclo[3.1.0]hexane

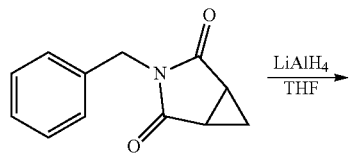

To a solution of 3-benzyl-3-azabicyclo[3.1.0]hexane-2,4-dione (2.0 g, 10.0 mmol) in THF (30 mL) was added LAH (1.5 g, 40.0 mmol). The resulting mixture was heated at reflux 4 h and then it was cooled to 0° C. The cold reaction mixture was carefully quenched with saturated $NH_4Cl$ and then it was filtered. The filtrate was concentrated to afford the title compound (1.5 g, 86.7%) as a clear oil. $MH^+$ 174.

Step 3 3-azabicyclo[3.1.0]hexane hydrochloride

A mixture of 3-benzyl-3-azabicyclo[3.1.0]hexane (1.3 g, 7.5 mmol), 10% Pd/C (130 mg) and conc. HCl (0.63 mL, 7.5 mmol) in MeOH (20 mL) was stirred at RT under an atmosphere of hydrogen (balloon) for 18 h. The reaction was filtered through Celite and the filtrate was concentrated to give the title compound (850 mg, 95%) as a white solid. $MH^+$ 84

Preparation 14 2'-(3-azabicyclo[3.1.0]hexan-3-yl)-[2,5'-bipyrimidin]-4-amine

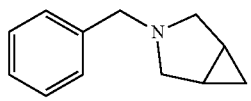

Step 1 3-(5-bromopyrimidin-2-yl)-3-azabicyclo [3.1.0]hexane

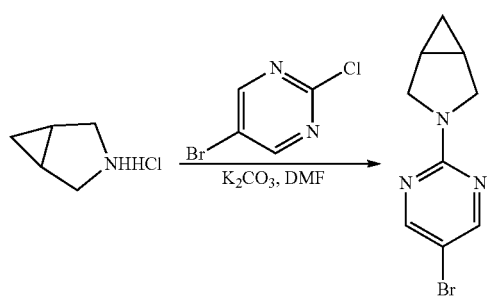

A sealed tube was charged with 5-bromo-2-chloropyrimidine (671.7 mg, 3.5 mmol), 3-azabicyclo[3.1.0]hexane hydrochloride (416.7 mg, 3.5 mmol), K₂CO₃ (967.5 mg, 7.0 mmol) and DMF (4 mL). The tube was sealed and stirred at 130° C. for 2 h. The reaction was cooled to RT and poured into cold water (4 mL). The solid that formed was collected and dried to give 3-(5-bromopyrimidin-2-yl)-3-azabicyclo [3.1.0]hexane (480 mg, 57.4%) as a white solid. MH⁺ 240.

Step 2 (2-(3-azabicyclo[3.1.0]hexan-3-yl)pyrimidin-5-yl)boronic acid

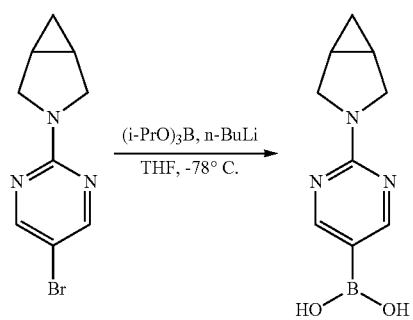 [SMILES: Brc1cnc(N2CC3CC3C2)nc1 ; OB(O)c1cnc(N2CC3CC3C2)nc1]

To a solution of 3-(5-bromopyrimidin-2-yl)-3-azabicyclo [3.1.0]hexane (480 mg, 2.0 mmol) and triisopropyl borate (0.7 mL, 3.0 mmol) in THF (6 mL) was added n-BuLi (1.1 mL, 2.4 M in hexane, 2.6 mmol) dropwise at −78° C. The reaction was stirred at −78° C. for 2 hr and then it was quenched with water and warmed to RT. The reaction was concentrated and the aqueous residue was extracted with ether (2×20 mL). The aqueous layer was separated, adjusted to pH 6 with 1N HCl and extracted with EA (3×20 mL). The combined organic phase was washed with brine, dried over Na₂SO₄, and concentrated to give the title product (200 mg, 48.5%) as a white solid. MH⁺ 206.

Step 3 2'-(3-azabicyclo[3.1.0]hexan-3-yl)-[2,5'-bipyrimidin]-4-amine

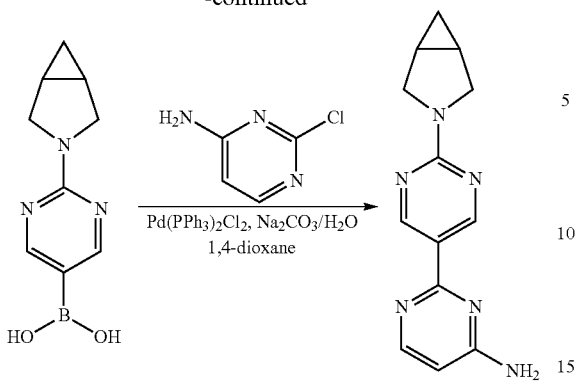

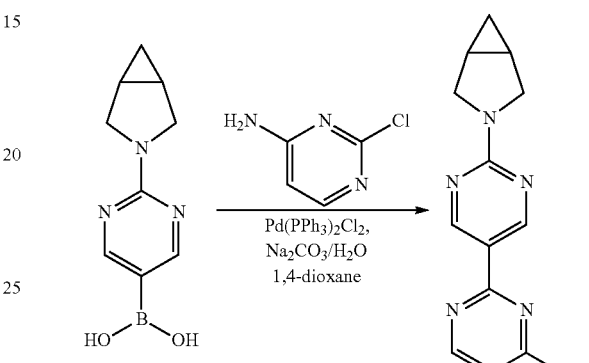

A mixture of (2-(3-azabicyclo[3.1.0]hexan-3-yl)pyrimidin-5-yl)boronic acid (150.0 mg, 1.2 mmol), 2-chloropyrimidin-4-amine (237.9 mg, 1.2 mmol), Pd(PPh₃)₂Cl₂ (86.0 mg, 0.1 mmol) and Na₂CO₃ (245.9 mg, 2.3 mmol) in 1,4-dioxane (5 mL) and water (1 mL) was degassed with nitrogen and stirred at 80° C. overnight. The reaction was cooled to RT and poured into EA. The organic phase was separated, washed with water and brine, dried over Na₂SO₄ and concentrated. The residue was dissolved in ether. An insoluble residue was removed by filtration and the filtrate was concentrated to give 2'-(3-azabicyclo[3.1.0]hexan-3-yl)-[2,5'-bipyrimidin]-4-amine (100 mg, 33.8%) as a white solid. MH⁺ 255.

Preparation 15 N-(2'-(3-azabicyclo[3.1.0]hexan-3-yl)-[2,5'-bipyrimidin]-4-yl)-2-chloro acetamide

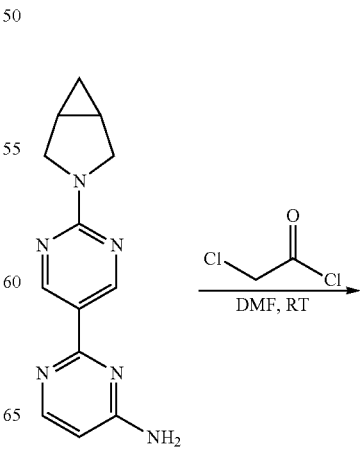

-continued

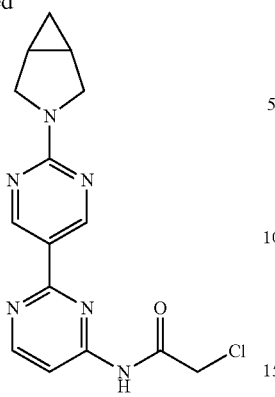

To a solution of 2'-(3-azabicyclo[3.1.0]hexan-3-yl)[2,5'-bipyrimidin]-4-amine (40 mg, 0.2 mmol) in DMF (2 mL) was added dropwise 2-chloroacetyl chloride (0.02 mL, 0.3 mmol) at 0° C. The reaction was stirred at RT for 2 h, then poured into EA. The organic layer was extracted with water and brine, dried over $Na_2SO_4$, and concentrated to give N-(2'-(3-azabicyclo[3.1.0]hexan-3-yl)-[2,5'-bipyrimidin]-4-yl)-2-chloroacet amide (50 mg, 96.2%) as a yellow solid. $MH^+$ 329.

Preparation 16 2'-(3-(trifluoromethyl)pyrrolidin-1-yl)-[2,5'-bipyrimidin]-4-amine

Step 1 5-bromo-2-(3-(trifluoromethyl)pyrrolidin-1-yl)pyramidine

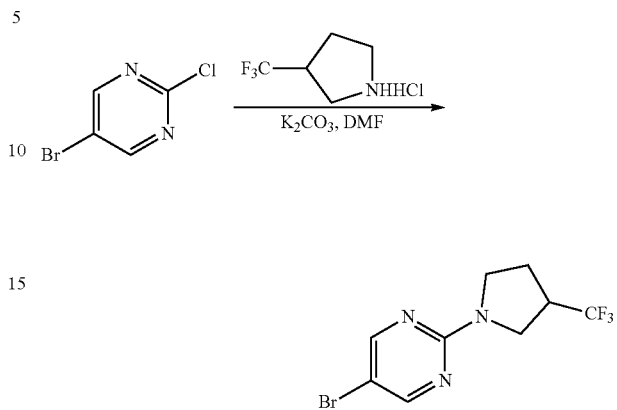

A sealed tube was charged with 5-bromo-2-chloropyrimidine (441.4 mg, 2.3 mmol), 3-(trifluoromethyl)pyrrolidine hydrochloride (402.6 mg, 2.1 mmol), $K_2CO_3$ (635.8 mg, 4.6 mmol) and DMF (3 mL). The tube was sealed and stirred at 130° C. for 2 h; then it was poured into water (4 mL). The solid was collected and dried to give 5-bromo-2-(3,3-difluoroazetidin-1-yl)pyrimidine (500 mg, 73.7%) as a white solid. $MH^+$ 296.

Step 2 (2-(3-(trifluoromethyl)pyrrolidin-1-yl)pyrimidin-5-yl)boronic acid

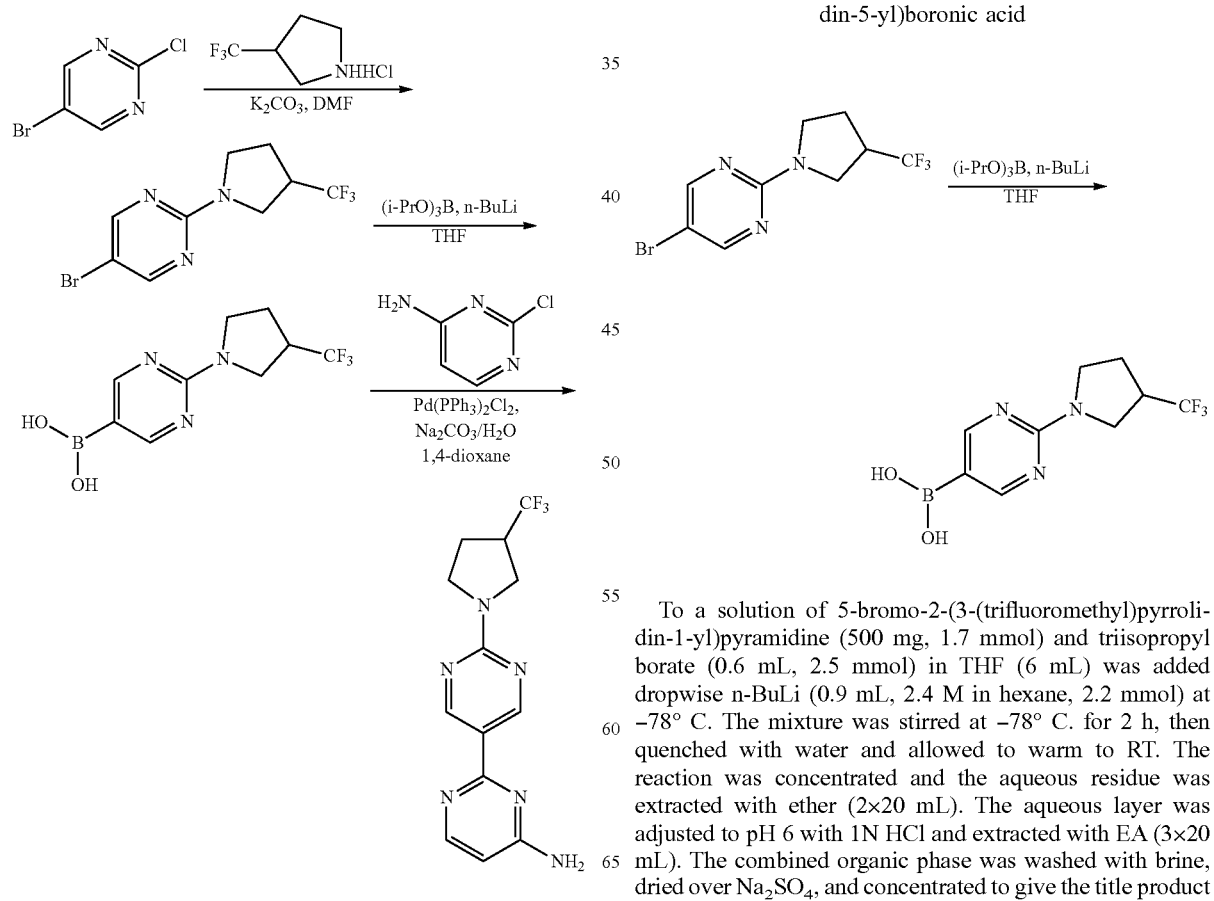

To a solution of 5-bromo-2-(3-(trifluoromethyl)pyrrolidin-1-yl)pyramidine (500 mg, 1.7 mmol) and triisopropyl borate (0.6 mL, 2.5 mmol) in THF (6 mL) was added dropwise n-BuLi (0.9 mL, 2.4 M in hexane, 2.2 mmol) at −78° C. The mixture was stirred at −78° C. for 2 h, then quenched with water and allowed to warm to RT. The reaction was concentrated and the aqueous residue was extracted with ether (2×20 mL). The aqueous layer was adjusted to pH 6 with 1N HCl and extracted with EA (3×20 mL). The combined organic phase was washed with brine, dried over $Na_2SO_4$, and concentrated to give the title product (320 mg, 72.3%) as a white solid. $MH^+$ 260.

Step 3 2'-(3-(trifluoromethyl)pyrrolidin-1-yl)-[2,5'-bipyrimidin]-4-amine

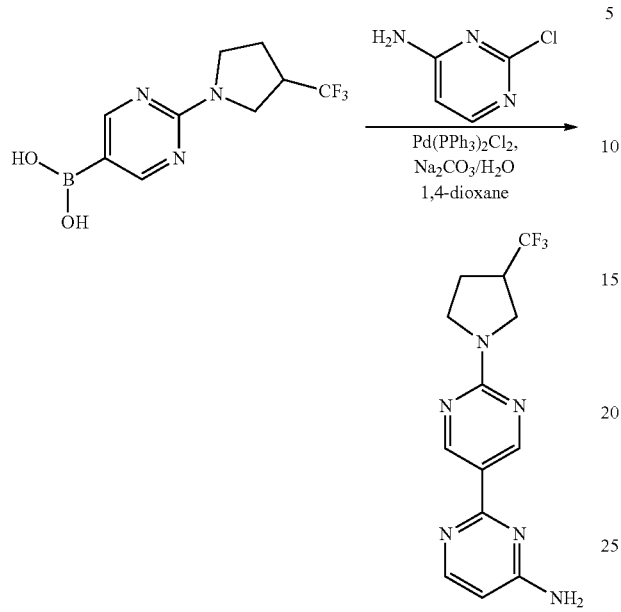

A mixture of (2-(3-(trifluoromethyl)pyrrolidin-1-yl)pyrimidin-5-yl)boronic acid (320.0 mg, 1.2 mmol), 2-chloropyrimidin-4-amine (158.1 mg, 1.2 mmol), Pd(PPh$_3$)$_2$Cl$_2$ (86.0 mg, 0.1 mmol) and Na$_2$CO$_3$ (260.0 mg, 2.5 mmol) in 1,4-dioxane (5 mL) and water (1 mL) was degassed with nitrogen and stirred at 90° C. overnight. The reaction was cooled to RT and poured into EA. The organic phase was washed with water and brine, dried over Na$_2$SO$_4$ and concentrated. The residue was dissolved in ether. An insoluble residue was removed by filtration and the filtrate was concentrated to give 2'-(3-(trifluoromethyl)pyrrolidin-1-yl)-[2,5'-bipyrimidin]-4-amine (200 mg, 52.6%) as a white solid. MH$^+$ 311.

Preparation 17 2-chloro-N-(2'-(3-(trifluoromethyl)pyrrolidin-1-yl)-[2,5'-bipyrimidin]-4-yl)acetamide

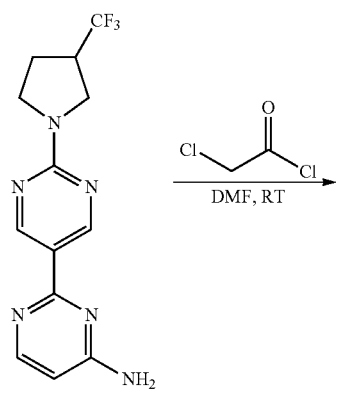

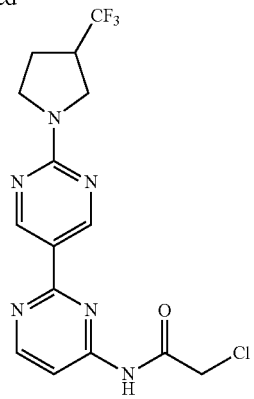

To a solution of 2'-(3-(trifluoromethyl)pyrrolidin-1-yl)-[2,5'-bipyrimidin]-4-amine (93 mg, 0.3 mmol) in DMF (2 mL) was added dropwise 2-chloroacetyl chloride (0.04 mL, 0.45 mmol) at 0° C. The reaction was stirred at RT for 2 h, then poured into EA. The organic phase was extracted with water and brine, dried over Na$_2$SO$_4$, and concentrated to give 2-chloro-N-(2'-(3-(trifluoromethyl)pyrrolidin-1-yl)-[2,5'-bipyrimidin]-4-yl)acetamide (100 mg, 86.4%) as a yellow solid. MH$^+$ 387.

Preparation 18 2-(2-(3-(trifluoromethyl)azetidin-1-yl)pyrimidin-5-yl)pyrimidin-4-amine

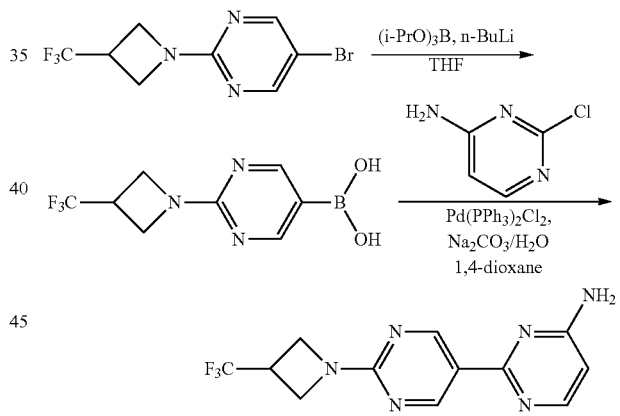

Step 1 2-(3-(trifluoromethyl)azetidin-1-yl)pyrimidin-5-ylboronic acid

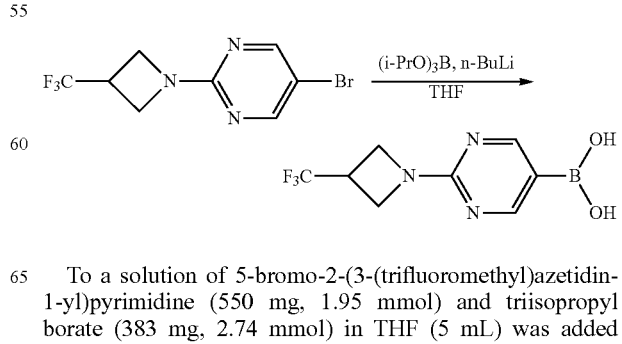

To a solution of 5-bromo-2-(3-(trifluoromethyl)azetidin-1-yl)pyrimidine (550 mg, 1.95 mmol) and triisopropyl borate (383 mg, 2.74 mmol) in THF (5 mL) was added dropwise n-BuLi (1.1 mL, 2.4 M in hexane) at −78° C. The reaction was stirred at −78° C. for 2 h. The reaction was quenched with water (5 mL) and allowed to warm to RT. The reaction was concentrated and the aqueous residue was extracted with ether (2×2 mL). The aqueous layer was adjusted pH to 5 with 1N HCl and extracted with EA (3×5 mL). The combined organic phase was dried over Na$_2$SO$_4$ and concentrated to afford 2-(3-(trifluoromethyl)azetidin-1-yl)pyrimidin-5-ylboronic acid (450 mg, 93.7%) as an off-white solid. MH$^+$ 248.

Step 2 2-(2-(3-(trifluoromethyl)azetidin-1-yl)pyrimidin-5-yl)pyrimidin-4-amine

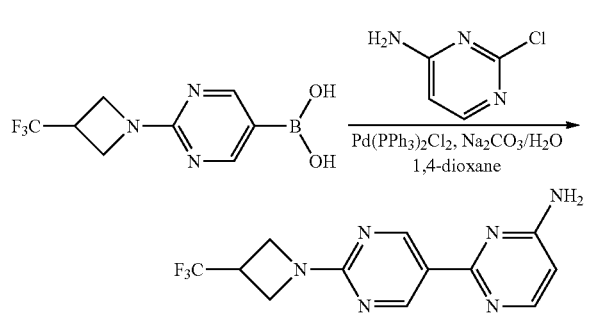

To a mixture of 2-(3-(trifluoromethyl)azetidin-1-yl)pyrimidin-5-ylboronic acid (450 mg, 1.82 mmol), 2-chloropyrimidin-4-amine (213 mg, 1.65 mmol) and saturated Na$_2$CO$_3$ (2.5 mL) in dioxane (10 mL) was added Pd(PPh$_3$)$_2$Cl$_2$ (58 mg, 0.08 mmol) and degassed three times with nitrogen. The reaction was stirred at 90° C. overnight. The reaction was cooled to RT and filtered through Celite. The filtrate was extracted with EA (2×4 mL). The combined organic phase was dried over Na$_2$SO$_4$ and concentrated. The residue was purified via chromatography eluting with PE:acetone (3:1) to afford 2-(2-(3-(trifluoromethyl)azetidin-1-yl)pyrimidin-5-yl)pyrimidin-4-amine (350 mg, 71.4%) as a white solid. MH$^+$ 297.

Preparation 19 2-chloro-N-(2-(2-(3-(trifluoromethyl)azetidin-1-yl)pyrimidin-5-yl)pyrimidin-4-yl)acetamide

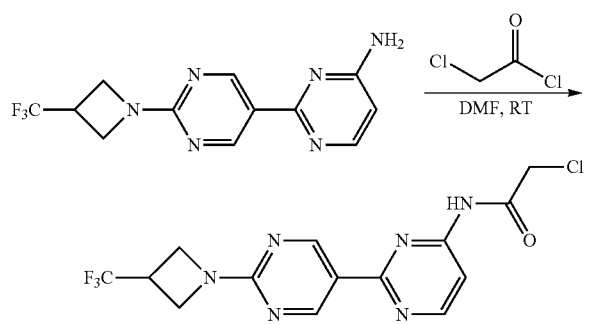

To a solution of 2-(2-(3-(trifluoromethyl)azetidin-1-yl)pyrimidin-5-yl)pyrimidin-4-amine (100 mg, 0.34 mmol) in DMF (2 mL) was added dropwise 2-chloroacetyl chloride (0.045 mL, 0.51 mmol) at 0° C. The mixture was stirred at room temperature for 2 h, then poured into EA. The organic phase was extracted with water and brine, dried over Na$_2$SO$_4$, and concentrated to give 2-chloro-N-(2'-(3,3-difluoroazetidin-1-yl)-[2,5'-bipyrimidin]-4-yl)acetamide (70 mg, 56%) as a yellow oil. MH$^+$ 373.1.

Preparation 20 2'-(4,4-difluoropiperidin-1-yl)-2,5'-bipyrimidin-4-amine

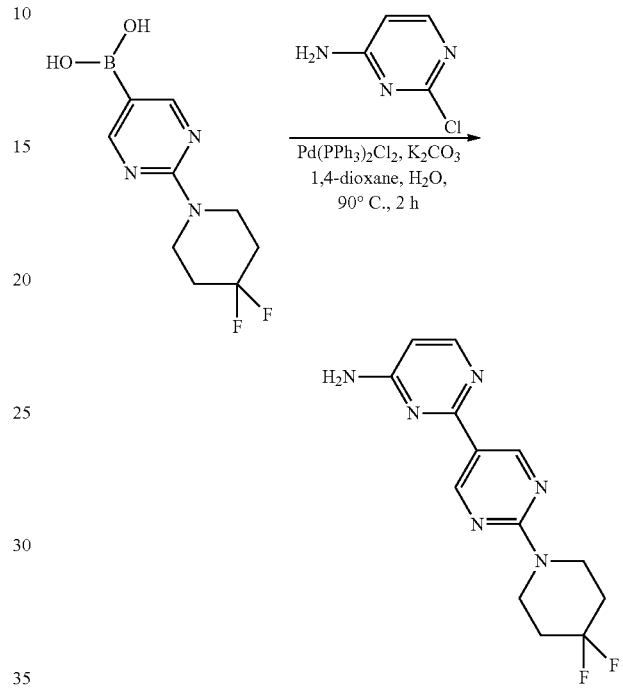

A mixture of (2-(4,4-difluoropiperidin-1-yl)pyrimidin-5-yl)boronic acid (142 mg, 0.58 mmol), 2-chloropyrimidin-4-amine (68.5 mg, 0.53 mmol), Pd(PPh3)$_2$Cl$_2$ (37.3 mg, 0.05 mmol), K$_2$CO$_3$ (146.8 mg, 1.06 mmol), 1,4-dioxane (3 mL) and water (0.5 mL) was degassed with nitrogen and stirred at 90° C. for 2 h. The resulting mixture was cooled to RT and poured into EA. The organic layer was separated, washed with water and brine, dried over anhydrous Na$_2$SO$_4$ and concentrated. The residue was purified with column chromatography eluting with DCM/MeOH (50:1) to give 2'-(4,4-difluoropiperidin-1-yl)-[2,5'-bipyrimidin]-4-amine (15 mg, 10%) as a white solid. MH$^+$ 293.

Preparation 21 (S)-2'-(2-methylpiperidin-1-yl)-2,5'-bipyrimidin-4-amine

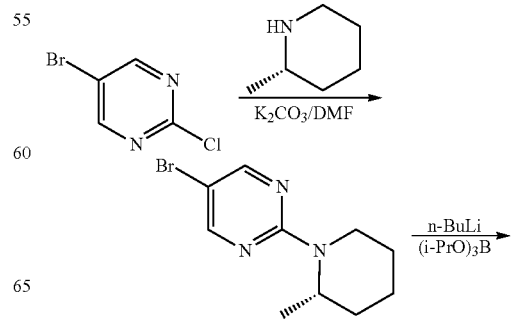

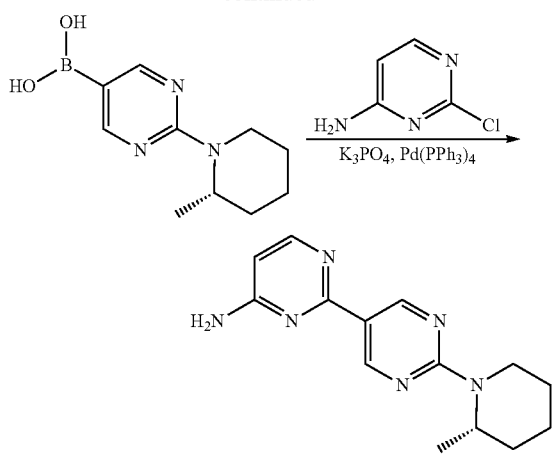

Step 1 (S)-5-bromo-2-(2-methylpiperidin-1-yl)pyrimidine

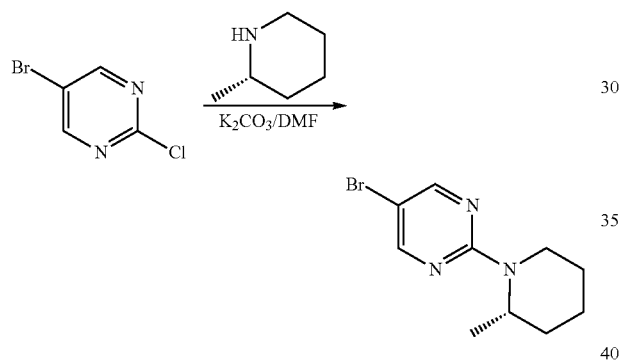

To a solution of 5-bromo-2-chloropyrimidine (1.41 g, 7.35 mmol) in DMF (20 mL) was added (S)-2-methylpiperidine (800 mg, 8.08 mmol) and $K_2CO_3$ (1.52 g, 11.03 mmol). The reaction was stirred at RT overnight. The reaction was poured into ice water and extracted with EA (3×20 mL). The combined organic phase was washed with brine, dried over $Na_2SO_4$, and concentrated. The residue was purified by chromatography eluting with PE:EA (80:1) to afford the title product (1.07 g, 56.9%) as a white solid. MH$^+$ 240.

Step 2 (S)-2-(2-methylpiperidin-1-yl)pyrimidin-5-ylboronic acid

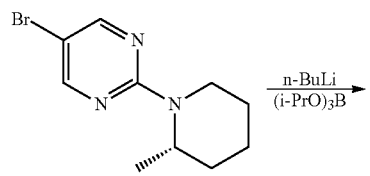

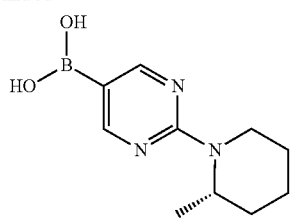

To a solution of (S)-5-bromo-2-(2-methylpiperidin-1-yl)pyrimidine (1.07 g, 4.2 mmol) and triisopropyl borate (1.1 g, 5.87 mmol) in THF (20 mL) was added n-BuLi (5.25 mL, 1.6 M in hexane, 8.4 mmol) dropwise at −70° C. The reaction was stirred at −70° C. for 3 h, then was quenched with water. The reaction was concentrated and the aqueous residue was extracted with ether (2×20 mL). The aqueous phase was adjusted to pH 6 with 1N HCl and extracted with EA (3×20 mL). The combined organic phase was washed with brine, dried over $Na_2SO_4$, and concentrated to give the title product (900 mg, 96%) as a white solid, which was directly used without purification. MH$^+$ 222.

Step 3 (S)-2'-(2-methylpiperidin-1-yl)-2,5'-bipyrimidin-4-amine

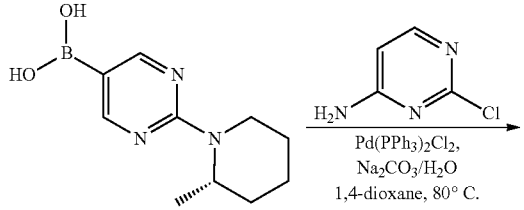

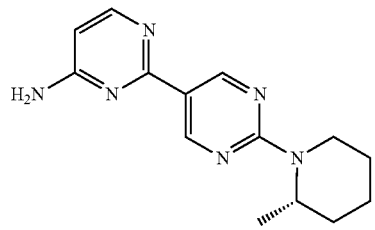

A mixture of (S)-2-(2-methylpiperidin-1-yl)pyrimidin-5-ylboronic acid (752 mg, 3.4 mmol), 4-amino-2-chloropyrimidine (400 mg, 3.09 mmol), Pd(PPh$_3$)$_2$Cl$_2$ (216.0 mg, 0.3 mmol) and Na$_2$CO$_3$ (655 mg, 6.18 mmol) in 1,4-dioxane (10 mL) and water (2.5 mL) was degassed with nitrogen and stirred at 80° C. for 2 h. The reaction was cooled to RT and partitioned between EA (20 mL) and water (15 mL). The organic phase was washed with water and brine, dried over Na$_2$SO$_4$ and concentrated. The residue was dissolved in ether. An insoluble residue was removed by filtration and the filtrate was concentrated to give (S)-2'-(2-methylpiperidin-1-yl)-2,5'-bipyrimidin-4-amine (682 mg, 81.8%) as a white solid. MH$^+$ 271.

Preparation 22 (S)-2-chloro-N-(2'-(2-methylpiperidin-1-yl)-2,5'-bipyrimidin-4-yl)acetamide

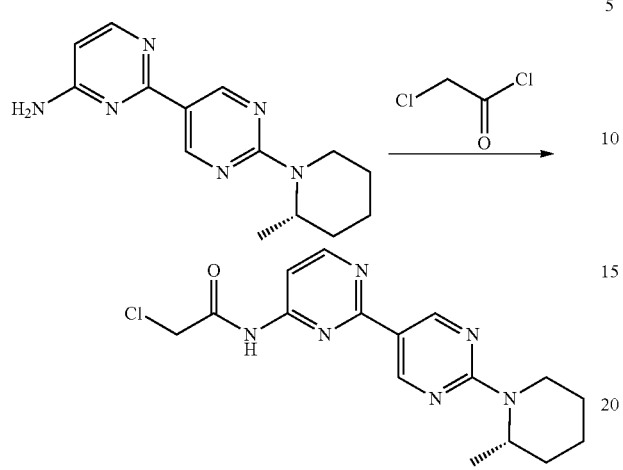

To a solution of (S)-2'-(2-methylpiperidin-1-yl)-2,5'-bipyrimidin-4-amine (400 mg, 1.48 mmol) in DMF (8 mL) was added 2-chloroacetyl chloride (0.17 mL, 2.24 mmol) dropwise at 0° C. The reaction was stirred at RT overnight, then poured into ice-water and extracted with EA (3×20 mL). The combined organic phase was washed with brine, dried over $Na_2SO_4$, and concentrated to afford the desired product (510 mg, 99%) as a yellow syrup. $MH^+$ 347.

Preparation 23 2-chloro-N-(2'-(2,2-dimethylpyrrolidin-1-yl)-[2,5'-bipyrimidin]-4-yl)acetamide (LJ-262-64)

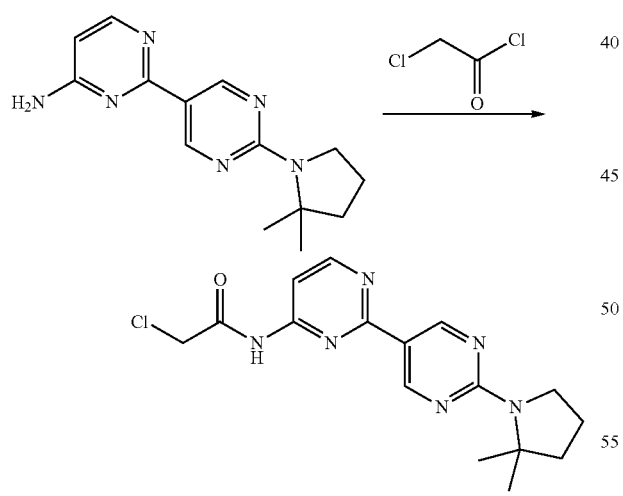

To a solution of 2'-(2,2-dimethylpyrrolidin-1-yl)-[2,5'-bipyrimidin]-4-amine (400 mg, 1.48 mmol) in DMF (5 mL) was added dropwise 2-chloroacetyl chloride (251 mg, 2.22 mmol) at 0° C. After stirring at RT overnight, the reaction mixture was partitioned with EA and water. The organic phase was washed with water and brine, dried over $Na_2SO_4$, and concentrated to give 2-chloro-N-(2'-(2,2-dimethylpyrrolidin-1-yl)-[2,5'-bipyrimidin]-4-yl)acetamide (500 mg, 97.4%) as a yellow solid. $MH^+$ 347.

Preparation 24 (S)-2'-(2-methylpyrrolidin-1-yl)-2,5'-bipyrimidin-4-amine

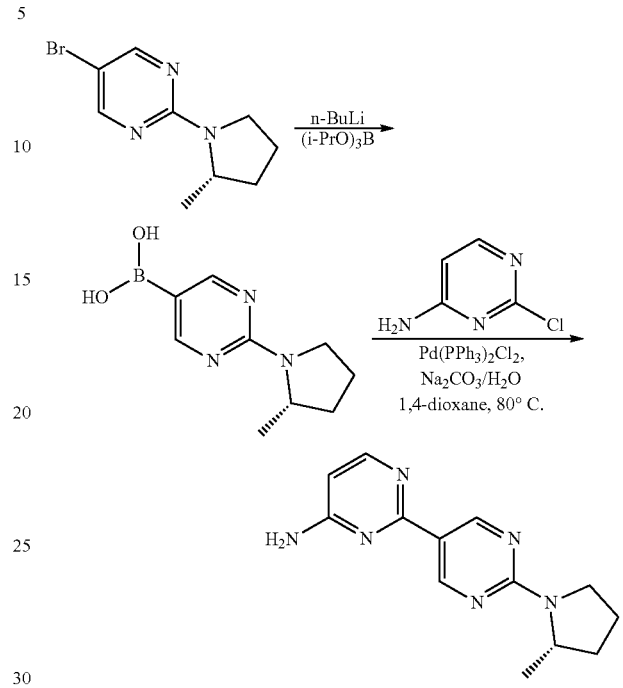

Step 1 (S)-2-(2-methylpyrrolidin-1-yl)pyrimidin-5-ylboronic acid

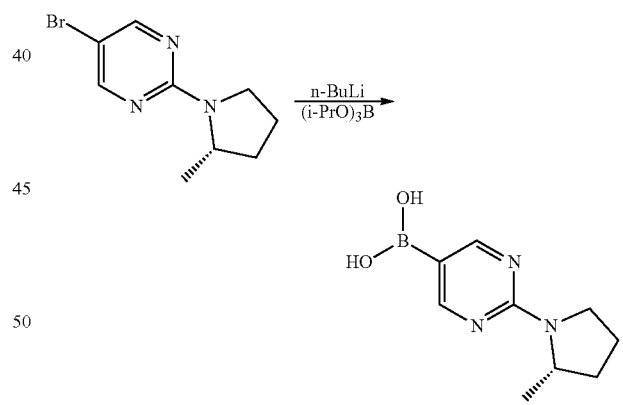

To a solution of (S)-5-bromo-2-(2-methylpyrrolidin-1-yl)pyrimidine (7 g, 30.8 mmol, prepared using the method described in WO2013/023102) and triisopropyl borate (8.12 g, 43.2 mmol) in THF (70 mL) was added n-BuLi (28.9 mL, 1.6 M in hexane, 46.3 mmol) dropwise at −70° C. The reaction was stirred at −70° C. for 3 h; then it was quenched with water. The reaction was concentrated and the aqueous residue was extracted with ether (2×20 mL). The aqueous layer was adjusted to pH 6 with 1N HCl and extracted with EA (3×20 mL). The combined organic phase was washed with brine, dried over $Na_2SO_4$, and concentrated to give the title product (4.8 g, 75.3%) as a white solid. $MH^+$ 208.

Step 2 (S)-2'-(2-methylpyrrolidin-1-yl)-2,5'-bipyrimidin-4-amine

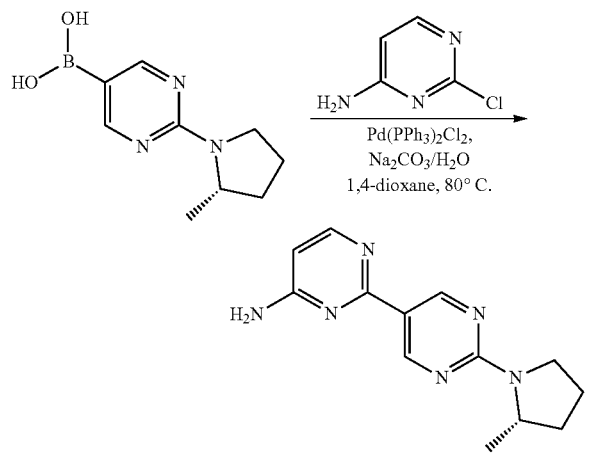

A mixture of (S)-2-(2-methylpyrrolidin-1-yl)pyrimidin-5-ylboronic acid (2.53 g, 12.23 mmol), 4-amino-2-chloropyrimidine (1.44 g, 11.12 mmol), Pd(PPh$_3$)$_2$Cl$_2$ (432.0 mg, 0.6 mmol) and Na$_2$CO$_3$ (2.35 g, 22.24 mmol) in 1,4-dioxane (40 mL) and water (10 mL) was degassed with nitrogen and stirred at 80° C. for 2 h. The reaction was cooled to RT and poured into EA. The organic phase was washed with water and brine, dried over Na$_2$SO$_4$ and concentrated. The residue was taken up in ether. An insoluble residue was removed by filtration and the filtrate was concentrated to give (S)-2'-(2-methylpyrrolidin-1-yl)-2,5'-bipyrimidin-4-amine (1.5 g, 54%) as white solid. MH$^+$ 257.

Preparation 25 (S)-2-chloro-N-(2'-(2-methylpyrrolidin-1-yl)-[2,5'-bipyrimidin]-4-yl)acetamide

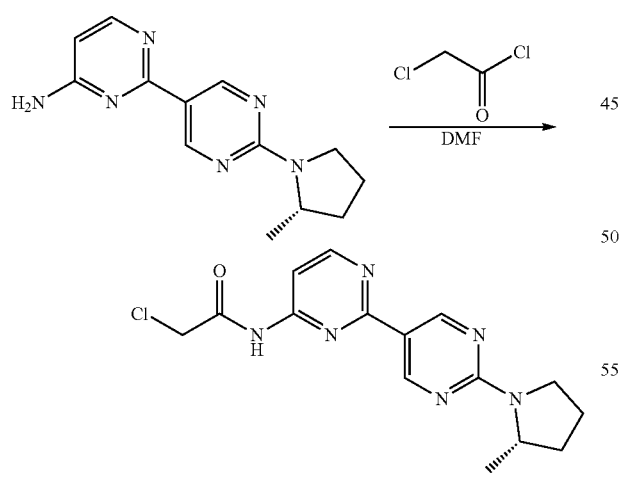

To a solution of (S)-2'-(2-methylpyrrolidin-1-yl)-[2,5'-bipyrimidin]-4-amine (256 mg, 1 mmol) in DMF (5 mL) was added dropwise 2-chloroacetyl chloride (170 mg, 1.5 mmol) at 0° C. After stirred at RT overnight, the reaction mixture was partitioned with EA and water. The organic layer was washed with water and brine, dried over Na$_2$SO$_4$, and concentrated to give (S)-2-chloro-N-(2'-(2-methylpyrrolidin-1-yl)-[2,5'-bipyrimidin]-4-yl)acetamide (280 mg, 84.1%) as a yellow solid. MH$^+$ 333.

Preparation 26 2-chloro-N-(2'-((S)-2-methylpyrrolidin-1-yl)-2,5'-bipyrimidin-4-yl)propanamide

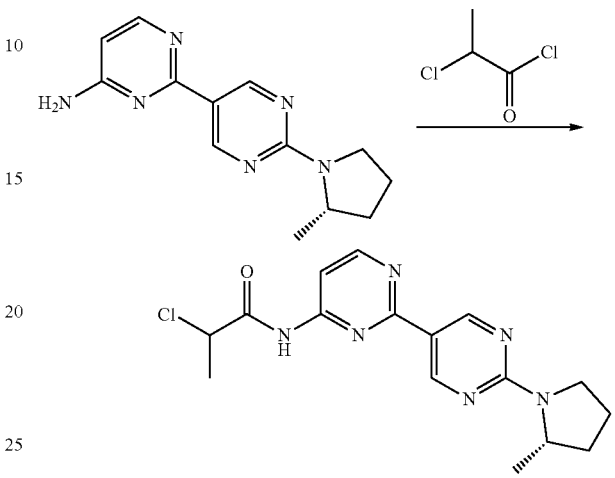

To a solution of (S)-2'-(2-methylpyrrolidin-1-yl)-2,5'-bipyrimidin-4-amine (800 mg, 3.12 mmol) in DMF (15 mL) was added 2-chloropropanoyl chloride (0.33 mL, 3.43 mmol) dropwise at 0° C. The reaction was stirred at RT overnight. The reaction was poured into ice water and extracted with EA (3×20 mL). The combined organic phase was washed with brine, dried over Na$_2$SO$_4$, and concentrated. The crude product was purified by chromatography eluting with PE:EA (5:1) to give 2-chloro-N-(2'-((S)-2-methylpyrrolidin-1-yl)-2,5'-bipyrimidin-4-yl)propanamide (600 mg, 56%) as a viscous oil. MH$^+$ 347.

Preparation 27 2-(3-methyl-2,6-dioxo-2,3-dihydro-1H-purin-7(6H)-yl)acetic acid

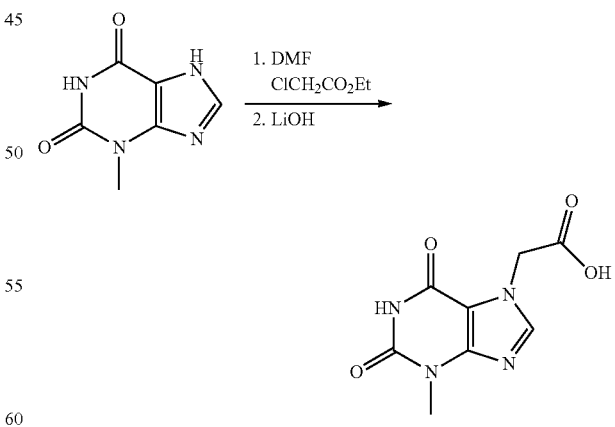

A mixture of 3-methyl-1H-purine-2,6(3H,7H)-dione (15 g, 90 mmol), K$_2$CO$_3$ (13.73 g, 99 mmol), DMF (451 mL), and ethyl 2-chloroacetate (9.62 mL, 90 mmol) was heated at 90° C. for 0.5 h. The reaction was cooled to RT and water (450 mL) was added. To the stirred solution was added LiOH (4.32 g, 181 mmol) in water (100 mL). The reaction was stirred at RT for 1 h. The reaction was adjusted to pH 4 with 6N HCl. The precipitate that formed was collected and dried to yield 2-(3-methyl-2,6-dioxo-2,3-dihydro-1H-purin-7(6H)-yl)acetic acid (18,670 g, 92%) as a white powder. $^1$H NMR (DMSO-d$_6$) δ 13.51 (s, 1H), 8.01 (s, 1H), 5.03 (s, 2H), 3.36 (s, 3H).

Preparation 28 2-(1-methyl-3-methyl-d3-2,6-dioxo-2,3-dihydro-1H-purin-7(6H)-yl)acetic acid

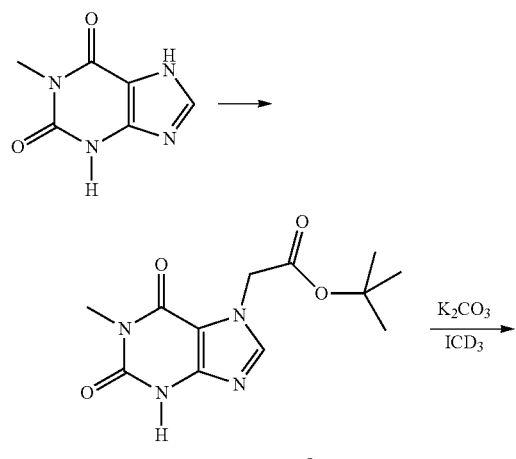

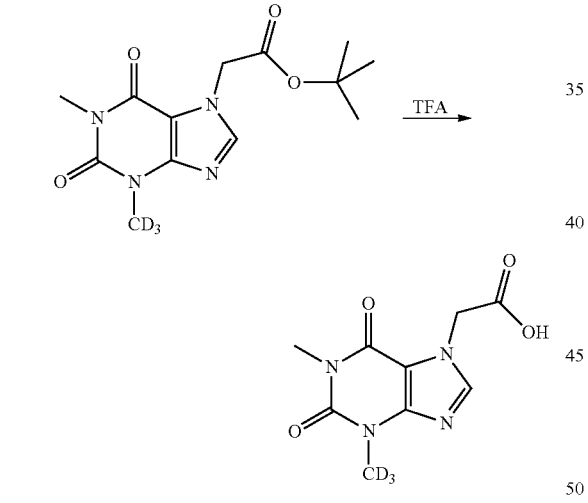

Step 1 tert-butyl 2-(1-methyl-2,6-dioxo-2,3-dihydro-1H-purin-7(6H)-yl)acetate

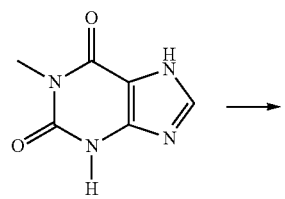

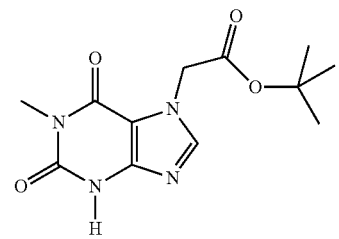

To a solution of 1-methylxanthine (9.049 g, 54.4 mmol) and potassium carbonate (8.258 g, 59.8 mmol) in DMF (200 mL), was added tert-butyl 2-bromoacetate (8.03 mL, 54.4 mmol) dropwise. The reaction was stirred at 90° C. for 1 h and cooled to room temperature. The mixture was poured into water and acidified with HCl (6N, aq.) to pH 4. The mixture was then extracted with EA (200 mL×3). The combined organic layers were washed with water (200 mL), dried over Na$_2$SO$_4$ and concentrated in vacuo. The crude product was purified by chromatography eluting with MaOH:DCM (2:100) to give tert-butyl 2-(1-methyl-2,6-dioxo-2,3-dihydro-1H-purin-7(6H)-yl)acetate (6.539 g, 43%) as yellow solid. MH$^+$ 281.

Step 2 tert-butyl 2-(1-methyl-3-methyl-d3-2,6-dioxo-2,3-dihydro-1H-purin-7(6H)-yl)acetate

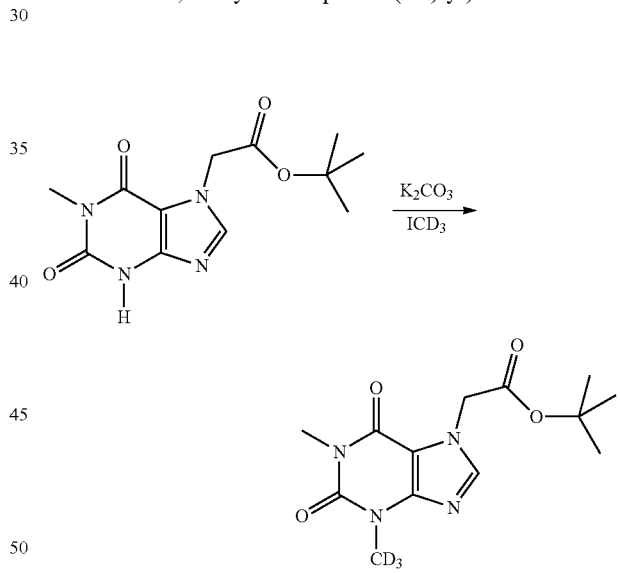

To a solution of tert-butyl 2-(1-methyl-2,6-dioxo-2,3-dihydro-1H-purin-7(6H)-yl)acetate (1.158 g, 4.13 mmol) in DMF (20.66 mL) at RT was added K$_2$CO$_3$ (0.857 g, 6.20 mmol) and iodomethane-D3 (0.334 mL, 5.37 mmol). The reaction was heated at 65° C. for 2 h. Additional iodomethane-D3 (0.2 equiv) was added and heating was continued 1 h longer. The reaction was cooled to RT, diluted with water and extracted three times with EA. The combined organic phase was washed with brine, dried over MgSO$_4$ and concentrated. The residue was purified by chromatography (0-100% EA:hexane) to afford tert-butyl 2-(1-methyl-3-methyl-d3-2,6-dioxo-2,3-dihydro-1H-purin-7(6H)-yl)acetate (1.35 g, impure). MH$^+$ 298. The impure product was used without further purification.

Step 3 2-(1-methyl-3-methyl-d3-2,6-dioxo-2,3-dihydro-1H-purin-7(6H)-yl)acetic acid

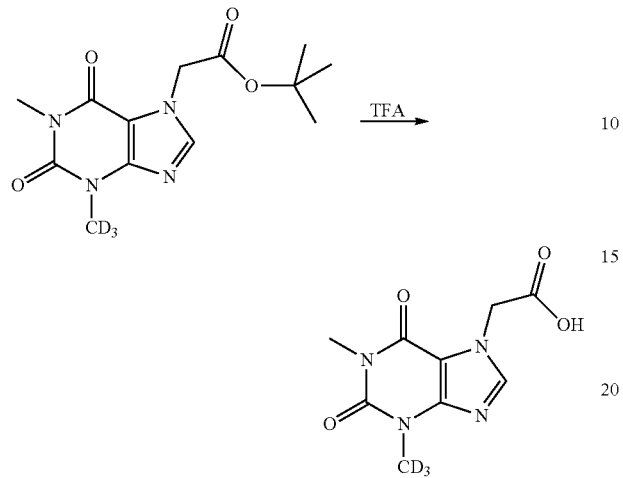

A solution of tert-butyl 2-(1-methyl-3-methyl-d3-2,6-dioxo-2,3-dihydro-1H-purin-7(6H)-yl)acetate (1.35 g, 4.54 mmol) in DCM (27.2 mL) was treated with TFA (18.16 mL). The reaction was stirred at RT for 2 h. The reaction was concentrated to an oil that was used without purification. MH+ 242.

Preparation 29 2'-(6,6-difluoro-3-azabicyclo[3.1.0]hexan-3-yl)-[2,5'-bipyrimidin]-4-amine

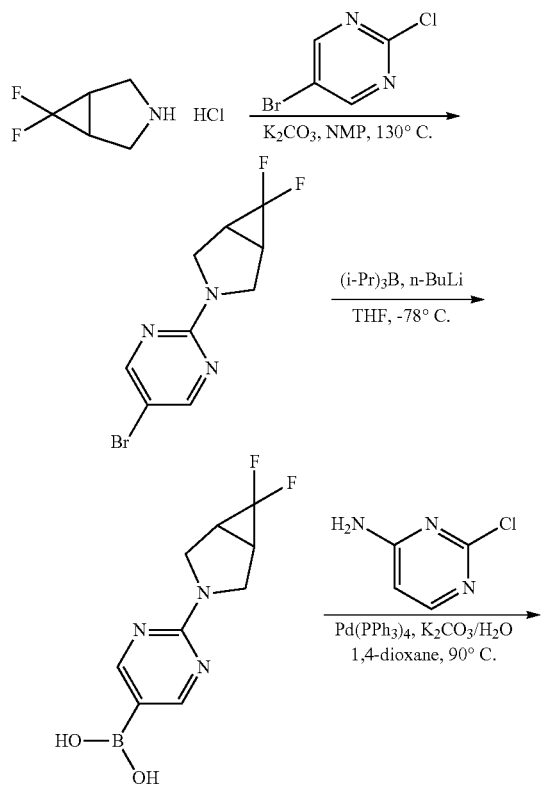

Step 1 3-(5-bromopyrimidin-2-yl)-6,6-difluoro-3-azabicyclo[3.1.0]hexane

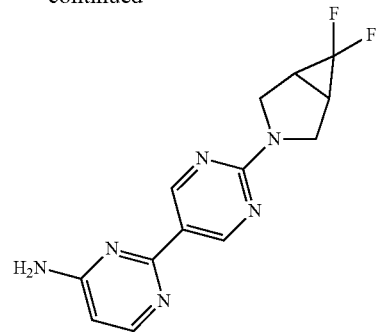

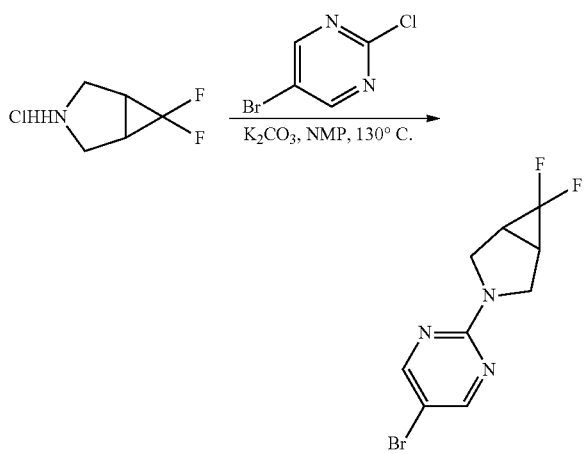

A sealed tube was charged with 5-bromo-2-chloropyrimidine (748.5 mg, 3.9 mmol), 6,6-difluoro-3-azabicyclo[3.1.0]hexane hydrochloride (604.6 mg, 3.9 mmol), $K_2CO_3$ (1.1 g, 7.8 mmol) and NMP (3 mL). The mixture was stirred at 130° C. for 3 h; then it was cooled to RT and poured into water (4 mL). The solid was collected by filtration and dried under vacuum to give 3-(5-bromopyrimidin-2-yl)-6,6-difluoro-3-azabicyclo[3.1.0]hexane (1.0 g, 93.2% yield) as a white solid. MH+ 276.

Step 2 (2-(6,6-difluoro-3-azabicyclo[3.1.0]hexan-3-yl)pyrimidin-5-yl)boronic acid

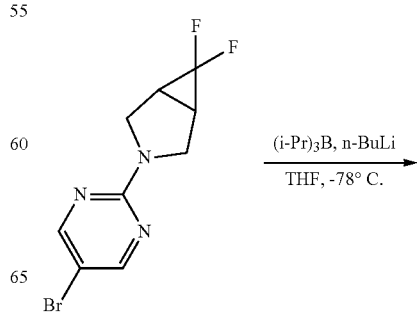

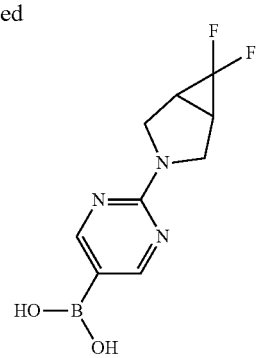

To a solution of 3-(5-bromopyrimidin-2-yl)-6,6-difluoro-3-azabicyclo[3.1.0]hexane (1.1 g, 4.1 mmol) and (i-PrO)₃B (1.4 mL, 6.2 mmol) in THF (20 mL) was added n-BuLi (3.9 mL, 1.6 M in hexane, 6.2 mmol) dropwise at −78° C. The reaction was stirred at −78° C. for 2 h; then it was quenched with water and warmed to RT. The solvent was removed under reduced pressure and the aqueous layer was washed with ether (2×50 mL). The aqueous layer was then adjusted to pH 6 with 1N HCl and extracted with EA (3×50 mL). The combined organic layers were washed with brine, dried over Na₂SO₄, and concentrated to give 2-(6,6-difluoro-3-azabicyclo[3.1.0]hexan-3-yl)pyrimidin-5-yl)boronic acid (700 mg, 72.6% yield) as a white solid.

Step 3 2'-(6,6-difluoro-3-azabicyclo[3.1.0]hexan-3-yl)-[2,5'-bipyrimidin]-4-amine

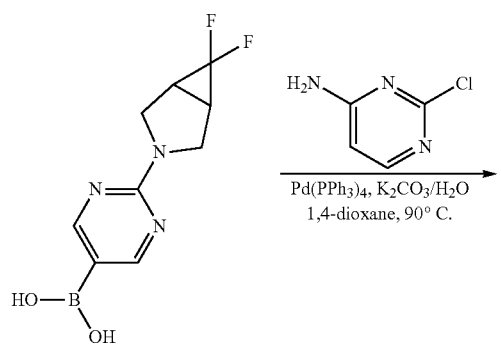

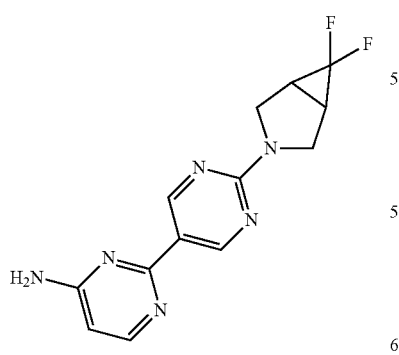

A mixture of (2-(6,6-difluoro-3-azabicyclo[3.1.0]hexan-3-yl)pyrimidin-5-yl)boronic acid (241.0 mg, 1.0 mmol), 2-chloropyrimidin-4-amine (129.0 mg, 1.0 mmol), Pd(PPh₃)₄ (57.8 mg, 0.05 mmol) and K₂CO₃ (276.4 mg, 2.0 mmol) in 1,4-dioxane (5 mL) and water (1 mL) was degassed and purged with N₂ three times. The reaction was heated at 90° C. with stirring for 3 h. The resulting mixture was cooled to RT and poured into EA. The organic phase was separated, washed with water and brine, dried over Na₂SO₄ and concentrated. The residue was purified with chromatography eluting with DCM:MeOH (50:1) to afford 2'-(6,6-difluoro-3-azabicyclo[3.1.0]hexan-3-yl)-[2,5'-bipyrimidin]-4-amine (210 mg, 72.3% yield) as a white solid. MH⁺ 291.

Preparation 30 (2R)-2-(1,3-dimethyl-2,6-dioxo-3,4,5,6-tetrahydro-1H-purin-7(2H)-yl)propanoic acid

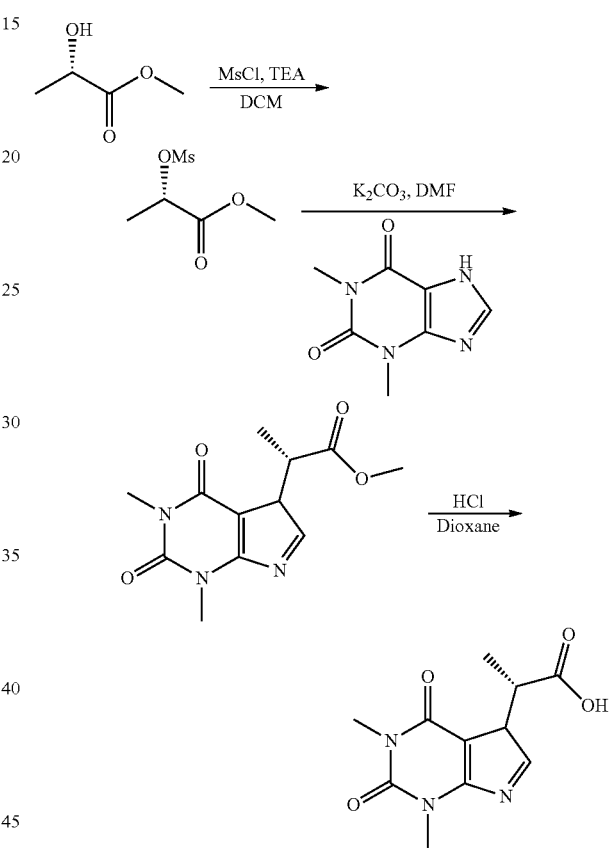

Step 1 (S)-methyl 2-(methylsulfonyloxy)propanoate

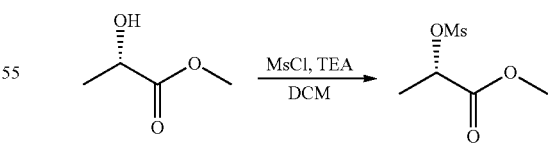

A solution of (S)-methyl 2-hydroxypropanoate (12.379 g, 119 mol) and TEA (17.4 mL, 125 mol) in DCM (100 mL) was chilled to 0° C. and methanesulfonyl chloride (12.4 mL, 125 mol) was added dropwise at 0° C. over 1 h. The mixture was stirred at 20° C. for 1.5 h. The resulting mixture was quenched with ice-water (100 mL). The organic layer was separated, washed with water (2×50 mL) and brine, dried over Na₂SO₄ and concentrated to afford the crude product (S)-methyl 2-(methylsulfonyloxy)propanoate (20.940 g, 97%) as brown oil which was used without purification.

Step 2 (R)-2-(1,3-dimethyl-2,6-dioxo-2,3-dihydro-1H-purin-7(6H)-yl)propanoic acid

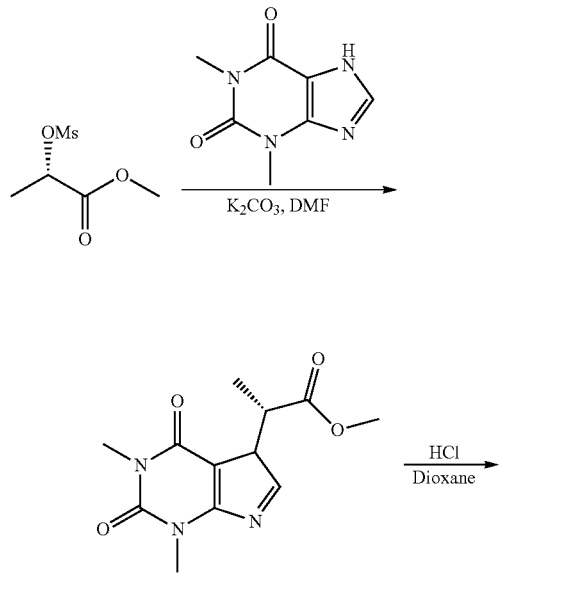

To a suspension of 1,3-dimethyl-3,4,5,7-tetrahydro-1H-purine-2,6-dione (4.588 g, 25.5 mol) and $K_2CO_3$ (7.038 g, 51 mol, 2 eq) in DMF (500 mL) at RT was added (s)-methyl 2-(methylsulfonyloxy)propanoate (6.953 g, 38.2 mol). The mixture was stirred at RT overnight, then quenched with saturated $NH_4Cl$. The resulting mixture was extracted with DCM (3×300 mL). The combined organic phase was washed with water and brine, dried over $Na_2SO_4$ and concentrated. The brown oil residue (8.633 g) was dissolved in dioxane (10 mL). To the solution was added 6N HCl (aq. 10 mL). The mixture was refluxed for 2 h, cooled to RT and then concentrated to remove the dioxane and most of the aqueous phase. The residue was purified with chromatography eluting with MeOH/DCM (0-10%) to afford (R)-2-(1,3-dimethyl-2,6-dioxo-2,3-dihydro-1H-purin-7(6H)-yl)propanoic acid (6.015 g, 93.6% yield) as white solid.

Synthesis of Compounds of Formula (I)

Example 1 (S)-2-(1,3-dimethyl-2,6-dioxo-2,3-dihydro-1H-purin-7(6H)-yl)-N-(2'-(2,2-dimethylpyrrolidin-1-yl)-[2,5'-bipyrimidin]-4-yl)propanamide

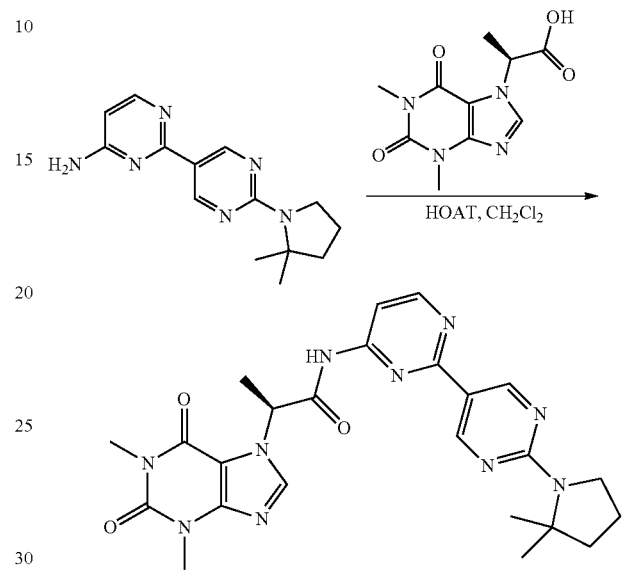

To a mixture of 2'-(2,2-dimethylpyrrolidin-1-yl)-[2,5'-bipyrimidin]-4-amine (4.2 g, 15.5 mmol) and (S)-2-(1,3-dimethyl-2,6-dioxo-2,3-dihydro-1H-purin-7(6H)-yl)propanoic acid (3.56 g, 14.1 mmol) in DCM (72 mL) was added HOAT (1.92 g, 14.1 mmol) at RT. The reaction was cooled to 0° C. and pyridine (2.23 g, 28.2 mmol) and DIC (2.67 g, 21.2 mmol) were added. The reaction was warmed to 25-28° C. and stirred overnight. The reaction mixture was quenched with 0.5 N HCl. The mixture was added dropwise to n-hexane and the precipitate that formed was collected and washed with MeOH to give (S)-2-(1,3-dimethyl-2,6-dioxo-2,3-dihydro-1H-purin-7(6H)-yl)-N-(2'-(2,2-dimethylpyrrolidin-1-yl)-[2,5'-bipyrimidin]-4-yl)propanamide (3 g, 19%). $^1H$ NMR ($CDCl_3$) δ 9.78 (s, 1H), 9.14 (s, 2H), 8.54 (d, J=5.6 Hz, 1H), 7.91 (s, 1H), 7.76 (d, J=5.6 Hz, 1H), 5.83 (q, J=7.2 Hz 1H), 3.77 (m, 2H), 3.63 (s, 3H), 3.50 (s, 3H), 1.96 (m, 7H), 1.60 (s, 6H).

Example 2 (S)-2-(1,3-dimethyl-2,6-dioxo-2,3-dihydro-1H-purin-7(6H)-yl)-N-(2'-((S)-2-(trifluoromethyl)pyrrolidin-1-yl)-[2,5'-bipyrimidin]-4-yl)propanamide (Compound 2)

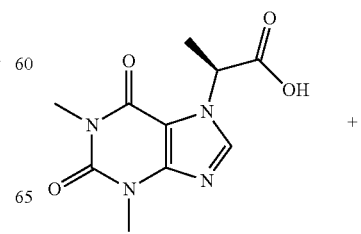

+

-continued

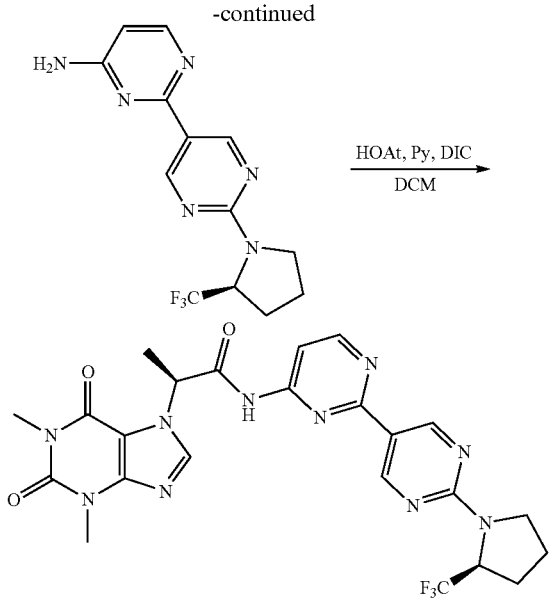

To a mixture of (S)-2-(1,3-dimethyl-2,6-dioxo-2,3-dihydro-1H-purin-7(6H)-yl)propanoic acid (2.44 g, 9.67 mmol) and (S)-2'-(2-(trifluoromethyl)pyrrolidin-1-yl)-2,5'-bipyrimidin-4-amine (3.3 g, 10.6 mmol) in DCM (48 mL) was added HOAT (1.3 g, 9.67 mmol) at RT. The mixture was cooled to 0° C. Pyridine (1.5 g, 19.3 mmol) was added dropwise over 30 min followed by dropwise addition of DIC (1.8 g, 14.5 mmol). The reaction was stirred at 35° C. for 16 h; then it was diluted with DCM (100 mL). The mixture was extracted with saturated NH$_4$Cl (50 mL, precooled to 0° C.) and brine, dried over Na$_2$SO$_4$, and concentrated. The residue was purified by chromatography eluting first with EA:PE (3:2) and then DCM:MeOH (30:1) and then recrystallized with EtOH to give the title compound (4.5 g, 78%) as a white solid. $^1$H NMR (DMSO-d$_6$) δ 11.46 (s, 1H), 9.22 (s, 2H), 8.66 (d, J=5.6 Hz, 1H), 8.31 (s, 1H), 7.81 (d, J=5.6 Hz, 1H), 5.82 (q, J=7.2 Hz 1H), 5.12 (t, 1H), 3.70 (m, 2H), 3.47 (s, 3H), 3.16 (s, 3H), 2.10 (m, 4H), 1.88 (d, J=7.2 Hz, 3H). MH$^+$ 545. diastereomeric excess (de): 99%*.
*Chiral HPLC Method condition: Column: CHIRALPAK IB, 150*4.6 mm, 5 μm; Mobile Phase: A: Hexane (HPLC GRADE); B: EtOH (HPLC GRADE); Flow Rate: 0.8 mL/min; Gradient: 30% B for 25 min. Results: Retention time of the desired diastereoisomer (S) is 14.16 min, the other isomer (R) is 9.66 min.

Example 3 (R)-2-(1,3-dimethyl-2,6-dioxo-2,3-dihydro-1H-purin-7(6H)-yl)-N-(2'-((S)-2-(trifluoromethyl)pyrrolidin-1-yl)-[2,5'-bipyrimidin]-4-yl)propanamide

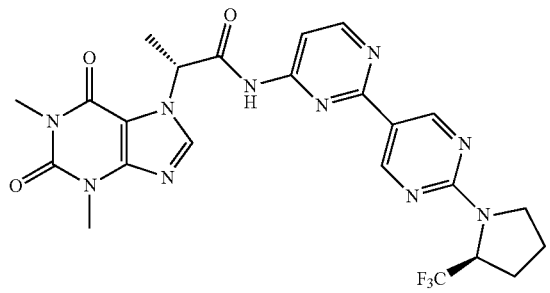 [SMILES: C[C@H](C(=O)Nc1ccnc(-c2cnc(N3CCC[C@H]3C(F)(F)F)nc2)n1)n1cnc2c1c(=O)n(C)c(=O)n2C]

The mother liquid after recrystallization from Example 2 in EtOH was concentrated. The residue was submitted for chiral preparative HPLC purification to give (R)-2-(1,3-dimethyl-2,6-dioxo-2,3-dihydro-1H-purin-7(6H)-yl)-N-(2'-((S)-2-(trifluoromethyl)pyrrolidin-1-yl)-[2,5'-bipyrimidin]-4-yl)propanamide as a white solid. $^1$H NMR (DMSO-d$_6$) δ 11.48 (s, 1H), 9.25 (s, 2H), 8.69 (d, J=5.6 Hz, 1H), 8.33 (s, 1H), 7.83 (d, J=5.6 Hz, 1H), 5.81 (q, J=7.2 Hz 1H), 5.13 (t, 1H), 3.71 (m, 2H), 3.69 (s, 3H), 3.17 (s, 3H), 2.14 (m, 4H), 1.88 (d, J=7.2 Hz, 3H). MH$^+$ 545. de: 99%.*

*Chiral HPLC Method condition: Column: CHIRALPAK IB, 150*4.6 mm, 5 μm; Mobile Phase: A: Hexane (HPLC GRADE); B: EtOH (HPLC GRADE); Flow Rate: 0.8 mL/min; Gradient: 30% B for 25 min.

Example 4 (S)-2-(1,3-dimethyl-2,6-dioxo-2,3-dihydro-1H-purin-7(6H)-yl)-N-(2'-((R)-2-(trifluoromethyl)pyrrolidin-1-yl)-[2,5'-bipyrimidin]-4-yl)propanamide

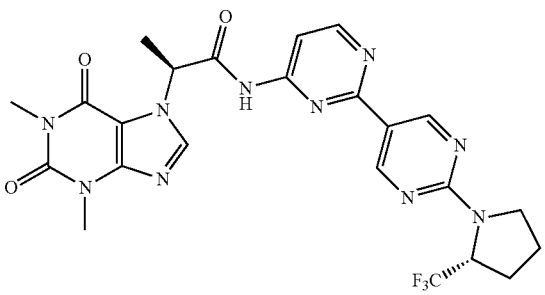 [SMILES: C[C@@H](C(=O)Nc1ccnc(-c2cnc(N3CCC[C@@H]3C(F)(F)F)nc2)n1)n1cnc2c1c(=O)n(C)c(=O)n2C]

The title compound was prepared using the method of Example 2 to yield a white solid. $^1$H NMR (DMSO-d$_6$) δ 11.46 (s, 1H), 9.25 (s, 2H), 8.70 (d, J=5.6 Hz, 1H), 8.33 (s, 1H), 7.83 (d, J=5.6 Hz, 1H), 5.81 (q, J=7.2 Hz 1H), 5.14 (t, 1H), 3.67 (m, 2H), 3.32 (s, 3H), 3.14 (s, 3H), 2.10 (m, 4H), 1.86 (d, J=7.2 Hz, 3H). MH$^+$ 545. de 98%*

*Chiral HPLC Method condition: Column: CHIRALPAK IB, 150*4.6 mm, 5 μm; Mobile Phase: A: Hexane (HPLC GRADE); B: EtOH (HPLC GRADE); Flow Rate: 0.8 mL/min; Gradient: 30% B for 25 min.

Example 5 (S)-2-(1-methyl-2,6-dioxo-2,3-dihydro-1H-purin-7(6H)-yl)-N-(2'-((S)-2-(trifluoromethyl)pyrrolidin-1-yl)-[2,5'-bipyrimidin]-4-yl)propanamide

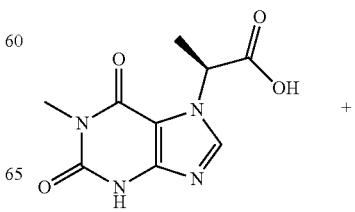 +

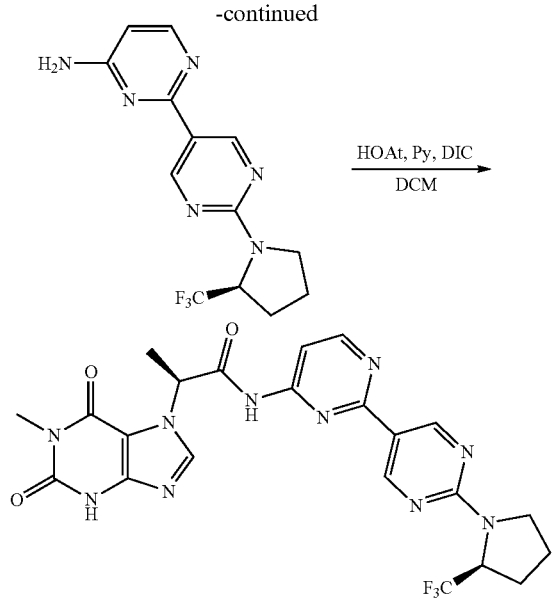

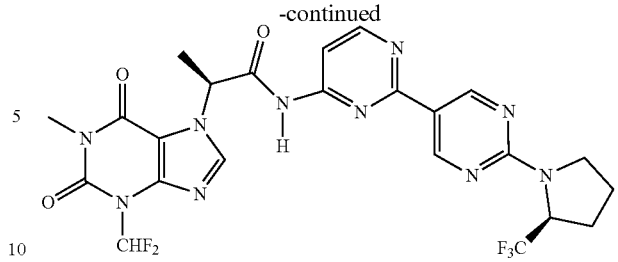

To a mixture of (2S)-2-(1-methyl-2,6-dioxo-3,4,5,6-tetrahydro-1H-purin-7(2H)-yl)propanoic acid (90.4 mg, 0.38 mmol) and (S)-2'-(2-(trifluoromethyl)pyrrolidin-1-yl)-2,5'-bipyrimidin-4-amine (119 mg, 0.38 mmol) in DCM (2 mL) was added HOAT (104 mg, 0.76 mmol) at RT. The reaction was cooled to 0° C. Pyridine (91 mg, 1.15 mmol) was added dropwise followed by dropwise addition of DIC (97 mg, 0.77 mmol). The reaction was stirred at 20° C. for 16 h; then it was diluted with DCM (10 mL). The mixture was washed with saturated NH$_4$Cl and brine, dried over Na$_2$SO$_4$ and concentrated. The residue was purified by chromatography eluting with DCM:MeOH (30:1) to give the title product (83 g, 41%) as a white solid. $^1$H NMR (DMSO-d$_6$) δ 11.94 (s, 1H), 11.44 (s, 1H), 9.25 (s, 2H), 8.71 (d, J=5.6 Hz, 1H), 8.23 (s, 1H), 7.84 (d, J=5.6 Hz, 1H), 5.78 (q, J=7.2 Hz 1H), 5.14 (t, 1H), 3.71 (m, 2H), 3.12 (s, 3H), 2.20 (m, 4H), 1.84 (d, J=7.2 Hz, 3H). MH$^+$ 531.

Example 6 (S)-2-(3-(difluoromethyl)-1-methyl-2,6-dioxo-2,3-dihydro-1H-purin-7(6H)-yl)-N-(2'-((S)-2-(trifluoromethyl)pyrrolidin-1-yl)-[2,5'-bipyrimidin]-4-yl)propanamide

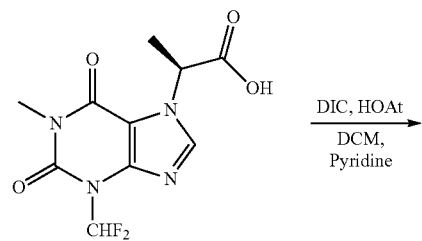

To a mixture of (S)-2-(3-(difluoromethyl)-1-methyl-2,6-dioxo-2,3-dihydro-1H-purin-7(6H)-yl)propanoic acid (61 mg, 0.21 mmol) and (S)-2'-(2-(trifluoromethyl)pyrrolidin-1-yl)-2,5'-bipyrimidin-4-amine (310 mg, 0.21 mmol) in DCM (1 mL) was added HOAT (57 mg, 0.42 mmol) at RT. The mixture was cooled to 0° C. Pyridine (50 mg, 0.63 mmol) was added dropwise followed by dropwise addition of DIC (53 mg, 0.42 mmol). The reaction was stirred at 20° C. for 16 h, then diluted with DCM (10 mL). The mixture was washed with saturated NH$_4$Cl and brine, dried over Na$_2$SO$_4$ and concentrated. The residue was purified by chromatography eluting with DCM:MeOH (30:1) to give the product (45.6 mg, 37%) as a white solid. $^1$H NMR (DMSO-d$_6$) δ 11.49 (s, 1H), 9.25 (s, 2H), 8.70 (s, 1H), 8.39 (s, 1H), 7.86 (t, J=5.6 Hz, 2H), 5.82 (q, J=8 Hz 1H), 5.14 (t, 1H), 3.74 (m, 2H), 3.16 (s, 3H), 2.22 (m, 4H), 1.87 (d, J=8 Hz, 3H). MH$^+$ 581.

Example 7 N-(2'-(3,3-difluoroazetidin-1-yl)-[2,5'-bipyrimidin]-4-yl)-2-(1,3-dimethyl-2,6-dioxo-2,3-dihydro-1H-purin-7(6H)-yl)acetamide

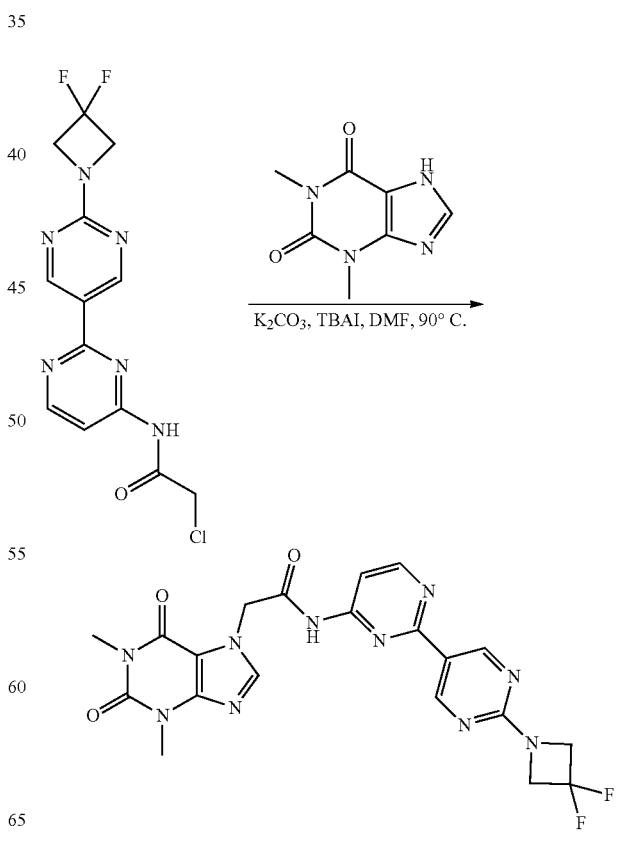

A mixture of 2-chloro-N-(2'-(3,3-difluoroazetidin-1-yl)-[2,5'-bipyrimidin]-4-yl)acetamide (50.0 mg, 0.1 mmol), K$_2$CO$_3$ (41.5 mg, 0.3 mmol), 1,3-dimethyl-1H-purine-2,6 (3H,7H)-dione (26.5 mg, 0.1 mmol) and TBAI (5.6 mg, 0.01 mmol) in DMF (3 mL) was stirred at 90° C. overnight. The reaction was cooled to RT and diluted with EA. The organic phase was washed with water, saturated NH$_4$Cl solution and brine, dried over Na$_2$SO$_4$, and concentrated. The residue was purified by preparative TLC (DCM/MeOH=30:1) to give N-(2'-(3,3-difluoroazetidin-1-yl)-[2,5'-bipyrimidin]-4-yl)-2-(1,3-dimethyl-2,6-dioxo-2,3-dihydro-1H-purin-7(6H)-yl) acetamide (4.0 mg, 5.6%) as a white solid. $^1$H NMR (DMSO-d$_6$) δ 11.48 (s, 1H), 9.26 (s, 2H), 8.73 (d, J=5.6 Hz, 1H), 8.08 (s, 1H), 7.83 (s, 1H), 5.36 (s, 2H), 4.60 (t, J=12.2 Hz, 4H), 3.46 (s, 3H), 3.19 (s, 3H). MH$^+$ 485.1.

Example 8 N-(2'-(4,4-difluoropiperidin-1-yl)-[2,5'-bipyrimidin]-4-yl)-2-(1,3-dimethyl-2,6-dioxo-2,3-dihydro-1H-purin-7(6H)-yl)acetamide

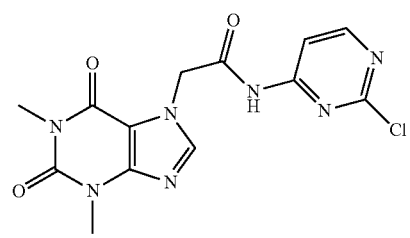
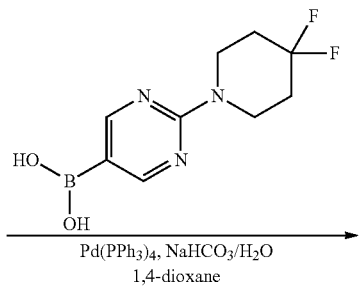

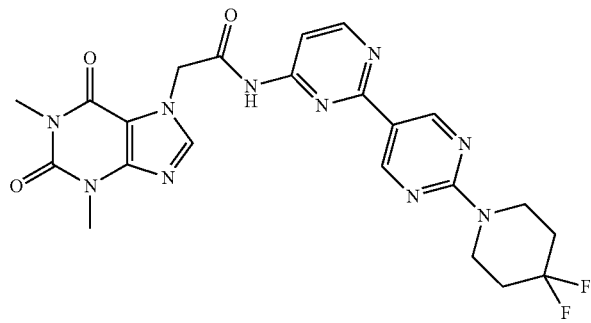

A mixture of N-(2-chloropyrimidin-4-yl)-2-(1,3-dimethyl-2,6-dioxo-2,3-dihydro-1H-purin-7(6H)-yl)acetamide (87.3 mg, 0.3 mmol), Pd(PPh$_3$)$_4$ (28.9 mg, 0.03 mmol), (2-(4,4-difluoropiperidin-1-yl)pyrimidin-5-yl)boronic acid (66.9 mg, 0.3 mmol) and NaHCO$_3$ (21.0 mg, 0.3 mmol) in 1,4-dioxane (3 mL) and water (0.5 mL) was degassed with nitrogen and stirred at 90° C. overnight. The reaction was cooled to RT and diluted with EA. The organic phase was separated, washed with water and brine, dried over Na$_2$SO$_4$ and concentrated. The residue was purified by preparative TLC (DCM/MeOH=30:1) to give N-(2'-(4,4-difluoropiperidin-1-yl)-[2,5'-bipyrimidin]-4-yl)-2-(1,3-dimethyl-2,6-dioxo-2,3-dihydro-1H-purin-7(6H)-yl)acetamide (8.0 mg, 6.2%) as a white solid. $^1$H-NMR (DMSO-d$_6$) δ 11.44 (s, 1H), 9.23 (s, 2H), 8.71 (d, J=5.7 Hz, 1H), 8.08 (s, 1H), 7.81 (s, 1H), 5.36 (s, 2H), 4.05-3.97 (m, 4H), 3.46 (s, 3H), 3.19 (s, 3H), 2.06 (dd, J=12.5, 6.6 Hz, 4H). MH$^+$ 513.1.

Example 9 (S)—N-(2'-(3,3-difluoroazetidin-1-yl)-2,5'-bipyrimidin-4-yl)-2-(1,3-dimethyl-2,6-dioxo-2,3-dihydro-1H-purin-7(6H)-yl)propanamide

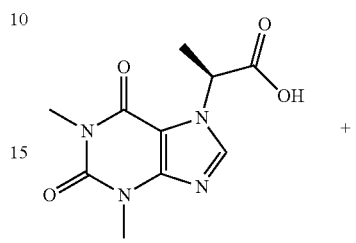

+

-continued

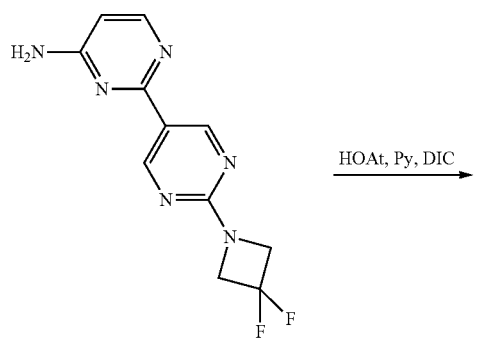

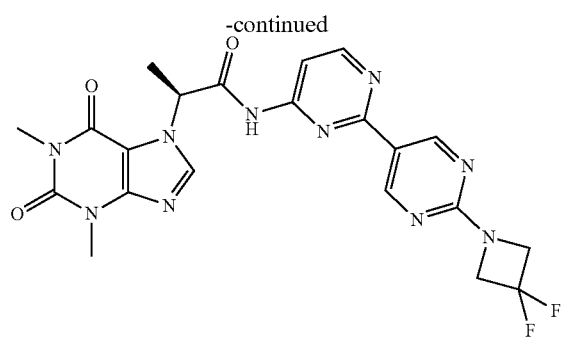

To a mixture of (S)-2-(1,3-dimethyl-2,6-dioxo-2,3-dihydro-1H-purin-7(6H)-yl)propanoic acid (57 mg, 0.23 mmol) and 2'-(3,3-difluoroazetidin-1-yl)-2,5'-bipyrimidin-4-amine (50 mg, 0.19 mmol) in DCM (3 mL) was added HOAT (31 mg, 0.23 mmol) at RT. The reaction was cooled to 0° C. then pyridine (30 mg, 0.38 mmol) was slowly added dropwise followed by dropwise addition of DIC (36 g, 0.29 mmol). The reaction was allowed to warm to RT and then warmed to 30° C. and stir 18 h. The reaction was extracted with water followed by saturated NH$_4$Cl. The organic phase was dried over Na$_2$SO$_4$, and concentrated. The residue was purified by preparative HPLC (DCM/MeOH=30:1) to give (S)—N-(2'-(3,3-difluoroazetidin-1-yl)-2,5'-bipyrimidin-4-yl)-2-(1,3-dimethyl-2,6-dioxo-2,3-dihydro-1H-purin-7(6H)-yl)propanamide (10 mg, 9%) as white a solid. $^1$H NMR (DMSO-d$_6$) δ 11.51 (s, 1H), 9.26 (s, 2H), 872 (d, 1H), 8.35 (s, 1H), 7.86 (d, 1H), 5.81 (q, 1H), 4.60 (t, 4H), 3.47 (s, 3H), 3.17 (s, 3H), 1.81 (d, 3H). MH$^+$ 499.

Example 10 N-(2'-(3-azabicyclo[3.1.0]hexan-3-yl)-[2,5'-bipyrimidin]-4-yl)-2-(1,3-dimethyl-2,6-dioxo-2,3-dihydro-1H-purin-7(6H)-yl)acetamide

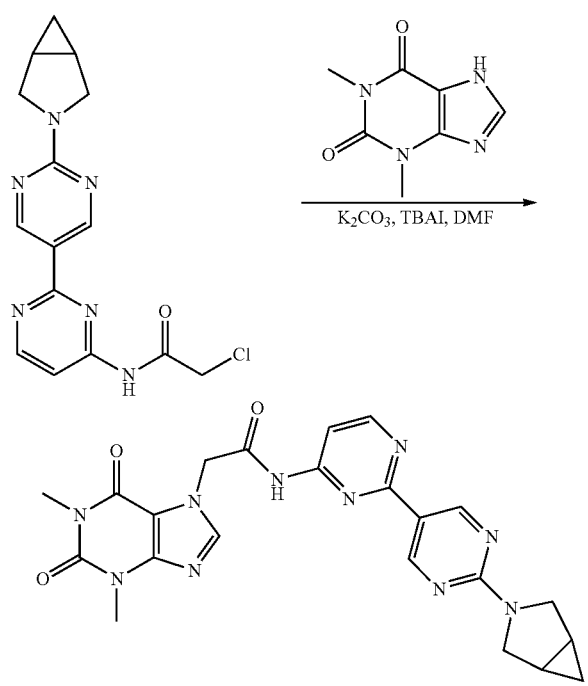

A mixture of N-(2'-(3-azabicyclo[3.1.0]hexan-3-yl)-[2,5'-bipyrimidin]-4-yl)-2-chloro acetamide (50.0 mg, 0.16 mmol), K$_2$CO$_3$ (44.3 mg, 0.32 mmol), 1,3-dimethyl-1H-purine-2,6(3H,7H)-dione (28.0 mg, 0.16 mmol) and TBAI (5.9 mg, 0.02 mmol) in DMF (3 mL) was stirred at 90° C. overnight. The reaction was cooled to RT and diluted with EA. The organic phase was extracted with water, saturated NH$_4$Cl and brine, dried over Na$_2$SO$_4$, and concentrated. The residue was purified by preparative TLC (DCM/MeOH=25:1) to give N-(2'-(3-azabicyclo[3.1.0]hexan-3-yl)-[2,5'-bipyrimidin]-4-yl)-2-(1,3-dimethyl-2,6-dioxo-2,3-dihydro-1H-purin-7(6H)-yl)acetamide (2.0 mg, 2.9%) as a white solid. $^1$H NMR (DMSO-d$_6$) δ 11.41 (s, 1H), 9.17 (s, 2H), 8.68 (d, J=5.7 Hz, 1H), 8.08 (s, 1H), 7.76 (s, 1H), 5.36 (s, 2H), 3.87 (d, J=11.5 Hz, 2H), 3.59 (s, 2H), 3.51 (s, 3H), 3.19 (s, 3H), 0.82 (m, 3H), 0.18 (s, 1H). MH$^+$475.

Example 11 2-(1,3-dimethyl-2,6-dioxo-2,3-dihydro-1H-purin-7(6H)-yl)-N-(2'43-(trifluoromethyl)pyrrolidin-1-yl)-[2,5'-bipyrimidin]-4-yl)

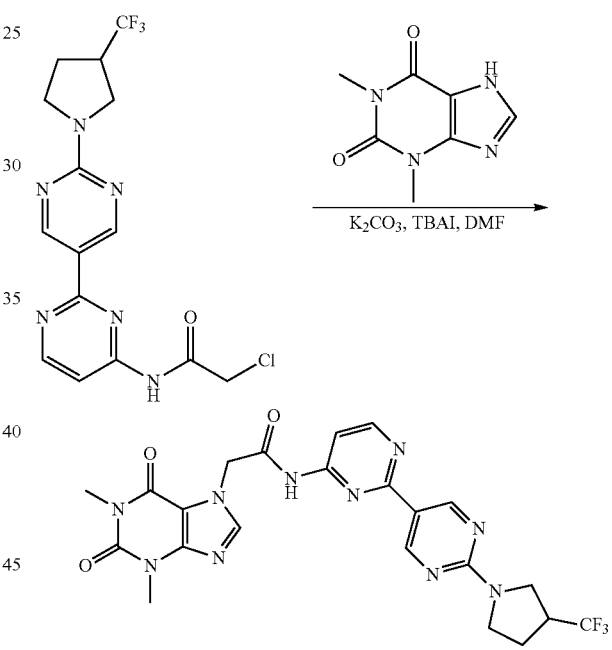

A mixture of 2-chloro-N-(2'-(3-(trifluoromethyl)pyrrolidin-1-yl)-[2,5'-bipyrimidin]-4-yl)acetamide (100.0 mg, 0.26 mmol), K$_2$CO$_3$ (53.7 mg, 0.39 mmol), 1,3-dimethyl-1H-purine-2,6(3H,7H)-dione (46.6 mg, 0.26 mmol) and TBAI (9.7 mg, 0.03 mmol) in DMF (3 mL) was stirred at 90° C. overnight. The reaction was cooled to RT and diluted with EA. The organic phase was washed with water, saturated NH$_4$Cl and brine, dried over Na$_2$SO$_4$, and concentrated. The residue was purified by preparative TLC (DCM/MeOH=30:1) to give 2-(1,3-dimethyl-2,6-dioxo-2,3-dihydro-1H-purin-7(6H)-yl)-N-(2'-(3-(trifluoromethyl)pyrrolidin-1-yl)-[2,5' bipyrimidin]-4-yl)acetamide (4.0 mg, 2.9%) as a white solid. $^1$HNMR (DMSO-d$_6$) δ 11.42 (s, 1H), 9.22 (s, 2H), 8.70 (d, J=5.7 Hz, 1H), 8.08 (s, 1H), 7.79 (s, 1H), 5.36 (s, 2H), 3.91 (dd, J=11.7, 8.1 Hz, 1H), 3.77 (s, 1H), 3.72-3.61 (m, 2H), 3.46 (s, 3H), 3.19 (s, 3H), 2.35-2.29 (m, 1H), 2.14 (dd, J=12.9, 7.3 Hz, 1H), 2.00 (d, J=7.9 Hz, 1H). MH$^+$ 531.

Example 12 N-(2'-(3,3-difluoroazetidin-1-yl)-[2,5'-bipyrimidin]-4-yl)-2-(1,3-dimethyl-2,6-dioxo-2,3-dihydro-1H-purin-7(6H)-yl)acetamide

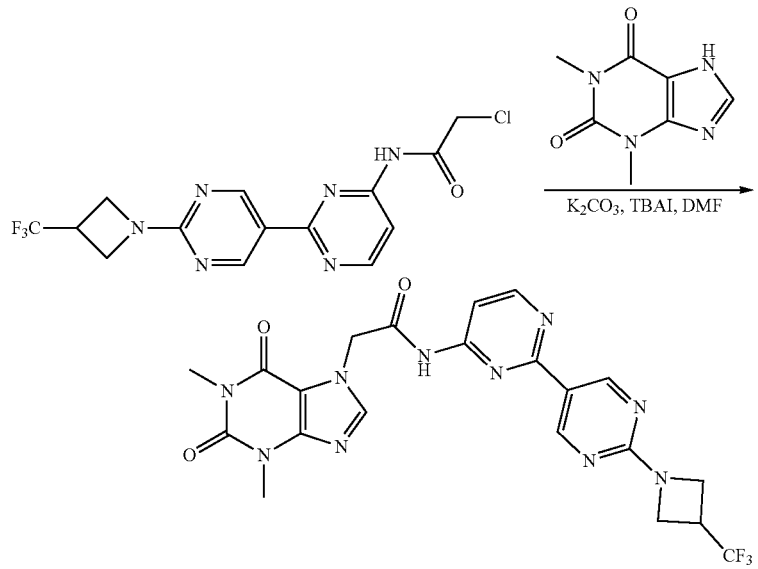

A mixture of 2-chloro-N-(2-(2-(3-(trifluoromethyl)azetidin-1-yl)pyrimidin-5-yl)pyrimidin-4-yl)acetamide (70 mg, 0.19 mmol), $K_2CO_3$ (51.9 mg, 0.38 mmol), 1,3-dimethyl-1H-purine-2,6(3H,7H)-dione (34.2 mg, 0.19 mmol) and TBAI (11.2 mg, 0.019 mmol) in DMF (2 mL) was stirred at 50° C. for 2 h. The reaction was cooled to RT and diluted with EA. The organic phase was washed with water and brine, dried over $Na_2SO_4$ and concentrated. The crude product which was triturated with MeOH, filtered, and dried to give the title product 2-(1,3-dimethyl-2,6-dioxo-1,2,3,6-tetrahydropurin-7-yl)-N-(2-(2-(3-(trifluoromethyl)azetidin-1-yl)pyrimidin-5-yl)pyrimidin-4-yl)acetamide (7.0 mg, 5.6%) as a white solid. $^1$H NMR (DMSO-$d_6$) δ 9.22 (s, 2H), 8.71 (d, J=6.0 Hz, 1H), 8.08 (s, 1H), 7.81 (d, J=4.8 Hz, 1H), 7.83 (s, 1H), 5.36 (s, 2H), 4.39-4.44 (m, 2H), 4.12-4.17 (m, 2H), 3.76-3.78 (m, 1H), 3.45 (s, 3H), 3.21 (s, 3H). MH$^+$ 517.

Example 13 (S)-2-(1,3-dimethyl-2,6-dioxo-2,3-dihydro-1H-purin-7(6H)-yl)-N-(2'-(3-(trifluoromethyl)azetidin-1-yl)-2,5'-bipyrimidin-4-yl)propanamide

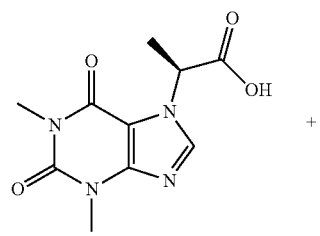

To a mixture of (S)-2-(1,3-dimethyl-2,6-dioxo-2,3-dihydro-1H-purin-7(6H)-yl)propanoic acid (85 mg, 0.34 mmol) and 2'-(3-(trifluoromethyl)azetidin-1-yl)-2,5'-bipyrimidin-4-amine (100 mg, 0.34 mmol) in DCM (3 mL) was added HOAT (46 mg, 0.34 mmol) at RT. The reaction was cooled to 0° C. Sequentially pyridine (54 mg, 0.68 mmol) and DIC (64 mg, 0.51 mmol) were slowly added dropwise. The reaction was warmed to 30° C. and stirred 18 h. The reaction was washed with water (5 mL), and saturated $NH_4Cl$ (5 mL). The organic phase was dried over $Na_2SO_4$ and concentrated. The residue was purified by chromatography eluting with PE:EA (1:1) to afford (S)-2-(1,3-dimethyl-2,6-dioxo-2,3-dihydro-1H-purin-7(6H)-yl)-N-(2'-(3-(trifluoromethyl)azetidin-1-yl)-2,5'-bipyrimidin-4-yl)propanamide (60 mg, 33.3%) as a white solid. ¹H NMR (DMSO-d₆) δ 11.49 (s, 1H), 9.22 (s, 2H), 8.70 (d, J=6.0 Hz, 1H), 8.34 (s, 1H), 7.84 (d, J=6.0 Hz, 1H), 5.81 (q, J=8.0 Hz 1H), 4.42 (t, J=8.8 Hz, 2H), 4.13-4.17 (m, 2H), 3.75-3.78 (m, 1H), 3.45 (s, 3H), 3.18 (s, 3H), 1.87 (d, J=8.8 Hz, 3H), MH⁺ 531.

Example 14 (S)—N-(2'-(4,4-difluoropiperidin-1-yl)-2,5'-bipyrimidin-4-yl)-2-(1,3-dimethyl-2,6-dioxo-2,3-dihydro-1H-purin-7(6H)-yl)propanamide

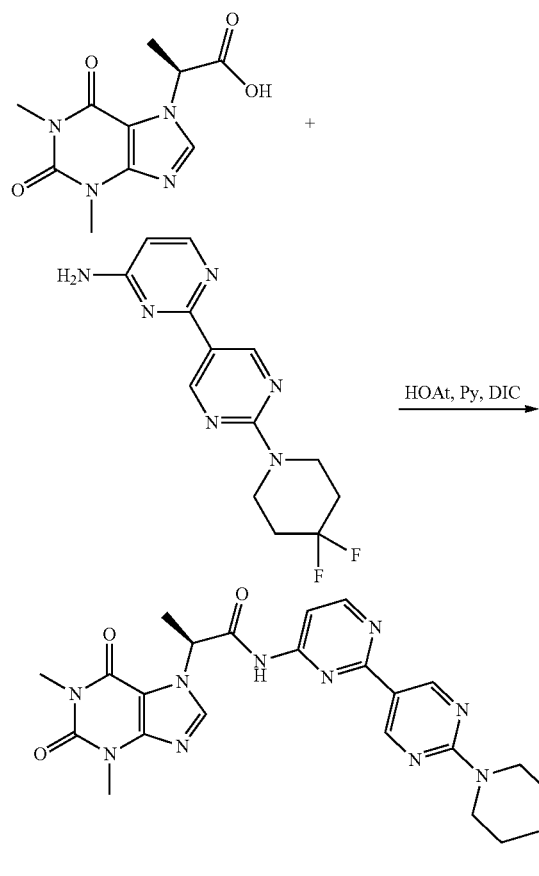

To a solution of (S)-2-(1,3-dimethyl-2,6-dioxo-2,3-dihydro-1H-purin-7(6H)-yl) propanoic acid (50 mg, 0.2 mmol) and 2'-(4,4-difluoropiperidin-1-yl)-2,5'-bipyrimidin-4-amine (58 mg, 0.2 mmol) in DCM (3 mL) was added HOAT (27 mg, 0.2 mmol) at RT. The reaction was cooled to 0° C. Sequentially pyridine (32 mg, 0.4 mmol) and then DIC (38 mg, 0.3 mmol) were added slowly dropwise. The reaction was warmed to 30° C. for 18 h. The reaction was extracted with water (5 mL), and saturated NH₄Cl (5 mL). The organic phase was dried over Na₂SO₄ and concentrated. The residue was purified via preparative TLC eluting with PE:EtOAc (1:1) to afford (S)—N-(2'-(4,4-difluoropiperidin-1-yl)-2,5'-bipyrimidin-4-yl)-2-(1,3-dimethyl-2,6-dioxo-2,3-dihydro-1H-purin-7(6H)-yl)propanamide (15 mg, 14.3%) as a white solid. ¹H NMR (DMSO-d₆) δ 9.22 (s, 2H), 8.70 (d, J=5.6 Hz, 1H), 8.34 (s, 1H), 7.83 (d, J=5.6 Hz, 1H), 5.81 (q, J=6.8 Hz 1H), 4.02 (t, J=5.6 Hz, 4H), 3.54 (s, 3H), 3.21 (s, 3H), 2.01-2.10 (m, 4H), 1.87 (d, J=6.8 Hz, 3H). MH⁺ 527.2.

Example 15 (2S)—N-(2'-(3-azabicyclo[3.1.0]hexan-3-yl)-2,5'-bipyrimidin-4-yl)-2-(1,3-dimethyl-2,6-dioxo-2,3-dihydro-1H-purin-7(6H)-yl)propanamide

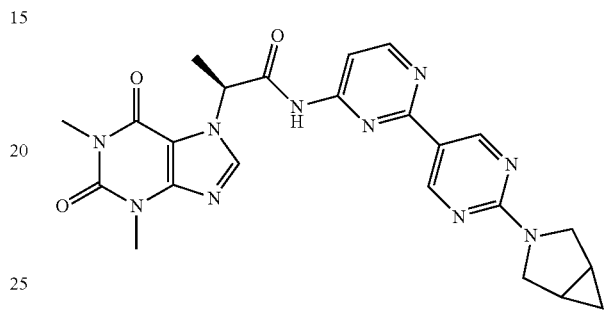

The title compound was prepared following the method of Example 14 with 20.7% yield as a white solid. ¹H NMR (DMSO-d₆) δ 11.42 (s, 1H), 9.16 (s, 2H), 8.66 (d, J=5.6 Hz, 1H), 8.33 (s, 1H), 7.79 (d, J=5.6 Hz, 1H), 5.81 (q, J=7.2 Hz 1H), 3.86 (d, J=11.2 Hz, 2H), 3.57 (d, J=11.6 Hz, 2H), 3.41 (s, 3H), 3.17 (s, 3H), 1.86 (d, J=7.6 Hz, 3H), 1.70 (t, J=3.6 Hz, 2H), 0.75-0.80 (m, 1H), 0.15-0.18 (m, 1H). MH⁺ 489.

Example 16 (2S)-2-(1,3-dimethyl-2,6-dioxo-2,3-dihydro-1H-purin-7(6H)-yl)-N-(2'-(3-(trifluoromethyl)pyrrolidin-1-yl)-2,5'-bipyrimidin-4-yl)propanamide

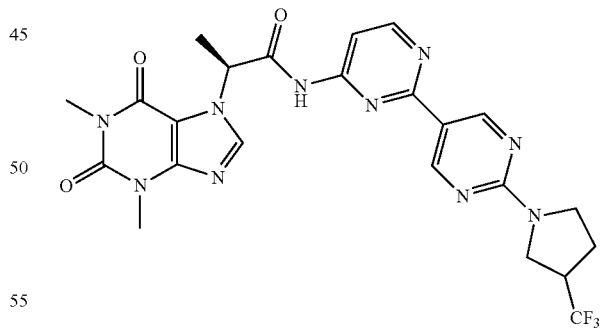

The title compound was prepared following the method of Example 14 with 39.1% yield as a white solid. ¹H NMR (DMSO-d₆) δ 11.46 (s, 1H), 9.22 (s, 2H), 8.69 (d, J=5.6 Hz, 1H), 8.34 (s, 1H), 7.81 (d, J=5.6 Hz, 1H), 5.82 (q, J=7.2 Hz, 1H), 3.88-3.94 (m, 1H), 3.69-3.78 (m, 1H), 3.62-3.67 (m, 2H), 3.50 (s, 3H), 3.43-3.49 (m, 1H), 3.20 (s, 3H), 2.30-2.35 (m, 2H), 2.12-2.17 (m, 1H), 1.87 (t, J=7.2 Hz, 3H). MH⁺ 545.2.

Example 17 (S)-2-(1,3-dimethyl-2,6-dioxo-2,3-dihydro-1H-purin-7(6H)-yl)-N-(2'-(2-methylpiperidin-1-yl)-2,5'-bipyrimidin-4-yl)acetamide

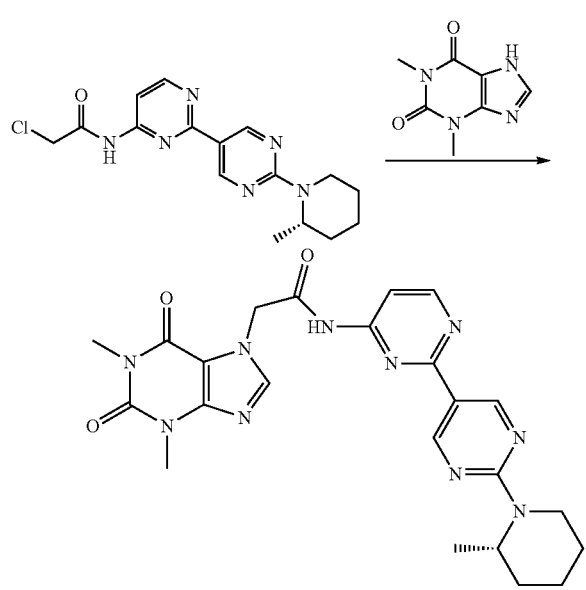

To a solution of 1,3-dimethyl-1H-purine-2,6(3H,7H)-dione (208 mg, 1.16 mmol) in DMF (8 mL) was added K$_2$CO$_3$ (320 mg, 2.32 mmol) and (S)-2-chloro-N-(2'-(2-methylpiperidin-1-yl)-2,5'-bipyrimidin-4-yl)acetamide (400 mg, 1.16 mmol). The reaction was stirred at RT for 1 h; then poured into ice-water. The solid precipitate was collected and triturated with MeOH to afford (S)-2-(1,3-dimethyl-2,6-dioxo-2,3-dihydro-1H-purin-7(6H)-yl)-N-(2'-(2-methylpiperidin-1-yl)-2,5'-bipyrimidin-4-yl)acetamide (220 mg, 45.5%) as a white solid. $^1$H NMR (DMSO-d$_6$) δ 11.38 (s, 1H), 9.17 (s, 2H), 8.68 (d, J=5.6 Hz, 1H), 8.07 (s, 1H), 7.75 (s, 1H), 5.36 (s, 2H), 5.12-5.14 (m, 1H), 4.67-4.71 (m, 1H), 3.45 (s, 3H), 3.19 (s, 3H), 3.00 (t, J=12 Hz, 1H), 1.57-1.75 (m, 5H), 1.22-1.40 (m, 1H), 1.19 (d, J=8 Hz, 3H). MH$^+$ 491.

Example 18 2-(1,3-dimethyl-2,6-dioxo-2,3-dihydro-1H-purin-7(6H)-yl)-N-(2'-(2,2-dimethylpyrrolidin-1-yl)-2,5'-bipyrimidin-4-yl)acetamide

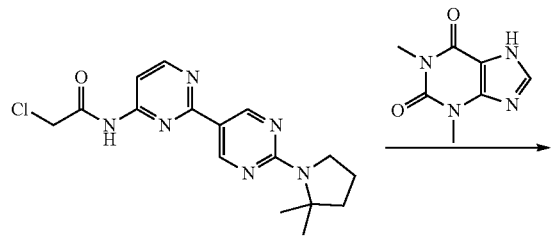

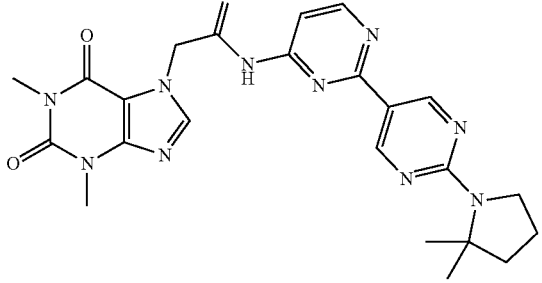

The title compound was prepared using the method of Example 17 with 43.1% yield as a white solid. $^1$H NMR (CDCl$_3$) δ 9.59 (s, 1H), 9.19 (s, 2H), 8.60 (d, J=5.2 Hz, 1H), 7.77 (s, 2H), 5.18 (s, 2H), 3.77 (t, J=6.4 Hz, 2H), 3.64 (s, 3H), 3.47 (s, 3H), 1.94-1.98 (m, 4H), 1.604 (s, 6H). MH$^+$ 491.

Example 19 (S)-2-(1,3-dimethyl-2,6-dioxo-2,3-dihydro-1H-purin-7(6H)-yl)-N-(2'-(2-methylpyrrolidin-1-yl)-2,5'-bipyrimidin-4-yl)acetamide

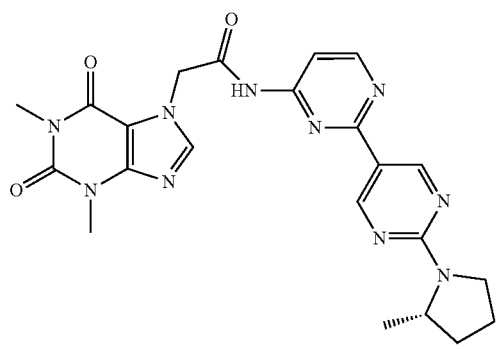

The title compound was prepared using the method of Example 17 with 46.7% yield as a white solid. $^1$H NMR (DMSO-d$_6$) δ 11.38 (s, 1H), 9.18 (s, 2H), 8.68 (d, J=5.2 Hz, 1H), 8.09 (s, 1H), 7.78 (s, 1H), 5.37 (s, 2H), 4.32 (t, J=5.2 Hz, 1H), 3.54-3.68 (m, 2H), 3.47 (s, 3H), 3.20 (s, 3H), 1.71-2.11 (m, 4H), 1.24 (d, J=6.4 Hz, 3H). MH$^+$ 477.

Example 20 2-(1,3-dimethyl-2,6-dioxo-2,3-dihydro-1H-purin-7(6H)-yl)-N-(2'-((S)-2-methylpyrrolidin-1-yl)-2,5'-bipyrimidin-4-yl)propanamide

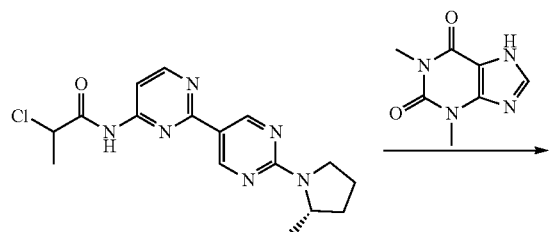

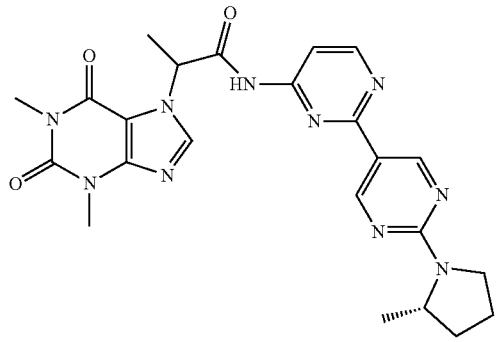

To a solution of 1,3-dimethyl-1H-purine-2,6(3H,7H)-dione (312 mg, 1.73 mmol) in DMF (8 mL) was added K$_2$CO$_3$ (477 mg, 3.46 mmol), 2-chloro-N-(2'-((S)-2-methylpyrrolidin-1-yl)-2,5'-bipyrimidin-4-yl)propanamide (600 mg, 1.73 mmol). The reaction was stirred at RT for 1 h; then poured into ice water. The solid precipitate was collected and washed with MeOH to afford 2-(1,3-dimethyl-2,6-dioxo-2,3-dihydro-1H-purin-7(6H)-yl)-N-(2'-((S)-2-methylpyrrolidin-1-yl)-2,5'-bipyrimidin-4-yl)propanamide (130 mg, 16%) as a white solid. $^1$H NMR (DMSO-d$_6$) δ 11.43 (s, 1H), 9.18 (s, 2H), 8.67 (d, J=5.6 Hz, 1H), 8.34 (s, 1H), 7.78 (d, J=5.6 Hz, 1H), 5.82 (d, J=7.2 Hz, 1H), 4.31 (t, J=5.2 Hz, 1H), 3.53-3.68 (m, 2H), 3.46 (s, 3H), 3.19 (s, 3H), 1.71-2.19 (m, 7H), 1.23 (d, J=6.4 Hz, 3H). MH$^+$ 491.

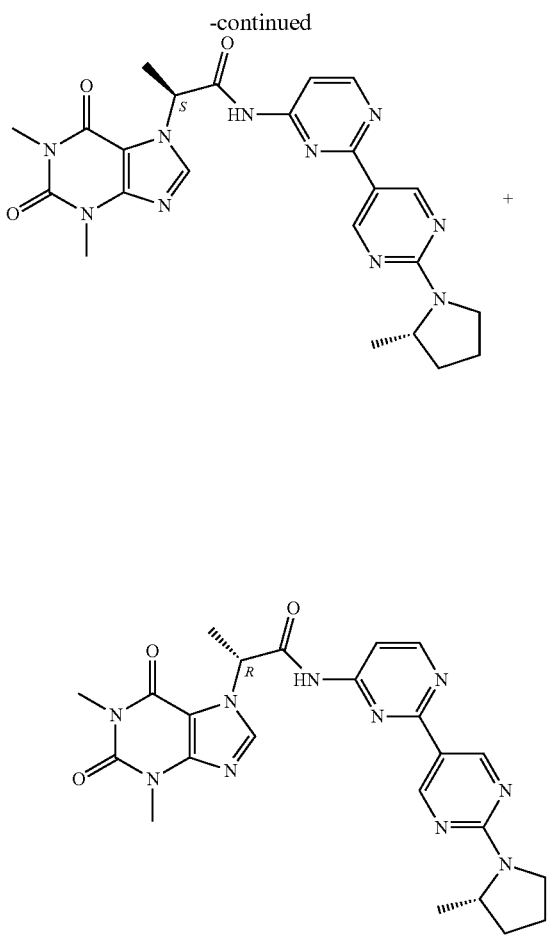

The diastereomeric product mixture from Example 20 was separated by supercritical fluid chromatography with a chiral column* to obtain (S)-2-(1,3-dimethyl-2,6-dioxo-2,3-dihydro-1H-purin-7(6H)-yl)-N-(2'-((S)-2-methylpyrrolidin-1-yl)-[2,5'-bipyrimidin]-4-yl)propanamide as colorless liquid (retention time 6.0 min). MH$^+$ 491.

* The chiral HPLC separation conditions 2.1×25.0 cm ChiralPak IC from Chiral Technologies (West Chester, Pa.), with 50% supercritical carbon dioxide and 50% of a 2:1:1 mixture of DCM:Hexane:Isopropanol at a flow rate of 80 mL/min.

Example 21 (S)-2-(1,3-dimethyl-2,6-dioxo-2,3-dihydro-1H-purin-7(6H)-yl)-N-(2'-((S)-2-methylpyrrolidin-1-yl)-[2,5'-bipyrimidin]-4-yl)propanamide

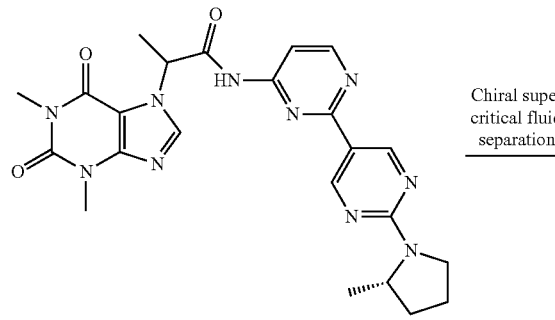

Chiral super critical fluid separation →

Example 22 (R)-2-(1,3-dimethyl-2,6-dioxo-2,3-dihydro-1H-purin-7(6H)-yl)-N-(2'-((S)-2-methylpyrrolidin-1-yl)-[2,5'-bipyrimidin]-4-yl)propanamide

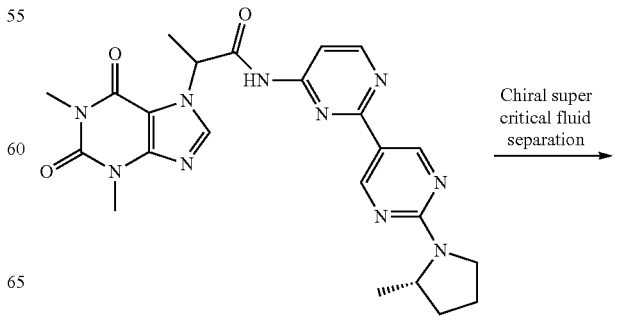

Chiral super critical fluid separation →

-continued

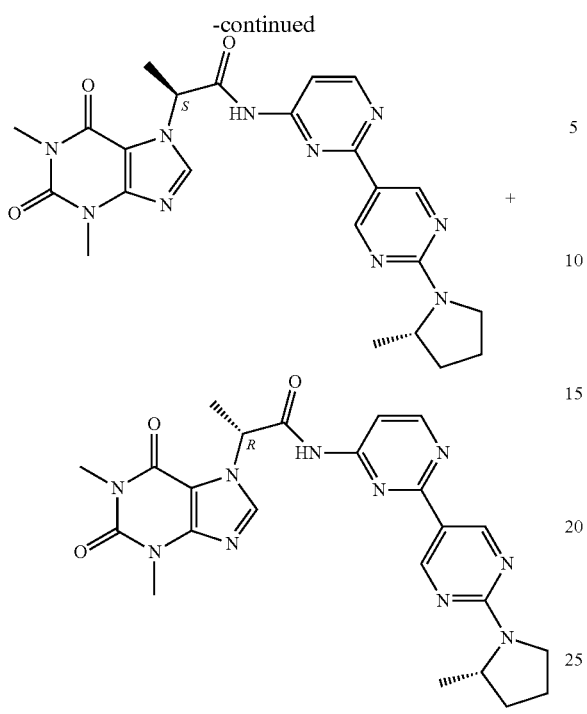

The diastereomeric product mixture from Example 20 was separated by supercritical fluid chromatography with a chiral column* to obtain (R)-2-(1,3-dimethyl-2,6-dioxo-2,3-dihydro-1H-purin-7(6H)-yl)-N-(2'-((S)-2-methylpyrrolidin-1-yl)-[2,5'-bipyrimidin]-4-yl)propanamide as colorless liquid (retention time 4.8 min). MH+ 491.

* The chiral HPLC separation conditions 2.1×25.0 cm ChiralPak IC from Chiral Technologies (West Chester, Pa.), with 50% supercritical carbon dioxide and 50% of a 2:1:1 mixture of DCM:Hexane:Isopropanol at a flow rate of 80 mL/min.

Example 23 2-(1,3-dimethyl-2,6-dioxo-2,3-dihydro-1H-purin-7(6H)-yl)-N-(2'-((S)-2-methylpiperidin-1-yl)-2,5'-bipyrimidin-4-yl)propanamide

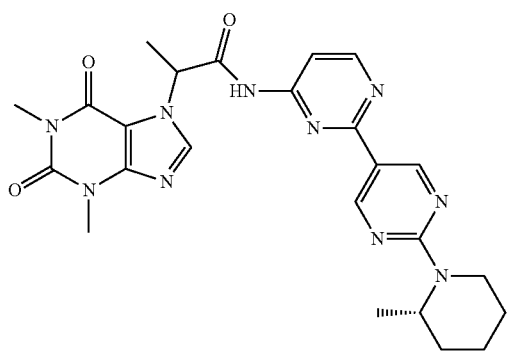 [SMILES: CC(C(=O)Nc1ccnc(-c2cnc(N3CCCC[C@@H]3C)nc2)n1)n1cnc2c1c(=O)n(C)c(=O)n2C]

The title product was prepared using the methods of Preparation 26 and Example 20 with 28.3% yield as a white solid. $^1$H NMR (CDCl$_3$) δ 9.73 (d, J=6.4 Hz, 1H), 9.17 (s, 2H), 8.56 (d, J=5.6 Hz, 1H), 7.86 (d, J=7.6 Hz, 1H) 7.79 (d, J=4 Hz, 1H), 5.76 (d, J=6.4 Hz, 1H), 4.76 (d, J=12.4 Hz, 1H), 3.60 (s, 3H), 3.47 (s, 3H), 3.02 (t, J=12 Hz, 1H), 1.90 (d, J=7.2 Hz, 3H), 1.48-1.78 (m, 6H), 1.23 (d, J=6.4 Hz, 3H). MH+ 505.

Example 24 (S)-2-(3-methyl-2,6-dioxo-2,3-dihydro-1H-purin-7(6H)-yl)-N-(2'-(2-methylpyrrolidin-1-yl)-[2,5'-bipyrimidin]-4-yl)acetamide

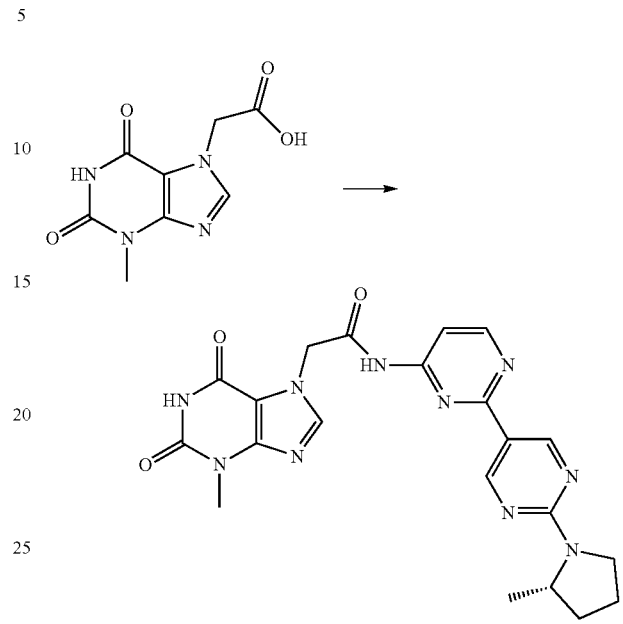

(S)-2'-(2-methylpyrrolidin-1-yl)-2,5'-bipyrimidin-4-amine (249 mg, 0.971 mmol), 2-(3-methyl-2,6-dioxo-2,3-dihydro-1H-purin-7(6H)-yl)acetic acid (436 mg, 1.943 mmol) and EDC (745 mg, 3.89 mmol) were added to pyridine (2.43 mL). The reaction was stirred 2 days at RT. The reaction was concentrated and the residue was purified by chromatography to afford (S)-2-(3-methyl-2,6-dioxo-2,3-dihydro-1H-purin-7(6H)-yl)-N-(2'-(2-methylpyrrolidin-1-yl)-[2,5'-bipyrimidin]-4-yl)acetamide (50 mg, 11%) as colorless liquid. MH+ 463.

Example 25 N-{2-[2-((2S)-2-methylpyrrolidinyl)pyrimidin-5-yl]pyrimidin-4-yl}-2-(1-methyl-3-methyl-d3-2,6-dioxo(1,3,7-trihydropurin-7-yl))acetamide

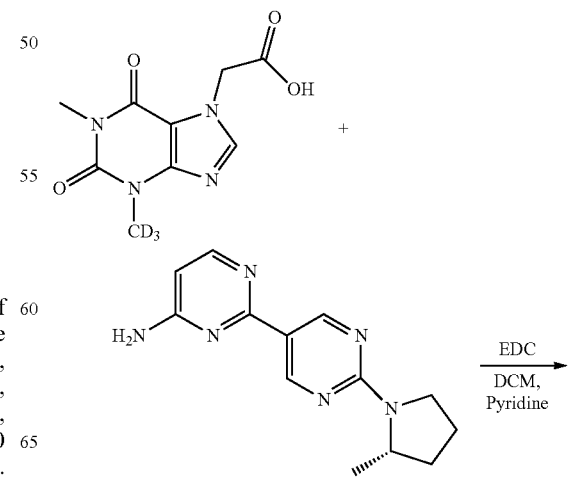

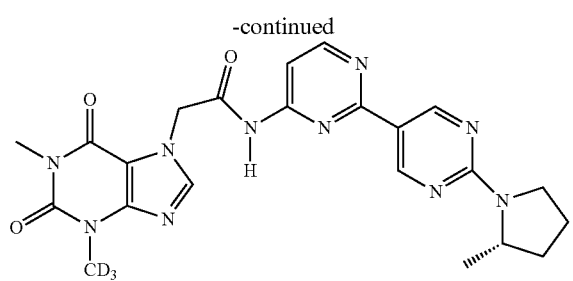

A mixture of 2-(1-methyl-3-methyl-d3-2,6-dioxo-2,3-dihydro-1H-purin-7(6H)-yl)acetic acid (0.200 g, 0.829 mmol), (S)-2'-(2-methylpyrrolidin-1-yl)-[2,5'-bipyrimidin]-4-amine (0.213 g, 0.829 mmol) and EDC (0.318 g, 1.658 mmol) was dissolved in pyridine (4.15 mL) at RT. The reaction was stirred overnight and then diluted with water. The reaction was extracted three times with EA. The organic phase was dried over MgSO$_4$ and concentrated. The residue was purified by chromatography to afford N-{2-[2-((2S)-2-methylpyrrolidinyl)pyrimidin-5-yl]pyrimidin-4-yl}-2-(1-methyl-3-methyl-d3-2,6-dioxo(1,3,7-trihydropurin-7-yl))acetamide (66.1 mg 17%) as colorless liquid. MH$^+$ 480.

Example 26 ((2S)—N-(2-(2-(3-azabicyclo[3.1.0]hexan-3-yl)pyramidin-5-yl)thiazol-4-yl)-2-(3-methyl-2,6-dioxo-1-(2-oxobutyl)-2,3-dihydro-1H-purin-7(6H)-yl)propanamide

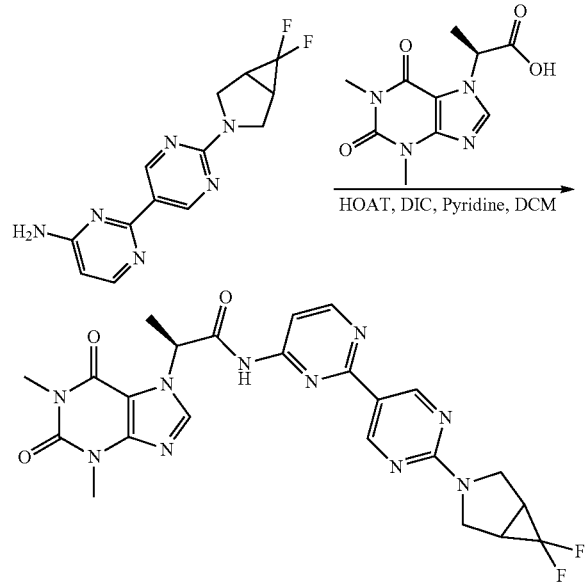

The title compound was prepared using the method of Example 14 in 8% yield as a white solid. $^1$H NMR (DMSO$_{d6}$) δ 11.47 (s, 1H), 9.20 (s, 2H), 8.69 (d, J=5.1 Hz, 1H), 8.35 (s, 1H), 7.82 (d, J=5.1 Hz, 1H), 5.83 (s, 1H), 4.01 (d, J=12.0 Hz, 2H), 3.87 (d, J=11.0 Hz, 2H), 3.46 (s, 3H), 3.18 (s, 3H), 2.71 (d, J=11.5 Hz, 2H), 1.87 (d, J=6.6 Hz, 3H). MH$^+$ 525.

Example 27 (S)-2-(1,3-dimethyl-2,6-dioxo-2,3-dihydro-1H-purin-7(6H)-yl)-N-(2'-(2-(trifluoromethyl)pyrrolidin-1-yl)-[2,5'-bipyrimidin]-4-yl)acetamide

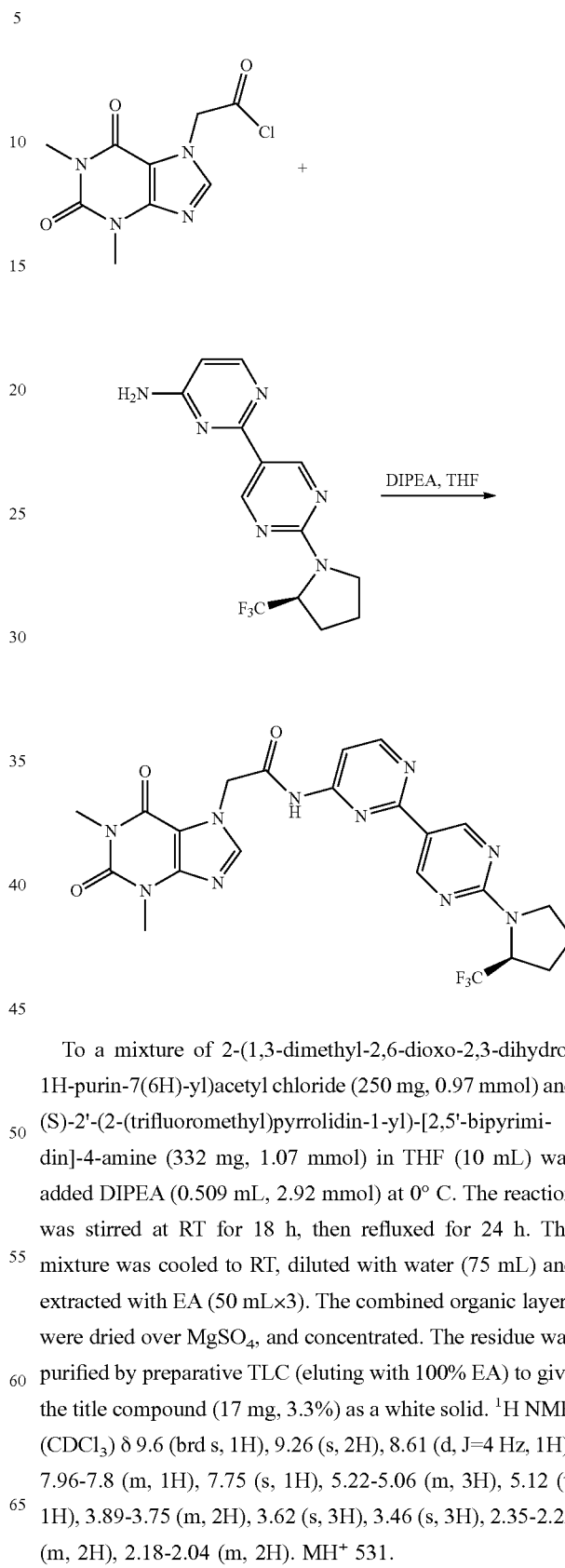

To a mixture of 2-(1,3-dimethyl-2,6-dioxo-2,3-dihydro-1H-purin-7(6H)-yl)acetyl chloride (250 mg, 0.97 mmol) and (S)-2'-(2-(trifluoromethyl)pyrrolidin-1-yl)-[2,5'-bipyrimidin]-4-amine (332 mg, 1.07 mmol) in THF (10 mL) was added DIPEA (0.509 mL, 2.92 mmol) at 0° C. The reaction was stirred at RT for 18 h, then refluxed for 24 h. The mixture was cooled to RT, diluted with water (75 mL) and extracted with EA (50 mL×3). The combined organic layers were dried over MgSO$_4$, and concentrated. The residue was purified by preparative TLC (eluting with 100% EA) to give the title compound (17 mg, 3.3%) as a white solid. $^1$H NMR (CDCl$_3$) δ 9.6 (brd s, 1H), 9.26 (s, 2H), 8.61 (d, J=4 Hz, 1H), 7.96-7.8 (m, 1H), 7.75 (s, 1H), 5.22-5.06 (m, 3H), 5.12 (t, 1H), 3.89-3.75 (m, 2H), 3.62 (s, 3H), 3.46 (s, 3H), 2.35-2.22 (m, 2H), 2.18-2.04 (m, 2H). MH$^+$ 531.

Example 28 (R)-2-(1,3-dimethyl-2,6-dioxo-2,3-dihydro-1H-purin-7(6H)-yl)-N-(2'-((R)-2-(trifluoromethyl)pyrrolidin-1-yl)-[2,5'-bipyrimidin]-4-yl)propanamide

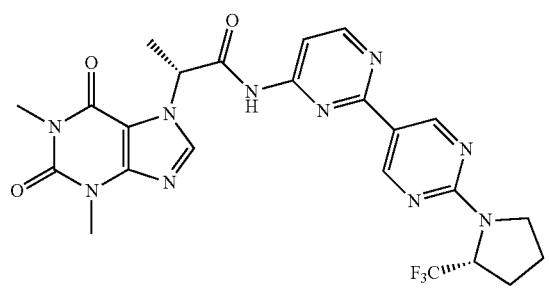 [SMILES: C[C@H](C(=O)Nc1ccnc(-c2cnc(N3CCC[C@@H]3C(F)(F)F)nc2)n1)n1cnc2c1c(=O)n(C)c(=O)n2C]

The title compound was prepared using the method of Example 2 to yield the title compound as a white solid. $^1$H NMR (DMSO-d$_6$) δ 11.46 (s, 1H), 9.22 (s, 2H), 8.66 (d, J=5.6 Hz, 1H), 8.31 (s, 1H), 7.81 (d, J=5.6 Hz, 1H), 5.82 (q, J=7.2 Hz 1H), 5.12 (t, 1H), 3.70 (m, 2H), 3.47 (s, 3H), 3.16 (s, 3H), 2.10 (m, 4H), 1.88 (d, J=7.2 Hz, 3H). MH$^+$ 545

Example 29 Process Scale Synthesis of (S)-2-(1,3-dimethyl-2,6-dioxo-2,3-dihydro-1H-purin-7(6H)-yl)-N-(2'-((S)-2-(trifluoromethyl)pyrrolidin-1-yl)-[2,5'-bipyrimidin]-4-yl)propanamide

Step 1 (R)-Methyl 2-(((trifluoromethyl)sulfonyl)oxy)propanoate

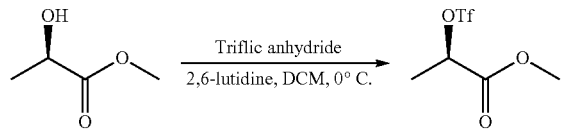

A 50 L reactor under a nitrogen atmosphere was charged with methylene chloride (30 L) and agitated. (R)-methyl lactate (1.44 kg, 13.83 mol) was added, followed by 2,6-lutidine (1.56 kg, 14.56 mol). The stirred mixture was cooled to −5 to 5° C. using a dry-ice/acetone bath. The reactor was carefully charged with trifluoromethane sulfonic anhydride (3.9 kg, 13.83 mol) using a peristaltic pump while maintaining the internal temperature between −5 and 5° C. This addition required more than 1 h. After addition was complete, the reaction was stirred 1 h more while maintaining the temperature between 0 and 5° C. The reaction was carefully quenched with deionized water (10 L) and vigorous stirring was continued 1 min longer. Stirring was stopped and the phases were allowed to separate. The bottom (methylene chloride) layer containing the product, was transferred to a holding container while the reactor was cleaned successively with acetone (2×10 L) and then methylene chloride (2×10 L). The intermediate triflate was used directly without purification.

Step 2 Methyl (S)-2-(1,3-dimethyl-2,6-dioxo-2,3-dihydro-1H-purin-7(6H)-yl)propanoate

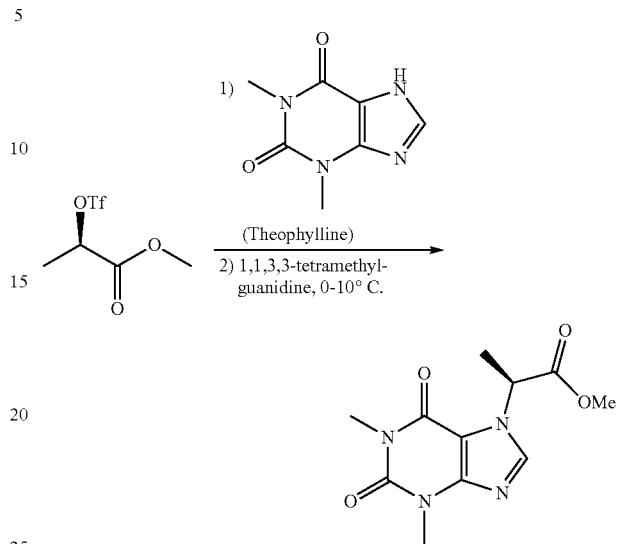

The methylene chloride product solution of R-Methyl 2-(((trifluoromethyl)sulfonyl)-oxy)propanoate was charged back to the clean 50 L reactor and the mixture was placed under a nitrogen atmosphere. The mixture was cooled with stirring to 0 to 5° C. with a dry ice/acetone bath. During cooling theophylline (2.0 kg, 11.1 mol) was charged to the reactor. 1,1,3,3-Tetramethylguanidine (1.34 kg, 11.66 mol) was slowly added to the reactor via peristaltic pump while maintaining the internal temperature below 10° C. After the addition was complete, the reaction was stirred for at least 1 h while maintaining the reaction temperature at 0 to 10° C. An aliquot taken after 30 min was tested by HPLC and confirmed the reaction was complete. Ice-cold 0.2N HCl (10 L) was added to the reactor to quench the reaction. The mixture was stirred vigorously for 1-2 min. Stirring was stopped and the phases were allowed to separate. The bottom methylene chloride product layer was transferred to a holding container. The upper aqueous layer was removed and discarded. The bottom methylene chloride layer was added back to the reactor and it was extracted with 5% aqueous NaHCO$_3$ (10 L) with vigorous stirring for 1-2 min. Stirring was stopped and the phases were allowed to separate. The bottom product layer was transferred to a holding container. The upper aqueous layer was removed and discarded. The bottom methylene chloride layer was added back to the reactor. Deionized water (10 L) was added to the reactor. The mixture was stirred vigorously for 1 min. Stirring was stopped and the phases were allowed to separate. The bottom product layer was transferred to a holding container. The upper aqueous layer was removed and discarded. The methylene chloride product-containing solution was transferred to a rotary evaporator and concentrated under vacuum (bath temperature 30-40° C.) until most of the methylene chloride distilled leaving crude methyl (S)-2-(1,3-dimethyl-2,6-dioxo-2,3-dihydro-1H-purin-7(6H)-yl)propanoate as a dark viscous syrup. HPLC analysis of a sample confirmed the product and its purity.

Step 3 (S)-2-(1,3-Dimethyl-2,6-dioxo-2,3-dihydro-1H-purin-7(6H)-yl)propanoic acid

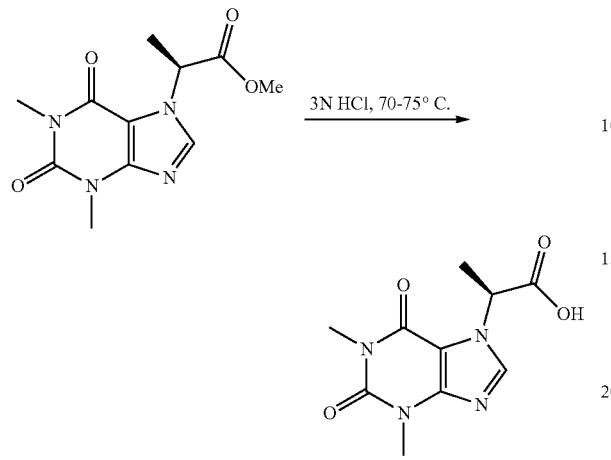

Methyl (S)-2-(1,3-dimethyl-2,6-dioxo-2,3-dihydro-1H-purin-7(6H)-yl)propanoate (7.16 kg, crude syrup from two batches from Steps 1 and 2) was transferred to a rotary evaporator bulb. Vacuum was applied and the bulb was rotated with a bath temperature of 30-40° C. until no more methylene chloride was distilled. Separately, a solution of 3N aqueous HCl (32 L, 4.5 equiv, based on 4 kg of theophylline) was prepared. The residue from the rotary evaporator bulb was transferred to a 50 L reactor. The bulb was rinsed with small portions of 3N HCl to remove all crude ester and transferred to the reactor, and the remaining 3N HCl was charged to the reactor. The reaction mixture was heated at 70-75° C. for at least 16 h. The reaction status at 16 h was checked by HPLC analysis of a small aliquot, and was deemed complete when the amount of ester was less than 10% compared to the acid product. The mixture was allowed to cool to room temperature with stirring for at least 16 h. The product was collected on a Buchner funnel and the solids were washed with ice-cold deionized water (2×2 L). The solids were dried on the vacuum funnel overnight until the mixture became a free-flowing solid (2.95 Kg). The crude product was 93.8% pure by HPLC analysis.

A portion of the crude (S)-2-(1,3-dimethyl-2,6-dioxo-2,3-dihydro-1H-purin-7(6H)-yl)propanoic acid (1 kg) was charged into a 22 L reactor. Deionized water (9 L, 9 volumes) was added to the reactor and stirring was started. The slurry was heated to 95° C. and held at that temperature until all the solids dissolved. A slurry of 40 g (4% by wt.) of Norite® activated carbon in 250 mL of deionized water was added to the hot mixture and stirring was continued at 90-95° C. for 1 h. The hot mixture was carefully transferred from the 22 L vessel through a filter funnel containing a glass microfiber filter into a clean 50 L reactor. This process was repeating two more times with 1 kg of the crude acid, each time filtering into the same 50 L reactor. The reactor was allowed to cool to below 30° C. with stirring. The solids were filtered and the product was washed with ice-cold deionized water (2×2 L). The product was dried at least 12 h on the filter funnel, then it was transferred to a vacuum oven and dried to a constant weight to afford (S)-2-(1,3-dimethyl-2,6-dioxo-2,3-dihydro-1H-purin-7(6H)-yl)propanoic acid (2.25 kg). The purified product was 99.31% pure by HPLC and had an enantiomeric purity of 100% by chiral HPLC. The overall yield of pure (S)-2-(1,3-dimethyl-2,6-dioxo-2,3-dihydro-1H-purin-7(6H)-yl)propanoic acid based on the theophylline starting material was 42.4%.

Step 4 (S)-5-bromo-2-(2-(trifluoromethyl)pyrrolidin-1-yl)pyrimidine

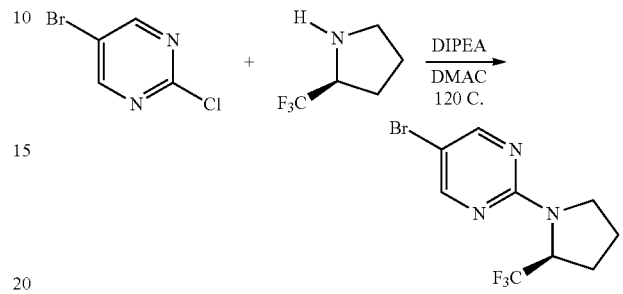

To a reaction vessel equipped with mechanical stirring, reflux condenser, nitrogen inlet, thermocouple, and an external heating mantle was charged with (S)-2-trifluoromethylpyrrolidine (1598 g, 11.49 mol), 5-bromo-2-chloropyrimidine (2000 g, 10.34 mol) and N,N-dimethylacetamide (9 L). The stirred mixture was warmed to 50° C. When the mixture became a solution, diisopropylethylamine (1633 g, 12.64 mol) was added and the reaction temperature was increased to 120° C. The reaction is stirred for 24-48 h until the reaction is complete by HPLC. The reaction is cooled to no less than 70° C. and the contents are transferred to a second stirred vessel containing water (90 L). This mixture was stirred and allowed to cool to 20° C., then further cooled to 5 to 10° C. and held at this temperature for 2 h. The solid product is collected by filtration and washed with cold water (3×5 L) The product was dried under vacuum at 50° C. to constant weight to afford (S)-5-bromo-2-(2-(trifluoromethyl)pyrrolidin-1-yl)pyrimidine (2898 g, 94.6%) as a light brown solid that was ~99% pure by HPLC.

Step 5 (S)-5-(4,4,5,5-tetramethyl-1,3,2-dioxaborolan-2-yl)-2-(2-(trifluoromethyl)pyrrolidin-1-yl)pyrimidine

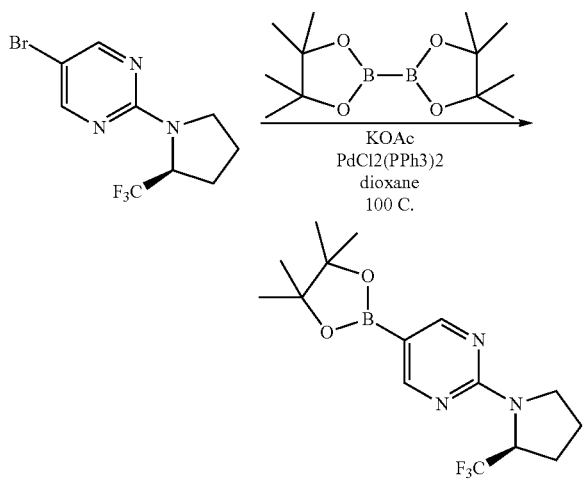

A reaction vessel equipped with mechanical stirring, reflux condenser, nitrogen inlet, thermocouple, and an external heating mantle was charged with dioxane (8 L) and gentle stirring was initiated. The reaction was charged with (S)-5-bromo-2-(2-(trifluoromethyl)pyrrolidin-1-yl)pyrimidine (1600 g, 5.40 mol), 4,4,4',4',5,5,5',5'-octamethyl-2,2'-bi(1,3,2-dioxaborolane) (2058 g, 8.11 mol), and potassium acetate (1059 g, 10.81 mol). Additional dioxane (17 L) was added and nitrogen gas was bubbled through the mixture. Bis-(triphenylphosphine) palladium chloride catalyst (113.7 g, 0.161 mol) was added to the reaction. The reaction was heated with nitrogen still bubbling through the mixture. When the reaction temperature reached 50° C., nitrogen was no longer bubbled through the mixture. However a nitrogen atmosphere was maintained, venting through the condenser. The reaction temperature was increased to 95 to 100° C. and maintained at this temperature until HPLC analysis indicated the reaction was complete, after about 16-24 h. The reaction was cooled to no less than 60° C., and transferred via peristaltic pump into a reactor containing 38 volumes of water. The transfer line was rinsed with 0.25 to 1.50 vol of dioxane. Additional water was added to the reactor when appropriate to facilitate product crystallization. The mixture was cooled to 10±5° C. and held for at least 1 hour. The product was collected in a Buchner funnel, washed with cold water (3×2 volumes), and dried under vacuum at 50-60° C. until a constant weight was achieved. (S)-5-(4,4,5,5-tetramethyl-1,3,2-dioxaborolan-2-yl)-2-(2-(trifluoromethyl)pyrrolidin-1-yl)pyrimidine was obtained as a light brown solid, 1964 g. This solid contained 12.7% water and was approximately 96% purity as determined by HPLC. The yield was estimated to be 1715 g, 91.4%. The material was suitable for further reaction without removal of residual water.

Step 6 (S)-2'-(2-(trifluoromethyl)pyrrolidin-1-yl)-[2,5'-bipyrimidin]-4-amine

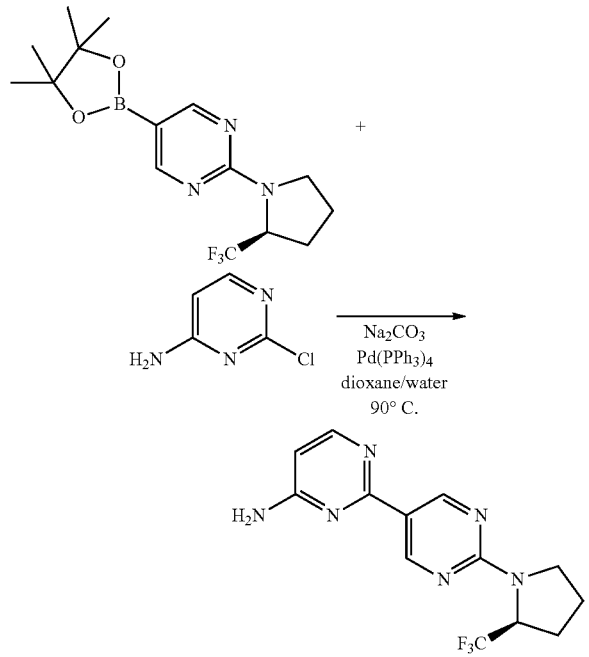

The wet (S)-5-(4,4,5,5-tetramethyl-1,3,2-dioxaborolan-2-yl)-2-(2-(trifluoromethyl)pyrrolidin-1-yl)pyrimidine (1964 g) from Step 5 was assayed for water content, and the stoichiometry was adjusted accordingly (1715 g, 5.0 mol). Dioxane (16 L) was added to a reaction vessel equipped with a heating mantle, thermocouple controller, nitrogen inlet, mechanical stirrer and reflux condenser. Compounds (S)-5-(4,4,5,5-tetramethyl-1,3,2-dioxaborolan-2-yl)-2-(2-(trifluoromethyl)pyrrolidin-1-yl)pyrimidine (corrected to 1715 g, 5.0 mol), 4-amino-2-chloropyrimidine (648 g, 5 mol) and sodium carbonate (962 g, 9.08 mol) were charged to the reaction vessel. Additional dioxane (8 L) is added. Nitrogen gas was bubbled through the solution for about 30-60 min., venting through the condenser. Tetrakis (triphenylphosphine) palladium (230 g 0.2 mol) was added, and the residual catalyst was rinsed into the reaction vessel with dioxane (1 L). Heating was started, and nitrogen bubbling was continued until the mixture reached about 50° C. At this time the nitrogen tube was retracted above the surface of the solution, but nitrogen the nitrogen atmosphere was maintained, venting through the condenser. The temperature was increased to 85-90° C. and maintained until the reaction was complete (1-4 h) as determined by HPLC. The reaction was cooled to no less than 60n ° C., and water (18 L) was added while maintaining temperature. The reaction mixture was filtered hot through GF-B glass fiber paper into a filter bottle. The filtrate was transferred while warm into a reactor, rinsing with 1:1 dioxane/water (0.5 to 3 L) as necessary, with the reactor jacket temperature set to 45° C. Water (36 L) was then added to the reactor, and the temperature was maintained during addition. The mixture was slowly cooled to 5±5° C., and additional water was added to the reactor as needed to maximize crystallization. The temperature was held for at 5±5° C. for at least 2 hours, after which the product was collected in a Buchner funnel and washed with cold water (3×3.5 L). The product was dried under vacuum at 50-60° C. until a constant weight was achieved to give (S)-2'-(2-(trifluoromethyl)pyrrolidin-1-yl)-[2,5'-bipyrimidin]-4-amine (1073 g, 70%) as an off-white solid.

A portion of this crude product (754 g, 2.43 mol) was slurried with 3N HCl (15 L) and filtered to remove impurities. The acidic solution was extracted with MTBE (4 L)) and heptane (4 L). These organic extracts were discarded to waste. The acidic solution was basified with 50% sodium hydroxide to pH 9-10. The mixture was cooled, and the precipitate collected by filtration. The solid was washed with cold water and dried under vacuum to yield an off-white solid, 695 g, 92% recovery. Residual palladium in this material was 782 ppm. This product was recrystallized from 50% aqueous acetonitrile (8 L). The mixture was cooled, and the product collected by filtration, rinsed with cold solvent and dried under vacuum to give 401.7 g (53% of the initial 754 g) of off-white solid, now with 181 ppm residual palladium. This off-white solid was dissolved in THF and treated with palladium scavenger SiliCycle® SiliaMetS® Thiol resin (25 g). The solvent was removed to give (S)-2'-(2-(trifluoromethyl)pyrrolidin-1-yl)-[2,5'-bipyrimidin]-4-amine as a white solid (390 g, 97% recovery) that was greater than 97% pure by HPLC and with less than 10 ppm residual palladium.

Step 7 (S)-2-(1,3-dimethyl-2,6-dioxo-2,3-dihydro-1H-purin-7(6H)-yl)-N-(2'-((S)-2-(trifluoromethyl)pyrrolidin-1-yl)-2,5'-bipyrimidin-4-yl)propanamide

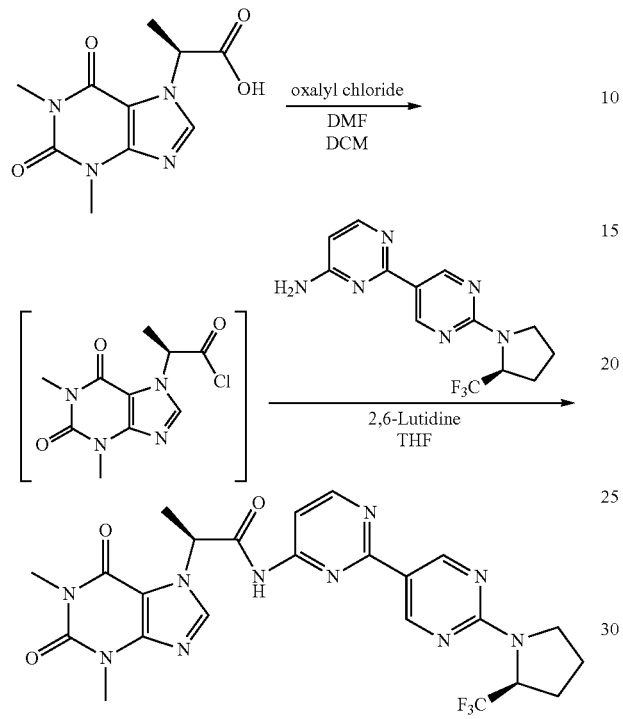

To a 100 L reactor with agitator, nitrogen inlet, and condenser was added dichloromethane (20 L), (S)-2-(1,3-dimethyl-2,6-dioxo-2,3-dihydro-1H-purin-7(6H)-yl)propanoic acid (1.0 kg, 3.96 mol) and N,N-dimethylformamide (14.5 mL, 0.2 mol). Additional dichloromethane (10 L) was added and the stirred mixture was chilled to 10-15° C. Oxalyl chloride (1.51 kg, 11.9 mol) was slowly added while maintaining the temperature below 25° C. The reaction was stirred 30-60 min at 25° C. The solvent was distilled from the reaction under vacuum and with a nitrogen bleed and the reactor jacket temperature increased to 35° C. as necessary. Additional dichloromethane (20 L) was added and the solvent was again distilled from the reaction. The addition and distillation of dichloromethane was repeated. Tetrahydrofuran (10 L) was added and this yielded a white to beige slurry. To the reaction was added (S)-2'-(2-(trifluoromethyl)pyrrolidin-1-yl)-[2,5'-bipyrimidin]-4-amine (1.07 kg, 3.45 mol) and the addition vessel was rinsed with tetrahydrofuran (1.5 L) into the reaction mixture. The reaction was cooled to ≤0° C. and 2,6-lutidine (0.964 L, 8.28 mol) was added, maintaining the reaction temperature below 5° C. The reaction was stirred at about 0° C. until it was considered complete by HPLC (about 2% of (S)-2'-(2-(trifluoromethyl)pyrrolidin-1-yl)-[2,5'-bipyrimidin]-4-amine remaining). After about 14 h, the reaction was carefully quenched with 0.2 N HCl (40 L) and water (20 L) while maintaining the reaction temperature below 15° C. The solid product was collected and washed with deionized water twice. The solids were dried to constant weight under vacuum at 50-60° C. to afford 1,473 g (78%) of (S)-2-(1,3-dimethyl-2,6-dioxo-2,3-dihydro-1H-purin-7(6H)-yl)-N-(2'-((S)-2-(trifluoromethyl)pyrrolidin-1-yl)-2,5'-bipyrimidin-4-yl)propanamide. This product material was combined with 1,435 g of product from a similar reaction and recrystallized from 2% aqueous ethanol (86.8 L) to yield 2,250 g of purified (S)-2-(1,3-dimethyl-2,6-dioxo-2,3-dihydro-1H-purin-7(6H)-yl)-N-(2'-((S)-2-(trifluoro-methyl)pyrrolidin-1-yl)-2,5'-bipyrimidin-4-yl)propanamide as an off-white solid.

Example 30 Telescoped synthesis of (S)-2'42-(trifluoromethyl)pyrrolidin-1-yl)-[2,5'-bipyrimidin]-4-amine from (S)-5-bromo-2-(2-(trifluoromethyl)pyrrolidin-1-yl)pyrimidine

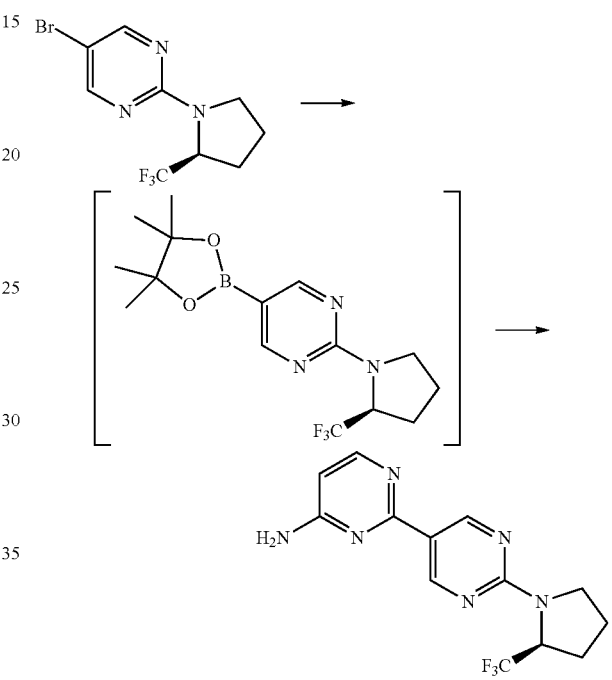

To a reaction vessel charged with dioxane (17.25 L) is added (S)-5-bromo-2-(2-(trifluoromethyl)pyrrolidin-1-yl)pyrimidine (1500 g, 5.066 mol), 4,4,4',4',5,5,5',5'-octamethyl-2,2'-bi(1,3,2-dioxaborolane) (1937 g, 7.628 mol), and potassium acetate (998 g, 10.17 mol). Additional dioxane (6.25 L) was added and nitrogen gas was bubbled through the mixture with gentle stirring for 30 to 60 min. Bis-(triphenylphosphine) palladium chloride catalyst (107 g, 0.152 mol) was added with a dioxane rinse (0.5 L), and the reaction was heated to 50° C. At this point, nitrogen was no longer bubbled through the mixture, although a nitrogen atmosphere was maintained, venting through the condenser. The reaction temperature was further increased to 95 to 100° C. and maintained at this temperature until the reaction was complete as indicated by HPLC analysis (about 24 h).

The reaction was then cooled to 60° C. and 4-amino-2-chloropyrimidine (623 g, 4.81 mol), sodium carbonate (975 g, 9.2 mol), and water (7.5 L) were added. Nitrogen gas was bubbled through the solution for about 30-60 min, venting through the condenser. Tetrakis (triphenylphosphine) palladium (129 g 0.11 mol) was added, and the residual catalyst was rinsed into the reaction vessel with dioxane (0.5 L). Heating was restarted, and nitrogen bubbling was continued until the mixture reached about 50° C. At this time the nitrogen tube was retracted above the surface of the solution, but the nitrogen atmosphere was maintained, venting through the condenser. The temperature was increased to 85-90° C. and maintained until the reaction was complete (1-24 h) as determined by HPLC. After cooling to no less than 60° C., water (15 L) was added while maintaining the temperature and the reaction mixture was filtered through GF-B glass fiber paper into a filter bottle. The filtrate was transferred while warm into a reactor, rinsing with 1:1 dioxane/water (0.5 to 3 L) as necessary, with the reactor jacket temperature set to 45° C. Water (42 L) was added to the reactor, and the mixture was slowly cooled to 5±5° C. Additional water was added to the reactor as needed to maximize crystallization, and the temperature was held at 5±5° C. for at least 2 hours. The product was then collected in a Buchner funnel, washed with cold water (3×3.5 L), then dried under vacuum at 50-60° C. until a constant weight was achieved to give (S)-2'-(2-(trifluoromethyl)pyrrolidin-1-yl)-[2,5'-bipyrimidin]-4-amine (1266 g, 70%) as an off-white solid. This product was purified as described in Example 29 (Step 7) to produce (S)-2'-(2-(trifluoromethyl)pyrrolidin-1-yl)-[2,5'-bipyrimidin]-4-amine with similar purity as described.

Characterization of Compounds of the Invention

Compounds of the invention are referred to herein by their respective example number. For example the compound produced by the method described in Example 1 may be referred to as "Compound of Example 1", "Example 1", or "Compound 1." All three names may be used herein interchangeably.

Example 31 Characterization of the Solid Crystalline Forms Obtained from Slurry Treatment of Compounds of Formula (I)

Certain compounds of the invention produced solvate crystalline forms after slurry treatment in a solvent or combination of solvents (e.g., water, ethanol, or a combination thereof). For example, Compound 2 produced a solvate crystalline form when slurried in ethanol or aqueous ethanol mixtures containing up to 3% water at room temperature, referred herein as Form A. The solid crystalline product obtained from the slurry was indexed using X-ray powder diffraction (XRPD) to define the unit cell (FIG. 1). The observed XPRD peaks are listed below in Table 1.

TABLE 1

Observed X-ray powder diffraction peaks from a solid crystalline form of Compound 2 (Form A) obtained from an ethanol slurry

| °2θ | d space (Å) | Intensity (%) |
|---|---|---|
| 5.71 ± 0.20 | 15.452 ± 0.540 | 16 |
| 6.13 ± 0.20 | 14.396 ± 0.469 | 27 |
| 7.67 ± 0.20 | 11.515 ± 0.300 | 86 |
| 8.75 ± 0.20 | 10.094 ± 0.230 | 15 |
| 9.05 ± 0.20 | 9.763 ± 0.215 | 8 |
| 9.58 ± 0.20 | 9.229 ± 0.192 | 33 |
| 10.62 ± 0.20 | 8.325 ± 0.156 | 23 |
| 11.73 ± 0.20 | 7.536 ± 0.128 | 10 |
| 12.31 ± 0.20 | 7.183 ± 0.116 | 13 |
| 12.52 ± 0.20 | 7.067 ± 0.112 | 56 |
| 12.91 ± 0.20 | 6.851 ± 0.106 | 9 |
| 13.12 ± 0.20 | 6.744 ± 0.102 | 7 |
| 13.49 ± 0.20 | 6.559 ± 0.097 | 100 |
| 13.81 ± 0.20 | 6.408 ± 0.092 | 14 |
| 14.12 ± 0.20 | 6.268 ± 0.088 | 36 |
| 14.95 ± 0.20 | 5.921 ± 0.079 | 17 |
| 15.40 ± 0.20 | 5.747 ± 0.074 | 19 |
| 16.10 ± 0.20 | 5.501 ± 0.068 | 19 |
| 16.44 ± 0.20 | 5.388 ± 0.065 | 13 |
| 16.60 ± 0.20 | 5.336 ± 0.064 | 19 |

TABLE 1-continued

Observed X-ray powder diffraction peaks from a solid crystalline form of Compound 2 (Form A) obtained from an ethanol slurry

| °2θ | d space (Å) | Intensity (%) |
|---|---|---|
| 17.36 ± 0.20 | 5.105 ± 0.058 | 8 |
| 17.59 ± 0.20 | 5.038 ± 0.057 | 12 |
| 17.85 ± 0.20 | 4.964 ± 0.055 | 12 |
| 18.90 ± 0.20 | 4.692 ± 0.049 | 28 |
| 19.31 ± 0.20 | 4.593 ± 0.047 | 55 |
| 19.69 ± 0.20 | 4.505 ± 0.045 | 13 |
| 19.88 ± 0.20 | 4.463 ± 0.044 | 14 |
| 20.33 ± 0.20 | 4.366 ± 0.043 | 15 |
| 20.55 ± 0.20 | 4.318 ± 0.042 | 13 |
| 20.86 ± 0.20 | 4.255 ± 0.040 | 24 |
| 20.97 ± 0.20 | 4.232 ± 0.040 | 21 |
| 21.60 ± 0.20 | 4.111 ± 0.038 | 13 |
| 22.17 ± 0.20 | 4.007 ± 0.036 | 19 |
| 22.72 ± 0.20 | 3.911 ± 0.034 | 15 |
| 23.04 ± 0.20 | 3.857 ± 0.033 | 14 |
| 23.18 ± 0.20 | 3.834 ± 0.033 | 33 |
| 23.32 ± 0.20 | 3.811 ± 0.032 | 15 |
| 23.69 ± 0.20 | 3.752 ± 0.031 | 20 |
| 24.21 ± 0.20 | 3.673 ± 0.030 | 16 |
| 24.39 ± 0.20 | 3.646 ± 0.029 | 18 |
| 24.51 ± 0.20 | 3.629 ± 0.029 | 36 |
| 25.15 ± 0.20 | 3.538 ± 0.028 | 17 |
| 25.92 ± 0.20 | 3.434 ± 0.026 | 18 |
| 26.77 ± 0.20 | 3.327 ± 0.024 | 7 |
| 27.55 ± 0.20 | 3.235 ± 0.023 | 8 |
| 28.29 ± 0.20 | 3.152 ± 0.022 | 10 |
| 28.85 ± 0.20 | 3.092 ± 0.021 | 7 |
| 29.13 ± 0.20 | 3.063 ± 0.021 | 25 |
| 29.42 ± 0.20 | 3.033 ± 0.020 | 8 |
| 30.16 ± 0.20 | 2.961 ± 0.019 | 12 |

Drying of crystals of compound of Formula (I) obtained from slurry treatment was capable of producing alternate polymorphs. For example, vacuum treatment (−80° C. for one day) of crystals of Compound 2 obtained from slurry treatment in 97% ethanol/3% water produced a stable, anhydrous solid crystalline form, referred to herein as Form B. This resulting crystalline form was characterized by using a variety of methods, including XRPD, polarized light microscopy, differential scanning calorimetry (DSC), thermal gravimetric analysis (TGA), and dynamic vapor sorption (DVS) with post-DVS XRPD.

FIG. 2 shows the XRPD pattern of a sample of the anhydrous solid crystalline form of Compound 2, and the observed peaks are listed below in Table 2. The successful indexing of this sample indicates that it is composed of a single crystalline phase. After storage of this solid crystalline form at ambient conditions for three months, the sample was subjected to XRPD analysis again. The resulting XRPD pattern matches the original indexed pattern shown in FIG. 2.

TABLE 2

Observed X-ray powder diffraction peaks from an anhydrous solid crystalline form of Compound 2 (Form B) from an ethanol slurry

| °2θ | d space (Å) | Intensity (%) |
|---|---|---|
| 5.70 ± 0.20 | 15.496 ± 0.543 | 35 |
| 7.86 ± 0.20 | 11.242 ± 0.286 | 11 |
| 8.20 ± 0.20 | 10.769 ± 0.262 | 24 |
| 9.41 ± 0.20 | 9.394 ± 0.199 | 14 |
| 9.78 ± 0.20 | 9.033 ± 0.184 | 55 |
| 10.21 ± 0.20 | 8.654 ± 0.169 | 8 |
| 10.98 ± 0.20 | 8.049 ± 0.146 | 25 |
| 11.45 ± 0.20 | 7.721 ± 0.134 | 17 |
| 11.75 ± 0.20 | 7.528 ± 0.128 | 21 |

TABLE 2-continued

Observed X-ray powder diffraction peaks from an anhydrous solid crystalline form of Compound 2 (Form B) from an ethanol slurry

| °2θ | d space (Å) | Intensity (%) |
|---|---|---|
| 12.54 ± 0.20 | 7.053 ± 0.112 | 25 |
| 12.98 ± 0.20 | 6.813 ± 0.105 | 100 |
| 13.71 ± 0.20 | 6.453 ± 0.094 | 10 |
| 14.31 ± 0.20 | 6.184 ± 0.086 | 29 |
| 14.80 ± 0.20 | 5.982 ± 0.080 | 22 |
| 15.72 ± 0.20 | 5.632 ± 0.071 | 21 |
| 15.97 ± 0.20 | 5.544 ± 0.069 | 10 |
| 16.40 ± 0.20 | 5.400 ± 0.065 | 13 |
| 16.90 ± 0.20 | 5.243 ± 0.062 | 13 |
| 17.32 ± 0.20 | 5.116 ± 0.059 | 15 |
| 17.65 ± 0.20 | 5.020 ± 0.056 | 18 |
| 17.88 ± 0.20 | 4.957 ± 0.055 | 16 |
| 18.10 ± 0.20 | 4.898 ± 0.054 | 14 |
| 18.84 ± 0.20 | 4.707 ± 0.050 | 12 |
| 19.20 ± 0.20 | 4.619 ± 0.048 | 61 |
| 19.67 ± 0.20 | 4.509 ± 0.045 | 65 |
| 20.58 ± 0.20 | 4.312 ± 0.041 | 10 |
| 21.16 ± 0.20 | 4.196 ± 0.039 | 10 |
| 22.03 ± 0.20 | 4.031 ± 0.036 | 8 |
| 23.04 ± 0.20 | 3.857 ± 0.033 | 14 |
| 23.42 ± 0.20 | 3.795 ± 0.032 | 19 |
| 24.49 ± 0.20 | 3.633 ± 0.029 | 31 |
| 25.00 ± 0.20 | 3.558 ± 0.028 | 11 |
| 26.16 ± 0.20 | 3.403 ± 0.026 | 10 |
| 27.09 ± 0.20 | 3.289 ± 0.024 | 13 |
| 28.04 ± 0.20 | 3.180 ± 0.022 | 9 |
| 28.83 ± 0.20 | 3.094 ± 0.021 | 17 |
| 29.74 ± 0.20 | 3.002 ± 0.020 | 24 |
| 30.01 ± 0.20 | 2.975 ± 0.019 | 19 |

Figure 4:
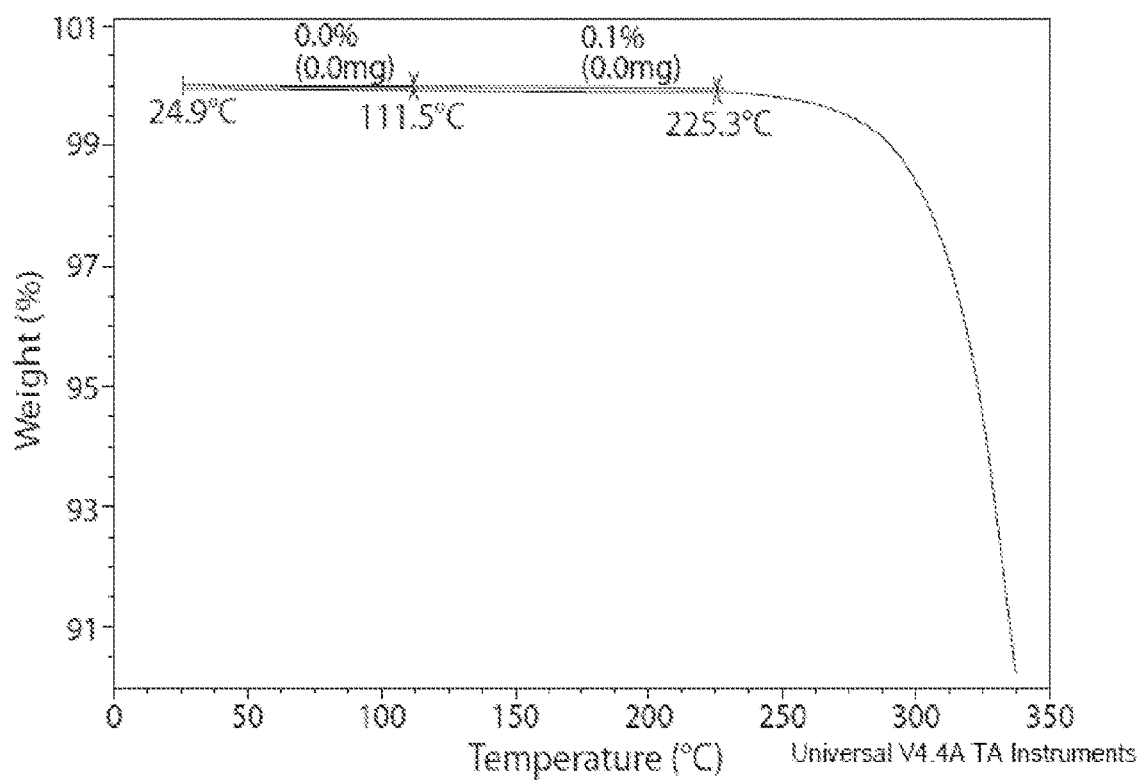
FIG. 4 is a graph depicting the results of thermal gravimetric analysis (TGA) on an anhydrous solid crystalline form of Compound 2 (Form B).

Differential scanning calorimetry (DSC) and thermal gravimetric analysis (TGA) were also carried out on the anhydrous solid crystalline form of Compound 2 (Form B); the resulting data are shown in FIG. 3 and FIG. 4. The DSC shows a minor broad endotherm with a peak maximum at 48.5° C. which is often indicative of a volatilization event; however there is no corresponding weight loss event in the TGA. The broad endotherm at 48.5° C. may indicate the presence of absorbed water in the sample during storage which is consistent with the moisture sorption (DVS) data. The DSC also shows a broad endotherm with a calculated onset of 185.4° C. that likely corresponds to a melting event and coincides with a minor TGA weight loss of 0.1% weight indicating that the sample may contain a small amount of an unidentified volatile component.

Figure 5:
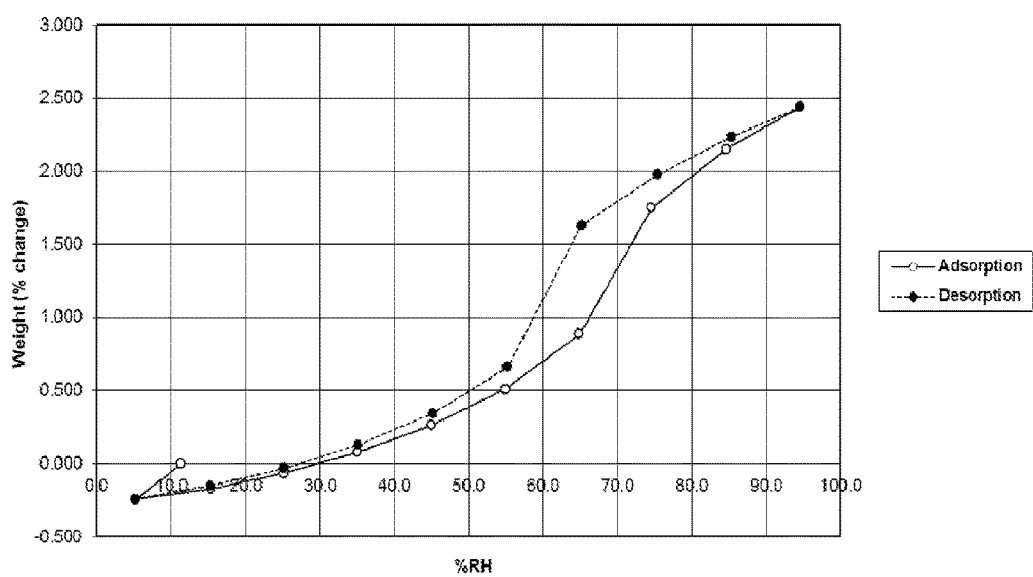
FIG. 5 is a graph depicting the results of dynamic vapor sorption (DVS) analysis on an anhydrous solid crystalline form of Compound 2 (Form B).

Dynamic vapor sorption (DVS) analysis of the anhydrous solid crystalline form of Compound 2 (Form B) was also carried out. The resulting isotherm plot is depicted in FIG. 5, and shows a 0.2% weight loss on equilibrium at 5% relative humidity (RH), followed by a reversible adsorption/desorption of 2.7% weight with negligible hysteresis. Based on this behavior, Form B appears to be a variable hydrate, in which the water content will depend on the ambient relative humidity. Taken together, the XRPD, DSC, TGA, and DVS data are all consistent with Form B being a crystalline, variable hydrate material that becomes anhydrous upon drying.

Figure 6:
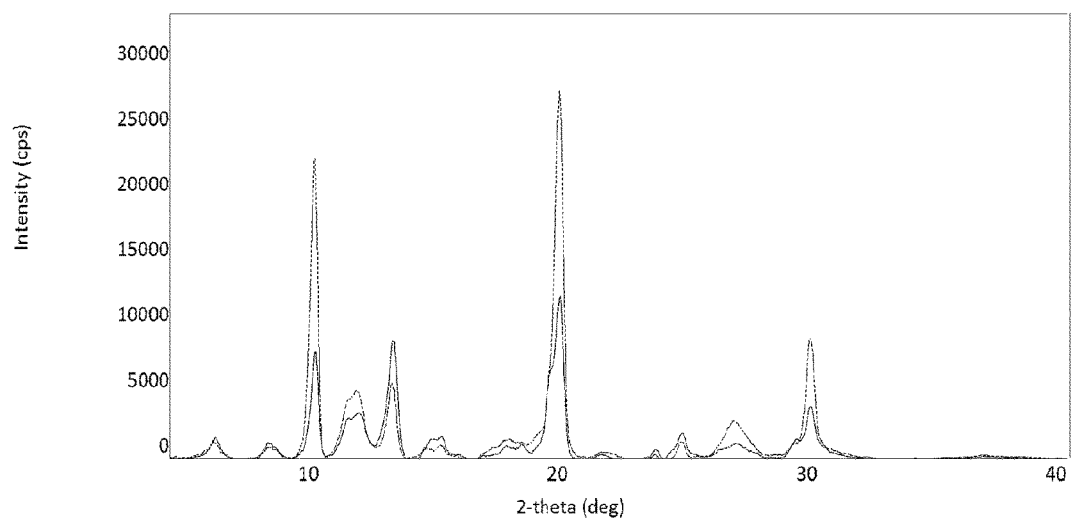
FIG. 6 is a spectrum depicting the overlaid results of XRPD analysis of the anhydrous solid crystalline form of Compound 2 (Form B) before (light gray trace) and after (dark gray trace) microionization to a $d_{90}$ value of less than 10 microns.

Crystals of Compound 2 obtained from ethanol or aqueous ethanol mixtures form long thin needles. XRPD patterns of such crystalline materials are often complicated by the phenomenon of preferred orientation, resulting from the crystals predominantly aligning in two dimensions. Thus the XRPD patterns of compounds of Formula (I), e.g., Compound 2, obtained from recrystallized samples look different from those obtained from the slurry experiments described above. It is known that particle size reduction can reduce the magnitude of preferred orientation artifacts. FIG. 6 illustrates examples of XRPD patterns of the solid crystalline form of Compound 2 (Form B) recrystallized from ethanol and dried, before (light gray trace) and after micronization (dark gray trace trace) to a $d_{90}$ value of less than 10 microns.

Example 32 Measuring Kinetic Solubilities of the Compounds of Formula (I)

The solubilities of the compounds of Formula (I) were tested using the procedure outlined in Kerns, E. H., *J Pharm Sci* (2001) 90:1838-1858, incorporated herein by reference and described below. Data for solubility was obtained by this method for compounds of Formula (I) and included in Table 3. The chromatographic data was performed by HPLC using an Xbridge Shield RP18 column with the following column dimensions: 4.6×30 mm, 3.5 µm. The mobile phase consisted of deionized water (MPA) with trifluoroacetic acid added in at 0.1% (v/v) (MPC) and HPLC-grade acetonitrile (MPB). The mobile phase flow rate was 2.5 mL/min with the column and sampling operating at ambient temperature. UV detection was set to 280 nm. For all samples used for solubility determination, the mobile phase gradient used is as shown in Table 4.

TABLE 3

Exemplary solubilities for selected compounds of Formula (I):

| Compound | pH 4.0 solubility (µg/mL) | pH 7.4 solubility (µg/mL) | pH 9.0 solubility (µg/mL) |
|---|---|---|---|
| 1 | 4 | 3 | 2 |
| 2 | 85 | 71 | 69 |
| 17 | 11 | 12 | 9 |
| 23 | 20 | 31 | 14 |
| 25 | 45 | 29 | 11 |
| 22 | 50 | 89 | 70 |
| 18 | 51 | 41 | 17 |
| 21 | 34 | 20 | 10.5 |
| 19 | 6 | 10 | 3.5 |

Samples for analysis of the compounds of Formula (I) were prepared at a % v/v=1/19 (i.e., 10 µL of the stock solution into 190 µL of buffer) by spiking stock solutions of the compounds of Formula (I) into buffered solutions. Three buffered solution systems were prepared: pH 4.0 prepared from 50 mM sodium acetate in a 5% dextrose in water solution, pH 7.4 prepared from 75 mM sodium phosphate in a 1:1 ratio of sterilized water for injection to a 5% dextrose in water solution, and pH 9.0 prepared from 50 mM sodium bicarbonate in a 1:2 ratio of sterilized water for injection to a 5% dextrose in water solution. The samples were incubated on a microplate shaker at 300 rpm for 24 hours at ambient temperature. Following incubation, the samples were centrifuged for five minutes at 13 k rpm at ambient temperature. The resulting supernatant was extracted for HPLC analysis.

TABLE 4

Mobile phase gradient used for solubility determination

| Time (min) | % MPA | % MPB | % MPC |
|---|---|---|---|
| 0.00 | 70 | 20 | 10 |
| 1.08 | 0 | 90 | 10 |
| 1.20 | 0 | 90 | 10 |

TABLE 4-continued

Mobile phase gradient used for solubility determination

| Time (min) | % MPA | % MPB | % MPC |
|---|---|---|---|
| 1.21 | 70 | 20 | 10 |
| 1.50 | 70 | 20 | 10 |

For example, compounds of the invention may allow acceptable levels of drug to reach therapeutic targets.

Figure 10:
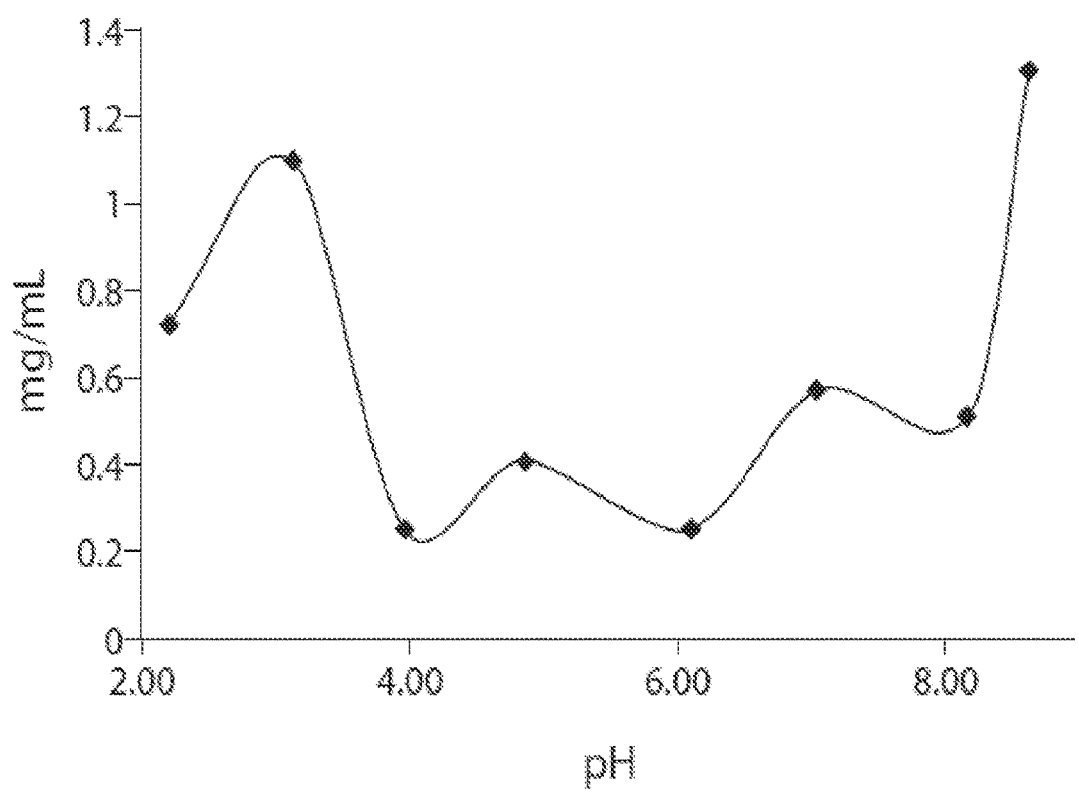
FIG. 10 is a graph depicting the solubility of a micronized formulation of Compound 2 over the pH range of 2.00 to 8.00.

Solubility of a micronized formulation of Compound 2 was further evaluated using McIlvain's citrate-phosphate buffer recipes (0.2M $Na_2HPO_4$ and 0.1M citric acid) from pH 2.2 to 8.64. Samples were agitated for 30 hours and sampled, centrifuged, and analyzed by UPLC. The highest solubility was seen at pH 8.6 and 3.1 while the effect of pH was narrow ranging from 0.2 to 1.3 mg/ml. Results are shown in FIG. 10.

Solubility was also determined in a fasted-state simulated intestinal fluid (FaSSIF) assay. Briefly, Compound 2 was added to the FaSSIF medium (bile salts, NaOH (0.420 g), NaH2PO4 (3.438 g), NaCl (6.186 g), pH to 6.5, at 25° C., and brought to a 1 L volume) agitated for 30 hours and sampled, centrifuged, and analyzed by UPLC. Solubility in the FaSSIF model was determined to be 1.19 mg/ml.

Solubility was further assessed in simulated gastrointestinal fluid (SGF) (HCl 0.1N at 25° C.). Briefly, compound was agitated for 30 hours and sampled, centrifuged, and analyzed by UPLC. Solubility in SGF was found to be 1.05 mg/ml. The results from these studies indicate that solubility of Compound 2 is not significantly dependent on pH of the media, but may have some increased solubility based on the presence of bile salts.

Compounds of the invention were also tested for solubility in Normal Ringer Solution. Briefly, compound solubility was determined by dissolving a standard range of volumes of 10 mM DMSO stock of compounds in Normal Ringer Solution (145 mM NaCl, 4.5 mM KCl, 2 mM $CaCl_2$, 1 mM $MgCl_2$, 10 mM HEPES, 10 mM glucose; pH 7.4 at room temperature). Following vortex and incubation for 40 minutes at room temperature, solutions were filtered, quenched with acetonitrile, and analyzed by liquid chromatography. Solubility limits were determined by comparison to a standard curve. The solubility limit was determined to be greater than 31.3 µM. Solubility is reported as "greater than" if the observed increase between the last 2 dilutions tested is greater than 2-fold. Table 5 shows the values achieved for the compounds tested.

TABLE 5

Solubility of compounds of Formula (I) in Normal Ringer Solution

| Compound | Solubility (nM) |
|---|---|
| 1 | >14300 |
| 2 | ~32400 |
| 4 | >31300 |
| 5 | 4370 |
| 6 | ~23000 |
| 13 | >77600 |
| 15 | 16300 |
| 19 | >18200 |
| 16 | >47000 |
| 26 | >15100 |

Binding of Compound 2 to human, rat, dog, and cynomolgus monkey plasma proteins was tested using an equilibrium dialysis approach. With this method, free compound is separated from protein-bound compound by dialysis across a semi-permeable membrane. At a concentration of 1 µM, Compound 2 demonstrated 98.5% binding to human, 95.3% binding to rat, 94.5% to dog and 98.0% to cynomolgus monkey plasma proteins (Table 6).

The protein binding was tested at a concentration of 1 µM. Pooled human, cynomolgus monkey, dog, and rat K2EDTA plasma was thawed and centrifuged at 2000×g for 10 minutes at 4° C. to remove particulates; any lipid on the top of the supernatant was also removed by aspiration. The plasma was warmed to 37° C. for 10 minutes before use. Test compounds were spiked into 2 ml plasma in a polypropylene plate to a final concentration of 1 µM. Triplicate 400 µl aliquots of spiked plasma were transferred into the Thermo RED dialysis units and dialyzed against 600 µl of PBS buffer. The RED devices were incubated at 37° C. with gentle shaking using a Boekel Jitterbug 130000; the plates were also protected from light. After 6 hours dialysis, triplicate 50 µl aliquots were removed from the RED plate, matrix-matched with either PBS buffer or blank plasma, as appropriate, and quenched with 4 volumes of ACN containing an internal standard. The extracted samples were then centrifuged at 2000×g for 5 minutes at 4° C. The supernatant (50 µl) was removed and diluted with 100 µl water prior to LC/MS/MS bioanalysis.

TABLE 6

Comparison of binding of Compound 2 and warfarin to plasma proteins

| | Species | Mean % Bound ± SD |
|---|---|---|
| Compound ID | | |
| Compound 2 | Human | 98.5 ± 0.1 |
| Compound 2 | Sprague dawley rat | 95.3 ± 0.8 |
| Compound 2 | Beagle dog | 94.5 ± 0.5 |
| Compound 2 | Cynomolgus monkey | 98.0 ± 0.1 |
| Controls | | |
| Warfarin | Human | 99.1 ± 0.2 |
| Warfarin | Sprague dawley rat | 99.1 ± 0.1 |
| Warfarin | Beagle dog | 93.5 ± 0.4 |
| Warfarin | Cynomolgus monkey | 98.9 ± 0.3 |

The change in $IC_{50}$ block in the presence of albumin and plasma was also studied. It is assumed that the pharmacological effect of a drug correlates to unbound plasma levels, which is known as the "free drug hypothesis". The aim of this study was to estimate the change in $IC_{50}$ for block of human TRPA1 (hTRPA1) by Compound 2 in the presence of physiologically relevant concentrations of albumin and plasma (see Table 7). The human form of TRPA1 was used to assess protein binding in all species due to technical issues. The whole-cell patch clamp technique as described in del Camino, D. et al. *J Neurosci* 74 (2010) 30:15165 was employed to measure current through hTRPA1 upon activation by allyl isothiocyanate (AITC), the active ingredient in mustard oil, in the presence of 1% (w/v) serum albumin or 25% (v/v) plasma from various species including human plasma (hPlasma), human serum albumin (HSA), rat plasma (rPlasma), rat serum albumin (RSA), dog plasma, and sheep serum albumin (sheepSA). Compound 2 was sub-diluted from a 10 mM stock in DMSO to 10 and 100 µM in DMSO, then diluted into Ringer solution at the concentrations referenced in Table 7 and Table 8.

The subsequent introduction of Compound 2 resulted in dose-dependent and reversible blockade of hTRPA1. In the presence of 25% (v/v) human plasma (hPlasma) hTRPA1 currents were blocked with an $IC_{50}$ of 95±2 nM, which is 14-fold higher than the $IC_{50}$ in the absence of serum (see Table 8). Experiments performed on hTRPA1 in the presence of rat plasma (rPlasma) and rat serum albumin (RSA) yielded a potency of block by Compound 2 of 68±8 nM and 95±9 nM, respectively indicating a degree of protein binding similar to that observed with human plasma. The $IC_{50}$ for block by Compound 2 was somewhat higher in the presence of dog plasma (221±54 nM). In the presence of 1% (w/v) sheep serum albumin (SheepSA) hTRPA1 currents were blocked with an $IC_{50}$ of 70±10 nM. Both block with Compound 2 and reversal upon washout were complete within 2-3 minutes. These experiments indicate that Compound 2 will exert pharmacological effects at lower plasma levels than previously identified compounds, because more free drug is available to interact with the target.

Based on the shift in $IC_{50}$ observes in the presence of plasma, it may be concluded that Compound 2 displays significant binding to plasma proteins across the four species tested in the range of 90-97%. This represents an improvement over past compounds of similar potency.

TABLE 7

Compound 2 hTRPA1 $IC_{50}$ determination in albumin and plasma

| Test | Ion Channel | Tested Concs. (nm) | n | Current Activation | $IC_{50}$ (nM) | Fold Shift |
|---|---|---|---|---|---|---|
| $IC_{50}$ + hPlasma | hTRPA1 | 32, 100, 320 | 3 | 20 µM AITC | 95 ± 2 | 14X |
| $IC_{50}$ + rPlasma | hTRPA1 | 32, 100, 320, 1000 | 4 | 20 µM AITC | 68 ± 8 | 10X |
| $IC_{50}$ + RSA | hTRPA1 | 32, 100, 320 | 3 | 20 µM AITC | 95 ± 9 | 14X |
| $IC_{50}$ + dog Plasma | hTRPA1 | 32, 100, 320, 1000, 3200 | 4 | 20 µM AITC | 221 ± 54 | 32X |
| $IC_{50}$ + SheepSA | hTRPA1 | 32, 100, 320 | 3 | 20 µM AITC | 70 ± 10 | 10X |

TABLE 8

Compound 2 $IC_{50}$ determination for hTRPA1 from various mammalian sources

| Test | Ion Channel | Species | Tested concs. (nm) | Current Activation | n | $IC_{50}$ Inward current (nM) |
|---|---|---|---|---|---|---|
| $IC_{50}$ | hTRPA1 | Human | 1, 3.2, 10, 32, 100 | 10 µM AITC | 13 | 6.9 ± 3.1 |
| $IC_{50}$ | rTRPA1 | Rat | 10, 32, 100 | 10 µM AITC | 3 | 22.9 ± 4.6 |
| $IC_{50}$ | dogTRPA1 | Dog | 3.2, 10, 32, 100 | 10 µM AITC | 4 | 23.5 ± 6.4 |
| $IC_{50}$ | mTRPA1 | Mouse | 10, 32, 100, 320 | 10 µM AITC | 3 | 26.6 ± 3.3 |
| $IC_{50}$ | sheepTRPA1 | Sheep | 1000, 3200, 10000 | 20 µM AITC | 3 | 3280 ± 640 |

Metabolic Stability

Metabolic stability of the compounds of Formula (I) was determined by standard liver microsome assays. Briefly, metabolic stability was tested by adding the compound to be tested dissolved in DMSO to human, dog, or rat liver microsomes. Assays were run with a starting concentration of 1 µM test compound. The reaction was initiated by addition of nicotinamide adenine dinucleotide phosphate-oxidase (NADPH) regeneration components at 37° C., at which time an aliquot was immediately quenched in an ice-cold acetonitrile/methanol/water solution. Reaction mixture was incubated at 37° C. on a shaker, and additional aliquots were taken at 7, 15, 30 and 60 minutes. Following quench and centrifugation, samples were analyzed on HPLC/MS/MS. Results are shown in Table 9, Table 10, and Table 11 below.

TABLE 9

Half life and hepatic clearance of compounds in human liver microsomes

| Compound | Human Liver Microsomes Half-Life (min) | Human Liver Microsomes Hepatic Clearance (mL/min/kg) |
|---|---|---|
| 1 | 9 | 16 |
| 2 | 43 | 8 |
| 4 | 19.8 | |
| 5 | 37.8 | |
| 6 | 27.4 | |
| 8 | 38.4 | |
| 13 | >60 | |
| 15 | 88.8 | |
| 17 | 8 | 16 |
| 18 | 12 | 15 |

TABLE 9-continued

Half life and hepatic clearance of compounds in human liver microsomes

| Compound | Human Liver Microsomes Half-Life (min) | Human Liver Microsomes Hepatic Clearance (mL/min/kg) |
|---|---|---|
| 19 | 50 | 9 |
| 21 | 30 | 10.5 |
| 22 | 26 | 12 |
| 23 | 4 | 18 |
| 25 | 43 | 8 |
| 16 | 52.4 | |
| 26 | >120 | |

TABLE 10

Half life and hepatic clearance of compounds in dog liver microsomes

| Compound | Female Half-Life (min) | Male Half-Life (min) | Half-Life both sexes (min) | Female Hepatic Clearance (mL/min/kg) | Male Hepatic Clearance (mL/min/kg) | Hepatic Clearance (mL/min/kg) |
|---|---|---|---|---|---|---|
| 1 | 18 | 10 | | 18 | 22 | |
| 2 | 22.9 | | 22.9 | | | |
| 5 | | | >120 | | | |
| 19 | | | 44 | | | 11 |
| 21 | 66 | | | 8 | | |

TABLE 11

Half life and hepatic clearance of compounds in rat liver microsomes

| Compound | Female Half-Life (min) | Male Half-Life (min) | Half-Life Both sexes (min) | Female Hepatic Clearance (mL/min/kg) | Male Hepatic Clearance (mL/min/kg) | Hepatic Clearance (mL/min/kg) |
|---|---|---|---|---|---|---|
| 1 | 46 | 22 | 39.2 | 20 | 29 | |
| 2 | | 786.6667 | >60 | | 2 | |
| 4 | | | 72.6 | | | |
| 5 | | | 113 | | | |
| 6 | | | 118 | | | |
| 8 | | | 115 | | | |
| 13 | | | 60 | | | |
| 15 | | | 72.7 | | | |
| 17 | | | | | | 22 |
| 18 | | | 21.8 | | | 24 |
| 19 | | 36 | 63.8 | | 25 | |
| 21 | | 16 | | | 34 | 11 |

Bioavailability

Early bioavailability studies in rat were conducted with solutions of the compounds of the invention. Compounds were delivered via oral administration as a solution in an appropriate excipient. Example formulations include, but are not limited to: 4% DMSO, 10% Solutol HS-15, and 86% water or 4% DMSO, 5% Tween, 25% Cremophor EL. Target concentrations were typically 1 mg/mL, and administered via oral gavage to non-fasted rats. The absolute bioavailability is the dose-corrected area under the curve (AUC) non-intravenous divided by the dose corrected AUC intravenous. The formula for calculating F for a drug administered by the oral route (PO) is given below:

% $F$ = AUC PO×Dose IV/AUC IV×Dose PO

The respective bioavailability for rats for the compounds tested is shown in Table 12.

TABLE 12

Bioavailability of compounds in non-fasted rats

| Compound | Rat % F |
|---|---|
| 1 | 46 |
| 2 | 100 |
| 4 | 100 |
| 15 | 35 |
| 19 | 77 |

Figure 11:
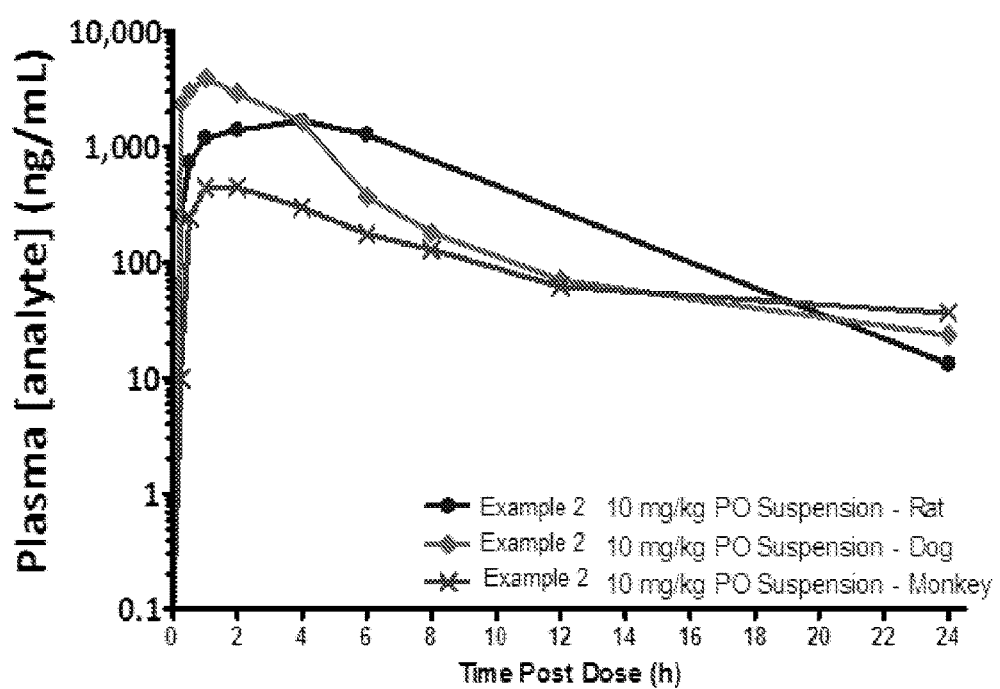
FIG. 11 is a graph depicting plasma levels of Compound 2 (i.e., Example 2) in rat, dog, or monkey models after administration of a 10 mg/kg oral dose.

Additional studies were conducted with micronized Compound 2 in rat, dogs (beagles), and cynomolgus monkeys. Animals received a 10 mg/kg dose oral dose of compound formulated as a suspension in 0.5% methyl cellulose in water for injection at a target concentration of 1 mg/mL, and administered a dose volume of 10 mL/kg by oral gavage in rats or fasted dogs and via oral delivery in fasted cynomolgus monkeys. The % F for the rats in these studies was 85%, 36% for the dogs, and 19% for the monkeys. FIG. 11 depicts the pharmacokinetic profile for these species.

Several in vivo studies were performed to characterize the bioavailability of Compound 2. In Sprague-Dawley rats, a single oral dose of 10 mg/kg to 1000 mg/kg of Compound 2 were compared in a series of experiments. Compound 2 used in these studies was recrystallized from ethanol and micronized. Exposures based on area under the curve (AUC) and maximum plasma concentration ($C_{max}$) increased with doses up to 1000 mg/kg.

Three studies were conducted in dogs (beagles). In one study, three fasted dogs were administered 10 mg/kg of a suspension of micronized Compound 2 by gavage. Blood samples were collected from these dogs before dosing and at 0.25, 0.50, 1, 2, 4, 6, 8, 12, and 24 hours post-administration. Blood samples were analyzed to determine plasma levels of Compound 2 by LC/MS/MS. In subsequent studies, pharmacokinetic (PK) parameters were determined following a single oral dose of suspensions of micronized Compound 2 (recrystallized from ethanol) administered to fasted dogs at dose levels of 10, 100, 300, 600, or 1000 mg/kg. Blood samples were taken before dosing and at 0.5, 1, 2, 4, 8, 12, 24 and 48 hours post-dosing and analyzed to determine plasma levels of Compound 2. Exposures on an AUC and $C_{max}$ basis increased with doses up to 600 mg/kg.

Three studies were conducted in fasted cynomolgus monkeys to determine the PK profile and bioavailability of a suspension formulation of Compound 2. Three monkeys were administered a suspension containing 10 mg/kg micronized Compound 2 by oral gavage. Monkeys were bled before dosing and at 0.25, 0.50, 1, 2, 4, 6, 12, and 24 hours post-dosing. Compound 2 plasma levels were determined by LC/MS/MS. Additional studies were conducted to evaluate the PK profile at higher dose levels of Compound 2 administered to fasted monkeys as an oral suspension. Blood samples were collected prior to dosing and up to 24 hours post-dosing. An additional 48 hour blood sample was collected from monkeys dosed with 300 mg/kg Compound 2. Plasma levels of Compound 2 were determined by LC/MS/MS. Exposures on an AUC and $C_{max}$ basis increased with doses up to 1000 mg/kg.

Figure 12:
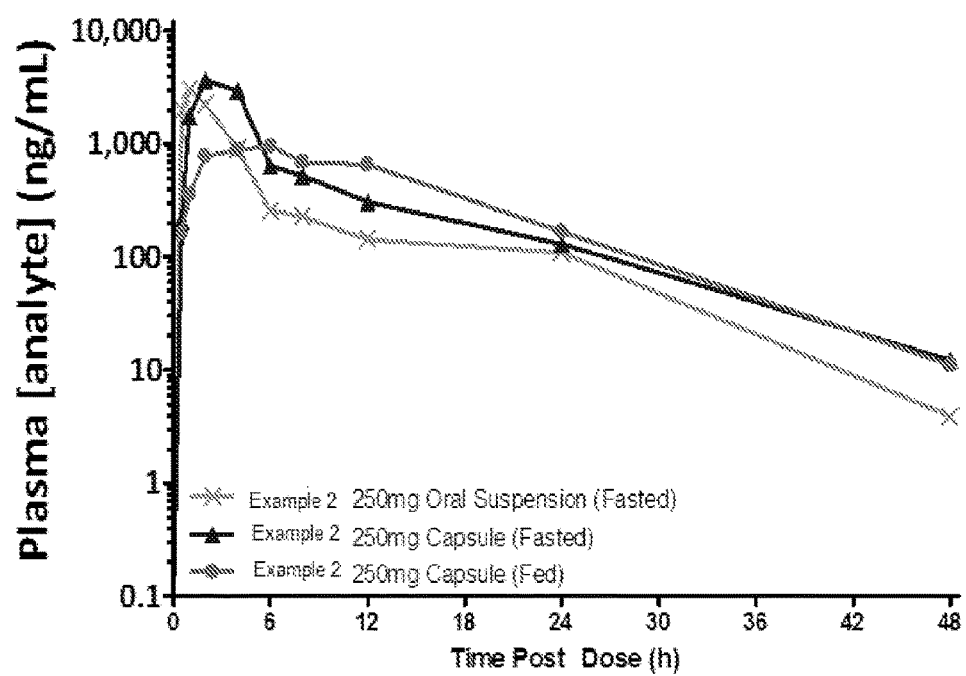
FIG. 12 is a graph depicting a comparison of the pharmacokinetic profile of Compound 2 (i.e., Example 2) in capsule and suspension formulations in fed and fasted monkeys.

Another study was conducted to compare the PK parameters of capsule and suspension formulations of Compound 2. All monkeys were dosed with 250 mg Compound 2. Two groups were dosed with the capsule formulation: one fasted and one allowed food ad libitum. The animals that received the suspension formulation were dosed using a nasogastric tube and were fasted. As seen in FIG. 12 and summarized in Table 13 below, the capsule formulation appeared to be associated with an increased bioavailability compared to the suspension, although the numerical difference was small. When the PK profile of the capsule formulation was compared in both fasted and fed monkeys, the bioavailability of Compound 2 capsules was numerically greater in fasted monkeys.

TABLE 13

Comparison of PK parameters of Compound 2: capsule and suspension formulations

| Compound 2 Dose (mg) | Compound 2 Formulation | F (%) |
| --- | --- | --- |
| 250 | Suspension (fasted) | 7.8 |
| 250 | Capsule (fasted) | 13 |
| 250 | Capsule (fed) | 10 |

Example 33 Method for Measuring Inhibition of the TRPA1 Ion Channel

Compounds of Formula (I) inhibit the TRPA1 channel, as shown by measuring the in vitro inhibition of human TRPA1, provided in data tables shown in Table 14, using the procedure outlined in del Camino et al., *J Neurosci* (2010) 30(45):15165-15174, which is incorporated herein by reference and summarized below. Data for TRPA1 inhibition was obtained by this method for the indicated compounds of Formula (I), with the relevant data included in Table 14 below. All currents were recorded in whole-cell configuration using EPC-9 and EPC-10 amplifiers and Patchmaster software (HEKA). Patch pipettes had a resistance of 1.5-3 M and up to 75% of the series resistance was compensated. The standard pipette solution consisted of 140 mM CsAsp, 10 mM EGTA, 10 mM HEPES, 2.27 mM, 20 $MgCl_2$, 1.91 mM $CaCl_2$, and up to 0.3 mM $Na_2GTP$, with pH adjusted to 7.2 with CsOH. In addition, a solution containing 145 mM CsCl, 10 mM HEPES, 10 mM EGTA, and up to 0.3 mM $Na_2GTP$ and 1 mM $MgCl_2$ (pH 7.2 adjusted with CsOH) can be used. The standard bath solution contained 150 mM NaCl, 10 mM HEPES, 10 mM glucose, 4.5 mM KCl, 1 mM EGTA, 3 mM $MgCl_2$, with pH adjusted to 7.4 with NaOH. In some instances, 2 mM $CaCl_2$ was added in place of EGTA and the concentration of $MgCl_2$ was reduced to 1 mM.

Data were collected either by continuous recordings at −60 mV or by applying voltage ramps from a holding potential of 0 mV every 4 s. Continuous recordings were collected at 400 Hz and digitally filtered off-line at 10 Hz for presentation. Voltage ramps were applied from −100 mV to 100 mV over the course of 400 ms, and data were collected at 10 kHz and filtered at 30 2.9 kHz. Inward and outward currents were analyzed from the ramps at −80 and 80 mV, respectively. Liquid junction potential correction was not used.

Solutions were switched using a gravity-fed continuous focal perfusion system. To achieve rapid temperature changes, two temperature control, and perfusion systems were employed simultaneously. For temperatures greater than or equal to 22° C., a Warner Instruments bipolar temperature controller (TC-344B) and inline heater (SHM-8) were used. For temperatures below 22° C. a Warner Instruments temperature controller (CL-100) and thermal cooling module (TCM-1) were used. Temperatures were confirmed using a thermistor (Warner Instruments, TA-29), with temperatures at the recorded cell estimated to be within +/−2° C. of those reported.

Table 14 shows data obtained from the in vitro assay described above. The antagonist effects of compounds of Formula (I) against human TRPA1 ("hTRPA1") in a whole cell patch configuration were evaluated using the in vitro assay protocol described above.

TABLE 14

Antagonist effects of Compounds of Formula (I) against human TRPA1

| Compound | hTRPA1 (nM) |
| --- | --- |
| 1 | 5.15 |
| 2 | 6.87 |
| 3 | 2290 |
| 4 | 11.3 |
| 5 | 663 |
| 6 | 29.7 |
| 7 | 922 |
| 8 | 71.9 |
| 9 | 462 |
| 10 | 93.5 |
| 11 | 124 |
| 12 | 387 |
| 13 | 62.9 |
| 14 | 94.8 |
| 15 | 26.7 |
| 16 | 24.9 |
| 17 | 41.2 |
| 18 | 10.4 |
| 19 | 96.1 |
| 21 | 51 |
| 22 | >3200 |
| 23 | 60.7 |
| 24 | 436 |
| 25 | 107 |
| 26 | 21.8 |
| 27 | 255 |
| 28 | 65.9 |

Example 34 Effect on Cold Hypersensitivity

Embodiments of the invention may be efficacious in the treatment of inflammatory pain. Compound 2 tested by the CFA-induced pain test method. Compound 2 was formulated as a clear solution in 4% DMSO, 10% Solutol, 86% DWI, pH 5.9 for oral administration (PO).

Briefly, the hind paw is sensitized to cold temperature (allodynic), by administering 0.1 mL of Complete Freund's Adjuvant (CFA) is administered to the right hind paw. Three days later, the time taken for the animal to lift its CFA-injected paw is recorded compared to its un-injected normal left hind paw. Animals are placed on the surface of the cold plate (1° C.) and the operator stops testing at the instant when the animal displays discomfort by flinching or lifting its paw from the plate (paw withdrawal latency, or PWL). To avoid tissue damage the maximum cut-off time is 5 minutes. Animals that are allodynic (average PWL to the first three pain behaviors <150 seconds for the CFA-injected hind paw: ~≥50% difference between the normal and CFA-injected paw) are included in the study and subsequently randomized across treatment groups. The following day, the animals are dosed under blinded conditions. Following the 1-2 hour pre-treatment time, the post-dose PWL readings are again taken. The efficacy of the drug treatment is assessed by comparing the PWL in the drug treatment animals to those animals that receive the vehicle.

Figure 7:
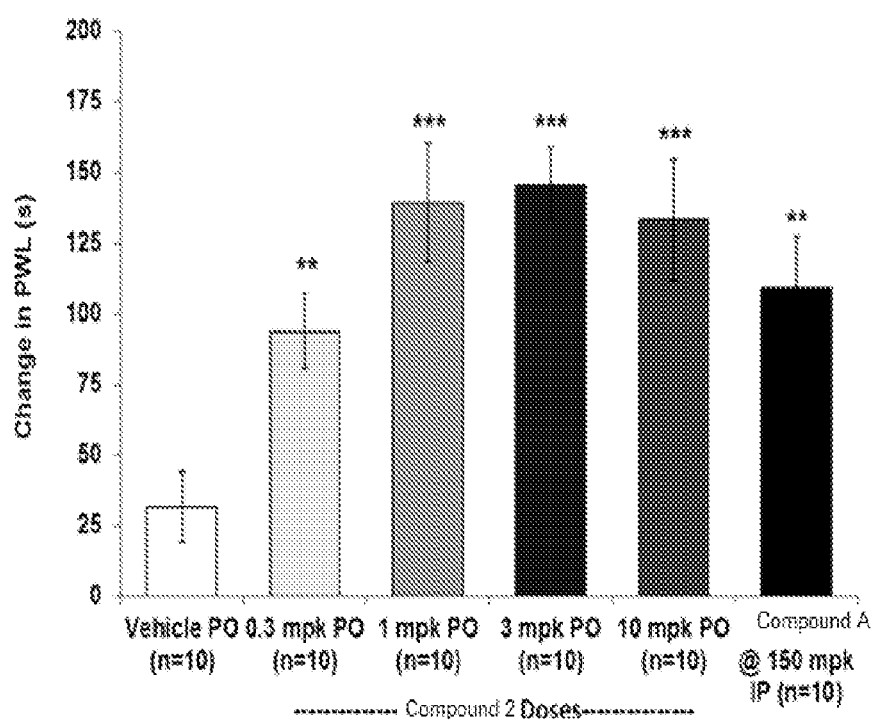
FIG. 7 is a graph depicting the effect of varying dosage amounts of Compound 2 administered orally in the CFA-induced cold hyperalgesia model in the rat.

As shown in FIG. 7 and Table 15, Compound 2 attenuated cold hypersensitivity after oral doses of 0.3 to 10 mg/kg. The positive comparator TRPA1 antagonist Compound A also reduced cold hypersensitivity at a higher dose of 150 mg/kg delivered via intraplantar injection. Importantly, the vehicle delivered orally (4% DMSO, 10% Solutol, 86% DWI) had no effect on paw withdrawal latency, compared to pre-administration baseline measurements.

TABLE 15

Attenuation of cold hypersensitivity by Compound 2 at varying oral dosages

| Dosage of Compound 2 | Pre-RX PWL (seconds) | Post RX PWL (seconds) |
| --- | --- | --- |
| Vehicle PO (n = 10) | 104.5 | 136.1 |
| 0.3 mpk PO (n = 10) | 104.0 | 197.7 |
| 1 mpk PO (n = 10) | 103.7 | 243.0 |
| 3 mpk PO (n = 10) | 103.9 | 249.6 |
| 10 mpk PO (n = 10) | 104.0 | 237.3 |
| Compound A @ 150 mpk IP (n = 10) | 104.2 | 213.2 |

Table 16 summarizes the average plasma levels of Compound 2 and Compound A. Approximately dose proportional exposures of Compound 2 were observed throughout the dose range tested. Decreased plasma binding of Compound 2 indicates an improved bioavailability of Compound 2 to the subjects over Compound A.

TABLE 16

Plasma levels of Compound 2 and Compound A

| Treatment Group | Dose (mg/kg) | Route | PLASMA (ng/mL) |
| --- | --- | --- | --- |
| Compound 2 | 0.3 | PO | 70 ± 11 |
| Compound 2 | 1 | PO | 265 ± 56 |
| Compound 2 | 3 | PO | 800 ± 160 |
| Compound 2 | 10 | PO | 2780 ± 425 |
| Compound A | 150 | IP | 7830 ± 3970 |

There were no differences in behavior between the vehicle and treatment groups (see Table 17). However lethargy/slow movement was noted in 5/10 animals treated with the positive comparator, Compound A, demonstrating that Compound 2 does not induce a significant sedative effect.

TABLE 17

Examination of animal behavior upon administration of Compound 2

| Treatment Group | Dose (mg/kg) | Route | # Animals with low activity/slow movement or frank lethargy* |
| --- | --- | --- | --- |
| Vehicle | — | PO | 2/10 |
| Compound 2 | 0.3 | PO | 1/10 |
| Compound 2 | 1 | PO | 1/10 |
| Compound 2 | 3 | PO | 2/10 |
| Compound 2 | 10 | PO | 2/10 |
| Compound A | 150 | IP | 5/10 |

Compound 4 was also tested using the methods disclosed. Compound 4 was formulated as a suspension in 0.5% methylcellulose and administered at the doses indicated in Table 18.

TABLE 18

Attenuation of cold hypersensitivity by Compound 4 at varying oral dosages

| Treatment | Pre-Rx PWL (seconds) | Post-Rx PWL (seconds) | PWL Change (seconds) |
| --- | --- | --- | --- |
| Vehicle, PO (n = 10) | 101.9 | 100.6 | −1.3 |
| Compound 4 1 mg/kg, PO (n = 10) | 101.7 | 250.3 | 148.6 |
| Compound 4 3 mg/kg, PO (n = 10) | 101.1 | 242.1 | 140.9 |
| Compound 4 10 mg/kg, PO (n = 10) | 101.5 | 234.1 | 132.6 |
| Compound A 150 mg/kg, IP (n = 8) | 104.9 | 210.8 | 105.9 |

Figure 13:
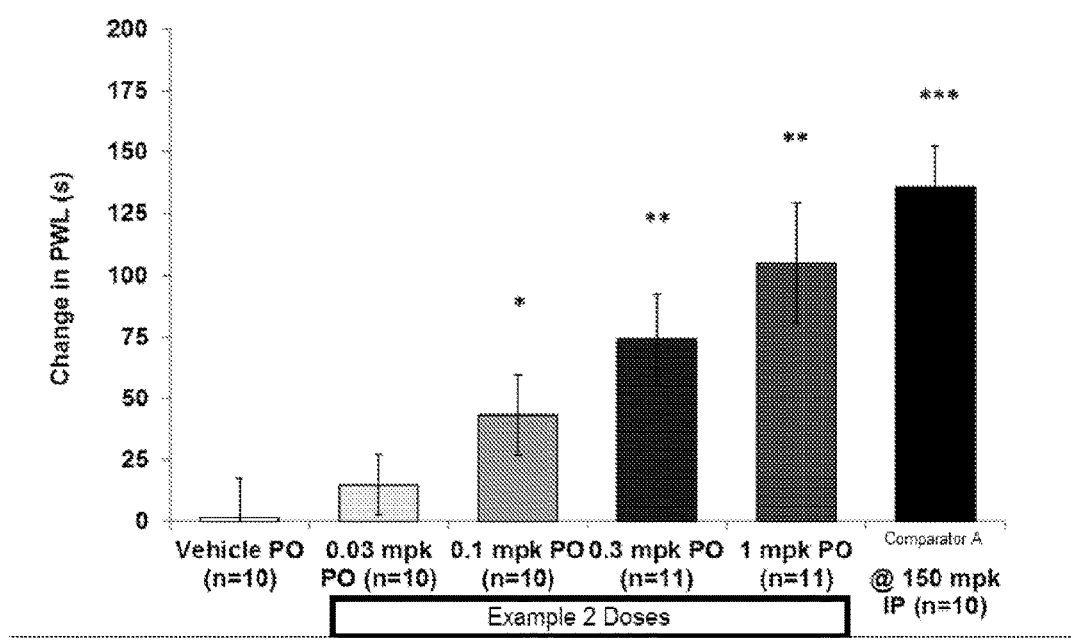
FIG. 13 is a chart depicting the analgesic effects observed upon low doses of orally administered Compound 2 (i.e., Example 2) and a control (Compound A, i.e., Comparator A) in the CFA model.

In a further study, compounds of the invention were tested for efficacy at low doses for the treatment of inflammatory pain. Using the methods disclosed in above, Compound 2 was dosed at ranges of 0.1 to 1 mg/kg PO. The positive comparator TRPA1 antagonist Compound A was also tested at a dose of 150 mg/kg IP. Compound 2 was formulated as a clear solution in 4% DMSO, 10% Solutol, 86% DWI, pH 5.9 for oral administration (PO) at a dose volume of 10 ml/kg. Oral drug delivery was accomplished using a 20-gauge 11/2" oral gavage needle and a 5 cc syringe. Fed rats received a single oral gavage of Compound 2 at 0.03, 0.1, 0.3, or 1 mg/kg or Vehicle, 2 hours prior to testing As seen in Table 19 and FIG. 13, Compound 2, when dosed at 0.1, 0.3, and 1 mg/kg PO, showed a significant reversal of CFA-induced cold hypersensitivity, as assayed by measuring paw withdrawal latency. 0.03 mg/kg dose levels did not exert a statistically significant effect. The positive comparator, the prototypic TRPA1 antagonist Compound A, also showed a significant reversal of cold hypersensitivity when dosed at 150 mg/kg IP.

TABLE 19

Reversal of CFA-induced cold hypersensitivity by Compound 2

| Dosage | PWL Change (Sec) | SEM |
| --- | --- | --- |
| Vehicle PO (n = 10) | 1.6 | 15.7 |
| Compound 2 @ 0.03 mpk PO (n = 10) | 14.8 | 12.2 |
| Compound 2 @ 0.1 mpk PO (n = 10) | 43.1 | 16.4 |
| Compound 2 @ 0.3 mpk PO (n = 11) | 74.1 | 18.1 |
| Compound 2 @ 1 mpk PO (n = 11) | 104.8 | 24.7 |
| Compound A @ 150 mpk IP (n = 10) | 135.8 | 16.6 |

In summary, these studies suggest that compounds of the invention have the potential to be efficacious in the treatment of inflammatory pain following oral administration.

Example 35 Formalin Model

Compound 2 was tested in the formalin-induced pain test reported by Dubuisson et al., Pain (1977) December; 4(2): 161-74. Dubuisson et al describe a method for assessing pain and analgesia in rats and cats. Briefly, dilute formalin (50 µL of 3% formalin) is injected into the plantar surface of the hind paw of a rat. The animal is promptly returned to an observation arena (standard Plexiglass rat cage), at which point a trained observer records the time the animal spends exhibiting pain behaviors (flinching, licking, biting of the injected paw/leg) in two distinct phases. The initial phase (Phase I: 0-5 min) is thought to have a significant component that is dependent upon direct activation of afferent fibers by formalin and functional TRPA1 (McNamara et al., 2007). The individual responsible for counting the pain behaviors in a particular study is blinded to the treatment groups.

Figure 14:
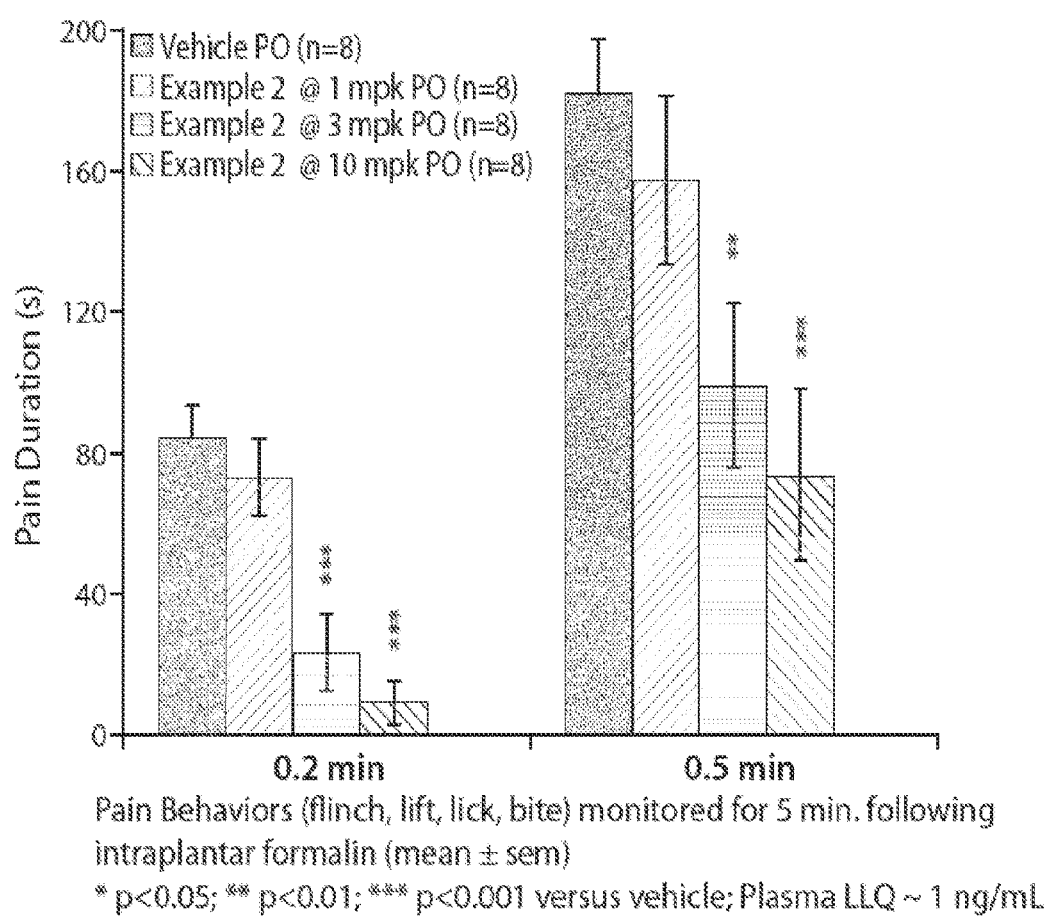
FIG. 14 is a chart depicting the dose response observed upon oral administration of Compound 2 (i.e., Example 2) in the formalin model.

Investigators studied oral administration of Compound 2 at 1, 3 and 10 mg/kg on pain behaviors in the formalin model in the rat. Compound 2 was prepared as solutions in 4% DMSO, 10% Solutol HS15, 86% WFI. Animals were dosed orally with Vehicle (4% DMSO, 10% Solutol, 86% WFI), or Compound 2 at 1, 3 or 10 mg/kg one hour prior to intraplantar formalin. FIG. 14 shows the duration of pain behaviors observed in the first two minutes (Left) or the duration of pain behaviors during the entire study period; five minutes (Right). (n=8 per group) (*=$p<0.05$, =$p<0.01$, * $p<0.001$:1-tailed T-test)

Oral administration of Compound 2 significantly reduced the nociceptive responses in Phase 1 of the formalin model at 3 and 10 mg/kg as seen in Table 20 and FIG. 14. Compared to vehicle treated animals, animals treated with Compound 2 at 1 mg/kg resulted in a ~14% decrease in the duration of pain behaviors from 0-2 minutes following intraplantar formalin, although this reduction was not statistically significant. At doses of 3 and 10 mg/kg PO, Compound 2 resulted in a significant decrease in formalin-induced pain behaviors from 0-2 minutes by ~72% and ~89%, respectively, compared to vehicle treated animals.

A similar reduction in the duration of pain behaviors was also observed with Compound 2 from 0-5 minutes post-formalin administration. At 1 mg/kg PO, Compound 2 reduced pain behaviors by ~14%, but did not reach statistical significance compared to vehicle treated animals. At 3 and 10 mg/kg PO, Compound 2 significantly reduced the duration of formalin-induced pain behaviors by 46% and ~60%, respectively.

TABLE 20

Dose response of Compound 2 administered orally using the formalin model

| Dose | Duration (seconds) 0-2 min | Duration (seconds) 0-5 min |
| --- | --- | --- |
| Vehicle PO (n = 8) | 84.50 | 182.00 |
| Compound 2 @ 1 mpk PO (n = 8) | 73.00 | 157.38 |
| Compound 2 @ 3 mpk PO (n = 8) | 23.25 | 99.00 |
| Compound 2 @ 10 mpk PO (n = 8) | 9.25 | 73.50 |

Figure 15:
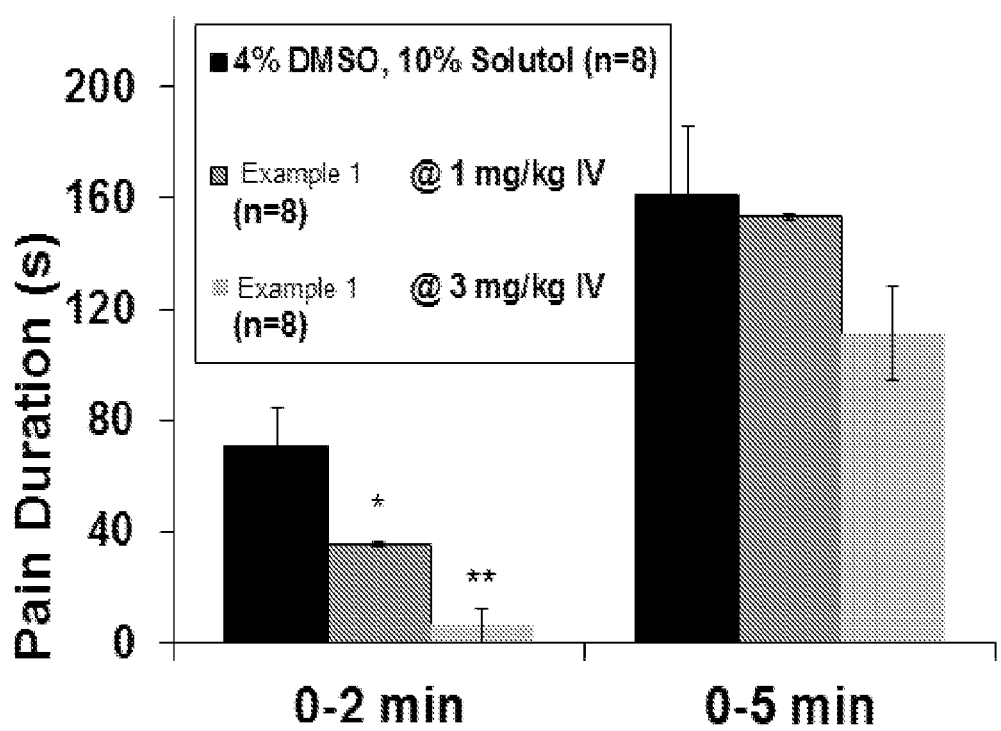
FIG. 15 is a chart depicting the efficacy observed with doses of intravenously administered Compound 1 (i.e., Example 1) in the formalin model.

A reduction in the duration of pain behaviors was also observed with Compound 1 from 0-5 minutes post-formalin administration. At 1 mg/kg and 3 mg/kg delivered intravenously to rats, Compound 1 reduced the duration of formalin-induced pain behaviors as shown in Table 21 and FIG. 15.

TABLE 21

Dose response of Compound 1 administered intravenously using the formalin model

| Dose | Duration (seconds) 0-2 min | Duration (seconds) 0-5 min |
| --- | --- | --- |
| Vehicle (n = 8) | 71.00 | 160.75 |
| Compound 1 @ 1 mg/kg IV (n = 8) | 35.50 | 153.25 |
| Compound 1 @ 3 mg/kg IV (n = 8) | 6.25 | 111.25 |

A reduction in the duration of pain behaviors was also observed with Compound 4 from 0-5 minutes post-formalin administration. Using the methods described above for the formalin assay, Compound 4 was formulated as a solution in 4% DMSO; 5% Tween-80; 20% Cremophor EL; and 71% WFI and administered by oral gavage to rats. Compound 4 reduced the duration of formalin-induced pain behaviors as shown in Table 22.

TABLE 22

Dose response of Compound 4 administered orally using the formalin model

| Dose | Duration (seconds) 0-2 min | Duration (seconds) 0-5 min |
| --- | --- | --- |
| Vehicle PO (n = 8) | 91.50 | 237.25 |
| Compound 4 @ 1 mpk PO (n = 8) | 76.13 | 197.88 |
| Compound 4 @ 3 mpk PO (n = 8) | 45.25 | 175.88 |
| Compound 4 @ 10 mpk PO (n = 8) | 47.13 | 191.00 |

Using the methods described above for the formalin assay, Compound 4 was formulated as a suspension in 0.5% methylcellulose and administered by oral gavage to rats. Compound 4 reduced the duration of formalin-induced pain behaviors as shown in Table 23.

TABLE 23

Dose response of Compound 4 administered orally using the formalin model

| Dose | Duration (seconds) 0-2 min | Duration (seconds) 0-5 min |
| --- | --- | --- |
| Vehicle PO (n = 8) | 94.25 | 192.75 |
| Compound 4 @ 1 mpk PO (n = 8) | 80.38 | 186.25 |
| Compound 4 @ 3 mpk PO (n = 8) | 51.13 | 163.25 |
| Compound 4 @ 10 mpk PO (n = 8) | 38.13 | 144.25 |

Figure 8:
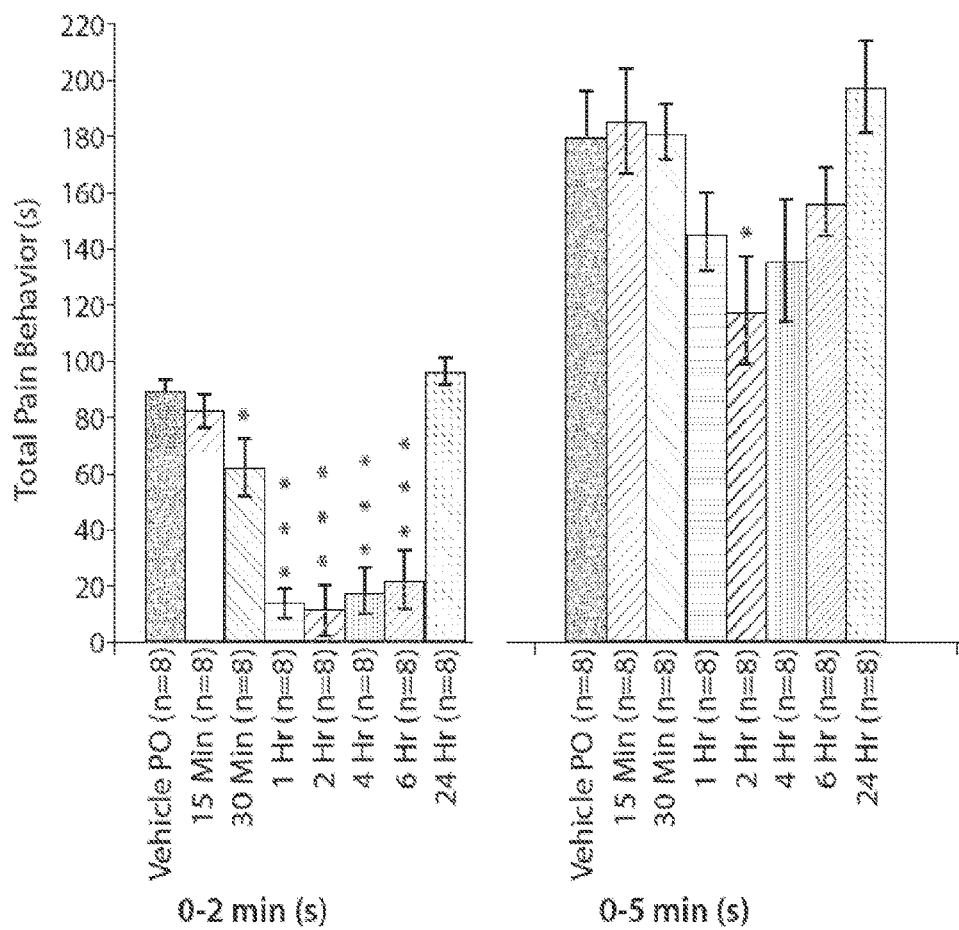
FIG. 8 is a chart depicting the duration of formalin-mediated pain behaviors post oral administration of Compound 2. Compound 2 was dosed at 15 minutes, 30 minutes, 1 hour, 2 hours, 4 hours, 6 hours, or 24 hours prior to formalin injection to assess the persistence of the benefit provided by treatment.

The persistence of the response was also studied. Compound 2 was prepared as a solution in 4% DMSO, 10% Solutol HS15, and 86% WFI. Rats were treated with 10 mg/kg of oral doses of Compound 2 or with the vehicle (PO). FIG. 8 shows that pre-treatment with oral dose formulation of Compound 2 at 10 mg/kg PO from 30 minutes to 6 hours prior to formalin injection significantly decreased the duration of formalin-mediated pain behaviors.

Compared to vehicle treated animals, 15 minute to 6 hour pre-treatment with oral Compound 2 at 10 mg/kg PO resulted in an ~30-87% decrease in the duration of formalin-induced pain behaviors 0-2 minutes following formalin injection, with the maximum decrease in pain behavior observed in the 2 hour pre-treatment group as shown in Table 24.

TABLE 24

Duration of pain response upon oral administration of Compound 2 using the formalin model

| Dose | Duration (seconds) 0-2 min | Duration (seconds) 0-5 min |
| --- | --- | --- |
| Vehicle PO (n = 8) | 89.63 | 179.73 |
| 15 Min (n = 8) | 82.50 | 185.43 |
| 30 Min (n = 8) | 62.50 | 181.40 |
| 1 Hr (n = 8) | 14.50 | 146.14 |
| 2 Hr (n = 8) | 12.00 | 118.10 |
| 4 Hr (n = 8) | 19.00 | 135.84 |
| 6 Hr (n = 8) | 22.75 | 156.61 |
| 24 Hr (n = 8) | 96.63 | 197.15 |

Compound 2 was also tested in the sheep model of allergic bronchoconstriction and airway hyperresponsiveness according to the methods disclosed in Abraham, W. M Puim *Pharmacol Ther* (2008) 21:743-754. Allergic sheep challenged with Ascaris suum show a substantial, biphasic increase in pulmonary resistance (RL). The first four hours are considered the early asthmatic response (EAR); the next four hours (hours 4-8) are considered to be the late asthmatic response (LAR). To assess airway responsiveness (AHR), the cumulative carbachol dose in breath units that increased pulmonary resistance 400% over the post-buffer value (PC 400) was calculated from the dose response curve. One breath unit was defined as one breath of a 1% w/v carbachol solution. A pre-challenge PC 400 was obtained 1-3 days before the start of dosing.

Compound 2 was formulated as a micronized powder suspended in 0.5% methylcellulose at a concentration of 6 mg/ml and administered orally at a dose of 30 mg/kg once a day for 4 days, at the same approximate time each day. Sheep were given 30 mg/kg Compound 2 orally daily four days. Two hours after the final dose of Compound 2, the sheep were subjected to an allergen (Ascaris) challenge. Each sheep was restrained in a prone position and its head was immobilized prior to topical anesthesia of the nasal passages. A balloon catheter was advanced through one nostril into the lower esophagus. Each sheep was intubated with a cuffed endotracheal tube through the other nostril. Tracheal and pleural pressures were determined using the endotracheal tube and balloon catheter, respectively. The trans-pulmonary pressure, i.e., the difference between the tracheal and pleural pressures, was measured using a differential pressure transducer catheter system. $R_L$ was determined by connecting the distal end of the endotracheal tube to a pneumotachograph. Data were collected from five to ten breaths to a computer and used to calculate $R_L$. Data from the same sheep challenged with Ascaris prior to the initiation of Compound 2 treatment were used to establish baseline values. Monitoring conditions for the control and drug trials were identical.

On the day of challenge and two hours after the final dose of Compound 2, an aerosol of Ascaris suum (82,000 protein nitrogen units/mL) was generated using a nebulizer and delivered to the sheep using a Harvard respirator. $R_L$ was determined one hour prior to challenge, immediately following Ascaris challenge, and hourly thereafter for eight hours. Challenge to 4 hours is considered the EAR while 4 to 8 hours is considered the LAR.

Sheep were also challenged with aerosolized carbachol, a cholinergic agonist that has a negative impact on AHR. The carbachol concentration in breath units that increased RL 400% (PC400) determinations were performed 24 hours following Ascaris challenge without Compound 2 dosing (historical baseline) or 24 hours after administration of the final dose of Compound 2.

Figure 16:
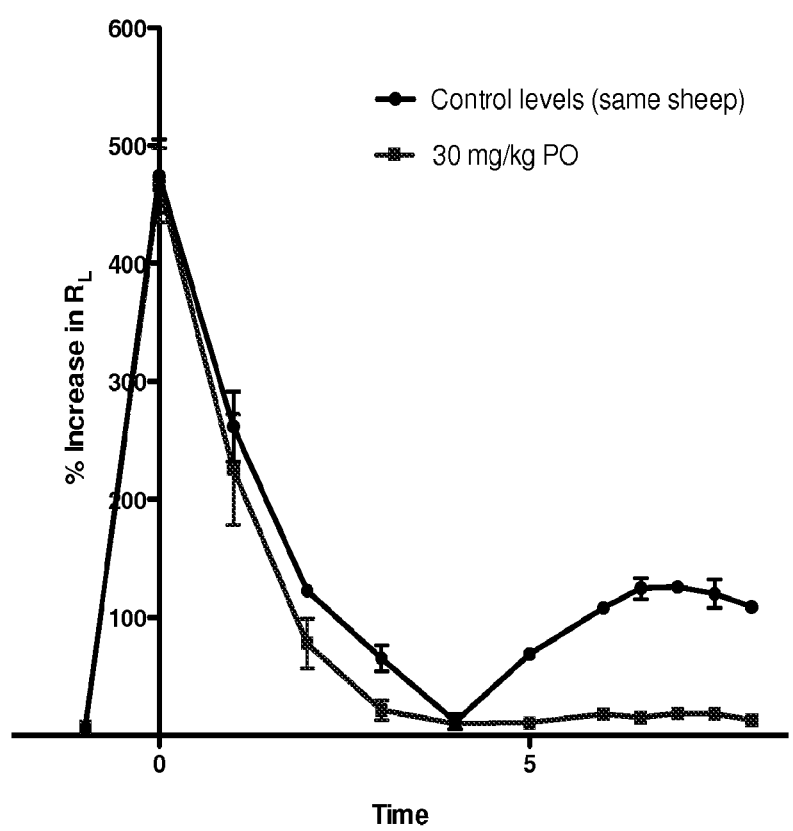
FIG. 16 is a graph depicting the change in lung resistance (early and late asthmatic response) in sheep challenged with allergen after administration of Compound 2.

FIG. 16 shows the antigen-induced responses in sheep at baseline (control) levels and following treatment with Compound 2 (30 mg/kg). Compound 2 did not affect the peak early airway responses. However, it dramatically attenuated the late airway responses (85% protection). In the control trial the average late airway responses was 126±4.7%, whereas in the treatment trial the average LAR was only 19±2.3% (P=0.002).

Figure 17:
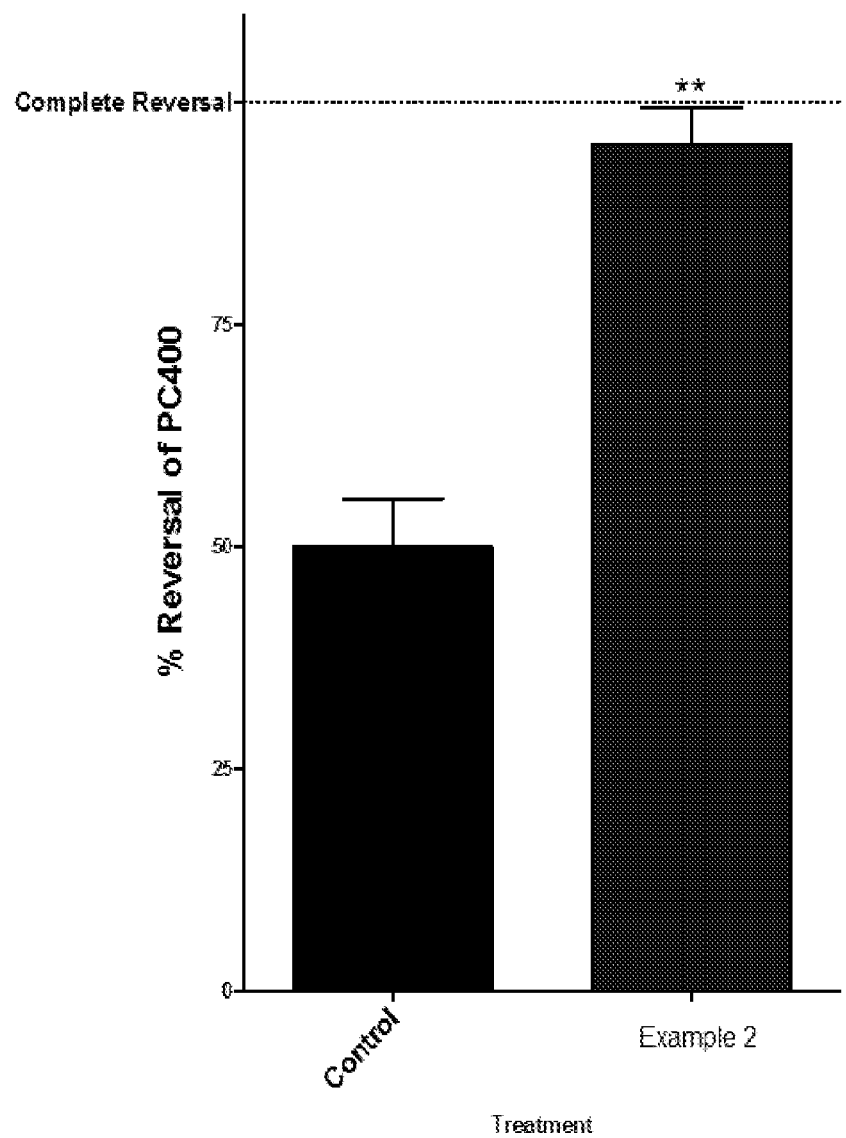
FIG. 17 is a chart depicting the effect of Compound 2 (i.e., Example 2) on measurement of airway hyperresponsiveness in the sheep model of allergic asthma.

FIG. 17 further shows the effect of Compound 2 (30 mg/kg) on PC400, a measurement of airway hyperresponsiveness representing the concentration of carbachol that induces a 400% increase in lung resistance.

In summary, treatment with Compound 2 reduced the airway hyperresponsiveness to levels similar to those observed in sheep that were not challenged with Ascaris suum.

Example 36 Pharmaceutical Profile

Compounds of the invention may not have significant drug/drug interactions, making administration preferable to patients taking multiple medications.

The ability of Compound 2 to inhibit human CYP450 enzymes was evaluated. Compound 1 and Compound 2 were tested in standard P450 Cyp-inhibition luminescent assay. Results are shown in Table 25 below.

TABLE 25

Inhibition of CYP450 enzymes by Compounds 1 and 2

| Compound | CYP 1A2: % Inhibition | CYP 2C19: % Inhibition | CYP 2C9: % Inhibition | CYP 2D6: % Inhibition | CYP 3A4: % Inhibition |
| --- | --- | --- | --- | --- | --- |
| 1 | 4.2 | 45.9 | 71.4 | 9 | 26.9 |
| 2 | 0.299 | 29.1 | 39.6 | 6.3 | 2.7 |

Compound 2 achieved a maximum block of human CYP450 enzymes of up to 37% at 10 μM for the seven isozymes tested; these values indicate that calculated $IC_{50}$ values would be >10 μM (Table 26).

Figure 9:
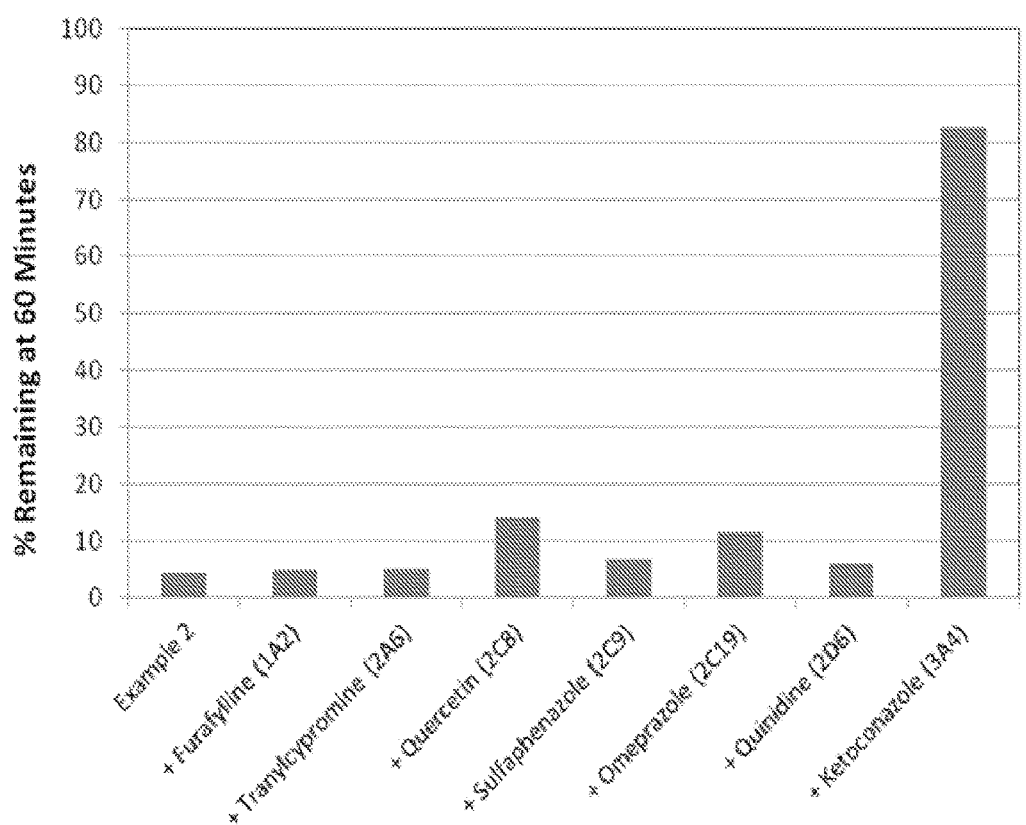
FIG. 9 is a chart depicting an exemplary profile of CYP450 reaction phenotyping with Compound 2, also referred to herein as Example 2.

CYP450 reaction phenotyping of Compound 2 was conducted by incubating the test article with human liver microsomes in the presence and absence of selective CYP450 inhibitors. The metabolic half-lives were not significantly affected by any of the CYP450 inhibitors except for ketoconazole, indicating that the in vitro metabolism of Compound 2 involved mainly the CYP3A4 isozymes (FIG. 9).

TABLE 26

CYP450 inhibition at 10 µM by Compound
2 and appropriate reference compounds

|  | CYP450 Isozyme | CYP450 Substrate | Mean % Inhibition at 10 µM |
|---|---|---|---|
| Compound ID |  |  |  |
| Compound 2 | 1A2 | Phenacetin | 9.0 |
| Compound 2 | 2B6 | Buproprion | 15.1 |
| Compound 2 | 2C8 | Amodiaquine | 3.2 |
| Compound 2 | 2C9 | Diclofenac | 22.0 |
| Compound 2 | 2C19 | Mephenytoin | 37.1 |
| Compound 2 | 2D6 | Dextromethorphan | 9.5 |
| Compound 2 | 3A4 | Midazolam | 0.0 |
| Compound 2 | 3A4 | Testosterone | 2.8 |
| Controls: |  |  |  |
| Fluvoxamine | 1A2 | Phenacetin | 96.6 |
| Ticlopidine | 2B6 | Buproprion | 98.2 |
| Quercetin | 2C8 | Amodiaquine | 61.5 |
| Sulfaphenazole | 2C9 | Diclofenac | 95.3 |
| Omeprazole | 2C19 | Mephenytoin | 68.2 |
| Quinidine* | 2D6 | Dextromethorphan | 55.8 |
| Ketoconazole | 3A4 | Midazolam | 99.2 |
| Ketoconazole | 3A4 | Testosterone | 98.8 |

*1 µM Assay Concentration

Example 37 Hepatotoxicity Safety Profile in Dogs

Compound 2 in vehicle (0.5% methylcellulose [400 cps] in deionized water) was administered orally once daily for five consecutive days by gavage once to 3 groups of non-naïve male and female beagle dogs. Each group received one dose level. Dose levels were 300, 600, and 1000 mg/kg for each group. A concurrent control group received the vehicle on a comparable regimen. The dose volume was 10 ml/kg for all groups. Hepatoxicity was measured via the serum biomarkers of alanine aminotransferease [ALT], aspartate aminotransferase [AST], alkaline phosphastase [ALP] and gamma-glutamyl transferase [GGT] which represent hepatotoxicity or bile duct injury. Table 27 shows that Compound 2 in the dogs at each dose level indicated did not elevate the serum biomarkers up to and including a dose of 300 mg/kg.

TABLE 27

Hepatoxicity safety profile of Compound 2 in beagle dogs

| Serum Biomarker | 0 mg/kg (U/L) | 30 mg/kg (U/L) | 100 mg/kg (U/L) | 300 mg/kg (U/L) |
|---|---|---|---|---|
| ALP d-5 | 93.0 | 93.0 | 120.0 | 118.0 |
| ALP d5 | 102.0 | 143.0 | 141.0 | 101.0 |
| ALT d-5 | 24.0 | 19.0 | 21.0 | 28.0 |
| ALT d5 | 21.0 | 20.0 | 19.0 | 21.0 |
| AST d-5 | 23.0 | 20.0 | 20.0 | 22.0 |
| AST d5 | 30.0 | 22.0 | 21.0 | 22.0 |
| GGT d-5 | 0.0 | 0.0 | 0.0 | 0.0 |
| GGT d5 | 0.0 | 0.0 | 0.5 | 0.0 |
| n | 1 | 2 | 2 | 2 |

Figure 18:
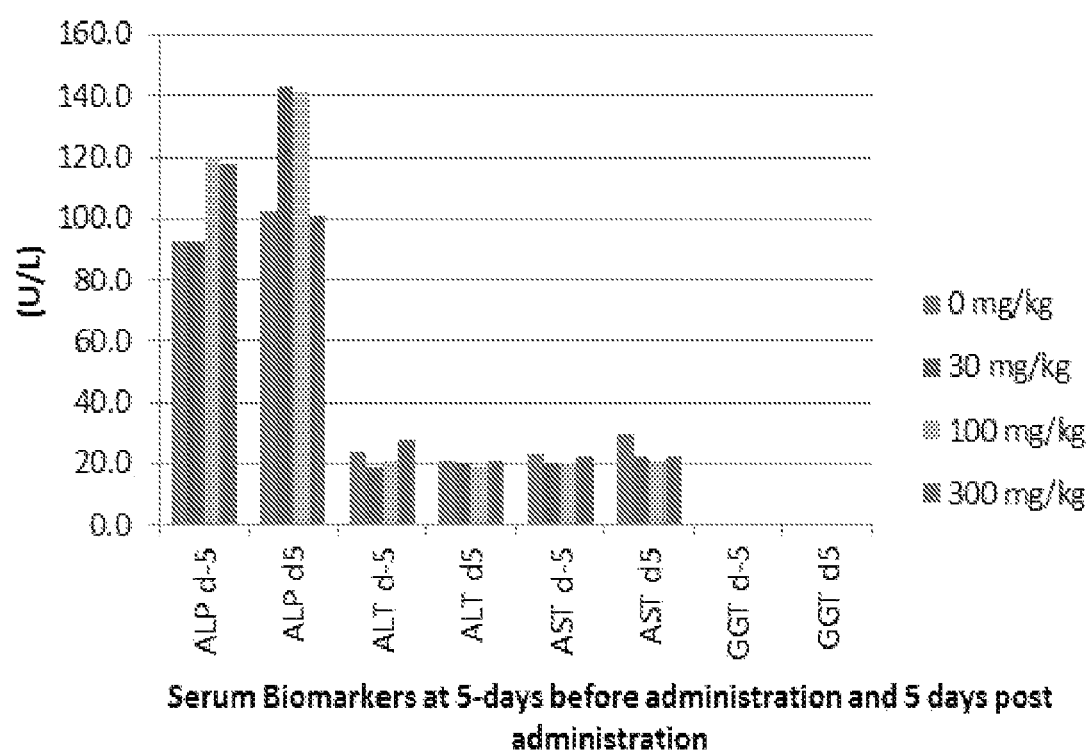
FIG. 18 is a chart depicting the serum biomarkers of hepatotoxicity in beagle dogs before and after receiving a once daily oral dose of Compound 2 over 5 days.
Figure 19:
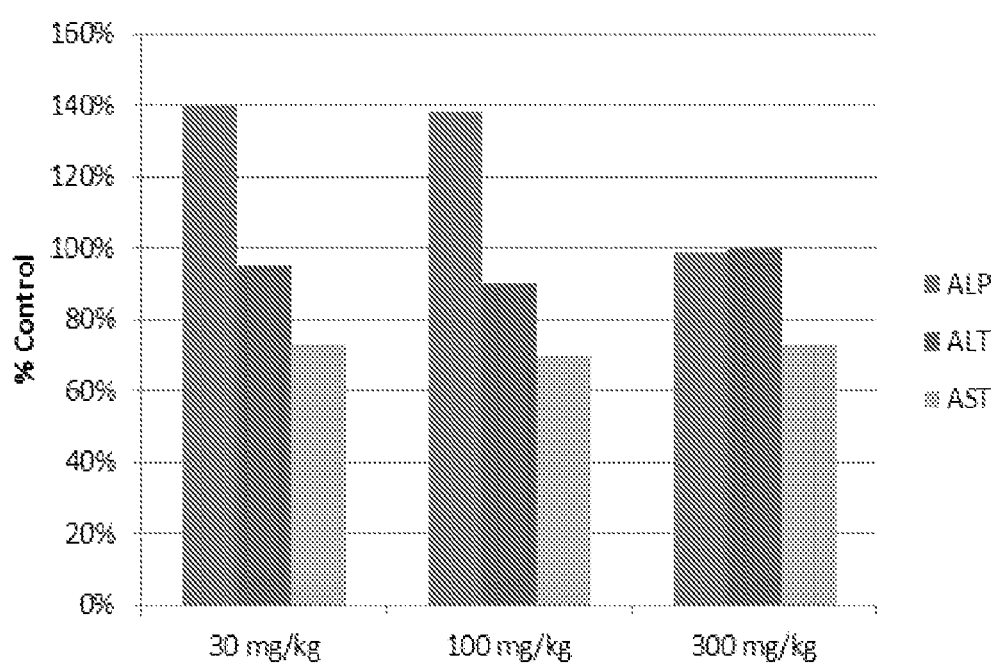
FIG. 19 is a chart depicting the change in serum biomarkers of hepatotoxicity between a control and Compound 2 (orally administered) in beagle dogs on Day 5 after receiving a once daily oral dose of Compound 2 over 5 days.

FIG. 18 further demonstrates that Compound 2 does not significantly elevate serum biomarker levels above normal ranges. FIG. 19 demonstrates that Compound 2 did not significantly elevate serum biomarker levels above base line measurements as demonstrated by a % difference over the vehicle.

Example 38 Hepatotoxicity Safety Profile in Rats

Compound 2 in the vehicle (0.5% methylcellulose [400 cps]) was administered orally by gavage once daily for a minimum of 28 consecutive days to 3 groups of sprague-dawley rats from Charles River Laboratories. Each group received one dosage level. Dosage levels were 30, 100, and 300 mg/kg/day for each group. Concurrent control groups received the vehicle on a comparable regimen. The dose volume was 10 ml/kg for all groups. Hepatoxicity was measured via the serum biomarkers of alanine aminotransferease [ALT], aspartate aminotransferase [AST], alkaline phosphastase [ALP] and gamma-glutamyl transferase [GGT] which represent hepatotoxicity or bile duct injury. Table 28 shows that Compound 2 in the rats as each dose level indicated did not elevate the serum biomarkers up to and including a dose of 300 mg/kg.

TABLE 28

Hepatotoxicity safety profile of Compound 2 in rats

| Serum Biomarker | Dose of Compound 2 (U/L) | | | |
|---|---|---|---|---|
|  | 0 mg/kg | 30 mg/kg | 100 mg/kg | 300 mg/kg |
| ALP d28 | 186.0 | 168.0 | 185.0 | 163.0 |
| ALT d28 | 36.0 | 33.0 | 34.0 | 43.0 |
| AST d28 | 116.0 | 98.0 | 100.0 | 115.0 |
| GGT d28 | 0.0 | 0.0 | 0.0 | 0.0 |
| n | 10.0 | 10.0 | 10.0 | 10.0 |

Figure 20:
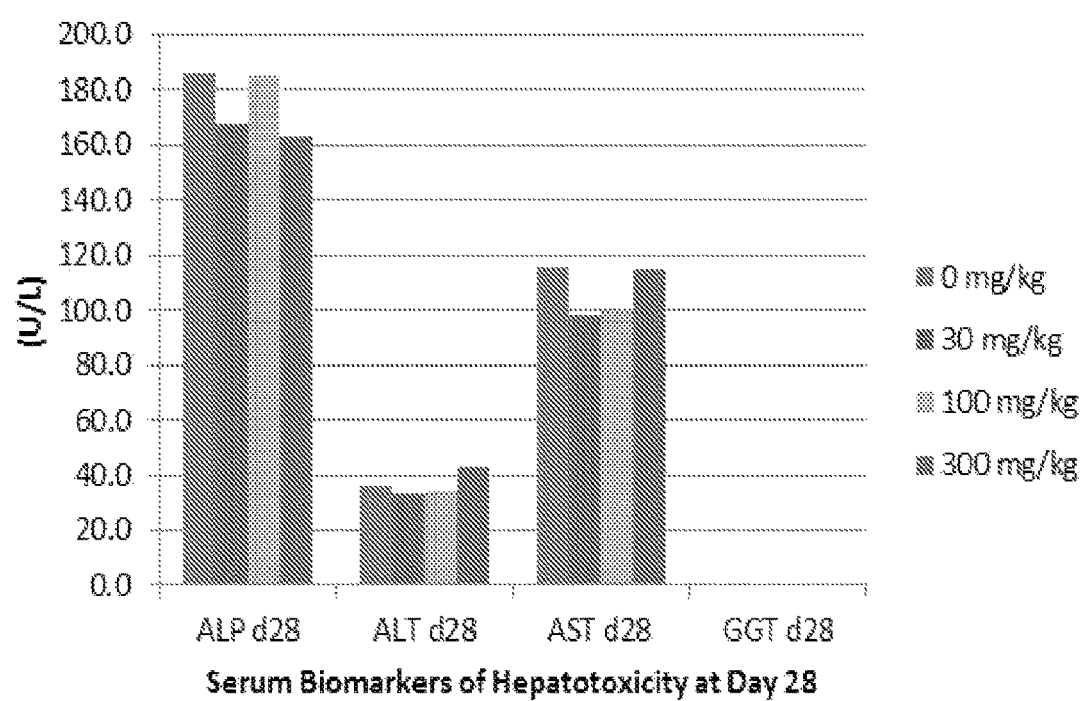
FIG. 20 is a chart depicting the change in serum biomarkers of hepatotoxicity in sprague-dawley rats after receiving a once daily oral dose of Compound 2 over 28 days.
Figure 21:
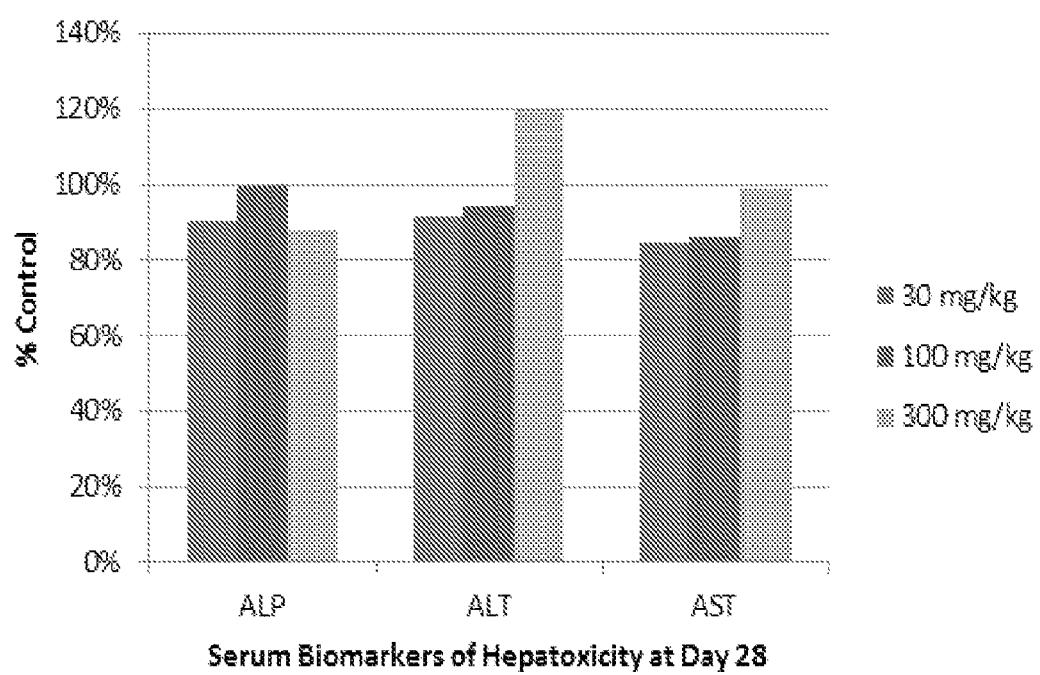
FIG. 21 is a chart depicting the change in serum biomarkers of hepatotoxicity between a control and Compound 2 (orally administered) in sprague-dawley rats on day 28 after receiving a once daily oral dose of Compound 2 over 28 days.

FIG. 20 further demonstrates that Compound 2 does not significantly elevate levels above normal ranges. FIG. 21 demonstrates that Compound 2 did not significantly elevate levels above base line measurements as demonstrated by a % difference over the vehicle.

Example 39 Hepatotoxicity Safety Profile in Monkeys

Compound 2 in the vehicle (0.5% methylcellulose, 400 cps) was administered via nasogastric intubation once daily for 28 or 29 consecutive days to 4 groups of cynomolgus monkeys. Each group received one dose level. Dosage levels were 10, 30, 100, and 300 mg/kg/day per group. A concurrent control group received the vehicle on a comparable regimen. The dosage volume was 10 ml/kg for all groups. Hepatoxicity was measured via the serum biomarkers of alanine aminotransferease [ALT], aspartate aminotransferase [AST], alkaline phosphastase [ALP] and gamma-glutamyl transferase [GGT] which represent hepatotoxicity or bile duct injury. Table 29 shows that Compound 2 in the monkeys at each dose level indicated did not elevate the serum biomarkers up to and including a dose of 300 mg/kg.

TABLE 29

Hepatotoxicity safety profile of Compound 2 in cynomolgus monkeys

| Serum Biomarker | Dosage of Compound 2 (U/L) | | | | |
|---|---|---|---|---|---|
|  | 0 mg/kg | 10 mg/kg | 30 mg/kg | 100 mg/kg | 300 mg/kg |
| ALP d28 | 565.0 | 744.0 | 461.0 | 532.0 | 441.0 |
| ALT d28 | 59.0 | 87.0 | 50.0 | 61.0 | 67.0 |
| AST d28 | 80.0 | 126.0 | 72.0 | 70.0 | 134.0 |
| GGT d28 | 67.6 | 64.0 | 49.0 | 53.7 | 54.8 |
| n | 5.0 | 3.0 | 3.0 | 3.0 | 5.0 |

Figure 22:
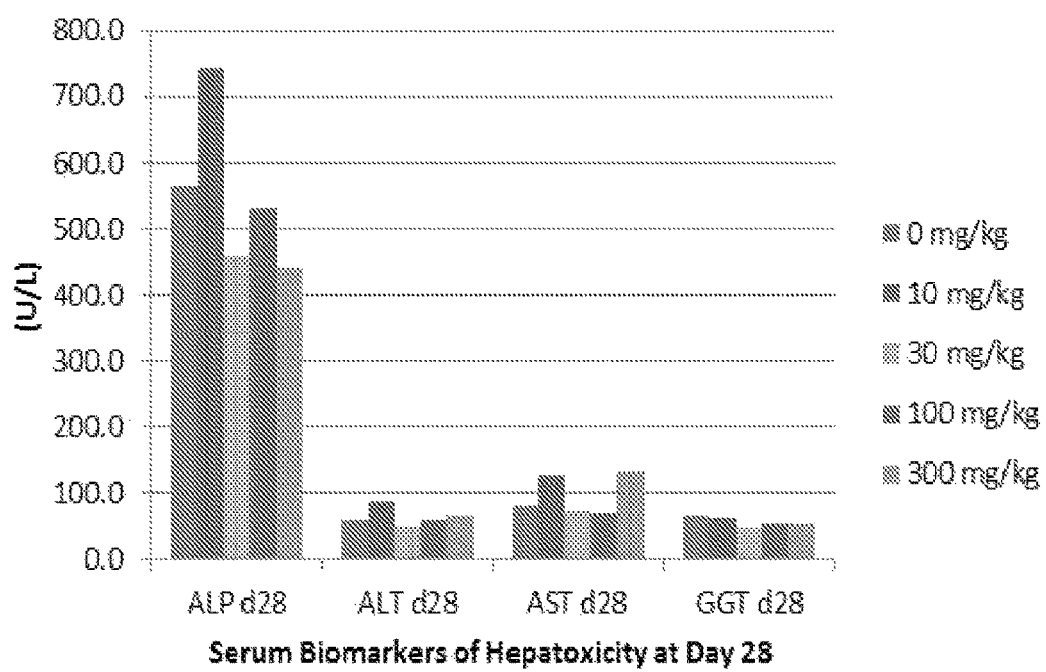
FIG. 22 is a chart depicting the serum biomarkers of hepatotoxicity in cynomolgus monkeys after receiving a once daily oral dose of Compound 2 over 28 days.
Figure 23:
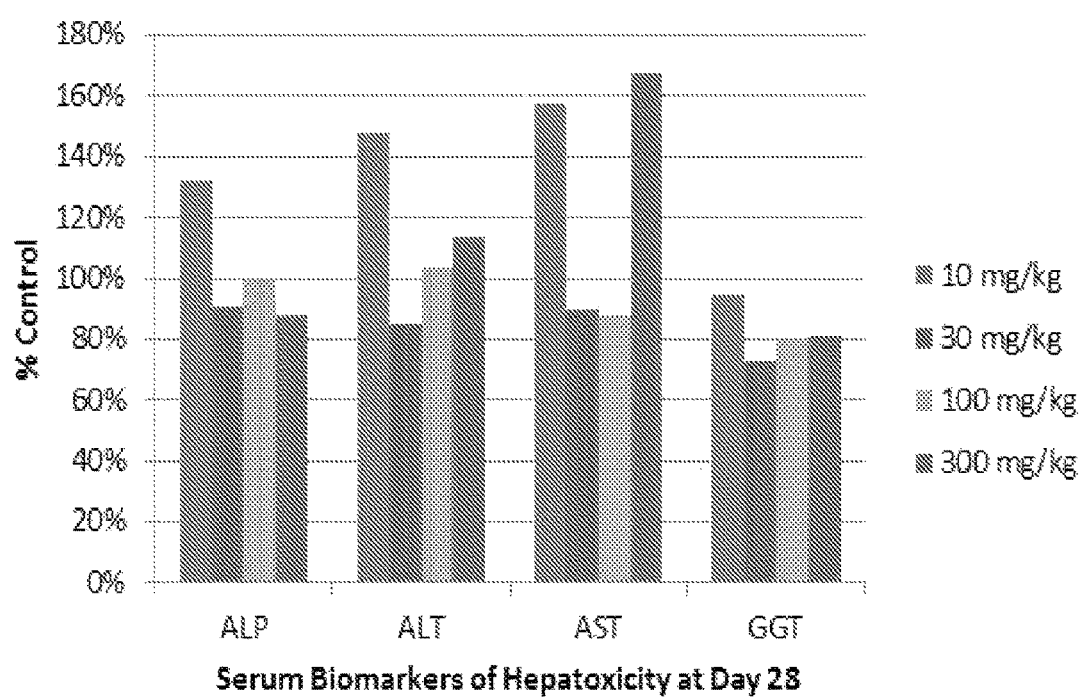
FIG. 23 is a chart depicting the change in serum biomarkers of hepatotoxicity between a control and Compound 2 (orally administered) in cynomolgus monkeys on day 28 after receiving a once daily oral dose of Compound 2 over 28 days.

FIG. 22 further demonstrates that Compound 2 does not significantly elevate levels above normal ranges. FIG. 23 demonstrates that Compound 2 did not significantly elevate levels above base line measurements as demonstrated by a % difference over the vehicle.

EQUIVALENTS

The disclosures of each and every patent, patent application, and publication cited herein are hereby incorporated herein by reference in their entirety. While this invention has been disclosed with reference to specific aspects, it is apparent that other aspects and variations of this invention may be devised by others skilled in the art without departing from the true spirit and scope of the invention. The appended claims are intended to be construed to include all such aspects and equivalent variations.

Any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference.

While this invention has been particularly shown and described with references to preferred embodiments thereof, it will be understood by those skilled in the art that various changes in form and details may be made therein without departing from the scope of the invention encompassed by the appended claims.

The invention claimed is:

1. A compound of the Formula (I) or a pharmaceutically acceptable salt thereof:

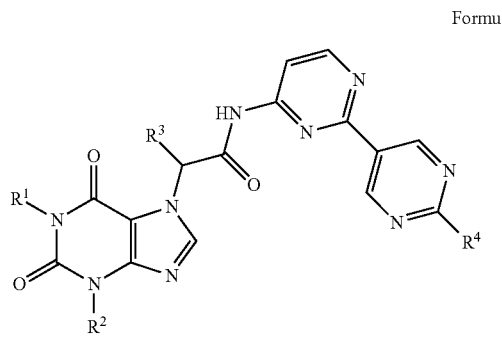

Formula (I)

wherein:
R$^1$ is H, C$_1$-C$_6$ alkyl, C$_2$-C$_6$ alkenyl, or C$_2$-C$_6$ alkynyl;
R$^2$ is H, C$_1$-C$_6$ alkyl, C$_2$-C$_6$ alkenyl, or C$_2$-C$_6$ alkynyl, optionally substituted with one or more R$^5$ groups;
R$^3$ is H, C$_1$-C$_6$ alkyl, C$_2$-C$_6$ alkenyl, or C$_2$-C$_6$ alkynyl;
R$^4$ is halo, hydroxy, alkoxy, thiol, alkylthio, amino, alkylamino, dialkylamino, cyano, nitro, amido, alkylamido, dialkylamido, thioyl, sulfonyl, cyclyl, heterocyclyl, aryl, or heteroaryl, optionally substituted at one or more positions with 1-4 R$^6$ groups;
R$^5$ is independently H, halogen, alkyl, aralkyl, alkenyl, alkynyl, hydroxy, amino, amido, phosphonate, carboxyl, ether, alkylthio, haloalkyl, and cyano; and
R$^6$ is independently H, halogen, alkyl, aralkyl, alkenyl, alkynyl, cycloalkyl, hydroxy, amino, nitro, sulfhydryl, imino, amido, phosphate, phosphonate, phosphinate, carbonyl, carboxyl, silyl, ether, alkylthio, sulfonyl, ketone, aldehyde, ester, heterocycle, an aromatic or heteroaromatic ring, haloalkyl, and cyano.

2. The compound according to claim 1, wherein R$^1$ is C$_1$-C$_6$ alkyl.
3. The compound of claim 2, wherein R$^1$ is —CH$_3$.
4. The compound of claim 1, wherein R$^1$ is H.
5. The compound of claim 1, wherein R$^2$ is H.
6. The compound of claim 1, wherein R$^2$ is C$_1$-C$_6$ alkyl.
7. The compound of claim 6, wherein R$^2$ is —CH$_3$ or —CHF$_2$.
8. The compound of claim 1, wherein each of R$^1$ and R$^2$ is independently C$_1$-C$_6$ alkyl.
9. The compound of claim 8, wherein each of R$^1$ and R$^2$ is independently —CH$_3$.
10. The compound of claim 1, wherein each of R$^1$ and R$^2$ is independently —CH$_3$ and R$^3$ is H.
11. The compound of claim 1, wherein R$^3$ is H.
12. The compound of claim 1, wherein R$^3$ is C$_1$-C$_6$ alkyl.
13. The compound of claim 12, wherein R$^3$ is —CH$_3$.
14. The compound of claim 1, wherein each of R$^1$, R$^2$, and R$^3$ is independently C$_1$-C$_6$ alkyl.
15. The compound of claim 14, wherein each of R$^1$, R$^2$ and R$^3$ is independently —CH$_3$.
16. The compound of claim 1, wherein the compound is of the Formula (Ia):

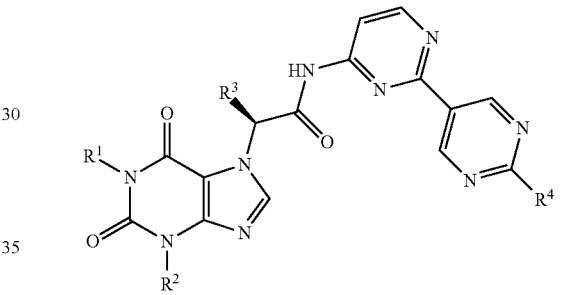

Formula (Ia), or a pharmaceutically acceptable salt thereof.

17. The compound of claim 1, wherein the compound is of the Formula (Ib):

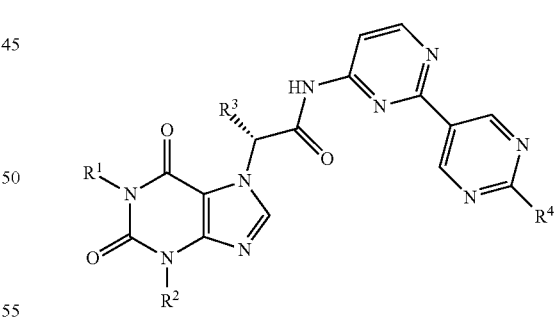

Formula (Ib), or a pharmaceutically acceptable salt thereof.

18. The compound of claim 1, wherein R$^4$ is heterocyclyl.
19. The compound of claim 18, wherein the heterocyclyl is a 4 to 8-membered ring.
20. The compound of claim 18, wherein the heterocyclyl is linked through a nitrogen atom.
21. The compound of claim 18, wherein R$^4$ is substituted heterocyclyl.
22. The compound of claim 21, wherein R$^4$ is selected from the group:

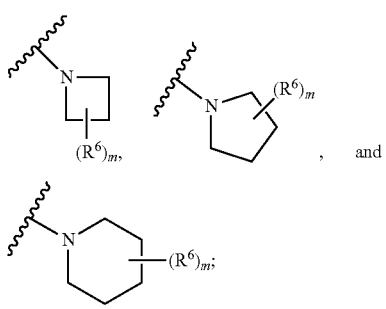

wherein m is 1, 2, 3, or 4.

23. The compound of claim 22, wherein $R^4$ is selected from the group:

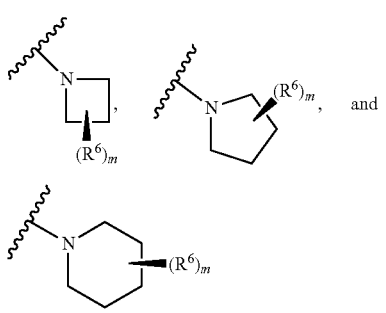

and m is 1.

24. The compound of claim 23, wherein $R^4$ is selected from the group:

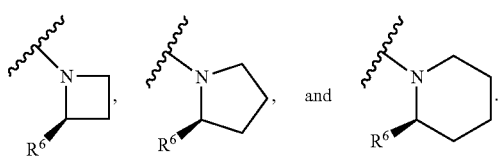

25. The compound of claim 22, wherein $R^4$ is selected from the group:

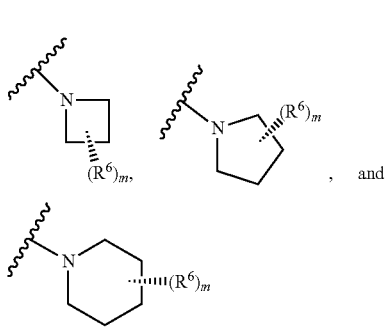

and m is 1.

26. The compound of claim 25, wherein $R^4$ is selected from the group:

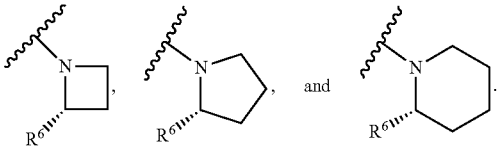

27. The compound of claim 22, wherein m is 1.

28. The compound of claim 1, wherein $R^6$ is alkyl, haloalkyl, or cyano.

29. The compound of claim 28, wherein $R^6$ is alkyl or haloalkyl.

30. The compound of claim 29, wherein $R^6$ is —$CF_3$.

31. The compound of claim 20, wherein $R^4$ is selected from the group:

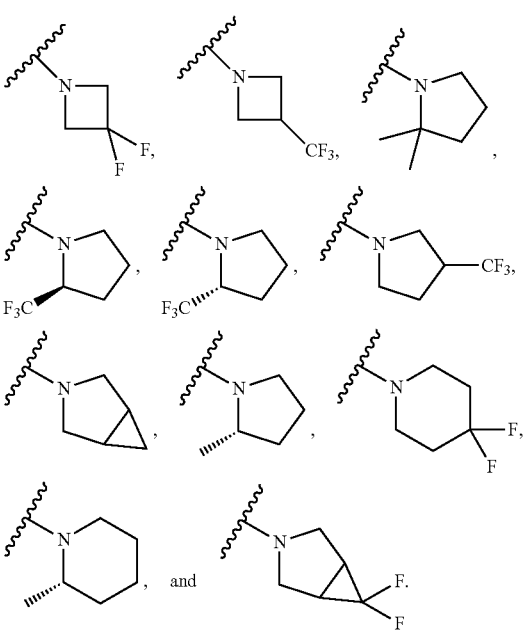

32. The compound of claim 1, wherein the compound of Formula (I) is of the Formula (II):

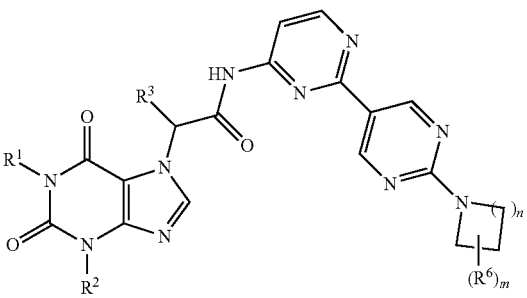

Formula (II)

wherein:
n is an integer from 0 to 4; and
m is selected from an integer from 0 to 4.

33. The compound of claim 1, wherein the compound of Formula (I) is of the Formula (IIa):

Formula (IIa)
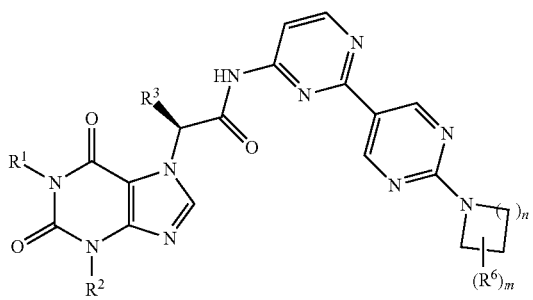
wherein:
n is an integer from 0 to 4; and
m is selected from an integer from 0 to 4.
34. The compound of claim 1, wherein the compound of Formula (I) is of the Formula (b):
Formula (IIb)
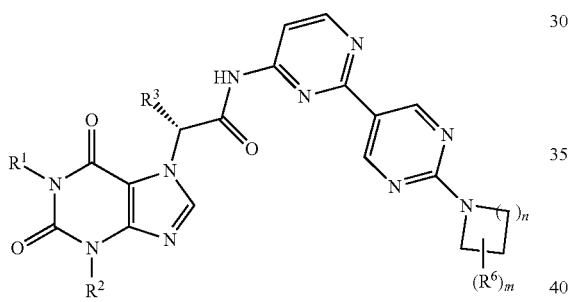
wherein:
n is an integer from 0 to 4; and
m is selected from an integer from 0 to 4.
35. The compound of claim 1, wherein the compound is selected from the following group:
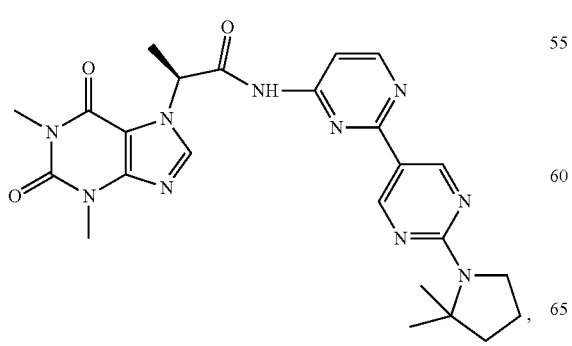
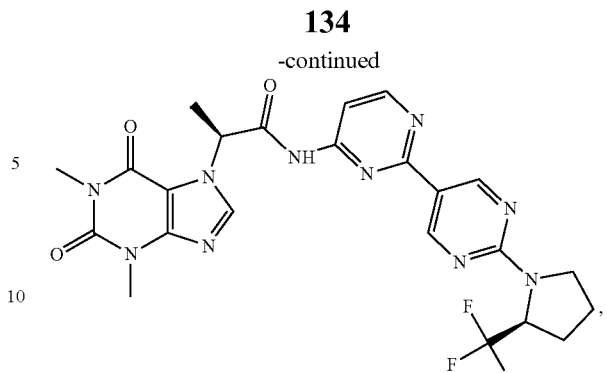
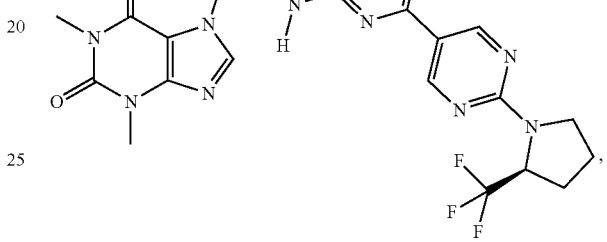
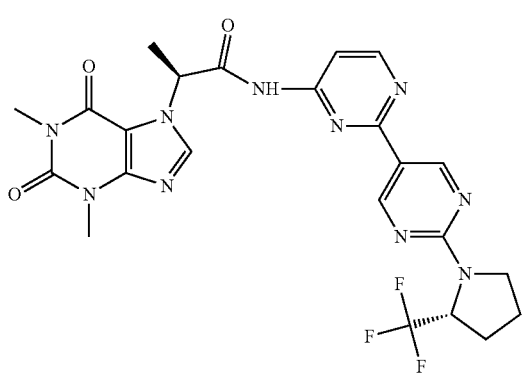
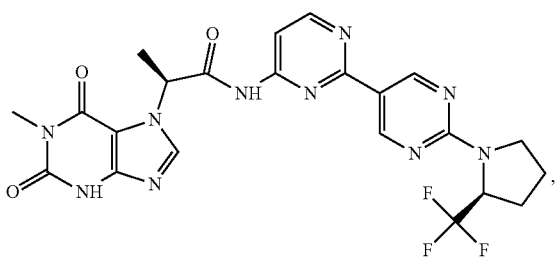
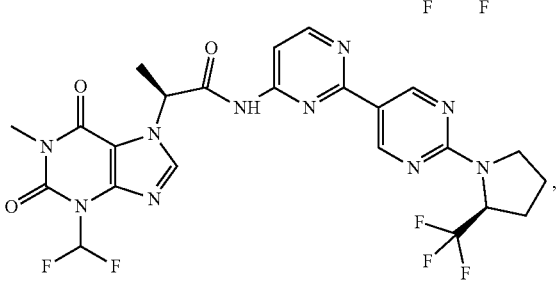

135
-continued
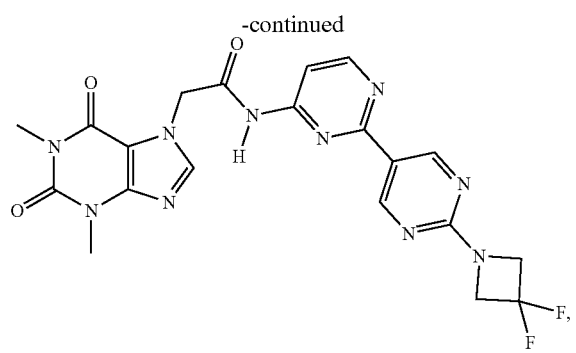
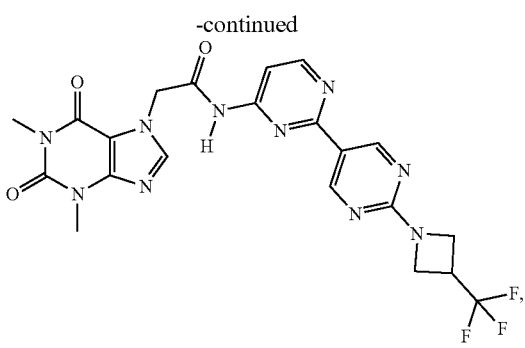
136
-continued
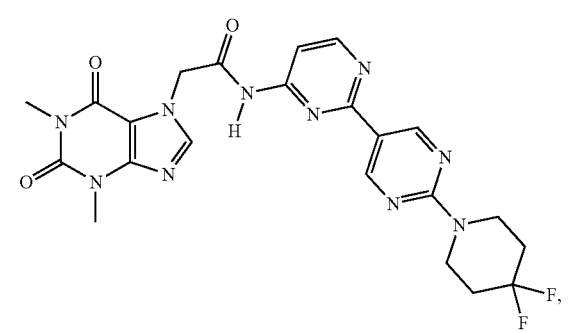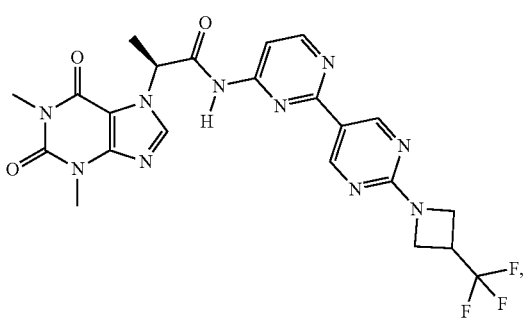
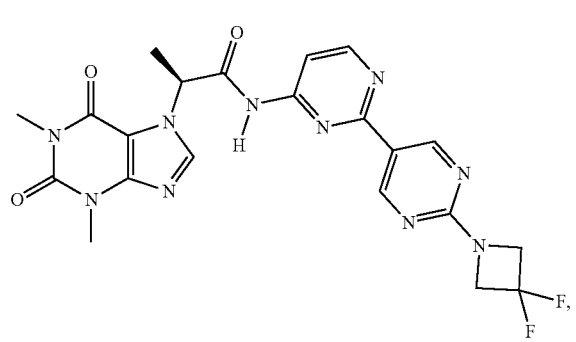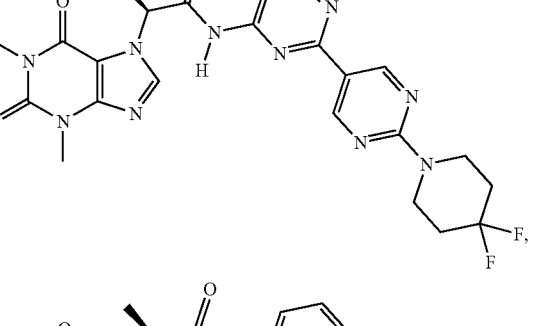
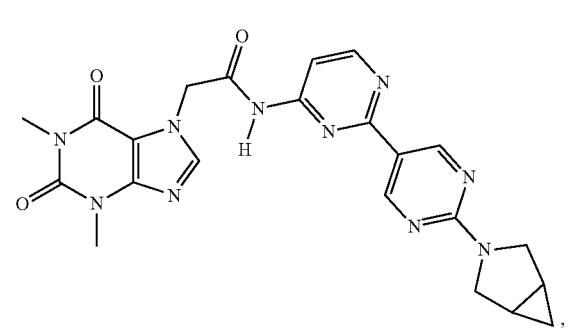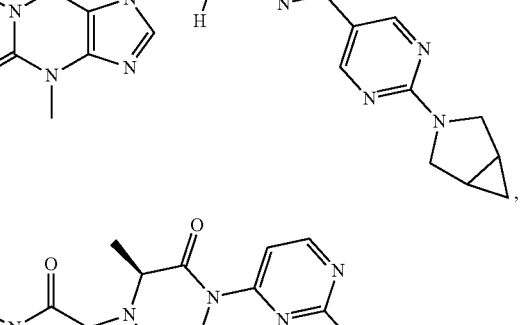
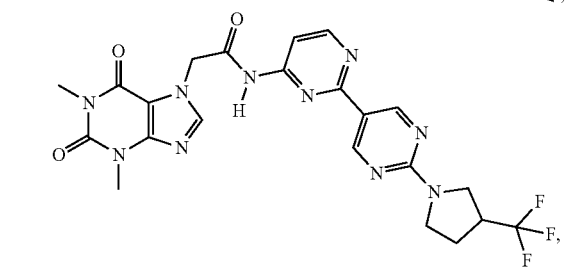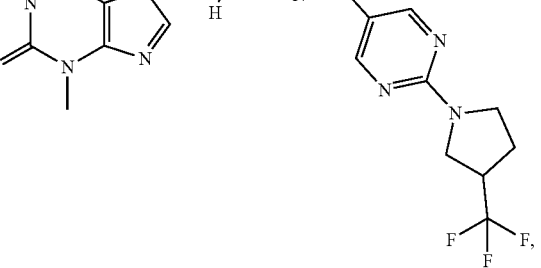

137
-continued
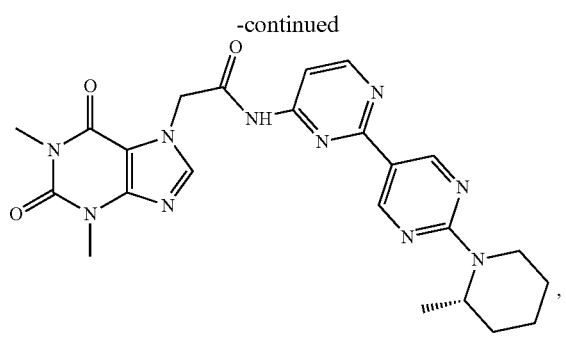
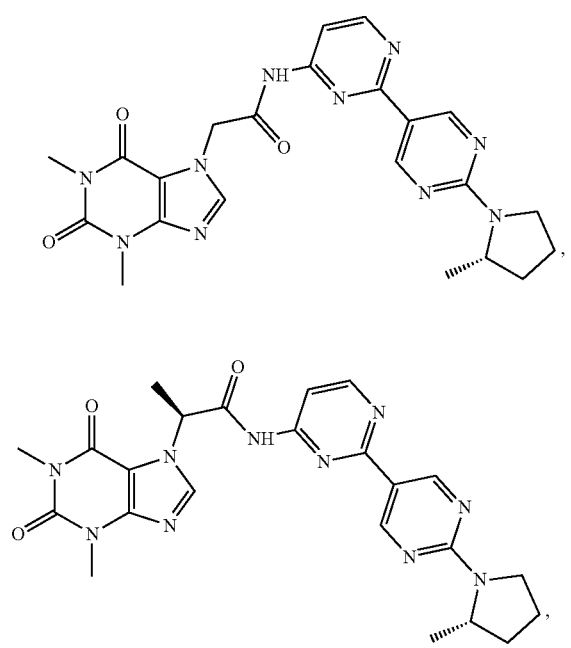
138
-continued
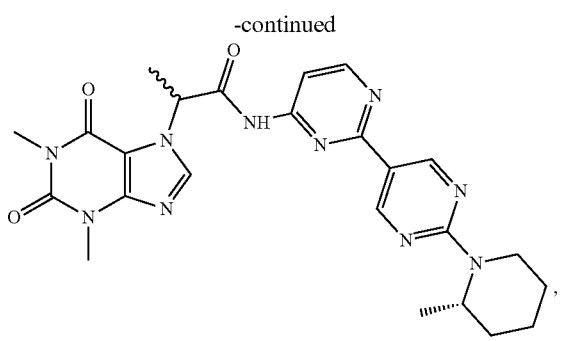
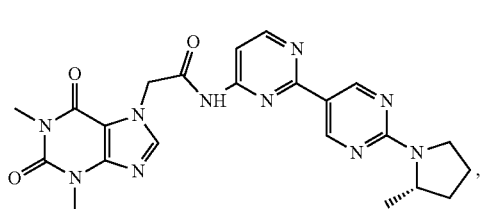
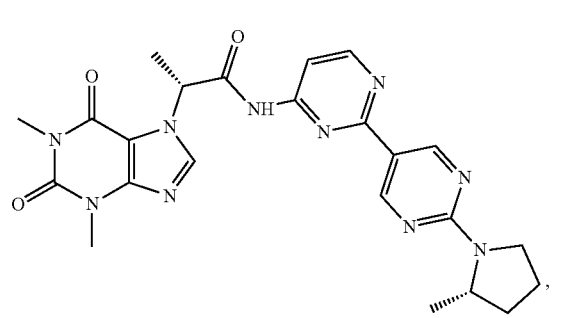
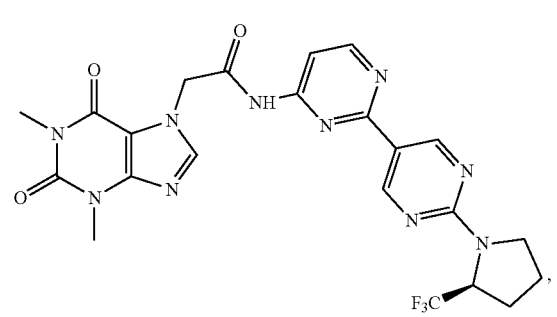

-continued

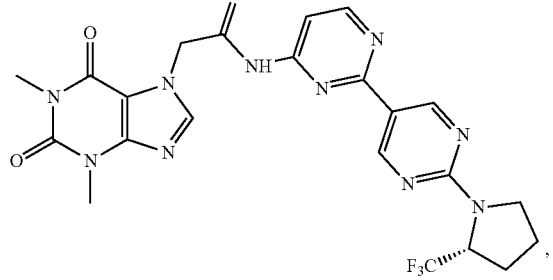

or a pharmaceutically acceptable salt thereof.

36. The compound of claim 1, wherein the compound is:

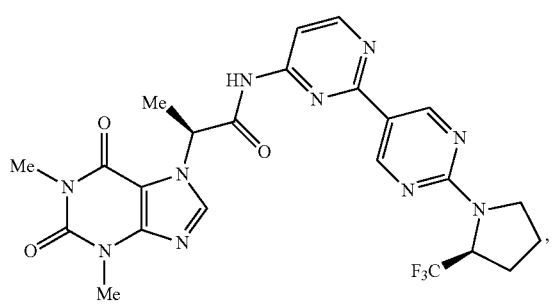 [SMILES: C[C@@H](C(=O)Nc1ccnc(-c2cnc(N3CCC[C@H]3C(F)(F)F)nc2)n1)n1cnc2c1c(=O)n(C)c(=O)n2C]

or a pharmaceutically acceptable salt thereof.

37. The compound of claim 36, wherein a solid crystalline form of the compound has an X-ray powder diffraction pattern comprising characteristic peaks, expressed in terms of 2θ, at about 7.67°, about 12.52°, about 13.49°, and about 19.31°.

38. The compound of claim 36, wherein a solid crystalline form of the compound has an X-ray powder diffraction pattern comprising characteristic peaks, expressed in terms of 2θ, at about 9.78°, about 12.98°, about 19.20°, and about 19.67°.

39. The compound of claim 1, wherein a solid crystalline form of the compound has a melting point of greater than or equal to 150° C.

40. The compound of claim 1, wherein a solid crystalline form of the compound has a melting point in the range of about 180° C. to about 205° C.

41. The compound of claim 1, wherein a solid crystalline form of the compound has a melting point in the range of about 190° C. to about 200° C.

42. A purified pharmaceutical preparation comprising a compound of Formula (I) or a pharmaceutically acceptable salt thereof:

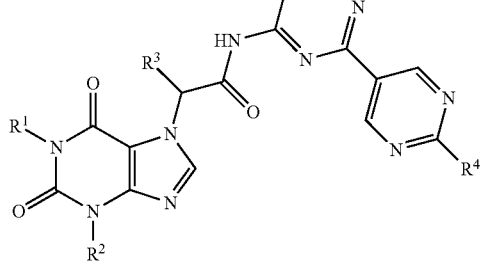

Formula (I)

wherein:

$R^1$ is H, $C_1$-$C_6$ alkyl, $C_2$-$C_6$ alkenyl, or $C_2$-$C_6$ alkynyl;

$R^2$ is H, $C_1$-$C_6$ alkyl, $C_2$-$C_6$ alkenyl, or $C_2$-$C_6$ alkynyl optionally substituted with one or more $R^5$ groups;

$R^3$ is H, $C_1$-$C_6$ alkyl, $C_2$-$C_6$ alkenyl, or $C_2$-$C_6$ alkynyl;

$R^4$ is halo, hydroxy, alkoxy, thiol, alkylthio, amino, alkylamino, dialkylamino, cyano, nitro, amido, alkylamido, dialkylamido, thioyl, sulfonyl, cyclyl, heterocyclyl, aryl, or heteroaryl, optionally substituted at one or more positions with 1-4 $R^6$ groups;

$R^5$ is independently H, halogen, alkyl, aralkyl, alkenyl, alkynyl, hydroxy, amino, amido, phosphonate, carboxyl, ether, alkylthio, haloalkyl, and cyano; and $R^6$ is independently H, halogen, alkyl, aralkyl, alkenyl, alkynyl, cycloalkyl, hydroxy, amino, nitro, sulfhydryl, imino, amido, phosphate, phosphonate, phosphinate, carbonyl, carboxyl, silyl, ether, alkylthio, sulfonyl, ketone, aldehyde, ester, heterocycle, an aromatic or heteroaromatic ring, haloalkyl, and cyano.

43. The preparation of claim 42, wherein the compound is:

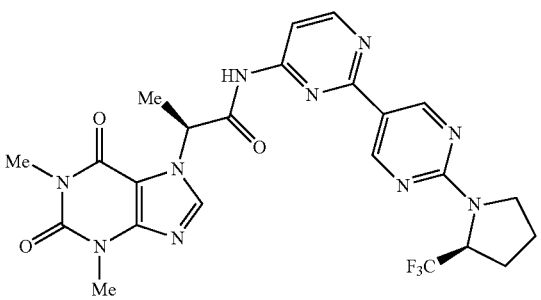 [SMILES: C[C@@H](C(=O)Nc1ccnc(-c2cnc(N3CCC[C@H]3C(F)(F)F)nc2)n1)n1cnc2c1c(=O)n(C)c(=O)n2C]

or a pharmaceutically acceptable salt thereof.

44. The preparation of claim 43, wherein the preparation comprises a diastereomeric excess of greater than or equal to 99%.

45. The preparation of claim 43, wherein the preparation has a moisture content of less than or equal to 0.1%.

46. A method for treating pain in a subject, the method comprising administering an effective amount of a compound of Formula (I), or a pharmaceutically acceptable salt thereof, to a subject in need thereof:

Formula (I)

wherein:

$R^1$ is H, $C_1$-$C_6$ alkyl, $C_2$-$C_6$ alkenyl, or $C_2$-$C_6$ alkynyl;

$R^2$ is H, $C_1$-$C_6$ alkyl, $C_2$-$C_6$ alkenyl, or $C_2$-$C_6$ alkynyl optionally substituted with one or more $R^5$ groups;

$R^3$ is H, $C_1$-$C_6$ alkyl, $C_2$-$C_6$ alkenyl, or $C_2$-$C_6$ alkynyl;

$R^4$ is halo, hydroxy, alkoxy, thiol, alkylthio, amino, alkylamino, dialkylamino, cyano, nitro, amido, alkylamido, dialkylamido, thioyl, sulfonyl, cyclyl, heterocyclyl, aryl, or heteroaryl, optionally substituted at one or more positions with 1-4 $R^6$ groups;

$R^5$ is independently H, halogen, alkyl, aralkyl, alkenyl, alkynyl, hydroxy, amino, amido, phosphonate, carboxyl, ether, alkylthio, haloalkyl, and cyano; and $R^6$ is independently H, halogen, alkyl, aralkyl, alkenyl, alkynyl, cycloalkyl, hydroxy, amino, nitro, sulfhydryl, imino, amido, phosphate, phosphonate, phosphinate, carbonyl, carboxyl, silyl, ether, alkylthio, sulfonyl, ketone, aldehyde, ester, heterocycle, an aromatic or heteroaromatic ring, haloalkyl, and cyano, to thereby treat the subject.

47. The method of claim 46, wherein the pain is neuropathic pain.

48. The method of claim 46, wherein the pain is inflammatory pain.

49. The method of claim 46, wherein the pain is PDN or CIPN.

50. The method of claim 46, wherein the pain is visceral pain.

51. The method of claim 46, wherein the pain is selected from the group: cancer pain, burn pain, oral pain, crush and injury-induced pain, incisional pain, bone pain, sickle cell disease pain, fibromyalgia and musculoskeletal pain.

52. The method of claim 46, wherein the pain is from hyperalgesia or allodynia.

53. A method for treating neuropathy in a subject, the method comprising administering an effective amount of a compound of Formula (I), or a pharmaceutically acceptable salt thereof, to a subject in need thereof:

Formula (I)

wherein:

$R^1$ is H, $C_1$-$C_6$ alkyl, $C_2$-$C_6$ alkenyl, or $C_2$-$C_6$ alkynyl;

$R^2$ is H, $C_1$-$C_6$ alkyl, $C_2$-$C_6$ alkenyl, or $C_2$-$C_6$ alkynyl optionally substituted with one or more $R^5$ groups;

$R^3$ is H, $C_1$-$C_6$ alkyl, $C_2$-$C_6$ alkenyl, or $C_2$-$C_6$ alkynyl;

$R^4$ is halo, hydroxy, alkoxy, thiol, alkylthio, amino, alkylamino, dialkylamino, cyano, nitro, amido, alkylamido, dialkylamido, thioyl, sulfonyl, cyclyl, heterocyclyl, aryl, or heteroaryl, optionally substituted at one or more positions with 1-4 $R^6$ groups;

$R^5$ is independently H, halogen, alkyl, aralkyl, alkenyl, alkynyl, hydroxy, amino, amido, phosphonate, carboxyl, ether, alkylthio, haloalkyl, and cyano; and $R^6$ is independently H, halogen, alkyl, aralkyl, alkenyl, alkynyl, cycloalkyl, hydroxy, amino, nitro, sulfhydryl, imino, amido, phosphate, phosphonate, phosphinate, carbonyl, carboxyl, silyl, ether, alkylthio, sulfonyl, ketone, aldehyde, ester, heterocycle, an aromatic or heteroaromatic ring, haloalkyl, and cyano, to thereby treat the subject.

54. The method of claim 53, wherein the neuropathy is from diabetes, chemical injury, chemotherapy, and or trauma.

55. A method for treating a dermatological disorder in a subject, the method comprising administering an effective amount of a compound of Formula (I), or a pharmaceutically acceptable salt thereof, to a subject in need thereof:

Formula (I)

wherein:

$R^1$ is H, $C_1$-$C_6$ alkyl, $C_2$-$C_6$ alkenyl, or $C_2$-$C_6$ alkynyl;

$R^2$ is H, $C_1$-$C_6$ alkyl, $C_2$-$C_6$ alkenyl, or $C_2$-$C_6$ alkynyl optionally substituted with one or more $R^5$ groups;

$R^3$ is H, $C_1$-$C_6$ alkyl, $C_2$-$C_6$ alkenyl, or $C_2$-$C_6$ alkynyl;

$R^4$ is halo, hydroxy, alkoxy, thiol, alkylthio, amino, alkylamino, dialkylamino, cyano, nitro, amido, alkylamido, dialkylamido, thioyl, sulfonyl, cyclyl, heterocyclyl, aryl, or heteroaryl, optionally substituted at one or more positions with 1-4 $R^6$ groups;

$R^5$ is independently H, halogen, alkyl, aralkyl, alkenyl, alkynyl, hydroxy, amino, amido, phosphonate, carboxyl, ether, alkylthio, haloalkyl, and cyano; and $R^6$ is independently H, halogen, alkyl, aralkyl, alkenyl, alkynyl, cycloalkyl, hydroxy, amino, nitro, sulfhydryl, imino, amido, phosphate, phosphonate, phosphinate, carbonyl, carboxyl, silyl, ether, alkylthio, sulfonyl, ketone, aldehyde, ester, heterocycle, an aromatic or heteroaromatic ring, haloalkyl, and cyano, to thereby treat the subject, wherein the dermatological disorder is selected from atopic dermatitis, acute pruritus, psoriasis, hives, eczema, dyshidrotic eczema, mouth ulcers, and diaper rash.

56. A method for treating a pulmonary disease in a subject, the method comprising administering an effective amount of a compound of Formula (I), or a pharmaceutically acceptable salt thereof, to a subject in need thereof:

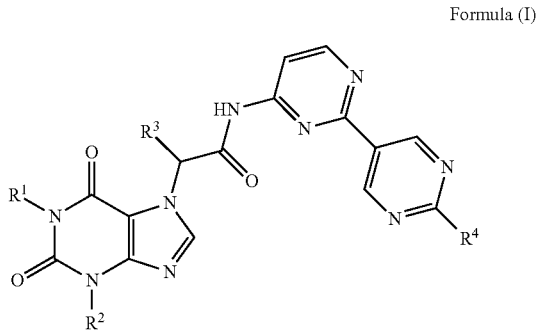

Formula (I)

wherein:
$R^1$ is H, $C_1$-$C_6$ alkyl, $C_2$-$C_6$ alkenyl, or $C_2$-$C_6$ alkynyl;
$R^2$ is H, $C_1$-$C_6$ alkyl, $C_2$-$C_6$ alkenyl, or $C_2$-$C_6$ alkynyl optionally substituted with one or more $R^5$ groups;
$R^3$ is H, $C_1$-$C_6$ alkyl, $C_2$-$C_6$ alkenyl, or $C_2$-$C_6$ alkynyl;
$R^4$ is halo, hydroxy, alkoxy, thiol, alkylthio, amino, alkylamino, dialkylamino, cyano, nitro, amido, alkylamido, dialkylamido, thioyl, sulfonyl, cyclyl, heterocyclyl, aryl, or heteroaryl, optionally substituted at one or more positions with 1-4 $R^6$ groups;
$R^5$ is independently H, halogen, alkyl, aralkyl, alkenyl, alkynyl, hydroxy, amino, amido, phosphonate, carboxyl, ether, alkylthio, haloalkyl, and cyano; and
$R^6$ is independently H, halogen, alkyl, aralkyl, alkenyl, alkynyl, cycloalkyl, hydroxy, amino, nitro, sulfhydryl, imino, amido, phosphate, phosphonate, phosphinate, carbonyl, carboxyl, silyl, ether, alkylthio, sulfonyl, ketone, aldehyde, ester, heterocycle, an aromatic or heteroaromatic ring, haloalkyl, and cyano, to thereby treat the subject, wherein the pulmonary disease is chronic obstructive pulmonary disease or asthma.

57. A method for treating cough in a subject, the method comprising administering an effective amount of a compound of Formula (I), or a pharmaceutically acceptable salt thereof, to a subject in need thereof:

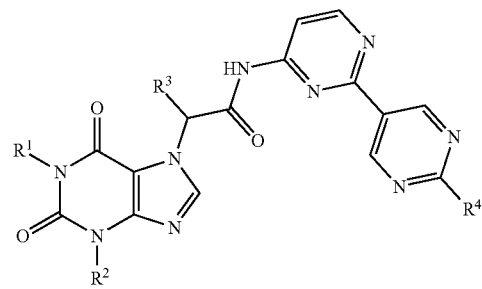

Formula (I)

wherein:
$R^1$ is H, $C_1$-$C_6$ alkyl, $C_2$-$C_6$ alkenyl, or $C_2$-$C_6$ alkynyl;
$R^2$ is H, $C_1$-$C_6$ alkyl, $C_2$-$C_6$ alkenyl, or $C_2$-$C_6$ alkynyl optionally substituted with one or more $R^5$ groups;
$R^3$ is H, $C_1$-$C_6$ alkyl, $C_2$-$C_6$ alkenyl, or $C_2$-$C_6$ alkynyl;
$R^4$ is halo, hydroxy, alkoxy, thiol, alkylthio, amino, alkylamino, dialkylamino, cyano, nitro, amido, alkylamido, dialkylamido, thioyl, sulfonyl, cyclyl, heterocyclyl, aryl, or heteroaryl, optionally substituted at one or more positions with 1-4 $R^6$ groups;
$R^5$ is independently H, halogen, alkyl, aralkyl, alkenyl, alkynyl, hydroxy, amino, amido, phosphonate, carboxyl, ether, alkylthio, haloalkyl, and cyano; and
$R^6$ is independently H, halogen, alkyl, aralkyl, alkenyl, alkynyl, cycloalkyl, hydroxy, amino, nitro, sulfhydryl, imino, amido, phosphate, phosphonate, phosphinate, carbonyl, carboxyl, silyl, ether, alkylthio, sulfonyl, ketone, aldehyde, ester, heterocycle, an aromatic or heteroaromatic ring, haloalkyl, and cyano, to thereby treat the subject.

58. The method of claim 57, wherein the cough is allergy-induced cough.

* * * * *

UNITED STATES PATENT AND TRADEMARK OFFICE
CERTIFICATE OF CORRECTION

PATENT NO. : 10,428,072 B2  
APPLICATION NO. : 15/940253  
DATED : October 1, 2019  
INVENTOR(S) : Blaise S. Lippa et al.

Page 1 of 1

It is certified that error appears in the above-identified patent and that said Letters Patent is hereby corrected as shown below:

In the Claims

In Column 133, Line 22, In Claim 34, delete "(b):" and insert -- (IIb): --, therefor.

In Column 138, Lines 55-65, through Column 139, Lines 1-14

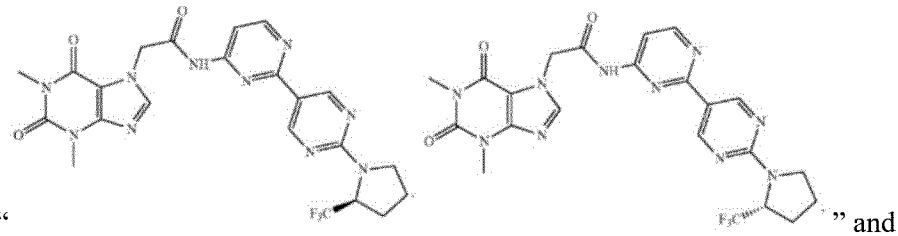

In Claim 35, delete " [structure] " and insert -- [structure], and [structure] --, therefor.

In Column 142, Line 38, In Claim 54, delete "and or" and insert -- and/or --, therefor.

Signed and Sealed this  
Seventeenth Day of December, 2019

Andrei Iancu  
*Director of the United States Patent and Trademark Office*